US012630652B2

(12) United States Patent
Chen et al.

(10) Patent No.: US 12,630,652 B2
(45) Date of Patent: *May 19, 2026

(54) BISPECIFIC ANTIBODY AND USE THEREOF

(71) Applicant: Keymed Biosciences (Chengdu) Co., LTD, Chengdu (CN)

(72) Inventors: Bo Chen, Chengdu (CN); Gang Xu, Chengdu (CN); Changyu Wang, Chengdu (CN)

(73) Assignee: Keymed Biosciences (Chengdu) Co., LTD, Chengdu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 19/229,907

(22) Filed: Jun. 5, 2025

(65) Prior Publication Data

US 2025/0346685 A1      Nov. 13, 2025

Related U.S. Application Data

(63) Continuation of application No. 18/038,159, filed as application No. PCT/CN2021/132195 on Nov. 22, 2021.

(30) Foreign Application Priority Data

Nov. 23, 2020    (CN) .......................... 202011325843.0

(51) Int. Cl.
| | |
|---|---|
| C07K 16/46 | (2006.01) |
| A61K 40/10 | (2025.01) |
| A61K 40/42 | (2025.01) |
| C12N 15/63 | (2006.01) |

(52) U.S. Cl.
CPC ............ C07K 16/468 (2013.01); A61K 40/10 (2025.01); A61K 40/4215 (2025.01); A61K 40/4221 (2025.01); A61K 40/4261 (2025.01); C12N 15/63 (2013.01); A61K 2239/31 (2023.05); A61K 2239/38 (2023.05); A61K 2239/48 (2023.05); A61K 2239/53 (2023.05); C07K 2317/31 (2013.01); C07K 2317/52 (2013.01); C07K 2317/565 (2013.01)

(58) Field of Classification Search
CPC .............. C07K 16/468; C07K 2317/31; C07K 16/2809; C07K 16/2878
See application file for complete search history.

(56) References Cited

U.S. PATENT DOCUMENTS

| | | | |
|---|---|---|---|
| 5,635,483 | A | 6/1997 | Pettit et al. |
| 5,780,588 | A | 7/1998 | Pettit et al. |
| 6,214,345 | B1 | 4/2001 | Firestone et al. |
| 7,229,619 | B1 | 6/2007 | Young et al. |
| 2013/0025295 | A1 | 1/2013 | Brehm et al. |
| 2017/0174781 | A1 | 6/2017 | Brownstein |
| 2017/0267783 | A1 | 9/2017 | Nezu et al. |

| | | | |
|---|---|---|---|
| 2020/0024356 | A1 | 1/2020 | Smith et al. |
| 2023/0330257 | A1 | 10/2023 | Wang et al. |
| 2024/0002540 | A1 | 1/2024 | Chen et al. |

FOREIGN PATENT DOCUMENTS

| | | | |
|---|---|---|---|
| CN | 103261220 A | 8/2013 | |
| CN | 105121467 A | 12/2015 | |
| CN | 111201031 A | 5/2020 | |
| CN | 111454357 A | 7/2020 | |
| EP | 4209512 A1 | 7/2023 | |
| EP | 4257607 A1 | 10/2023 | |
| EP | 4257612 A1 | 10/2023 | |
| JP | 2013524498 A | 6/2013 | |
| JP | 2015535828 A | 12/2015 | |
| JP | 2018520642 A | 8/2018 | |
| JP | 2018525005 A | 9/2018 | |
| WO | WO-2002088172 | 11/2002 | |
| WO | WO-2003026577 A2 | 4/2003 | |
| WO | WO-2004010957 A2 | 2/2004 | |
| WO | WO-2005081711 A2 | 9/2005 | |
| WO | WO-2005082023 A2 | 9/2005 | |
| WO | WO-2005084390 A2 | 9/2005 | |
| WO | WO-2006132670 A2 | 12/2006 | |
| WO | WO-2007008603 A1 | 1/2007 | |
| WO | WO-2007011968 A2 | 1/2007 | |
| WO | WO-2011097603 A1 | 8/2011 | |
| WO | WO-2012023053 A2 | 2/2012 | |
| WO | WO-2012059882 A2 | 5/2012 | |
| WO | WO-2014047231 A1 | 3/2014 | |
| WO | WO-2014087248 A2 | 6/2014 | |
| WO | WO-2015026894 A2 * | 2/2015 | .............. A61P 35/00 |
| WO | WO-2016179003 A1 | 11/2016 | |
| WO | WO-2016194992 A1 | 12/2016 | |

(Continued)

OTHER PUBLICATIONS

Fischer et al (Nature Communications 2015, vol. 6, article 6113) (Year: 2015).*

Anderson et al., Drugs of the Future—Bispecific Antibodies An investigation of future development needs, Biology Education Center, Uppsala University, 2019, 70 pages.

Armour et al., Recombinant Human IgG Molecules lacking Fcgamma Receptor I binding and Monocyte Triggering Activities, Eur J Immunnol, Aug. 1999, 29(8):2613-2624 pages.

Atwell et al., "Stable heterodimers from remodeling the domain interface of a homodimer using a phage display library," JMol Biol, Jul. 4, 1997, 270(1):26-35.

European Appln. No. 21894071.6, Extended European Search Report mailed on Sep. 13, 2024, 12 pages.

(Continued)

*Primary Examiner* — Karen A. Canella
(74) *Attorney, Agent, or Firm* — Goodwin Procter LLP

(57)          ABSTRACT

Provided are a bispecific antibody or an antigen-binding fragment thereof, a nucleic acid encoding the same, a cell comprising the nucleic acid, a composition comprising the bispecific antibody or antigen-binding fragment thereof, the nucleic acid and/or the cell, and related applications of the bispecific antibody or antigen-binding fragment thereof in the treatment of cancer.

41 Claims, 47 Drawing Sheets

Specification includes a Sequence Listing.

(56) References Cited

FOREIGN PATENT DOCUMENTS

| | | |
|---|---|---|
| WO | WO-2017031104 A1 | 2/2017 |
| WO | WO-2020018820 A1 | 1/2020 |
| WO | 2021027674 A1 | 2/2021 |
| WO | WO-2022105924 A1 | 5/2022 |

OTHER PUBLICATIONS

Fischer et al., Exploiting light chains for the scalable generation and platform purification of native human bispecfic IgG, Nature Communications, Feb. 12, 2025, 6(1): 12 pages.

Idusogie et al., "Mapping of the Clq binding site on rituxan, a chimeric antibody with a human IgGl Fe," J Immunol, Apr. 15, 2000, 164(8):4178-4184.

Japanese Appln. No. 2023-530940, Office Action mailed on Apr. 19, 2024, 12 pages (with English translation).

Kipriyanov, Generation and characterization of bispecific tandem diabodies for tumor therapy, Recombinant Antibodies for Cancer Therapy: Methods and Protocols, 2003, 19: 13 pages.

Merchant et al., "An efficient route to human bispecific IgG," Nat Biotechnol, Jul. 1998, 16(7):677-681.

Newman et al., "Modification of the Fe region of a primatized IgG antibody to human CD4 retains its ability to modulate CD4 receptors but does not deplete CD4( +) T cells in chimpanzees," Clin Immunol, Feb. 2011, 98(2): 164-174.

PCT/CN2021/132195 International Search Report mailed on Feb. 15, 2022, 9 pages (with English translation).

Perez et al., Specific targeting of cytotoxic T cells by anti-T3 linked to anti-target cell antibody, Nature, Jul. 1985, 316(6026):354-356.

Schaefer et al., Immunoglobulin domain crossover as a generic approach for the production of bispecfic IgG antibodies, Proceedings of the National Academy of Sciences, Jul. 5, 2011, 108(27): 11187-11192.

Staerz et al., "Hybrid antibodies can target sites for attack by T cells," Nature, Apr. 1985, 314(6012):628-631.

Wang et al., "A systematic approach for analysis and characterization of mispairing in bispecific antibodies with asymmetric architecture," Mabs, Nov.-Dec. 2018, available online Sep. 20, 2018, 10(8):1226-1235.

Brinkman, Ulrich et al., The making of Biospecifc Antibodies, MABS, vol. 9, No. 2, Jan. 10, 2017 (Jan. 10, 2017), pp. 182-212, XP055374463, US, ISSN: 1942-0862, DOI: 10.1080/19420862.2016.1268307, * p. 189, right-hand column * table *.

* cited by examiner

κ light chain     λ light chain

κλ001

κλ002

κλ003

κλ004

κλ005

BCMAxCD3 κλ005

BCMAxCD3 κλ006

REGN 5458

SEQUENCE LISTING

```
Sequence total quantity: 95
SEQ ID NO: 1            moltype = AA  length = 306
FEATURE                 Location/Qualifiers
source                  1..306
                        mol_type = protein
                        organism = Homo sapiens
SEQUENCE: 1
QSIKGNHLVK VYDYQEDGSV LLTCDAEAKN ITWFKDGKMI GFLTEDKKKW NLGSNAKDPR   60
GMYQCKGSQN KSKPLQVYYR MCQNCIELNA PEAAGGPSVF LFPPKPKDTL MISRTPEVTC  120
VVVDVSHEDP EVKFNWYVDG VEVHNAKTKP REEQYNSTYR VVSVLTVLHQ DWLNGKEYKC  180
KVSNKALPAS IEKTISKAKG QPREPQVCTL PPSRDELTKN QVSLSCAVKG FYPSDIAVEW  240
ESNGQPENNY KTTPPVLDSD GSFFLVSKLT VDKSRWQQGN VFSCSVMHEA LHNHYTQKSL  300
SLSPGK                                                            306

SEQ ID NO: 2            moltype = AA  length = 339
FEATURE                 Location/Qualifiers
source                  1..339
                        mol_type = protein
                        organism = Homo sapiens
SEQUENCE: 2
QDGNEEMGGI TQTPYKVSIS GTTVILTCPQ YPGSEILWQH NDKNIGGDED DKNIGSDEDH   60
LSLKEFSELE QSGYYVCYPR GSKPEDANFY LYLRARVCEN CMEMDAPEAA GGPSVFLFPP  120
KPKDTLMISR TPEVTCVVVD VSHEDPEVKF NWYVDGVEVH NAKTKPREEQ YNSTYRVVSV  180
LTVLHQDWLN GKEYKCKVSN KALPASIEKT ISKAKGQPRE PQVYTLPPCR DELTKNQVSL  240
WCLVKGFYPS DIAVEWESNG QPENNYKTTP PVLDSDGSFF LYSKLTVDKS RWQQGNVFSC  300
SVMHEALHNH YTQKSLSLSP GKGSGLNDIF EAQKIEWHE                         339

SEQ ID NO: 3            moltype = AA  length = 305
FEATURE                 Location/Qualifiers
source                  1..305
                        mol_type = protein
                        organism = Macaca fascicularis
SEQUENCE: 3
QSFEENRKLN VYNQEDGSVL LTCHVKNTNI TWFKEGKMID ILTAHKNKWN LGSNTKDPRG   60
VYQCKGSKDK SKTLQVYYRM CQNCIELNAP EAAGGPSVFL FPPKPKDTLM ISRTPEVTCV  120
VVDVSHEDPE VKFNWYVDGV EVHNAKTKPR EEQYNSTYRV VSVLTVLHQD WLNGKEYKCK  180
VSNKALPASI EKTISKAKGQ PREPQVCTLP PSRDELTKNQ VSLSCAVKGF YPSDIAVEWE  240
```

-continued

```
SNGQPENNYK TTPPVLDSDG SFFLVSKLTV DKSRWQQGNV FSCSVMHEAL HNHYTQKSLS   300
LSPGK                                                                305

SEQ ID NO: 4              moltype = AA   length = 330
FEATURE                   Location/Qualifiers
source                    1..330
                          mol_type = protein
                          organism = Macaca fascicularis
SEQUENCE: 4
QDGNEEMGSI TQTPYQVSIS GTTVILTCSQ HLGSEAQWQH NGKNKEDSGD RLFLPEFSEM   60
EQSGYYVCYP RGSNPEDASH HLYLKARVCE NCMEMDAPEA AGGPSVFLFP PKPKDTLMIS   120
RTPEVTCVVV DVSHEDPEVK FNWYVDGVEV HNAKTKPREE QYNSTYRVVS VLTVLHQDWL   180
NGKEYKCKVS NKALPASIEK TISKAKGQPR EPQVYTLPPC RDELTKNQVS LWCLVKGFYP   240
SDIAVEWESN GQPENNYKTT PPVLDSDGSF FLYSKLTVDK SRWQQGNVFS CSVMHEALHN   300
HYTQKSLSLS PGKGSGLNDI FEAQKIEWHE                                     330

SEQ ID NO: 5              moltype = AA   length = 109
FEATURE                   Location/Qualifiers
source                    1..109
                          mol_type = protein
                          organism = Homo sapiens
SEQUENCE: 5
QAVVTQEPSL TVSPGGTVTL TCRSSTGAVT TSNYANWVQQ KPGQAPRGLI GGTNKRAPWT   60
PARFSGSLLG GKAALTLSGA QPEDEAEYYC ALWYSNLWVF GGGTKLTVL                109

SEQ ID NO: 6              moltype = DNA   length = 327
FEATURE                   Location/Qualifiers
source                    1..327
                          mol_type = other DNA
                          organism = Homo sapiens
SEQUENCE: 6
caggctgtgg tcacacaaga gcctagcctg acagtgtctc ctggcggcac agtgaccctg   60
acctgtagat cttctacagg cgccgtgacc accagcaact acgctaattg ggtgcagcag   120
aagcccggcc aggctcctag aggactgatc ggcggaagca acaagagagc cccttggaca   180
cccgccagat tctctggatc tctgctcggc ggaaaggccg ctctgacact ttctggtgct   240
cagcctgagg acgaggccga gtactattgt gccctgtggt acagcaacct gtgggtgttc   300
ggcggaggca ccaaactgac agttctg                                       327

SEQ ID NO: 7              moltype = AA   length = 14
FEATURE                   Location/Qualifiers
source                    1..14
                          mol_type = protein
                          organism = Homo sapiens
SEQUENCE: 7
RSSTGAVTTS NYAN                                                      14

SEQ ID NO: 8              moltype = AA   length = 8
FEATURE                   Location/Qualifiers
source                    1..8
                          mol_type = protein
                          organism = Homo sapiens
SEQUENCE: 8
GGTNKRAP                                                             8

SEQ ID NO: 9              moltype = AA   length = 9
FEATURE                   Location/Qualifiers
source                    1..9
                          mol_type = protein
                          organism = Homo sapiens
SEQUENCE: 9
ALWYSNLWV                                                            9

SEQ ID NO: 10             moltype = AA   length = 109
FEATURE                   Location/Qualifiers
source                    1..109
                          mol_type = protein
                          organism = Homo sapiens
SEQUENCE: 10
QAVVTQEPSL TVSPGGTVTL TCRSSTGAVT TSNYANWVQE KPGQAPRGLI GGTNKRAPWT   60
PARFSGSLLG GKAALTLSGA QPEDEAEYYC ALWYSNLWVF GGGTKLTVL                109

SEQ ID NO: 11             moltype = DNA   length = 327
FEATURE                   Location/Qualifiers
source                    1..327
                          mol_type = other DNA
                          organism = Homo sapiens
SEQUENCE: 11
caggctgtgg tcacacaaga gcctagcctg acagtgtctc ctggcggcac agtgaccctg   60
acctgtagat cttctacagg cgccgtgacc accagcaact acgctaattg ggtgcaggag   120
```

-continued

```
aagcccggcc aggctcctag aggactgatc ggcggaacaa acaagagagc cccttggaca  180
cccgccagat tctctggatc tctgctcggc ggaaaggccg ctctgacact ttctggtgct  240
cagcctgagg acgaggccga gtactattgt gccctgtggt acagcaacct gtgggtgttc  300
ggcggaggca ccaaactgac agttctg                                      327

SEQ ID NO: 12              moltype = AA   length = 109
FEATURE                    Location/Qualifiers
source                     1..109
                           mol_type = protein
                           organism = Homo sapiens
SEQUENCE: 12
EAVVTQEPSL TVSPGGTVTL TCESSDGAVT TSNYANWVQE KPGQAPRGLI GGTNKEAPWT  60
PARFSGSLLG GKAALTLSGA QPEDEAEYYC ALWYSNLWVF GGGTKLTVL             109

SEQ ID NO: 13              moltype = DNA   length = 327
FEATURE                    Location/Qualifiers
source                     1..327
                           mol_type = other DNA
                           organism = Homo sapiens
SEQUENCE: 13
gaggctgtgg tcacacaaga gcctagcctg acagtgtctc ctggcggcac agtgaccctg  60
acctgtgagt cttctgacgg cgccgtgacc accagcaact acgctaattg ggtgcaggag  120
aagcccggcc aggctcctag aggactgatc ggcggaacaa acaaggaggc cccttggaca  180
cccgccagat tctctggatc tctgctcggc ggaaaggccg ctctgacact ttctggtgct  240
cagcctgagg acgaggccga gtactattgt gccctgtggt acagcaacct gtgggtgttc  300
ggcggaggca ccaaactgac agttctg                                      327

SEQ ID NO: 14              moltype = AA   length = 14
FEATURE                    Location/Qualifiers
source                     1..14
                           mol_type = protein
                           organism = Homo sapiens
SEQUENCE: 14
ESSDGAVTTS NYAN                                                     14

SEQ ID NO: 15              moltype = AA   length = 8
FEATURE                    Location/Qualifiers
source                     1..8
                           mol_type = protein
                           organism = Homo sapiens
SEQUENCE: 15
GGTNKEAP                                                            8

SEQ ID NO: 16              moltype = AA   length = 109
FEATURE                    Location/Qualifiers
source                     1..109
                           mol_type = protein
                           organism = Homo sapiens
SEQUENCE: 16
QAVVTQEPSL TVSPGGTVTL TCESSDGAVT TSNYANWVQE KPGQAPRGLI GGTNKEAPWT  60
PARFSGSLLG GKAALTLSGA QPEDEAEYYC ALWYSNLWVF GGGTKLTVL             109

SEQ ID NO: 17              moltype = DNA   length = 327
FEATURE                    Location/Qualifiers
source                     1..327
                           mol_type = other DNA
                           organism = Homo sapiens
SEQUENCE: 17
caggctgtgg tcacacaaga gcctagcctg acagtgtctc ctggcggcac agtgaccctg  60
acctgtgagt cttctgacgg cgccgtgacc accagcaact acgctaattg ggtgcaggag  120
aagcccggcc aggctcctag aggactgatc ggcggaacaa acaaggaggc cccttggaca  180
cccgccagat tctctggatc tctgctcggc ggaaaggccg ctctgacact ttctggtgct  240
cagcctgagg acgaggccga gtactattgt gccctgtggt acagcaacct gtgggtgttc  300
ggcggaggca ccaaactgac agttctg                                      327

SEQ ID NO: 18              moltype = AA   length = 109
FEATURE                    Location/Qualifiers
source                     1..109
                           mol_type = protein
                           organism = Homo sapiens
SEQUENCE: 18
QAVVTQEPSL TVSPGGTVTL TCRSSTGAVT TSNYANWVQE KPGQAPRGLI GGTNKRAPWT  60
PARFSGSLLG GKAALTITGA QAEDEAEYYC VLWYSNLWVF GGGTKLTVL             109

SEQ ID NO: 19              moltype = DNA   length = 327
FEATURE                    Location/Qualifiers
source                     1..327
                           mol_type = other DNA
                           organism = Homo sapiens
```

```
SEQUENCE: 19
caggctgtgg tcacacaaga gcctagcctg acagtgtctc ctggcggcac agtgaccctg    60
acctgtagat cttctacagg cgccgtgacc accagcaact acgctaattg ggtgcaggag   120
aagcccggcc aggctcctag aggactgatc ggcggaacaa acaagagagc cccttggaca   180
cccgccagat tctctggatc tctgctcggc ggaaaggccg ctctgacaat cactggtgct   240
caggctgagg acgaggccga gtactattgt gtgctgtggt acagcaacct gtgggtgttc   300
ggcggaggca ccaaactgac agttctg                                       327

SEQ ID NO: 20            moltype = AA   length = 8
FEATURE                  Location/Qualifiers
source                   1..8
                         mol_type = protein
                         organism = Homo sapiens
SEQUENCE: 20
YGTNKRAP                                                               8

SEQ ID NO: 21            moltype = AA   length = 9
FEATURE                  Location/Qualifiers
source                   1..9
                         mol_type = protein
                         organism = Homo sapiens
SEQUENCE: 21
VLWYSNLWV                                                              9

SEQ ID NO: 22            moltype = AA   length = 109
FEATURE                  Location/Qualifiers
source                   1..109
                         mol_type = protein
                         organism = Homo sapiens
SEQUENCE: 22
QAVVTQEPSL TVSPGGTVTL TCRSSTGAVT TSNYANWFQE KPGQAPRGLI YGTNKRAPWT    60
PARFSGSLLG GKAALTLSGA QAEDEAEYYC VLWYSNLWVF GGGTKLTVL               109

SEQ ID NO: 23            moltype = DNA   length = 327
FEATURE                  Location/Qualifiers
source                   1..327
                         mol_type = other DNA
                         organism = Homo sapiens
SEQUENCE: 23
caggctgtgg tcacacaaga gcctagcctg acagtgtctc ctggcggcac agtgaccctg    60
acctgtagat cttctacagg cgccgtgacc accagcaact acgctaattg gttccaggag   120
aagcccggcc aggctcctag aggactgatc tacggaacaa acaagagagc cccttggaca   180
cccgccagat tctctggatc tctgctcggc ggaaaggccg ctctgacact ttctggtgct   240
caggctgagg acgaggccga gtactattgt gtcctgtggt acagcaacct gtgggtgttc   300
ggcggaggca ccaaactgac agttctg                                       327

SEQ ID NO: 24            moltype = AA   length = 125
FEATURE                  Location/Qualifiers
source                   1..125
                         mol_type = protein
                         organism = Homo sapiens
SEQUENCE: 24
EVQLVESGGG LVQPGGSLRL SCAASGFTFN TYAMNWVRQA PGKGLEWVSR IRSKYNNYAT    60
YYADSVKDRF TISRDDSKNT LYLQMNSLRA EDTAVYYCVR HGNFGNSYVS WFAYWGQGTL   120
VTVSS                                                               125

SEQ ID NO: 25            moltype = DNA   length = 375
FEATURE                  Location/Qualifiers
source                   1..375
                         mol_type = other DNA
                         organism = Homo sapiens
SEQUENCE: 25
gaggtgcagc tggttgaatc tggcggagga ctggttcagc ctggcggatc tctgagactg    60
tcttgtgccg ccagcggctt caccttcaac acctacgcta tgaactgggt ccgacaggcc   120
cctggcaaag gactggaatg ggtgtccaga atcaggtcca agtacaacaa ctacgccacc   180
tactacgccg acagcgtgaa ggacagattc accatcagca gggacgacag caagaacacc   240
ctgtacctgc agatgaacag cctgagagcc gaggacaccg ccgtgtacta ctgtgtcaga   300
cacggcaact cggcaacag ctatgtgtct tggtttgcct actggggcca gggcacactg    360
gtcacagtta gctct                                                    375

SEQ ID NO: 26            moltype = AA   length = 6
FEATURE                  Location/Qualifiers
source                   1..6
                         mol_type = protein
                         organism = Homo sapiens
SEQUENCE: 26
NTYAMN                                                                 6

SEQ ID NO: 27            moltype = AA   length = 18
```

-continued

```
FEATURE           Location/Qualifiers
source            1..18
                  mol_type = protein
                  organism = Homo sapiens
SEQUENCE: 27
IRSKYNNYAT YYADSVKD                                          18

SEQ ID NO: 28    moltype = AA  length = 14
FEATURE           Location/Qualifiers
source            1..14
                  mol_type = protein
                  organism = Homo sapiens
SEQUENCE: 28
HGNFGNSYVS WFAY                                              14

SEQ ID NO: 29    moltype = AA  length = 125
FEATURE           Location/Qualifiers
source            1..125
                  mol_type = protein
                  organism = Homo sapiens
SEQUENCE: 29
EVQLVESGGG LVQPGGSLRL SCAASGFTFS TYAMNWVRKA PGKGLEWVSR IRSKYNNYAT  60
YYADSVKDRF TISRDDSKNT LYLQMNSLRA EDTAVYYCVR HGNFGNSYVS WFAYWGQGTL  120
VTVSS                                                        125

SEQ ID NO: 30    moltype = DNA  length = 375
FEATURE           Location/Qualifiers
source            1..375
                  mol_type = other DNA
                  organism = Homo sapiens
SEQUENCE: 30
gaggtgcagc tggttgaatc tggcggagga ctggttcagc ctggcggatc tctgagactg  60
tcttgtgccg ccagcggctt caccttctcc acctacgcta tgaactgggt ccgaaaggcc  120
cctggcaaag gactggaatg ggtgtccaga atcaggtcca agtacaacaa ctacgccacc  180
tactacgccg acagcgtgaa ggacagattc accatcagca gggacgacag caagaacacc  240
ctgtacctgc agatgaacag cctgagagcc gaggacaccg ccgtgtacta ctgtgtcaga  300
cacggcaact cggcaacagc ctatgtgtct tggtttgcct actggggcca gggcacactg  360
gtcacagtta gctct                                             375

SEQ ID NO: 31    moltype = AA  length = 6
FEATURE           Location/Qualifiers
source            1..6
                  mol_type = protein
                  organism = Homo sapiens
SEQUENCE: 31
STYAMN                                                       6

SEQ ID NO: 32    moltype = AA  length = 125
FEATURE           Location/Qualifiers
source            1..125
                  mol_type = protein
                  organism = Homo sapiens
SEQUENCE: 32
EVQLVESGGG LVQPGGSLRL SCAASGFTFS TYAMNWVRKA PGKGLEWVSR IRSKYNNYAT  60
YYADSVKDRF TISRDDSKNT LYLQMNSLRA EDTAVYYCVR HGNFGESYVS WFAYWGQGTL  120
VTVSS                                                        125

SEQ ID NO: 33    moltype = DNA  length = 375
FEATURE           Location/Qualifiers
source            1..375
                  mol_type = other DNA
                  organism = Homo sapiens
SEQUENCE: 33
gaggtgcagc tggttgaatc tggcggagga ctggttcagc ctggcggatc tctgagactg  60
tcttgtgccg ccagcggctt caccttctcc acctacgcta tgaactgggt ccgaaaggcc  120
cctggcaaag gactggaatg ggtgtccaga atcaggtcca agtacaacaa ctacgccacc  180
tactacgccg acagcgtgaa ggacagattc accatcagca gggacgacag caagaacacc  240
ctgtacctgc agatgaacag cctgagagcc gaggacaccg ccgtgtacta ctgtgtcaga  300
cacggcaact cggcgagagc ctatgtgtct tggtttgcct actggggcca gggcacactg  360
gtcacagtta gctct                                             375

SEQ ID NO: 34    moltype = AA  length = 14
FEATURE           Location/Qualifiers
source            1..14
                  mol_type = protein
                  organism = Homo sapiens
SEQUENCE: 34
HGNFGESYVS WFAY                                              14
```

```
SEQ ID NO: 35           moltype = AA  length = 125
FEATURE                 Location/Qualifiers
source                  1..125
                        mol_type = protein
                        organism = Homo sapiens
SEQUENCE: 35
EVQLVESGGG LVQPGGSLRL SCAASGFTFS TYAMNWVRKA PGKGLEWVSR IRSKYNNYAT   60
YYADSVKDRF TISRDDSKNT LYLQMNSLRA EDTAVYYCVR HGNFGQSYVS WFAYWGQGTL   120
VTVSS                                                               125

SEQ ID NO: 36           moltype = DNA  length = 375
FEATURE                 Location/Qualifiers
source                  1..375
                        mol_type = other DNA
                        organism = Homo sapiens
SEQUENCE: 36
gaggtgcagc tggttgaatc tggcggagga ctggttcagc ctggcggatc tctgagactg   60
tcttgtgccg ccagcggctt caccttctcc acctacgcta tgaactgggt ccgaaaggcc   120
cctggcaaag gactggaatg ggtgtccaga atcaggtcca agtacaacaa ctacgccacc   180
tactacgccg acagcgtgaa ggacagattc accatcagca gggacgacag caagaacacc   240
ctgtacctgc agatgaacag cctgagagcc gaggacaccg ccgtgtacta ctgtgtcaga   300
cacggcaact cggccagag ctatgtgtct tggtttgcct actggggcca gggcacactg   360
gtcacagtta gctct                                                   375

SEQ ID NO: 37           moltype = AA  length = 14
FEATURE                 Location/Qualifiers
source                  1..14
                        mol_type = protein
                        organism = Homo sapiens
SEQUENCE: 37
HGNFGQSYVS WFAY                                                     14

SEQ ID NO: 38           moltype = AA  length = 125
FEATURE                 Location/Qualifiers
source                  1..125
                        mol_type = protein
                        organism = Homo sapiens
SEQUENCE: 38
EVQLVESGGG LVQPGGSLRL SCAASGFTFS TYAMNWVRKA PGKGLEWVSR IRSKYNNYAT   60
YYADSVKDRF TISRDDSKNT LYLQMNSLRA EDTAVYYCVR HGNFGDSYVS WFAYWGQGTL   120
VTVSS                                                               125

SEQ ID NO: 39           moltype = DNA  length = 375
FEATURE                 Location/Qualifiers
source                  1..375
                        mol_type = other DNA
                        organism = Homo sapiens
SEQUENCE: 39
gaggtgcagc tggttgaatc tggcggagga ctggttcagc ctggcggatc tctgagactg   60
tcttgtgccg ccagcggctt caccttctcc acctacgcta tgaactgggt ccgaaaggcc   120
cctggcaaag gactggaatg ggtgtccaga atcaggtcca agtacaacaa ctacgccacc   180
tactacgccg acagcgtgaa ggacagattc accatcagca gggacgacag caagaacacc   240
ctgtacctgc agatgaacag cctgagagcc gaggacaccg ccgtgtacta ctgtgtcaga   300
cacggcaact cggcgacag ctatgtgtct tggtttgcct actggggcca gggcacactg   360
gtcacagtta gctct                                                   375

SEQ ID NO: 40           moltype = AA  length = 14
FEATURE                 Location/Qualifiers
source                  1..14
                        mol_type = protein
                        organism = Homo sapiens
SEQUENCE: 40
HGNFGDSYVS WFAY                                                     14

SEQ ID NO: 41           moltype = AA  length = 125
FEATURE                 Location/Qualifiers
source                  1..125
                        mol_type = protein
                        organism = Homo sapiens
SEQUENCE: 41
EVQLVESGGG LVQPGGSLRL SCAASGFTFS TYAMNWVRKA PGKGLEWVSR IRSKYNNYAT   60
YYADSVKDRF TISRDDSKNT LYLQMNSLRA EDTAVYYCVR HGNFGTSYVS WFAYWGQGTL   120
VTVSS                                                               125

SEQ ID NO: 42           moltype = DNA  length = 375
FEATURE                 Location/Qualifiers
source                  1..375
                        mol_type = other DNA
                        organism = Homo sapiens
```

-continued

```
SEQUENCE: 42
gaggtgcagc tggttgaatc tggcggagga ctggttcagc ctggcggatc tctgagactg   60
tcttgtgccg ccagcggctt caccttctcc acctacgcta tgaactgggt ccgaaaggcc  120
cctggcaaag gactggaatg ggtgtccaga atcaggtcca agtacaacaa ctacgccacc  180
tactacgccg acagcgtgaa ggacagattc accatcagca gggacgacag caagaacacc  240
ctgtacctgc agatgaacag cctgagagcc gaggacaccg ccgtgtacta ctgtgtcaga  300
cacggcaact tcggcaccag ctatgtgtct tggtttgcct actggggcca gggcacactg  360
gtcacagtta gctct                                                  375

SEQ ID NO: 43              moltype = AA  length = 14
FEATURE                    Location/Qualifiers
source                     1..14
                           mol_type = protein
                           organism = Homo sapiens
SEQUENCE: 43
HGNFGTSYVS WFAY                                                     14

SEQ ID NO: 44              moltype = AA  length = 125
FEATURE                    Location/Qualifiers
source                     1..125
                           mol_type = protein
                           organism = Homo sapiens
SEQUENCE: 44
EVQLVESGGG LVQPGGSLRL SCAASGFTFS DYAMNWVRKA PGKGLEWVSR IRSKYNNYAT   60
YYADSVEDRF TISRDDSKNT LYLQMNSLRA EDTAVYYCVR HGNFGNSYVS WFAYWGQGTL  120
VTVSS                                                              125

SEQ ID NO: 45              moltype = DNA  length = 375
FEATURE                    Location/Qualifiers
source                     1..375
                           mol_type = other DNA
                           organism = Homo sapiens
SEQUENCE: 45
gaggtgcagc tggttgaatc tggcggagga ctggttcagc ctggcggatc tctgagactg   60
tcttgtgccg ccagcggctt caccttctcc gactacgcta tgaactgggt ccgaaaggcc  120
cctggcaaag gactggaatg ggtgtccaga atcaggtcca agtacaacaa ctacgccacc  180
tactacgccg acagcgtgga ggacagattc accatcagca gggacgacag caagaacacc  240
ctgtacctgc agatgaacag cctgagagcc gaggacaccg ccgtgtacta ctgtgtcaga  300
cacggcaact tcggcaacag ctatgtgtct tggtttgcct actggggcca gggcacactg  360
gtcacagtta gctct                                                  375

SEQ ID NO: 46              moltype = AA  length = 6
FEATURE                    Location/Qualifiers
source                     1..6
                           mol_type = protein
                           organism = Homo sapiens
SEQUENCE: 46
SDYAMN                                                              6

SEQ ID NO: 47              moltype = AA  length = 18
FEATURE                    Location/Qualifiers
source                     1..18
                           mol_type = protein
                           organism = Homo sapiens
SEQUENCE: 47
IRSKYNNYAT YYADSVED                                                 18

SEQ ID NO: 48              moltype = AA  length = 125
FEATURE                    Location/Qualifiers
source                     1..125
                           mol_type = protein
                           organism = Homo sapiens
SEQUENCE: 48
EVQLVESGGG LVQPGGSLRL SCAASGFTFN TYAMNWVRKA PGKGLEWVGR IRSKYNNYAT   60
YYADSVKDRF TISRDDSKNS LYLQMNSLKT EDTAVYYCAR HGNFGNSYVS WFAYWGQGTL  120
VTVSS                                                              125

SEQ ID NO: 49              moltype = DNA  length = 375
FEATURE                    Location/Qualifiers
source                     1..375
                           mol_type = other DNA
                           organism = Homo sapiens
SEQUENCE: 49
gaggtgcagc tggttgaatc tggcggagga ctggttcagc ctggcggatc tctgagactg   60
tcttgtgccg ccagcggctt caccttcaac acctacgcta tgaactgggt ccgaaaggcc  120
cctggcaaag gactggaatg ggtgggaaga atcaggtcca agtacaacaa ctacgccacc  180
tactacgccg acagcgtgaa ggacagattc accatcagca gggacgacag caagaacagc  240
ctgtacctgc agatgaacag cctgaaaacc gaggacaccg ccgtgtacta ctgtgccaga  300
cacggcaact tcggcaacag ctatgtgtct tggtttgcct actggggcca gggcacactg  360
```

-continued

```
gtcacagtta gctct                                                     375

SEQ ID NO: 50              moltype = AA  length = 125
FEATURE                    Location/Qualifiers
source                     1..125
                           mol_type = protein
                           organism = Homo sapiens
SEQUENCE: 50
EVQLVESGGG LVQPGGSLRL SCAASGFTFN TYAMNWVRKA PGKGLEWVGR IRSKYNNYAT   60
YYADSVKDRF TISRDDSKNS LYLQMNSLKT EDTAVYYCVR HGNFGNSYVS WFAYWGQGTL   120
VTVSS                                                               125

SEQ ID NO: 51              moltype = DNA  length = 375
FEATURE                    Location/Qualifiers
source                     1..375
                           mol_type = other DNA
                           organism = Homo sapiens
SEQUENCE: 51
gaggtgcagc tggttgaatc tggcggagga ctggttcagc ctggcggatc tctgagactg   60
tcttgtgccg ccagcggctt caccttcaac acctacgcta tgaactgggt ccgaaaggcc   120
cctggcaaag gactggaatg ggtgggaaga atcaggtcca gtacaacaa ctacgccacc   180
tactacgccg acagcgtgaa ggacagattc accatcagcag ggacgacag caagaacagc   240
ctgtacctgc agatgaacag cctgaaaacc gaggacaccg ccgtgtacta ctgtgtcaga   300
cacggcaact cggcaacag ctatgtgtct tggtttgcct actggggcca gggcacactg   360
gtcacagtta gctct                                                   375

SEQ ID NO: 52              moltype = AA  length = 125
FEATURE                    Location/Qualifiers
source                     1..125
                           mol_type = protein
                           organism = Homo sapiens
SEQUENCE: 52
EVQLVESGGG LVQPGGSLRL SCAASGFTFN TYAMNWVRKA PGKGLEWVAR IRSKYNNYAT   60
YYADSVKDRF TISRDDSKNS LYLQMNSLKT EDTAVYYCVR HGNFGNSYVS WFAYWGQGTL   120
VTVSS                                                               125

SEQ ID NO: 53              moltype = DNA  length = 375
FEATURE                    Location/Qualifiers
source                     1..375
                           mol_type = other DNA
                           organism = Homo sapiens
SEQUENCE: 53
gaggtgcagc tggttgaatc tggcggagga ctggttcagc ctggcggatc tctgagactg   60
tcttgtgccg ccagcggctt caccttcaac acctacgcta tgaactgggt ccgaaaggcc   120
cctggcaaag gactggaatg ggtggccaga atcaggtcca gtacaacaa ctacgccacc   180
tactacgccg acagcgtgaa ggacagattc accatcagca gggacgacag caagaacagc   240
ctgtacctgc agatgaacag cctgaaaacc gaggacaccg ccgtgtacta ctgtgtcaga   300
cacggcaact cggcaacag ctatgtgtct tggtttgcct actggggcca gggcacactg   360
gtcacagtta gctct                                                   375

SEQ ID NO: 54              moltype = AA  length = 214
FEATURE                    Location/Qualifiers
source                     1..214
                           mol_type = protein
                           organism = Homo sapiens
SEQUENCE: 54
EIVLTQSPGT LSLSPGERAT LSCRASQSVS SYLAWYQQKP GQAPRLLIYD ASNRATGIPD   60
RFSGSGSGTD FTLTISRLEP EDFAVYYCQQ RSNWPITFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 55              moltype = DNA  length = 642
FEATURE                    Location/Qualifiers
source                     1..642
                           mol_type = other DNA
                           organism = Homo sapiens
SEQUENCE: 55
gagatcgtgc tgacacagag ccctggcaca ctgtcactgt ctccaggcga gagagccaca   60
ctgagctgta gagccagcca gagcgtgtcc tcttacctgg cctggtatca gcagaagcct   120
ggacaggctc ccagactgct gatctacgac gccagcaaca gagccacagg catcccccgat   180
agattcagcg gctctggctc tggcaccgac ttcaccctga caatcagcag actggaaccc   240
gaggacttcg ccgtgtacta ctgccagcag agaagcaact ggcccatcac attcggccag   300
ggcaccaagc tggaaatcaa gcgaactgtg gctgcaccat ctgtcttcat cttccccgca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                     642
```

-continued

```
SEQ ID NO: 56          moltype = AA   length = 449
FEATURE                Location/Qualifiers
source                 1..449
                       mol_type = protein
                       organism = Homo sapiens
SEQUENCE: 56
EVQLLESGGG VVQPGGSLRL SCAASGFTFN DYAMHWVRQA PGKGLEWVST ISWNSGSIGY      60
ADSVKGRFTI SRDNSKNTLY LQMNSLRAED TAVYYCAKDI QYGNYYYGMD YWGQGTLVTV     120
SSASTKGPSV FPLAPCSRST SESTAALGCL VKDYFPEPVT VSWNSGALTS GVHTFPAVLQ     180
SSGLYSLSSV VTVPSSSLGT KTYTCNVDHK PSNTKVDKRV ESKYGPPCPP CPAPEFEGGP     240
SVFLFPPKPK DTLMISRTPE VTCVVVDVSQ EDPEVQFNWY VDGVEVHNAK TKPREEQFNS     300
TYRVVSVLTV LHQDWLNGKE YKCKVSNKGL ASSIEKTISK AKGQPREPQV CTLPPSQEEM     360
TKNQVSLSCA VKGFYPSDIA VEWESNGQPE NNYKTTPPVL DSDGSFFLVS KLTVDKSRWQ     420
EGNVFSCSVM HEALHNHYTQ KSLSLSLGK                                       449

SEQ ID NO: 57          moltype = DNA   length = 1347
FEATURE                Location/Qualifiers
source                 1..1347
                       mol_type = other DNA
                       organism = Homo sapiens
SEQUENCE: 57
gaagtgcagc tgctggaatc tggtggcgga gttgttcagc ctggcggctc tctgagactg      60
tcttgtgctg ccagcggctt caccttcaac gactacgcta tgcactgggt ccgacaggcc     120
cctggcaaag gacttgaatg ggtgtccacc atcagctgga acagcggctc tatcggctac     180
gccgattccg tgaagggcag attcaccatc tccagagaca acagcaagaa caccctgtac     240
ctgcagatga acagcctgag agccgaggac accgccgtgt actactgtgc caaggacatc     300
cagtacggca actactacta cggcatggac tactgggggcc agggaacact ggttaccgtt     360
agctctgcta gcaccaaggg ccccagcgtg ttccccctgg cccccttgcag cagaagcacc     420
agcgagagca cagccgccct gggctgcctg gtgaaggact acttccccga gcccgtgacc     480
gtgtcctgga acagcggcgc tctgaccagc ggcgtgcata ccttccccgc cgtgctccag     540
agcagcggac tgtactccct gagcagcgtg gtgaccgtgc cttccagcag cctgggcacc     600
aagacctaca cctgcaacgt ggaccacaag cccagcaaca ccaaggtgga caagagagtg     660
gagagcaagt acggcccctcc ctgccccccct tgccctgccc ccgagttcga gggcggacct     720
agcgtgttcc tgttcccccc caagcccaag gacaccctga tgatcagcag aacccccgag     780
gtgacctgcg tggtggtgga cgtgtcccag gaggacccccg aggtccagtt taattggtac     840
gtggacggcg tggaagtgca taacgccaag accaagccca gagaggagca gttcaacagc     900
acctacagag tggtgtccgt gctgaccgtg ctgcaccagg actggctgaa cggcaaggaa     960
tacaagtgca aggtctccaa caagggcctg gccagcagca tcgagaagac catcagcaag    1020
gccaagggcc agccacggga gccccaggtc tgcaccctgc cacctagcca gagggagatg    1080
accaagaacc aggtgtccct gagctgtgcc gtgaaaggct ctatcccag cgatatcgcc    1140
gtggagtggg agagcaacgg ccagcccgag aacaactaca agaccacccc cctgtgctg    1200
gacagcgacg gcagcttctt cctggtttcc aagctgaccg tggacaagtc cagatggcag    1260
gagggcaacg tcttcagctg ctccgtgatg cacgaggccc tgcacaacca ctacacccag    1320
aagtccctga gcctgagcct gggcaag                                        1347

SEQ ID NO: 58          moltype = AA   length = 215
FEATURE                Location/Qualifiers
source                 1..215
                       mol_type = protein
                       organism = Homo sapiens
SEQUENCE: 58
QAVVTQEPSL TVSPGGTVTL TCRSSTGAVT TSNYANWVQQ KPGQAPRGLI GGTNKRAPWT      60
PARFSGSLLG GKAALTITGA QAEDEAEYYC VLWYSNLWVF GGGTKLTVLG QPKAAPSVTL     120
FPPSSEELQA NKATLVCLIS DFYPGAVTVA WKADSSPVKA GVETTTPSKQ SNNKYAASSY     180
LSLTPEQWKS HRSYSCQVTH EGSTVEKTVA PTECS                                215

SEQ ID NO: 59          moltype = DNA   length = 645
FEATURE                Location/Qualifiers
source                 1..645
                       mol_type = other DNA
                       organism = Homo sapiens
SEQUENCE: 59
caggctgtgg tcacacaaga gcctagcctg acagtgtctc ctggcggcac agtgaccctg      60
acctgtagat cttctacagg cgccgtgacc accagcaact acgctaattg ggtgcagcag     120
aagcccggcc aggctcctag aggactgatc ggcggaacaa acaagagagc cccttggaca     180
cccgccagat tctctggatc tctgctcggc ggaaaggccg ctctgacaat cactggtgct     240
caggctgagg acgaggccga gtactattgt gtgctgtggt acagcaacct gtgggtgttc     300
ggcggaggca ccaaactgac agttctgggt cagcccaagg cggcgccctc ggtcactctg     360
ttcccgccct cctctgagga gcttcaagcc aacaaggcca cactggtgtg tctcataagt     420
gacttctatc cgggagccgt gacagtggcc tggaaggcag atagcagccc cgtcaaggcg     480
ggagtggaga ccaccacacc ctccaaacaa agcaacaaca gtacgcggc cagcagctac     540
ctgagcctga cgcctgagca gtggaagtcc cacagaagct acagctgcca ggtcacgcat     600
gaagggagca ccgtggagaa gacagtggcc cctacagaat gttca                    645

SEQ ID NO: 60          moltype = AA   length = 452
FEATURE                Location/Qualifiers
source                 1..452
                       mol_type = protein
                       organism = Homo sapiens
```

```
SEQUENCE: 60
EVQLVESGGG LVQPGGSLRL SCAASGFTFN TYAMNWVRQA PGKGLEWVGR IRSKYNNYAT   60
YYADSVKDRF TISRDDSKNS LYLQMNSLKT EDTAVYYCVR HGNFGNSYVS WFAYWGQGTL  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFE  240
GGPSVFLFPP KPKDTLMISR TPEVTCVVVD VSQEDPEVQF NWYVDGVEVH NAKTKPREEQ  300
FNSTYRVVSV LTVLHQDWLN GKEYKCKVSN KGLASSIEKT ISKAKGQPRE PQVYTLPPCQ  360
EEMTKNQVSL WCLVKGFYPS DIAVEWESNG QPENNYKTTP PVLDSDGSFF LYSKLTVDKS  420
RWQEGNVFSC SVMHEALHNH YTQKSLSLSL GK                                452

SEQ ID NO: 61            moltype = DNA  length = 1356
FEATURE                  Location/Qualifiers
source                   1..1356
                         mol_type = other DNA
                         organism = Homo sapiens
SEQUENCE: 61
gaggtgcagc tggttgaatc tggcggagga ctggttcagc ctggcggatc tctgagactg   60
tcttgtgccg ccagcggctt caccttcaac acctacgcta tgaactgggt ccgacaggcc  120
cctggcaaag gactggaatg ggtgggaaga atcaggtcca agtacaacaa ctacgccacc  180
tactacgccg acagcgtgaa ggacagattc accatcagca gggacgacag caagaacagc  240
ctgtacctgc agatgaacag cctgaaaacc gaggacaccg ccgtgtacta ctgtgtcaga  300
cacggcaact tcggcaacag ctatgtgtct tggtttgcct actggggcca gggcacactg  360
gtcacagtta gctctgctag caccaagggc cccagcgtgt tccccctggc cccttgcagc  420
agaagcacca gcgagagcac agccgccctg ggctgcctgg tgaaggacta cttccccgag  480
cccgtgaccg tgtcctggaa cagcggcgct ctgaccagcg gcgtgcatac cttccccgcc  540
gtgctccaga gcagcggact gtactccctg agcagcgtgg tgaccgtgcc ttccagcagc  600
ctgggcacca gacctacac ctgcaacgtg accacaagc ccagcaacac caaggtggac  660
aagagagtgg agagcaagta cggccctccc tgccccccctt gccctgcccc cgagttcgag  720
ggcggaccta gcgtgttcct gttccccccc aagcccaagg acaccctgat gatcagcaga  780
acccccgagg tgacctgcgt ggtggtggac gtgtcccagg aggaccccga ggtccagttt  840
aattggtacg tggacggcgt ggaagtgcat aacgccaaga ccaagcccag agaggagcag  900
ttcaacagca cctacagagt ggtgtccgtg ctgaccgtgc tgcaccagga ctggctgaac  960
ggcaaggaat acaagtgcaa ggtctccaac aagggcctgg ccagcagcat cgagaagacc 1020
atcagcaagg ccaagggcca gccacgggag ccccaggtct acaccctgcc accttgtcaa 1080
gaggagatga ccaagaacca ggtgtccctg tggtgtctgg tgaaaggctt ctatcccagc 1140
gatatcgccg tggagtggga gagcaacggc cagcccgaga caaactacaa gaccaccccc 1200
cctgtgctgg acagcgacgg cagcttcttc ctgtactcca agctgaccgt ggacaagtcc 1260
agatggcagg agggcaacgt cttcagctgc tccgtgatgc acgaggccct gcacaaccac 1320
tacacccaga agtccctgag cctgagcctg ggcaag                            1356

SEQ ID NO: 62            moltype = AA  length = 214
FEATURE                  Location/Qualifiers
source                   1..214
                         mol_type = protein
                         organism = Homo sapiens
SEQUENCE: 62
EIVLTQSPGT LSLSPGERAT LSCRASQSVS SYLAWYQKKP GQAPRLLIYD ASNRATGIPD   60
RFSGSGSGTD FTLTISRLEP EDFAVYYCQQ RSNWPITFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 63            moltype = DNA  length = 642
FEATURE                  Location/Qualifiers
source                   1..642
                         mol_type = other DNA
                         organism = Homo sapiens
SEQUENCE: 63
gagatcgtgc tgacacagag ccctggcaca ctgtcactgt ctccaggcga gagagccaca   60
ctgagctgta gagccagcca gagcgtgtcc tcttacctgg cctggtatca gaagaagcct  120
ggacaggctc ccagactgct gatctacgac gccagcaaca gagccacagg catccccgat  180
agattcagcg gctctggctc tggcaccgac ttcaccctga caatcagcag actggaaccc  240
gaggacttcg ccgtgtacta ctgccagcag agaagcaact ggcccatcac attcggccag  300
ggcaccaagc tggaaatcaa gcgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 64            moltype = AA  length = 449
FEATURE                  Location/Qualifiers
source                   1..449
                         mol_type = protein
                         organism = Homo sapiens
SEQUENCE: 64
EVQLLESGGG VVQPGGSLRL SCAASGFTFN DYAMHWVREA PGKGLEWVST ISWNSGSIGY   60
ADSVKGRFTI SRDNSKNTLY LQMNSLRAED TAVYYCAKDI QYGNYYYGMD YWGQGTLVTV  120
SSSASTKGPSV FPLAPCSRST SESTAALGCL VKDYFPEPVT VSWNSGALTS GVHTFPAVLQ  180
SSGLYSLSSV TVPSSSLGT KTYTCNVDHK PSNTKVDKRV ESKYGPPCPP CPAPEFEGGP  240
```

```
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL ASSIEKTISK AKGQPREPQV CTLPPSQEEM    360
TKNQVSLSCA VKGFYPSDIA VEWESNGQPE NNYKTTPPVL DSDGSFFLVS KLTVDKSRWQ    420
EGNVFSCSVM HEALHNHYTQ KSLSLSLGK                                      449

SEQ ID NO: 65              moltype = DNA  length = 1347
FEATURE                    Location/Qualifiers
source                     1..1347
                           mol_type = other DNA
                           organism = Homo sapiens
SEQUENCE: 65
gaagtgcagc tgctggaatc tggtggcgga gttgttcagc ctggcggctc tctgagactg     60
tcttgtgctg ccagcggctt caccttcaac gactacgcta tgcactgggt ccgagaggcc    120
cctggcaaag gacttgaatg gggtgtccac atcagctggt atcggctac                180
gccgattccg tgaagggcag attcaccatc tccagagaca acagcaagaa caccctgtac    240
ctgcagatga acagcctgag agccgaggac accgccgtgt actactgtgc caaggacatc    300
cagtacggca actactacta cggcatggac tactggggcc agggaacact ggttaccgtt    360
agctctgcta gcaccaaggg ccccagcgtg ttccccctgg cccccttgcag cagaagcacc    420
agcgagagca cagccgccct gggctgcctg gtgaaggact acttccccga gcccgtgacc    480
gtgtcctgga cagcggcgc tctgaccagc ggcgtgcata ccttccccgc cgtgctccag    540
agcagcggac tgtactccct gagcagcgtg gtgaccgtgc cttccagcag cctgggcacc    600
aagacctaca cctgcaacgt ggaccacaag cccagcaaca ccaaggtgga caagagagtg    660
gagagcaagt acggcctcc ctgccccct tgcctgccc ccgagttcga gggcggacct      720
agcgtgttcc tgttcccccc caagcccaag gacaccctga tgatcagcag aaccccgag    780
gtgacctgcg tggtggtgga cgtgtcccag gaggacccg aggtccagtt taattggtac    840
gtggacggcg tggaagtgca taacgccaag accaagccca gaggagagca gttcaacagc    900
acctacagag tggtgtccgt gctgaccgtg ctgcaccagg actggctgaa cggcaaggaa    960
tacaagtgca aggtctccaa caagggcctg ccagcagca tcgagaagac catcagcaag   1020
gccaaggggc agccacggga gccccaggtc tgcaccctgc cacctagcca agaggagatg   1080
accaagaacc aggtgtccct gagctgtgcc gtgaaaggct tctatcccag cgatatcgcc   1140
gtggagtggg agagcaacgg ccagcccgag aacaactaca agaccacccc ccctgtgctg   1200
gacagcgacg gcagcttctt cctggtttcc aagctgaccg tggacaagtc cagatggcag   1260
gagggcaacg tcttcagctg ctccgtgatg cacgaggccc tgcacaacca ctacacccag   1320
aagtccctga gcctgagcct gggcaag                                      1347

SEQ ID NO: 66              moltype = AA  length = 215
FEATURE                    Location/Qualifiers
source                     1..215
                           mol_type = protein
                           organism = Homo sapiens
SEQUENCE: 66
QAVVTQEPSL TVSPGGTVTL TCRSSTGAVT TSNYANWVQE KPGQAPRGLI GGTNKRAPWT     60
PARFSGSLLG GKAALTITGA QAEDEAEYYC VLWYSNLWVF GGGTKLTVLG QPKAAPSVTL    120
FPPSSEELQA NKATLVCLIS DFYPGAVTVA WKADSSPVKA GVETTTPSKQ SNNKYAASSY    180
LSLTPEQWKS HRSYSCQVTH EGSTVEKTVA PTECS                              215

SEQ ID NO: 67              moltype = DNA  length = 645
FEATURE                    Location/Qualifiers
source                     1..645
                           mol_type = other DNA
                           organism = Homo sapiens
SEQUENCE: 67
caggctgtgg tcacacaaga gcctagcctg acagtgtctc ctggcggcac agtgaccctg     60
acctgtagat cttctacagg cgccgtgacc accagcaact acgctaattg ggtgcaggag    120
aagccggcc aggctcctag aggactgatc ggcggaacaa acaagagagc ccttggaca     180
cccgccagat tctctggatc tctgctcggc ggaaaggccg ctctgacaat cactggtgct    240
caggctgagg acgaggccga gtactattgt gtgctgtggt acagcaacct gtgggtgttc    300
ggcggaggca ccaaactgac agttctgggt cagcccaagg cggcgccctc ggtcactctg    360
ttcccgccct cctctgagga gcttcaagcc aacaaggcca cactggtgtg tctcataagt    420
gacttctatc cgggagccgt gacagtggcc tggaaggcag atagcagccc cgtcaaggcg    480
ggagtggaga ccaccacacc ctccaaacaa agcaacaaca gtacgcggc cagcagctac    540
ctgagcctga cgcctgagca gtggaagtcc cacagaagct acagctgcca ggtcacgcat    600
gaagggagca ccgtggagaa gacagtggcc cctacagaat gttca                  645

SEQ ID NO: 68              moltype = AA  length = 452
FEATURE                    Location/Qualifiers
source                     1..452
                           mol_type = protein
                           organism = Homo sapiens
SEQUENCE: 68
EVQLVESGGG LVQPGGSLRL SCAASGFTFN TYAMNWVRKA PGKGLEWVGR IRSKYNNYAT     60
YYADSVKDRF TISRDDSKNS LYLQMNSLKT EDTAVYYCVR HGNFGNSYVS WFAYWGQGTL    120
VTVSSASTKG PSVFPLAPCS RSTSESTAAL GCLVKDYFPE PVTVSWNSGA LTSGVHTFPA    180
VLQSSGLYSL SSVVTVPSSS LGTKTYTCNV DHKPSNTKVD KRVESKYGPP CPPCPAPEFE    240
GGPSVFLFPP KPKDTLMISR TPEVTCVVVD VSQEDPEVQF NWYVDGVEVH NAKTKPREEQ    300
FNSTYRVVSV LTVLHQDWLN GKEYKCKVSN KGLASSIEKT ISKAKGQPRE PQVYTLPPCQ    360
EEMTKNQVSL WCLVKGFYPS DIAVEWESNG QPENNYKTTP PVLDSDGSFF LYSKLTVDKS    420
RWQEGNVFSC SVMHEALHNH YTQKSLSLSL GK                                 452
```

```
SEQ ID NO: 69              moltype = DNA   length = 1356
FEATURE                    Location/Qualifiers
source                     1..1356
                           mol_type = other DNA
                           organism = Homo sapiens
SEQUENCE: 69
gaggtgcagc tggttgaatc tggcggagga ctggttcagc ctggcggatc tctgagactg     60
tcttgtgccg ccagcggctt caccttcaac acctacgcta tgaactgggt ccgaaaggcc    120
cctgcaaag gactggaatg ggtgggaaga atcaggtcca agtacaacaa ctacgccacc     180
tactacgccg acagcgtgaa ggacagattc accatcagca gggacgacag caagaacagc    240
ctgtacctgc agatgaacag cctgaaaacc gaggacaccg ccgtgtacta ctgtgtcaga    300
cacggcaact tcggcaacag ctatgtgtct tggtttgcct actgggggcca gggcacactg    360
gtcacagtta gctctgctag caccaagggc cccagcgtgt tccccctggc cccttgcagc    420
agaagcacca gcgagagcac agccgccctg ggctgcctgg tgaaggacta cttccccgag    480
cccgtgaccg tgtcctggaa cagcggcgct ctgaccagcg gcgtgcatac cttccccgcc    540
gtgctccaga gcagcggact gtactccctg agcagcgtgg tgaccgtgcc ttccagcagc    600
ctgggcacca agacctacac ctgcaacgtg accacaagc ccagcaacac caaggtggac     660
aagagagtgg agagcaagta cggccctccc tgcccccctt gccctgcccc cgagttcgag    720
ggcggaccta gcgtgttcct gttcccccc aagcccaagg acaccctgat gatcagcaga     780
accccccgagg tgacctgcgt ggtggtggac gtgtcccagg aggaccccga ggtccagttt    840
aattggtacg tggacggcgt ggaagtgcat aacgccaaga ccaagcccag agaggagcag    900
ttcaacagca cctacagagt ggtgtccgtg ctgaccgtgc tgcaccagga ctggctgaac    960
ggcaaggaat acaagtgcaa ggtctccaac aagggcctgg ccagcagcat cgagaagacc   1020
atcagcaagg ccaagggcca gccacgggag ccccaggtct acaccctgcc acccttgtcaa  1080
gaggagatga ccaagaacca ggtgtccctg tggtgtctgg tgaaaggctt ctatcccagc   1140
gatatcgccg tggagtggga gagcaacggc cagcccgagg acaactacaa gaccaccccc   1200
cctgtgctgg acagcgacgg cagcttcttc ctgtactcca agctgaccgt ggacaagtcc   1260
agatggcagg agggcaacgt cttcagctgc tccgtgatgc acgaggccct gcacaaccac   1320
tacacccaga agtccctgag cctgagcctg ggcaag                             1356

SEQ ID NO: 70              moltype = AA   length = 214
FEATURE                    Location/Qualifiers
source                     1..214
                           mol_type = protein
                           organism = Homo sapiens
SEQUENCE: 70
EIVLTQSPGT LSLSPGERAT LSCRASQSVS SYLAWYQKKP GQAPRLLIYD ASNRATGIPD     60
RFSGSGSGTD FTLTISRLEP EDFAVYYCQQ RSNWPITFGQ GTKLEIKRTV AAPSVFIFPP    120
SDKKLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 71              moltype = DNA   length = 642
FEATURE                    Location/Qualifiers
source                     1..642
                           mol_type = other DNA
                           organism = Homo sapiens
SEQUENCE: 71
gagatcgtgc tgacacagag ccctggcaca ctgtcactgt ctccaggcga gagagccaca     60
ctgagctgta gagccagcca gagcgtgtcc tcttacctgg cctggtatca gaagaagcct    120
ggacaggctc ccagactgct gatctacgac gccagcaaca gagccacagg catccccgat    180
agattcagcg gctctggctc tggcaccgac ttcaccctga caatcagcag actggaaccc    240
gaggacttcg ccgtgtacta ctgccagcag agaagcaact ggcccatcac attcggccag    300
ggcaccaagc tggaaatcaa gcgaactgtg gctgcaccat ctgtcttcat cttcccgcca    360
tctgataaga aattgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642

SEQ ID NO: 72              moltype = AA   length = 449
FEATURE                    Location/Qualifiers
source                     1..449
                           mol_type = protein
                           organism = Homo sapiens
SEQUENCE: 72
EVQLLESGGG VVQPGGSLRL SCAASGFTFN DYAMHWVREA PGKGLEWVST ISWNSGSIGY     60
ADSVKGRFTI SRDNSKNTLY LQMNSLRAED TAVYYCAKDI QYGNYYYGMD YWGQGTLVTV    120
SSASTKGPSV FPLAPCSRST SESTAALGCL VEDYFPEPVT VSWNSGALTS GVHTFPAVLQ    180
SSGLYSLSSV VTVPSSSLGT KTYTCNVDHK PSNTKVDERV ESKYGPPCPP CPAPEFEGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL ASSIEKTISK AKGQPREPQV CTLPPSQEEM    360
TKNQVSLSCA VKGFYPSDIA VEWESNGQPE NNYKTTPPVL DSDGSFFLVS KLTVDKSRWQ    420
EGNVFSCSVM HEALHNHYTQ KSLSLSLGK                                     449

SEQ ID NO: 73              moltype = DNA   length = 1347
FEATURE                    Location/Qualifiers
source                     1..1347
                           mol_type = other DNA
                           organism = Homo sapiens
```

```
SEQUENCE: 73
gaagtgcagc tgctggaatc tggtggcgga gttgttcagc ctggcggctc tctgagactg    60
tcttgtgctg ccagcggctt caccttcaac gactacgcta tgcactgggt ccgagaggcc   120
cctggcaaag gacttgaatg ggtgtccacc atcagctgga acagcggctc tatcggctac   180
gccgattccg tgaagggcag attcaccatc tccagagaca acagcaagaa cacctgtac   240
ctgcagatga acagcctgag agccgaggac accgccgtgt actactgtgc caaggcatc   300
cagtacggca actactacta cggcatggac tactgggggcc agggaacact ggttaccgtt   360
agctctgcta gcaccaaggg ccccagcgtg ttccccctgg cccccttgcag cagaagcacc   420
agcgagagca cagccgccct gggctgcctg gtggaggact acttccccga gcccgtgacc   480
gtgtcctgga acagcggcgc tctgaccagc ggcgtgcata ccttccccgc cgtgctccag   540
agcagcggac tgtactccct gagcagcgtg gtgaccgtgc cttccagcag cctgggcacc   600
aagacctaca cctgcaacgt ggaccacaag cccagcaaca ccaaggtgga cgagagagtg   660
gagagcaagt acggccctcc ctgcccccct tgccctgccc ccgagttcga aggcggacct   720
agcgtgttcc tgttcccccc caagcccaag gacaccctga tgatcagcag aacccccgag   780
gtgacctgcg tggtggtgga cgtgtcccag gaggaccccg aggtccagtt taattggtac   840
gtggacggcg tggaagtgca taacgccaag accaagccca gagaggagca gttcaacagc   900
acctacagag tggtgtccgt gctgaccgtg ctgcaccagg actggctgaa cggcaaggaa   960
tacaagtgca aggtctccaa caagggcctg ccagcagca tcgagaagac catcagcaag  1020
gccaagggcc agccacggga gcccaggtc tgcaccctgc cacctagcca agaggagatg  1080
accaagaacc aggtgtccct gagctgtgcc gtgaaaggct tctatcccag cgatatcgcc  1140
gtggagtggg agagcaacgg ccagcccgag aacaactaca agaccacccc ccctgtgctg  1200
gacagcgacg gcagcttctt cctggtttcc aagctgaccg tggacaagtc cagatggcag  1260
gagggcaacg tcttcagctg ctccgtgatg cacgaggccc tgcacaacca ctacacccag  1320
aagtccctga gcctgagcct gggcaag                                      1347

SEQ ID NO: 74        moltype = AA   length = 449
FEATURE              Location/Qualifiers
source               1..449
                     mol_type = protein
                     organism = Homo sapiens
SEQUENCE: 74
EVQLLESGGG VVQPGGSLRL SCAASGFTFN DYAMHWVREA PGKGLEWVST ISWNSGSIGY    60
ADSVKGRFTI SRDNSKNTLY LQMNSLRAED TAVYYCAKDI QYGNYYYGMD YWGQGTLVTV   120
SSASTKGPSV FPLAPCSRST SESTAALGCL VEDYFPEPVT VSWNSGALTS GVHTFPAVLQ   180
SSGLYSLSSV VTVPSSSLGT KTYTCNVDHK PSNTKVDERV ESKYGPPCPP CPAPEFEGGP   240
SVFLFPPKPK DTLMISRTPE VTCVVVDVSQ EDPEVQFNWY VDGVEVHNAK TKPREEQFAS   300
TYRVVSVLTV LHQDWLNGKE YKCKVSNKGL PSSIEKTISK AKGQPREPQV CTLPPSQEEM   360
TKNQVSLSCA VKGFYPSDIA VEWESNGQPE NNYKTTPPVL DSDGSFFLVS KLTVDKSRWQ   420
EGNVFSCSVM HEALHNHYTQ KSLSLSLGK                                     449

SEQ ID NO: 75        moltype = DNA   length = 1347
FEATURE              Location/Qualifiers
source               1..1347
                     mol_type = other DNA
                     organism = Homo sapiens
SEQUENCE: 75
gaagtgcagc tgctggaatc tggtggcgga gttgttcagc ctggcggctc tctgagactg    60
tcttgtgctg ccagcggctt caccttcaac gactacgcta tgcactgggt ccgagaggcc   120
cctggcaaag gacttgaatg ggtgtccacc atcagctgga acagcggctc tatcggctac   180
gccgattccg tgaagggcag attcaccatc tccagagaca acagcaagaa cacctgtac   240
ctgcagatga acagcctgag agccgaggac accgccgtgt actactgtgc caaggacatc   300
cagtacggca actactacta cggcatggac tactgggggcc agggaacact ggttaccgtt   360
agctctgcta gcaccaaggg ccccagcgtg ttccccctgg cccccttgcag cagaagcacc   420
agcgagagca cagccgccct gggctgcctg gtggaggact acttccccga gcccgtgacc   480
gtgtcctgga acagcggcgc tctgaccagc ggcgtgcata ccttccccgc cgtgctccag   540
agcagcggac tgtactccct gagcagcgtg gtgaccgtgc cttccagcag cctgggcacc   600
aagacctaca cctgcaacgt ggaccacaag cccagcaaca ccaaggtgga cgagagagtg   660
gagagcaagt acggccctcc ctgcccccct tgccctgccc ccgagttcga aggcggacct   720
agcgtgttcc tgttcccccc caagcccaag gacaccctga tgatcagcag aacccccgag   780
gtgacctgcg tggtggtgga cgtgtcccag gaggaccccg aggtccagtt taattggtac   840
gtggacggcg tggaagtgca taacgccaag accaagccca gagaggagca gttcgccagc   900
acctacagag tggtgtccgt gctgaccgtg ctgcaccagg actggctgaa cggcaaggaa   960
tacaagtgca aggtctccaa caagggcctg cctagcagca tcgagaagac catcagcaag  1020
gccaagggcc agccacggga gcccaggtc tgcaccctgc cacctagcca agaggagatg  1080
accaagaacc aggtgtccct gagctgtgcc gtgaaaggct tctatcccag cgatatcgcc  1140
gtggagtggg agagcaacgg ccagcccgag aacaactaca agaccacccc ccctgtgctg  1200
gacagcgacg gcagcttctt cctggtttcc aagctgaccg tggacaagtc cagatggcag  1260
gagggcaacg tcttcagctg ctccgtgatg cacgaggccc tgcacaacca ctacacccag  1320
aagtccctga gcctgagcct gggcaag                                      1347

SEQ ID NO: 76        moltype = AA   length = 223
FEATURE              Location/Qualifiers
source               1..223
                     mol_type = protein
                     organism = Homo sapiens
SEQUENCE: 76
EVQLVESGGG LVQPGGSLRL SCAASGFTFN TYAMNWVRKA PGKGLEWVGR IRSKYNNYAT    60
YYADSVKDRF TISRDDSKNS LYLQMNSLKT EDTAVYYCVR HGNFGNSYVS WFAYWGQGTL   120
VTVSSASTKG PSVFPLAPCS RSTSESTAAL GCLVKDYFPE PVTVSWNSGA LTSGVHTFPA   180
```

```
VLQSSGLYSL SSVVTVPSSS LGTKTYTCNV DHKPSNTKVD KRV                     223

SEQ ID NO: 77          moltype = DNA   length = 669
FEATURE                Location/Qualifiers
source                 1..669
                       mol_type = other DNA
                       organism = Homo sapiens
SEQUENCE: 77
gaggtgcagc tggttgaatc tggcggagga ctggttcagc ctggcggatc tctgagactg   60
tcttgtgccg ccagcggctt caccttcaac acctacgcta tgaactgggt ccgaaaggcc   120
cctggcaaag gactggaatg ggtgggaaga atcaggtcca agtacaacaa ctacgccacc   180
tactacgccg acagcgtgaa ggacagattc accatcagca gggacgacag caagaacagc   240
ctgtacctgc agatgaacag cctgaaaacc gaggacaccg ccgtgtacta ctgtgtcaga   300
cacggcaact tcggcaacag ctatgtgtct tggtttgcct actggggcca gggcacactg   360
gtcacagtta gctctgctag caccaagggc cccagcgtgt tccccctggc cccttgcagc   420
agaagcacca gcgagagcac agccgccctg ggctgcctgg tgaaggacta cttccccgag   480
cccgtgaccg tgtcctggaa cagcggcgct ctgaccagcg gcgtgcatac cttccccgcc   540
gtgctccaga gcagcggact gtactccctg agcagcgtgg tgaccgtgcc ttccagcagc   600
ctgggcacca gacctacac ctgcaacgtg gaccacaagc ccagcaacac caaggtggac    660
aagagagtg                                                          669

SEQ ID NO: 78          moltype = AA   length = 444
FEATURE                Location/Qualifiers
source                 1..444
                       mol_type = protein
                       organism = Homo sapiens
SEQUENCE: 78
QAVVTQEPSL TVSPGGTVTL TCRSSTGAVT TSNYANWVQE KPGQAPRGLI GGTNKRAPWT   60
PARFSGSLLG GKAALTITGA QAEDEAEYYC VLWYSNLWVF GGGTKLTVLG QPKAAPSVTL   120
FPPSSEELQA NKATLVCLIS DFYPGAVTVA WKADSSPVKA GVETTTPSKQ SNNKYAASSY   180
LSLTPEQWKS HRSYSCQVTH EGSTVEKTVA PTECSESKYG PPCPPCPAPE FEGGPSVFLF   240
PPKPKDTLMI SRTPEVTCVV VDVSQEDPEV QFNWYVDGVE VHNAKTKPRE EQFASTYRVV   300
SVLTVLHQDW LNGKEYKCKV SNKGLPSSIE KTISKAKGQP REPQVYTLPP CQEEMTKNQV   360
SLWCLVKGFY PSDIAVEWES NGQPENNYKT TPPVLDSDGS FFLYSKLTVD KSRWQEGNVF   420
SCSVMHEALH NHYTQKSLSL SLGK                                          444

SEQ ID NO: 79          moltype = DNA   length = 1332
FEATURE                Location/Qualifiers
source                 1..1332
                       mol_type = other DNA
                       organism = Homo sapiens
SEQUENCE: 79
caggctgtgg tcacacaaga gcctagcctg acagtgtctc ctggcggcac agtgaccctg   60
acctgtagat cttctacagg cgccgtgacc accagcaact acgctaattg ggtgcaggag   120
aagcccggcc aggctcctag aggactgatc ggcggaacaa acaagagagc ccctggaca   180
cccgccagat tctctggatc tctgctcggc ggaaaggccg ctctgacaat cactggtgct   240
caggctgagg acgaggccga gtactattgt gtgctgtggt acagcaacct gtgggtgttc   300
ggcggaggca ccaaactgac agttctgggt cagcccaagg cggcgccctc ggtcactctg   360
ttcccgccct cctctgagga gcttcaagcc aacaaggcca cactggtgtg tctcataagt   420
gacttctatc cgggagccgt gacagtggcc tggaaggcag atagcagccc cgtcaaggcg   480
ggagtggaga ccaccacacc ctccaaacaa agcaacaaca agtacgcggc cagcagctac   540
ctgagcctga cgcctgagca gtggaagtcc cacagaagct acagctgcca ggtcacgcat   600
gaagggagca ccgtggagaa gacagtggcc cctacagaat gttcagagag caagtacggc   660
cctccctgcc cccttgccc tgcccccgag ttcgagggcg acctagcgt gttcctgttc    720
cccccaagc ccaaggacac cctgatgatc agcagaaccc cgaggtgac ctgcgtggtg    780
gtggacgtgt cccaggagga ccccgaggtc cagtttaatt ggtacgtgga cggcgtggaa   840
gtgcataacg ccaagaccaa gcccagagag gagcagttcg ccagcaccta cagagtggtg   900
tccgtgctga ccgtgctgca ccaggactgg ctgaacggca aggaatacaa gtgcaaggtc   960
tccaacaagg gcctgcctag cagcatcgag aagaccatca aggccaagca gggccagcca   1020
cgggagcccc aggtctacac cctgccacct tgtcaagagg agatgaccaa gaaccaggtg   1080
tccctgtggt gtctggtgaa aggcttctat cccagcgata tcgccgtgga gtgggagagc   1140
aacggccagc ccgagaacaa ctacaagacc acccccctg tgctggacag cgacggcagc    1200
ttcttcctgt actccaagct gaccgtggac aagtccagat ggcaggaggg caacgtcttc   1260
agctgctccg tgatgcacga ggccctgcac aaccactaca cccagaagtc cctgagcctg   1320
agcctgggca ag                                                      1332

SEQ ID NO: 80          moltype = AA   length = 218
FEATURE                Location/Qualifiers
source                 1..218
                       mol_type = protein
                       organism = Homo sapiens
SEQUENCE: 80
DIVLTQSPAS LAVSPGQRAT ITCRASKSVS TSGYSYMHWY QKKPGQPPKL LIYLASNLES   60
GVPARFSGSG SGTDFTLTIN PVEAEDTANY YCQHSRELPW TFGQGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 81          moltype = DNA   length = 654
FEATURE                Location/Qualifiers
```

```
source                 1..654
                       mol_type = other DNA
                       organism = Homo sapiens
SEQUENCE: 81
gacatcgtgc tgacacagag ccctgcttct ctggctgtgt ctcctggcca gagagccacc    60
atcacctgta gagccagcaa gagcgtgtcc accagcggct actcttacat gcactggtat   120
cagaagaagc ccggccagcc tcctaagctg ctgatctacc tggctagcaa cctcgaaagc   180
ggagtgcctg ctagattttc tggcagcggc tctggcaccg acttcaccct gacaatcaac   240
cccgtggaag ccgaagacac cgccaactac tactgccagc acagcagaga gctgccctgg   300
acatttggcc agggcaccaa ggtggaaatc aagcgaactg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc   600
acccatcagg gcctgagctc gcccgtcaca aagagcttca acagggggaga gtgt         654

SEQ ID NO: 82           moltype = AA   length = 449
FEATURE                 Location/Qualifiers
source                  1..449
                        mol_type = protein
                        organism = Homo sapiens
SEQUENCE: 82
QVQLVQSGSE LKKPGASVKV SCKASGYIFT NFGMNWVREA PGQGLEWMGW INTYTGEQIY    60
ADGFTGRFVF SLDTSASTAY LQISSLKAED TAVYFCARGE IYYGYDVGFV YWGQGTLVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFEGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL ASSIEKTISK AKGQPREPQV CTLPPSQEEM   360
TKNQVSLSCA VKGFYPSDIA VEWESNGQPE NNYKTTPPVL DSDGSFFLVS KLTVDKSRWQ   420
EGNVFSCSVM HEALHNHYTQ KSLSLSLGK                                      449

SEQ ID NO: 83           moltype = DNA   length = 1347
FEATURE                 Location/Qualifiers
source                  1..1347
                        mol_type = other DNA
                        organism = Homo sapiens
SEQUENCE: 83
caggttcagc tggtgcagtc tggcagcgag ctgaagaaac ctggcgcctc tgtgaaggtg    60
tcctgcaagg ctagcggcta catcttcacc aacttcggca tgaactgggt ccgagaggct   120
cctggacagg gactcgaatg gatgggctgg atcaacacct acaccggcga gcagatctac   180
gccgatggct tcacaggcag attcgtgttc agcctggaca ccagcgccag cacagcttac   240
ctgcagatca gctctctgaa ggccgaggat accgccgtgt acttctgtgc cagaggcgag   300
atctactacg gctacgacgt gggctttgtg tactggggcc agggaacact ggtcaccgtt   360
agctctgcta gcaccaaggg ccccagcgtg ttcccctg ccccttgcag cagaagcacc     420
agcgagagca gccgcgccct gggctgcctg gtgaaggact acttccccga gcccgtgacc   480
gtgtcctgga caagcggcgc tctgaccagc ggcgtgcata ccttccccgc cgtgctccag   540
agcagcggac tgtactccct gagcagcgtg gtgaccgtgc cttccagcag cctgggcacc   600
aagacctaca cctgcaacgt ggaccacaag cccagcaaca ccaaggtgga caagagagtg   660
gagagcaagt acggccctcc ctgccccccc tgccctgccc ccgagttcga gggcggacct   720
agcgtgttcc tgttcccccc caagcccaag gacaccctga tgatcagcag aacccccgag   780
gtgacctgcg tggtggtgga cgtgtcccag gaggaccccg aggtccagtt taattggtac   840
gtggacggcg tggaagtgca taacgccaag accaagcccag agaggagca gttcaacagc   900
acctacagag tggtgtccgt gctgaccgtg ctgcaccagg actggctgaa cggcaaggaa   960
tacaagtgca aggtctccaa caagggcctg gccagcagca tcgagaagac catcagcaag  1020
gccaagggcc agccacggga gccccaggtc tgcacccctgc cacctagcca gagggagatg  1080
accaagaacc aggtgtccct gagctgtgcc gtgaaaggct tctatcccag cgatatcgcc  1140
gtggagtggg agagcaacgg ccagcccgag aacaactaca gaccacccc cctgtgctg   1200
gacagcgacg gcagcttctt cctggtttcc aagctgaccg tggacaagtc cagatggcag  1260
gagggcaacg tcttcagctg ctccgtgatg cacgaggccc tgcacaacca ctacacccag  1320
aagtccctga gcctgagcct gggcaag                                      1347

SEQ ID NO: 84           moltype = AA   length = 218
FEATURE                 Location/Qualifiers
source                  1..218
                        mol_type = protein
                        organism = Homo sapiens
SEQUENCE: 84
DIVLTQSPAS LAVSPGQRAT ITCRASKSVT TSGYSIHWY QKKPGQPPKL LIYLASDLEA     60
GVPARFSGSG SGTDFTLTIN PVEAEDTANY YCQHSRELPW TFGQGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                            218

SEQ ID NO: 85           moltype = DNA   length = 654
FEATURE                 Location/Qualifiers
source                  1..654
                        mol_type = other DNA
                        organism = Homo sapiens
SEQUENCE: 85
gacatcgtgc tgacacagag ccctgcttct ctggctgtgt ctcctggcca gagagccacc    60
```

```
atcacctgta gagccagcaa gagcgtgacc accagcggct actcttacat ccactggtat   120
cagaagaagc ccggccagcc tcctaagctg ctgatctacc tggccagcga tctggaagct   180
ggcgtgccag ctagattttc tggcagcggc tctggcaccg acttcaccct gacaatcaac   240
cccgtggaag ccgaagacac cgccaactac tactgccagc acagcagaga gctgccctgg   300
acatttggcc agggcaccaa ggtggaaatc aagcgaactg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc   600
acccatcagg gcctgagctc gcccgtcaca aagagcttca caggggagag tgt           654
```

SEQ ID NO: 86                    moltype = AA   length = 449
FEATURE                          Location/Qualifiers
source                           1..449
                                 mol_type = protein
                                 organism = Homo sapiens
SEQUENCE: 86
```
QVQLVQSGSE LKKPGASVKV SCKASGYIFT NFGMNWVREA PGQGLEWMGW INTYTGEQIY   60
ADGFTGRFVF SLDTSVSTAY LQISSLKAED TAVYFCARGE IYYGYDVGFV YWGQGTLVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFEGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL ASSIEKTISK AKGQPREPQV CTLPPSQEEM   360
TKNQVSLSCA VKGFYPSDIA VEWESNGQPE NNYKTTPPVL DSDGSFFLVS KLTVDKSRWQ   420
EGNVFSCSVM HEALHNHYTQ KSLSLSLGK                                     449
```

SEQ ID NO: 87                    moltype = DNA   length = 1347
FEATURE                          Location/Qualifiers
source                           1..1347
                                 mol_type = other DNA
                                 organism = Homo sapiens
SEQUENCE: 87
```
caggttcagc tggtgcagtc tggcagcgag ctgaagaaac ctggcgcctc tgtgaaggtg   60
tcctgcaagg ctagcggcta catcttcacc aacttcggca tgaactgggt ccgagaggct   120
cctggacagg gactcgaatg gatgggctgg atcaacacct acaccggcga gcagatctac   180
gccgatggct tcacaggcag attcgtgttc agcctggaca ccagcgtcag cacagcttac   240
ctgcagatca gctctctgaa ggccgaggat accgccgtgt acttctgtgc cagaggcgag   300
atctactacg gctacgacgt gggctttgtg tactggggcc agggaacact ggtcaccgtt   360
agctctgcta gcaccaaggg ccccagcgtg ttccccctgg cccccttgcag cagaagcacc   420
agcgagagca gcaccgccct gggctgcctg gtgaaggact acttccccga gcccgtgacc   480
gtgtcctgga caagcggcgc tctgaccagc ggcgtgcata ccttccccgc cgtgctccag   540
agcagcggac tgtactccct gagcagcgtg gtgaccgtgc cttccagcag cctgggcacc   600
aagacctaca cctgcaacgt ggaccacaag cccagcaaca ccaaggtgga caagagagtg   660
gagagcaagt acggccctcc ctgcccccct tgccctgccc ccgagttcga gggcggacct   720
agcgtgttcc tgttcccccc caagcccaag gacaccctga tgatcagcag aacccccgag   780
gtgacctgcg tggtggtgga cgtgtcccag gaggaccccg aggtccagtt taattggtac   840
gtggacggcg tggaagtgca taacgccaag accaagcca gaggagca gttcaacagc   900
acctacagag tggtgtccgt gctgaccgtg ctgcaccagg actggctgaa cggcaaggaa   960
tacaagtgca aggtctccaa caagggcctg gccagcagca tcgagaagac catcagcaag   1020
gccaaggggc agccacggga gccccaggtc tgcaccctgc cacctagcca agaggagatg   1080
accaagaacc aggtgtccct gagctgtgcc gtgaaaggct tctatcccag cgatatcgct   1140
gtggagtggg agagcaacgg ccagcccgag aacaactaca agaccacccc ccctgtgctg   1200
gacagcgacg gcagcttctt cctggtttcc aagctgaccg tggacaagtc cagatggcag   1260
gagggcaacg tcttcagctg ctccgtgatg cacgaggccc tgcacaacca ctacacccag   1320
aagtccctga gcctgagcct gggcaag                                        1347
```

SEQ ID NO: 88                    moltype = AA   length = 219
FEATURE                          Location/Qualifiers
source                           1..219
                                 mol_type = protein
                                 organism = Homo sapiens
SEQUENCE: 88
```
DVVMTQSPLS LPVTPGEPAS ISCRSSQSIV HSNGNTYLEW YLKKPGQSPQ LLIYKVSNRF   60
SGVPDRFSGS GSGTDFTLKI SRVEAEDVGV YFCLQVTHVP LTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219
```

SEQ ID NO: 89                    moltype = DNA   length = 657
FEATURE                          Location/Qualifiers
source                           1..657
                                 mol_type = other DNA
                                 organism = Homo sapiens
SEQUENCE: 89
```
gacgtggtca tgacacagag ccctctgagc ctgcctgtga cacctggcga acctgccagc   60
atcagctgta gaagcagcca gagcatcgtg cacagcaacg gcaacacata cctggagtgg   120
tatctgaaga gccccggcca gtctcctcag ctgctgatct acaaggtgtc caacagattc   180
agcggcgtgc ccgacagatt ctctggctct ggatctggca ccgacttcac cctgaagatc   240
tccagagtgg aagccgagga cgtgggcgtg tacttctgtc tccaggtcac acacgtgccc   300
ctgacatttg gccagggcac caagctggaa atcaagcgaa ctgtggctgc accatctgtc   360
```

-continued

```
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt      657
```

SEQ ID NO: 90        moltype = AA   length = 442
FEATURE                 Location/Qualifiers
source                  1..442
                        mol_type = protein
                        organism = Homo sapiens SEQUENCE: 90
```
QVQLVQSGAE VKKPGSSVKV SCKASGYTFA DYEIHWVREA PGQGLEWMGA IHPGSGGTAY   60
AQKFQGRVTL TADESSTTAY MELSSLRSED TAVYYCTRYY SFAYWGQGTL VTVSSASTKG   120
PSVFPLAPCS RSTSESTAAL GCLVKDYFPE PVTVSWNSGA LTSGVHTFPA VLQSSGLYSL   180
SSVVTVPSSS LGTKTYTCNV DHKPSNTKVD KRVESKYGPP CPPCPAPEFE GGPSVFLFPP   240
KPKDTLMISR TPEVTCVVVD VSQEDPEVQF NWYVDGVEVH NAKTKPREEQ FNSTYRVVSV   300
LTVLHQDWLN GKEYKCKVSN KGLASSIEKT ISKAKGQPRE PQVCTLPPSQ EEMTKNQVSL   360
SCAVKGFYPS DIAVEWESNG QPENNYKTTP PVLDSDGSFF LVSKLTVDKS RWQEGNVFSC   420
SVMHEALHNH YTQKSLSLSL GK                                           442
```

SEQ ID NO: 91        moltype = DNA   length = 1326
FEATURE                 Location/Qualifiers
source                  1..1326
                        mol_type = other DNA
                        organism = Homo sapiens SEQUENCE: 91
```
caggttcagc tggttcagtc tggcgccgaa gtgaagaaac ctggcagcag cgtgaaggtg   60
tcctgcaagg ctagcggcta caccttcgcc gactacgaga tccactgggt ccgagaggct   120
ccaggacagg gacttgaatg gatgggcgct atccatcctg gctctggcgg cacagcttac   180
gcccagaaat tccagggcag agtgaccctg accgccgacg agtctagcac caccgcctac   240
atggaactga gcagcctgag aagcgaggac accgccgtgt actactgcac ccggtactac   300
agcttcgcct actggggaca gggaaccctg gtcacagtca gctctgctag caccaagggc   360
cccagcgtgt tccccctggc ccccttgcagc agaagcacca gcgagagcac agccgccctg   420
ggctgcctgg tgaaggacta cttccccgag cccgtgaccg tgtcctggaa cagcggcgct   480
ctgaccagcg gcgtgcatac cttccccgcc gtgctccaga gcagcggact gtactccctg   540
agcagcgtgg tgaccgtgcc ttccagcagc ctgggcacca gacctacac ctgcaacgtg    600
gaccacaagc ccagcaacac caaggtggac aagagagtgg agagcaagta cggccctccc   660
tgcccccctt gccctgcccc cgagttcgag ggcggaccta gcgtgttcct gttcccccc    720
aagcccaagg acaccctgat gatcagcaga accccgagg tgacctgcgt ggtggtggac    780
gtgtcccagg aggaccccga ggtccagttt aattggtacg tggacggcgt ggaagtgcat   840
aacgccaaga ccaagcccag agaggagcag ttcaacagca cctacagagt ggtgtccgtg   900
ctgaccgtgc tgcaccagga ctggctgaac ggcaaggaat acaagtgcaa ggtctccaac   960
aagggcctgg ccagcagcat cgagaagacc atcagcaagg ccaagggcca gccacgggag   1020
ccccaggtct gcaccctgcc acctagccaa gaggagatga ccaagaacca ggtgtccctg   1080
agctgtgccg tgaaaggctt ctatcccagc gatatcgccg tggagtggga gagcaacggc   1140
cagcccgaga caactacaa gaccacccc cctgtgctgg acagcgacgg cagcttcttc     1200
ctggtttcca agctgaccgt ggacaagtcc agatggcagg agggcaacgt cttcagctgc   1260
tccgtgatgc acgaggccct gcacaaccac tacacccaga gtccctgag cctgagcctg    1320
ggcaag                                                             1326
```

SEQ ID NO: 92        moltype = AA   length = 219
FEATURE                 Location/Qualifiers
source                  1..219
                        mol_type = protein
                        organism = Homo sapiens SEQUENCE: 92
```
DVVMTQSPLS LPVTPGEPAS ISCRSSQSIV HSNGNTYLEW YLKKPGQSPQ LLIYKVSNRF   60
SGVPDRFSGS GSGTDFTLKI SRVEAEDVGV YFCLQVTHVP LTFGQGTKLE IKRTVAAPSV   120
FIFPPSDKKL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219
```

SEQ ID NO: 93        moltype = DNA   length = 657
FEATURE                 Location/Qualifiers
source                  1..657
                        mol_type = other DNA
                        organism = Homo sapiens SEQUENCE: 93
```
gacgtggtca tgacacagag ccctctgagc ctgcctgtga cacctggcga acctgccagc   60
atcagctgta gaagcagcca gagcatcgtg cacagcaacg gcaacacata cctggagtgg   120
tatctgaaga gccccggcca gtctcctcag ctgctgatct acaaggtgtc caacagattc   180
agcggcgtgc ccgacagatt ctctggctct ggatctggca ccgacttcac cctgaagatc   240
tccagagtgg aagccgagga cgtgggcgtg tacttctgtc tccaggtcac acacgtgccc   300
ctgacatttg gccagggcac caagctggaa atcaagcgaa ctgtggctgc accatctgtc   360
ttcatcttcc cgccatctga taagaaattg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt      657
```

-continued

```
SEQ ID NO: 94              moltype = AA  length = 442
FEATURE                    Location/Qualifiers
source                     1..442
                           mol_type = protein
                           organism = Homo sapiens
SEQUENCE: 94
QVQLVQSGAE VKKPGSSVKV SCKASGYTFA DYEIHWVREA PGQGLEWMGA IHPGSGGTAY   60
AQKFQGRVTL TADESSTTAY MELSSLRSED TAVYYCTRYY SFAYWGQGTL VTVSSASTKG  120
PSVFPLAPCS RSTSESTAAL GCLVEDYFPE PVTVSWNSGA LTSGVHTFPA VLQSSGLYSL  180
SSVVTVPSSS LGTKTYTCNV DHKPSNTKVD ERVESKYGPP CPPCPAPEFE GGPSVFLFPP  240
KPKDTLMISR TPEVTCVVVD VSQEDPEVQF NWYVDGVEVH NAKTKPREEQ FNSTYRVVSV  300
LTVLHQDWLN GKEYKCKVSN KGLASSIEKT ISKAKGQPRE PQVCTLPPSQ EEMTKNQVSL  360
SCAVKGFYPS DIAVEWESNG QPENNYKTTP PVLDSDGSFF LVSKLTVDKS RWQEGNVFSC  420
SVMHEALHNH YTQKSLSLSL GK                                          442

SEQ ID NO: 95              moltype = DNA  length = 1326
FEATURE                    Location/Qualifiers
source                     1..1326
                           mol_type = other DNA
                           organism = Homo sapiens
SEQUENCE: 95
caggttcagc tggttcagtc tggcgccgaa gtgaagaaac ctggcagcag cgtgaaggtg   60
tcctgcaagg ctagcggcta caccttcgcc gactacgaga tccactgggt ccgagaggct  120
ccaggacagg gacttgaatg gatgggcgct atccatcctg gctctggcgg cacagcttac  180
gcccagaaat tccagggcag agtgaccctg accgccgacg agtctagcac caccgcctac  240
atggaactga gcagcctgag aagcgaggac accgccgtgt actactgcac ccggtactac  300
agcttcgcct actggggaca gggaaccctg gtcacagtca gctctgctag caccaagggc  360
cccagcgtgt tccccctggc cccttgcagc agaagcacca gcgagagcac agccgccctg  420
ggctgcctgg tggaggacta cttccccgag cccgtgaccg tgtcctggaa cagcggcgct  480
ctgaccagcg gcgtgcatac cttccccgcc gtgctccaga gcagcggact gtactccctg  540
agcagcgtgg tgaccgtgcc ttccagcagc ctgggcacca agacctacac ctgcaacgtg  600
gaccacaagc ccagcaacac caaggtggac gagagagtgg agagcaagta cggccctccc  660
tgcccccctt gccctgcccc cgagttcgaa ggcggaccta gcgtgttcct gttccccccc  720
aagcccaagg acaccctgat gatcagcaga accccgaggt gacctgcgt ggtggtggac  780
gtgtcccagg aggaccccga ggtccagttt aattggtacg tggacggcgt ggaagtgcat  840
aacgccaaga ccaagcccag agaggagcag ttcaacagca cctacagagt ggtgtccgtg  900
ctgaccgtgc tgcaccagga ctggctgaac ggcaaggaat acaagtgcaa ggtctccaac  960
aagggcctgg ccagcagcat cgagaagacc atcagcaagg ccaagggcca gccacgggag 1020
ccccaggtct gcaccctgcc acctagccaa gaggagatga ccaagaacca ggtgtccctg 1080
agctgtgccg tgaaaggctt ctatcccagc gatatcgccg tggagtggga gagcaacggc 1140
cagcccgaga caaactacaa gaccaccccc cctgtgctgg acagcgacgg cagcttcttc 1200
ctggtttcca agctgaccgt ggacaagtcc agatggcagg agggcaacgt cttcagctgc 1260
tccgtgatgc acgaggccct gcacaaccac tacacccaga gtccctgag cctgagcctg 1320
ggcaag                                                          1326
```

BISPECIFIC ANTIBODY AND USE THEREOF

CROSS REFERENCE TO THE RELATED APPLICATIONS

This application is a continuation of, and claims priority to, U.S. patent application Ser. No. 18/038,159, filed May 22, 2023, which was a 35 U.S.C. § 371 National Phase entry of International Application No. PCT/CN2021/132195, filed on Nov. 22, 2021, which is based upon and claims priority to Chinese Patent Application No. 202011325843.0, filed on Nov. 23, 2020, the entire contents of each of which are incorporated herein by reference.

SEQUENCE LISTING STATEMENT

This application contains a Sequence Listing which has been submitted electronically in XML format. The Sequence Listing XML is incorporated herein by reference. The XML file, created on Jun. 3, 2025, is named "OURO-001C1_SL", and is 119,478 bytes in size.

TECHNICAL FIELD

The present disclosure relates to a bispecific antibody and use thereof, particularly a bispecific antibody that binds CD3 and another antigen, and use thereof.

BACKGROUND ART

A T-cell bispecific antibody (or T-cell adaptor) is a specific antibody molecule, through which recognizes a target cell surface antigen (antigen arm) at one end and binds to a T-cell CD3 receptor (CD3 arm) at the other end, CD3 on T-cells may be aggregated in a manner similar to TCR/peptide/HLA, thereby activating T-cells and killing tumors. In the 1980s, it was reported that tumor cells were killed by using bispecific antibodies (Staerz U D., Nature. 1985 Apr. 18-24; 314(6012):628-31; Perez P. et al. Nature. 1985 Jul. 25-31; 316(6026):354-6). After more than 30 years of research, the problem of antibody mismatch has been substantially solved, and three bispecific antibody drugs have been successively approved for marketing. Although these bispecific antibodies show very good therapeutic effects in approved indications, the concomitant side effects and limitations in use preclude widespread applications of these bispecific antibodies in the early days. For example: early-marketed catumaxomab has been withdrawn from the market, because the Fc fragment binds to Fcγ receptor expressed by liver Kupffer cells, which triggers a rapid cytokine release. Regarding the blinatumomab launched in 2014, due to the use of Fv antibody fragments, the biological half-life is only 2 hours, it requires a low-dose continuous intravenous infusion, and is approved by FDA together with a black-box warning on cytokine release syndrome and neurological toxicities.

During a normal immune response, TCR is binded with low affinity (about 1-100M) to foreign peptide-human leukocyte antigen complexes (HLA) on infected or mutated cells, an activation signal is transduced into the nucleus via CD3 signaling complexes (including CD3εγ, CD3εδ and CD3ζζ), activating the expression of transcription factors and their downstream proteins (cytokines, granzymes, perform, etc.), wherein the signal intensity generated by the TCR complexes will determine the fate of T-cells. The early developed CD3 bispecific antibodies, mostly based on a small number of murine antibodies such as OKT3, L2K, UCHT1, TR66 and the like, have high affinity, leading to excessive activation of T-cells and release of a large number of cytokines and resulting in cytokine storm syndrome. At the same time, the high affinity also leads to the enrichment of bispecific antibodies in secondary lymphoid organs, and reduces the exposure to tumor tissue.

The binding ability of Fc portion of the antibody to Fcγ receptor is another important factor affecting drug safety. Since Fcγ receptor is expressed in various normal tissues, after the bi-specific antibody binds to Fcγ receptor on cell membrane through Fc, it can result in cross-linking activation of CD3 receptor bound at the other end due to Fcγ receptor aggregation, thereby resulting in severe off-target toxicity. By using a human IgG2 subtype or IgG4 subtype which has a weak Fcγ receptor binding ability, or further performing amino acid substitutions at the corresponding positions in CH2, for example: positions 233-236 (EU sequence numbering) of IgG1 and IgG4 are substituted with the corresponding sequence of IgG2 by Armour etc. so as to reduce the binding to Fcγ receptors (Armour K L, et al, Recombinant human IgG molecules lacking Fcgamma receptor I binding and monocyte triggering activities, Eur J Immunol. 1999 Aug; 29(8):2613-24). Newman etc. introduced mutations Ser228Pro and Leu235Glu in IgG4, stabilizing the IgG4 structure while reducing binding to Fcγ receptors (Newman R, et al, Modification of the Fc region of a primatized IgG antibody to human CD4 retains its ability to modulate CD4 receptors but does not deplete CD4(+) T-cells in chimpanzees. Clin Immunol. 2001 Feb; 98(2):164-74). Idusogie etc. found that respectively substituting Asp270, Lys322, Pro329 or Pro331 with Ala could reduce the binding of IgG1 to complement C1q (Idusogie E E, et al, Mapping of the C1q binding site on rituxan, a chimeric antibody with a human IgG1 Fc. J Immunol. 2000 Apr. 15; 164(8):4178-84), etc.

Interstrand mismatches are major process difficulties in the development of natural IgG-like bispecific antibodies. A common light chain invented by Merchant A M etc. (Merchant A M, et al, An efficient route to human bispecific IgG. Nat Biotechnol. 1998. PMID: 9661204) or a common heavy chain developed by Fischer N etc. (Fischer N, et al, Exploiting light chains for the scalable generation and platform purification of native human bispecific IgG. Nat Commun. 2015 Feb. 12; 6:6113) often require complicated protein engineering-modifications or be produced from transgenic animals (McWhirter J, et al, Common light chain mouse. WO2011097603. 2011); Carter Pet al. (Atwell S, et al, Stable heterodimers from remodeling the domain interface of a homodimer using a phage display library, J Mol Biol. 1997 Jul. 4; 270(1):26-35), resolving mismatches between heavy chains by introducing a knobs-into-holes complementary mutation in the Fc portion of the antibody. Schaefer G etc. (Schaefer W, et al, Immunoglobulin domain crossover as a generic approach for the production of bispecific IgG antibodies, Proc Natl Acad Sci USA. 2011) developed the CrossMab technique that exchanges the Fab part or full length of the light and heavy chains to solve the mismatch problem of a light chain, wherein the partially exchanged CrossMab$^{VH-VL}$ and CrossMab$^{CH1-CL}$ require the introduction of additional peptide segments to achieve correct pairing, while the CrossMab$^{Fab}$ with full length exchange has a correct pairing rate of less than 50%.

SUMMARY OF THE INVENTION

In expressing bispecific antibodies, the inventor has unexpectedly discovered that, by combining a humanized anti-CD3 antibody having a X light chain with a targeting antibody having a k light chain, the X light chain of the anti-CD3 antibody is more likely to pair with a heavy chain of a homologous CD3, while the kappa light chain of the targeting antibody is more likely to pair with a heavy chain of a homologous targeting antibody. By further designing complementary charge pairs between the light and heavy chains, the efficiency of correct pairing can be improved. Furthermore, experimental examples prove that, the novel T-cell connector constructed by using antibodies having multiple targets such as CD20, BCMA and GPC3, and humanized anti-CD3 antibody may achieve a monomer purity of 98-100% and a very low mismatch ratio (<1%) after three-step purification.

The present disclosure provides a novel T-cell linker designed by using bispecific antibodies with different types of light chains x X, and a full-length IgG configuration, wherein in combination with the anti-CD3 antibody arms of target cells and T-cells, kappa light chain and lambda light chain are used to pair with their homologous heavy chains, and complementary charge pairs are introduced to enhance the correct pairing rate. By affinity optimization, activated T-cells can be recruited at low concentrations of the novel T-cell connector, resulting in effective killing of target cells, while T-cells are not activated in the absence of target cells. At the same time, κλ bispecific antibodies of the novel T-cell do not bind to FcγR receptors, reducing the risk of cytokine storm. The novel anti-CD20×CD3 κλ, bispecific antibody, anti-BCMA×CD3 κλ bispecific antibody, and anti-GPC3×CD3κλ, bispecific antibody constructed using the methods of the present disclosure have high purification yields, which can obtain a purity of >99% purity by three-step purification. Animals have a good tolerance to the novel CD20-CD3 κλ bispecific antibody. The efficacy and safety of the novel T-cell connector are superior to similar antibodies. In one aspect, the present disclosure provides a bispecific antibody or antigen-binding portion thereof.

In another aspect, the present disclosure provides nucleic acids encoding a bispecific antibody or antigen-binding portion thereof according to the previous aspect.

In another aspect, the present disclosure provides a vector comprising a nucleic acid of the previous aspect.

In another aspect, the present disclosure provides a cell comprising the vector of the previous aspect.

In the antibody or antigen-binding portion thereof according to any one of the preceding aspects, the antibody or antigen-binding portion thereof is humanized.

In another aspect, the present disclosure provides a pharmaceutical composition or the kit comprising the antibody or antigen-binding portion thereof, or nucleic acid encoding the same according to any of the preceding aspects, and a pharmaceutically acceptable carrier.

In another aspect, the present disclosure provides an antibody-drug conjugate, comprising the antibody or antigen-binding portion thereof, bispecific or multispecific molecule of any of the foregoing aspects which are covalently attached to a therapeutic moiety.

In another aspect, the present disclosure provides a method of treating a disease associated therewith, comprising the steps of: administering to the mammal a therapeutically effective amount of the antibody or antigen-binding fragment thereof, the nucleic acid, the vector, the cell and/or the pharmaceutical composition according to any of the preceding aspects.

In another aspect, the present disclosure provides a use of the antibody or antigen-binding fragment thereof, nucleic acid, vector, cell and/or pharmaceutical composition according to any of the preceding aspects in preparing a medicament or kit for treating a tumor antigen-related disease in a mammal.

The antibodies of the present disclosure can be used in a variety of applications, including detection of tumor antigens, diagnosis, treatment, or prevention of diseases associated with tumor antigens.

BRIEF DESCRIPTION OF THE DRAWINGS

FIG. 13A shows killing of Nalm-6 cells and FIG. 13B shows activation of T-cells.

FIG. 14A shows killing of TMD-8 cells and FIG. 14B shows activation of T-cells.

FIG. 15A shows killing of Toledo cells and FIG. 15B shows activation of T-cells.

FIG. 24A shows killing of NCI-H929 cells and FIG. 24B shows activation of T-cells.

FIG. 25A shows killing of RPMI-8226 cells and FIG. 25B shows activation of T-cells.

FIG. 34A shows killing of HepG2 cells and FIG. 34B shows activation of T-cells.

DETAILED DESCRIPTION OF EMBODIMENTS

Figure 1:
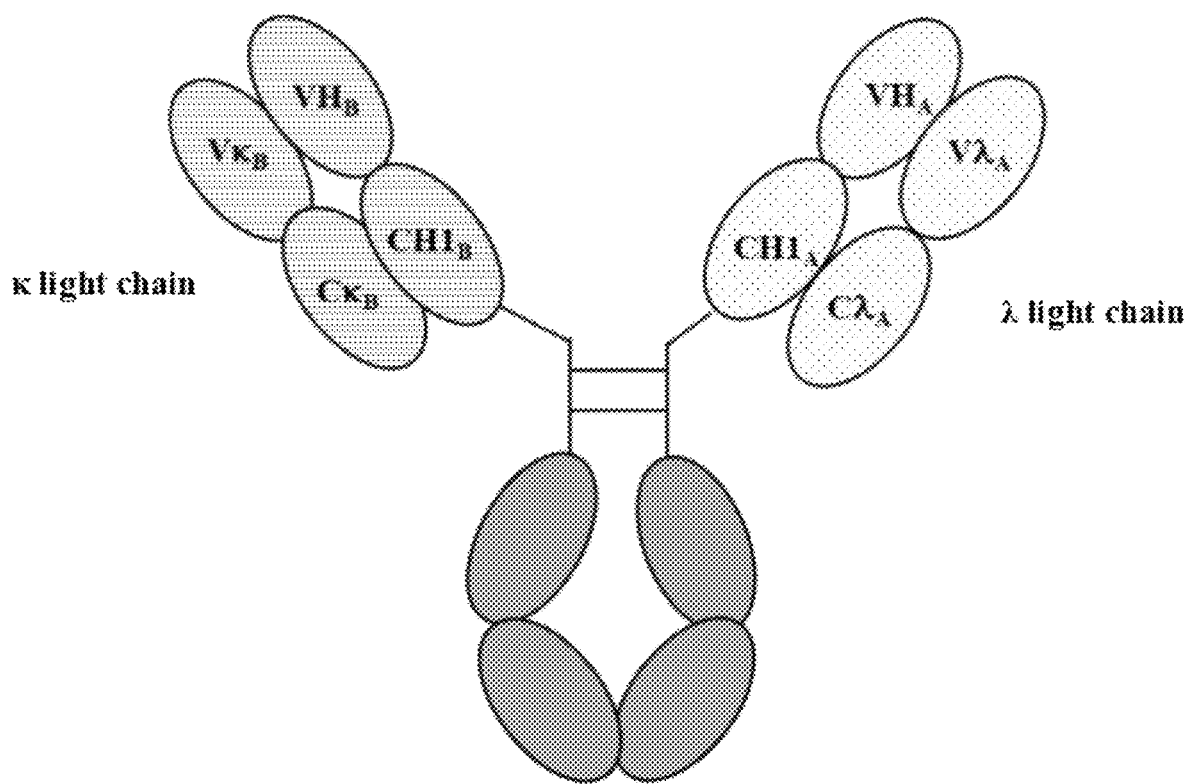
FIG. 1 shows a first antigen×CD3 κλ bispecific antibodies of the present disclosure.

In the present disclosure, the scientific and technical terms used herein have the meanings commonly understood by those skilled in the art, unless otherwise specified. Also, as used herein, protein and nucleic acid chemistry, molecular biology, cell and tissue culture, microbiology, immunology, and laboratory procedures used herein are terms and routine procedures widely used in the corresponding fields. Meanwhile, in order to better understand the present disclosure, definitions and explanations of related terms are provided below.

As used herein, a "tumor antigen" preferably refers to any antigen or antigenic determinant present in (or bound to) a tumor cell but not normally present in a normal cell, or an antigen or antigenic determinant present in or bound to a tumor cell in a greater amount than on a normal (non-tumor) cell, or an antigen or antigenic determinant present in a tumor cell in a form other than that found on a normal (non-tumor) cell. The term thus includes tumor-specific antigens, including tumor-specific antigens (TSA) or tumor-related antigens (TAA), including tumor-related membrane antigens, embryonic antigens on tumors, growth factor receptors, growth factor ligands and any other types of antigens associated with cancers. The tumor antigen can be, for example, a B-cell differentiation antigen (e.g. CD19, CD20, and CD37), a B-cell maturation antigen (B-cell maturation antigen, BCMA), a glypican 3 (GPC3), an epithelial cancer antigen (e.g. breast cancer, gastrointestinal cancer, lung cancer), a prostate-specific cancer antigen (PSA) or a prostate-specific membrane antigen (PSMA), a bladder cancer antigen, a lung (e.g. small cell lung) cancer antigen, a colon cancer antigen, an ovarian cancer antigen, a brain cancer antigen, a stomach cancer antigen, a renal cell carcinoma antigen, a pancreatic cancer antigen, a liver cancer antigen, an esophageal cancer antigen, a head and neck cancer antigen, or a colorectal cancer antigen.

TSA is (or is believed to be) unique to tumor cells and does not occur on other cells in the body (e.g. does not occur to a significant extent on other cells). TAA is not unique to tumor cells and is instead expressed on normal cells (e.g. under conditions that do not induce immune tolerance to the antigen). For example, when the immune system is immature and unable to respond, TAA may be antigens that are expressed on normal cells during fetal development, or they may be antigens that are normally present at very low levels on normal cells, but are expressed at higher levels on tumor cells.

Non-limiting examples of TSA or TAA antigens include: differentiation antigens such as MART-I/MelanA(MART-I), gp100(Pmel 17), tyrosinase, TRP-1, TRP-2 and tumor-specific multilineage antigens such as MAGE-1, MAGE-3, BAGE, GAGE-1, GAGE-2, p15; an overexpressed embryonic antigen, such as CEA; overexpressed oncogenes and mutated tumor suppressor genes such as p53, Ras, HER-2/neu; unique tumor antigens resulted from chromosomal translocations, such as BCR-ABL, E2A-PRL, H4-RET, IGH-IGK, MYL-RAR; and viral antigens such as the Epstein Barr virus antigen EBVA and the human HPV antigens E6 and E7. Other tumor antigens include TSP-180, MAGE-4, MAGE-5, MAGE-6, RAGE, NY-ESO, erbB, pl85erbB2, pl80erbB-3, c-met, nm-23H1, PSA, TAG-72, CA 19-9, CA72-4, CAM 17.1, NuMa, K-ras, β-catenin, CDK4, Mum-1, p15, p16, 43-9F, 5T4, 791Tgp 72, alpha-fetoprotein, D-HCG, BCA225, BTAA, CA125, CA15-3CA 27.29BCAA, CA195, CA242, CA-50, CAM43, CD68P1, CO-029, FGF-5, G250, Ga733EpCAM, HTgp-175, M344, MA-50, MG7-Ag, MOV18, NB/70K, NY-CO-1, RCAS1, SDCCAGi6, TA-90Mac-2 binding protein cyclophilin C-related protein, TAAL6, TAG72, TLP, MUC16, IL13Ra2, FRa, VEGFR2, Lewis Y, FAP, EphA2, CEACAM5, EGFR, CA6, CA9, GPNMB, EGP1, FOLR1, endothelial receptor, STEAP1, SLC 44A4, boundin-4, AGS-16, guanidinyl cyclase C, MUC-1, CFC1B, integrin α3 chain (a3bl chain, i.e. laminin receptor chain) and TPS. Other tumor antigens also include CD19, CD20, CD22, CD30, CD72, CD180, CD171 (L1 CAM), CD123, CD133, CD138, CD37, CD70, CD79a, CD79b, CD56, CD74, CD166, CD71, CLL-1/CLECK 12A, ROR1, BCMA, glypican3 (GPC3), mesothelin, CD33/IL3Ra, c-Met, PSCA, PSMA, glycolipid F77, EGFRvIII, GD-2, MY-ESO-1 or MAGEA3. As used herein, the term "CD20" refers to any native CD20 from any vertebrate source including mammals, such as primates (e.g. humans) and rodents (e.g. mice and rats).

The terms "anti-CD20 antibody" and "antibody that binds CD20" refer to an antibody that is capable of binding CD20 with sufficient affinity such that the antibody is used as a diagnostic and/or therapeutic agent in targeting CD20. In one embodiment, the degree of binding of an anti-CD20 antibody to an unrelated non-CD20 protein is less than about 10% of the binding of the antibody to CD20, as measured, for example, by a radioimmunoassay (RIA). In certain embodiments, an antibody that binds CD20 has a dissociation constant ($K_d$) of ≤1 μM, ≤100 nM, ≤10 nM, ≤1 nM, ≤0.1 nM, ≤0.01 nM, or ≤0.001 nM (e.g. $10^{-8}$M or less, e.g.

$10^{-8}$M to $10^{-13}$M, e.g. $10^{-9}$M to $10^{-13}$M). In certain embodiments, anti-CD20 antibodies bind to CD20 epitopes conserved among CD20 from different species.

As used herein, the term "BCMA" may refer to the concept of BCMA itself and any variants, isoforms and paralogs thereof, which are present together in animals and preferably in humans.

The term "human BCMA" refers to BCMA of human origin and may preferably have, but is not limited to, the amino acid sequence under Genbank accession number AB052772.1.

The terms "anti-BCMA antibody" and "antibody that binds to BCMA" refer to an antibody that is capable of binding to BCMA with sufficient affinity such that the antibody is used as a diagnostic and/or therapeutic agent in targeting BCMA. In one embodiment, the degree of binding of an anti-BCMA antibody to an unrelated non-BCMA protein is less than about 10% of the binding of the antibody to BCMA, as measured, for example, by a radioimmunoassay (RIA). In certain embodiments, an antibody that binds BCMA has a dissociation constant ($K_d$) of ≤1 M, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g. from $10^{-9}$M to $10^{-13}$M). In certain embodiments, anti-BCMA antibodies bind BCMA epitopes conserved among BCMA from different species.

As used herein, the term "GPC3" may refer to the concept of GPC3 itself and any variants, isoforms and paralogs thereof, which are present together in animals and preferably in humans.

The term "human GPC3" refers to GPC3 of human origin.

The terms "anti-GPC3 antibody" and "antibody that binds GPC3" refer to an antibody that is capable of binding GPC3 with sufficient affinity such that the antibody is used as a diagnostic and/or therapeutic agent in targeting GPC3. In one embodiment, the degree of binding of an anti-GPC3 antibody to an unrelated non-GPC3 protein is less than about 10% of the binding of the antibody to GPC3 as measured, for example, by a radioimmunoassay (RIA). In certain embodiments, an antibody that binds GPC3 has a dissociation constant ($K_d$) of ≤1 M, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g. from $10^{-9}$M to $10^{-13}$M). In certain embodiments, anti-GPC3 antibodies bind GPC3 epitopes conserved among GPC3 from different species.

"CD3" refers to any native CD3 from any vertebrate source, including mammals, such as primates (e.g. humans), non-human primates (e.g. cynomolgus monkeys), and rodents (e.g. mice and rats), unless otherwise specified. The term encompasses "full-length" unprocessed CD3 as well as any form of CD3 derived from processing in cells. The term also encompasses naturally occurring variants of CD3, such as splice variants or allelic variants. In one embodiment, the CD3 is human CD3, in particular the epsilon subunit (CD3ε) of human CD3. The amino acid sequence of human CD3ε is shown in UniProt (www.uniprot.org) under accession number P07766 (version 144), or NCBI (www.ncbi.nlm.nih.gov/) RefSeq NP_000724.1. The amino acid sequence of *Macaca fascicularis* CD3ε is shown in NCBI GenBank no.BAB71849.1.

The use of the term "cell surface" is in accordance with its normal meaning in the art, and thus includes the exterior of a cell accessible by binding to proteins and other molecules.

As used herein, unless otherwise specified, the term "about" or "approximately" means within plus or minus 10% of a given value or range. in the case that an integer is required, the term refers to rounding up or down to the nearest integer within plus or minus 10% of the given value or range.

The phrase "substantially identical" with respect to the polypeptide sequence an antibody chain is understood to mean an antibody chain that exhibits at least 60%, 65%, 70%, 75%, 80%, 85%, 90%, 95%, 96%, 97%, 98%, 99% or higher sequence identity to a reference polypeptide sequence. With respect to a nucleic acid sequence, the term is understood to mean a nucleotide sequence that exhibits at least greater than 60%, 65%, 70%, 75%, 80%, 85%, 90%, 95%, 96%, 97%, 98%, 99% or more sequence identity to a reference nucleic acid sequence.

Sequence "identity" or "homoousia" has its meanings widely acknowledged in this field, and the percentage of sequence identity between two nucleic acids or polypeptide molecules or regions can be calculated using published techniques. Sequence identity can be measured along the full length of a polynucleotide or polypeptide or along a region of the molecule. Although there are many methods of measuring identity between two polynucleotides or polypeptides, the term "identity" is well known to the skilled artisan (Carrillo, H. & Lipman, D., SIAM J Applied Math 48:1073 (1988)).

A "substitutional" variant is a variant in which at least one amino acid residue in the native sequence has been removed and inserted at its same position by a different amino acid. The substitution may be single, wherein only one amino acid in the molecule is substituted; or the substitution may be multiple, wherein the same molecule has two or more amino acids that are substituted. Multiple substitutions may be at consecutive positions. Likewise, an amino acid may be substituted with multiple residues, wherein such variants include both substitutions and insertions. An "insertional" variant is a variant in which one or more amino acids are inserted immediately adjacent to an amino acid at a particular position in a native sequence. An immediately adjacent amino acid means an amino acid attached to the (a-carboxy or a-amino functional group of the amino acid. A "deletional" variant is a variant in which one or more amino acids in the native amino acid sequence have been removed. Typically, deletional variants have one or two amino acids deleted in a particular region of the molecule.

With respect to the variable domains of the antibody, the term "variable" refers to certain portions of related molecules that differ widely in sequences between antibodies, and are used for specific recognition and binding of a particular antibody to its specific target. However, the variability is not uniformly distributed throughout the variable domain of the antibody. Variability is concentrated in what is known as complementary determinant regions (CDRs, i.e. CDR1, CDR2 and CDR3) or three segments of the hypervariable region, all of which are located in the variable domains of the light and heavy chains. The more conserved portions in the variable domains are referred to as framework (FR) regions or framework sequences. Each variable domain of a native heavy and light chain comprises four FR regions predominantly in a β-folded configuration, they are joined by three CDRs, and the CDRs forms loops, the loops are joined to the β-folded structure and in some cases form part of the β-folded structure. The CDRs of each chain are typically joined together in close proximity by FR regions and aid in the formation of antibody target binding sites (epitopes or determinants) by means of CDRs from other chains. As used herein, immunoglobulin amino acid residue numbering is performed in accordance with the immunoglobulin amino acid residue numbering system of Kabat et al., unless otherwise indicated. One CDR may have the ability to specifically bind to an associated epitope.

As used herein, an "antibody fragment" or "antigen-binding fragment" of an antibody refers to any portion of a full-length antibody that is less than full-length but comprises at least a portion of the variable region (e.g. one or more CDRs and/or one or more antibody binding sites) of the antibody that binds antigen, and thus retains binding specificity as well as at least a portion of the specific binding capacity of the full-length antibody. Thus, an antigen-binding fragment refers to an antibody fragment that comprises an antigen-binding portion that binds the same antigen as the antibody from the antibody fragment derived therefrom. Antibody fragments include antibody derivatives produced by enzymatic treatment of full-length antibodies, as well as synthetically produced derivatives, e.g. recombinantly produced derivatives. Antibodies include antibody fragments. Examples of antibody fragments include, but are not limited to, Fab, Fab', F(ab')$_2$, single chain Fv(scFv), Fv, dsFv, diabodies, Fd and Fd' fragments and other fragments including modified fragments (see, e.g. Methods in Molecular Biology, Vol 207: Recombinant Antibodies for Cancer Therapy Methods and Protocols (2003); Chapter 1; p 3-25, Kipriyanov). The fragments may comprise multiple chains linked together, for example by disulfide bonds and/or by peptide linkers. Antibody fragments generally comprise at least or about 50 amino acids, and typically at least or about 200 amino acids. Antigen-binding fragments include any antibody fragment that, when inserted into an antibody framework (e.g. by displacement of the corresponding region), results in an antibody that immunospecifically binds (i.e. exhibits a Ka of at least or at least about $10^7$-$10^8$M-1) an antigen. A "functional fragment" or "analog of an antibody" is a fragment or analog that prevents or substantially reduces the ability of the receptor to bind a ligand or initiate signal transduction. As used herein, functional fragments generally have the same meaning as "antibody fragments", and as far as antibodies are concerned, they may refer to fragments that prevent or substantially reduce the ability of the receptor to bind a ligand or initiate signal transduction, such as Fv, Fab, F(ab')$_2$, and the like. An "Fv" fragment consists of a dimer formed by a variable domain of a heavy chain and a variable domain of a light chain in the manner of a non-covalent association (V$_H$-V$_L$ dimer). In this configuration, the three CDRs of each variable domain interact to define a target binding site on the surface of the V$_H$-V$_L$ dimer, as is the case with intact antibodies. The six CDRs together confer target binding specificity to the intact antibody. However, even a single variable domain (or half of an Fv comprising only three target-specific CDRs) may still have the ability to recognize and bind targets.

As used herein, the term "bispecific antibody" (BsAb) refers to antibodies and/or antigen-binding molecules capable of specifically binding to two different antigenic determinants. Generally, a bispecific antibody and/or antigen-binding molecule comprises two antigen-binding sites, each of which is specific for a different antigenic determinant. In certain embodiments, the bispecific antibody and/or antigen-binding molecule is capable of binding two antigenic determinants simultaneously, particularly two antigenic determinants expressed on two different cells.

As used herein, "monoclonal antibody" refers to a population of identical antibodies, meaning that each individual antibody molecule in the population of monoclonal antibodies is identical to another antibody molecule. This property is in contrast to the property of a polyclonal population of the antibodies comprising antibodies having a plurality of different sequences. Monoclonal antibodies can be prepared by a number of well known methods (Smith et al. (2004) J. Clin. Pathol. 57, 912-917; and Nelson et al. J Clin Pathol (2000), 53, 111-117). For example, monoclonal antibodies can be prepared by immortalizing B cells, for example by fusion with myeloma cells to produce hybridoma cell lines or by infecting B cells with a virus, such as EBV. Recombinant techniques can also be used to prepare antibodies from clonal populations of host cells in vitro by transforming host cells with plasmids carrying artificial sequences encoding the nucleotides of the antibodies.

As used herein, the term "hybridoma" or "hybridoma cell" refers to a cell or cell line (typically a myeloma or lymphoma cell) resulted from the fusion of antibody-producing lymphocytes and non-antibody-producing cancer cells. As is known to those of ordinary skill in the art, hybridomas can be propagated and continuously supplied to produce a particular monoclonal antibody. Methods for producing hybridomas are known in the art (Harlow&Lane, 1988). When referring to the term "hybridoma" or "hybridoma cell", they also include subclones and progeny cells of hybridomas.

As used herein, a full-length antibody is an antibody having two full-length heavy chains (e.g. VH-CH1-CH2-CH3 or VH-CH1-CH2-CH3-CH4) and two full-length light chains (VL-CL) and a hinge region, e.g. an antibody naturally produced by an antibody secreting B cell as well as a synthetically produced antibody having the same domain.

The term "chimeric antibody" refers to an antibody in which the variable region sequences are derived from one species and the constant region sequences are derived from another species, for example, an antibody in which the variable region sequences are derived from a mouse antibody and the constant region sequences are derived from a human antibody.

A "humanized" antibody refers to a form of non-human (e.g. mouse) antibody that is a chimeric immunoglobulin, immunoglobulin chain or fragment thereof (e.g. Fv, Fab, Fab', F(ab')$_2$ or other antigen-binding subsequence of an antibody) and contains minimal sequence derived from a non-human immunoglobulin. Preferably, the humanized antibody is a human immunoglobulin (recipient antibody) in which residues of the complementarity-determining region (CDR) of the recipient antibody are replaced by CDR residues from a non-human species (donor antibody) such as mouse, rat or rabbit having the desired specificity, affinity and capacity.

Furthermore, in humanization process, it is also possible to mutate amino acid residues in the CDR1, CDR2 and/or CDR3 regions of VH and/or VL, thereby improving one or more binding properties (e.g. affinity) of the antibody. Mutations can be introduced, e.g. by PCR-mediated mutagenesis, and their effect on antibody binding or other functional properties can be assessed using the in vitro or in vivo assays described herein. Typically, conservative mutations are introduced. Such mutations may be amino acid substitutions, additions or deletions. In addition, mutations in CDR typically do not exceed one or two. Thus, the humanized antibodies of the present disclosure also encompass antibodies comprising one or two amino acid mutations in CDR.

As used herein, the term "CDR" refers to a complementarity-determining region, it is known that an antibody molecule has three CDR per heavy and three CDR per light chain. CDR is also known as a hypervariable region, is present in the variable region of each of the heavy and light chains of an antibody, and has a very high site of variability in a primary structure of CDR. In the present specification, the CDR of the heavy chain is represented by CDR1, CDR2, CDR3 at the amino terminus of the amino acid sequence of the heavy chain, and the CDR of the light chain is represented by CDR1, CDR2, CDR3 at the amino terminus of the amino acid sequence of the light chain. These sites are adjacent to each other in the tertiary structure and determine the specificity of the antigen to which the antibody binds.

As used herein, the term "epitope" refers to any antigenic determinant on an antigen to which the paratope of an antibody binds. Epitopic determinants usually comprise chemically active surface types of molecules, such as amino acids or sugar side chains, and usually have specific three-dimensional structural properties and specific charge properties.

As used herein, "specific binding" or "immunospecifically binding" with respect to an antibody or antigen-binding fragment thereof may be used interchangeably herein and refers to the ability of an antibody or antigen-binding fragment to form one or more non-covalent bonds with the same antigen through non-covalent interactions between the antibody and the antibody binding site of the antigen. The antigen may be an isolated antigen or present in a tumor cell. Generally, an antibody that immunospecifically binds (or specifically binds) an antigen is the one that binds the antigen with an affinity constant (Ka) of about or of $1 \times 10^7 M^{-1}$ or $1 \times 10^8 M^{-1}$ or greater (or a dissociation constant (Kd) of $1 \times 10^{-7} M$ or $1 \times 10^{-8} M$ or less). Affinity constants can be determined by standard kinetic methods for antibody reactions, e.g. immunoassays, surface plasmon resonance (SPR) (Rich and Myszka (2000) Curr. Opin. Biotechnol 11:54; Englebienne (1998) Analyst. 123:1599), isothermal titration calorimetry (ITC), or other kinetic interaction assays known in the art. Reference can also be made to U.S. Pat. No. 7,229,619 which describes an exemplary SPR and ITC method for calculating the binding affinity of an antibody). Instruments and methods for detecting and monitoring the rate of binding in real time are known and commercially available (with reference to Malmqvist (2000) Biochem. Soc. Trans. 27:335).

As used herein, the terms "polynucleotide" and "nucleic acid molecule" refer to an oligomer or polymer comprising at least two linked nucleotides or nucleotide derivatives, including deoxyribonucleic acid (DNA) and ribonucleic acid (RNA), typically linked together by phosphodiester bonds. As used herein, the term "nucleic acid molecule" is intended to include DNA molecules and RNA molecules. The nucleic acid molecule may be single-stranded or double-stranded, and may be cDNA.

As used herein, an isolated nucleic acid molecule is a nucleic acid molecule isolated from other nucleic acid molecules present in the natural source. An "isolated" nucleic acid molecule, such as a cDNA molecule, can be substantially free of other cellular material or culture medium when prepared by recombinant techniques, or substantially free of chemical precursors or other chemical components when chemically synthesized. Exemplary isolated nucleic acid molecules provided herein include isolated nucleic acid molecules encoding an antibody or antigen-binding fragment provided herein.

As used herein, "operably linked" with respect to a nucleic acid sequence, region, element or domain means that the nucleic acid regions are functionally related to one another. For example, a promoter may be operably linked to a nucleic acid encoding a polypeptide such that the promoter regulates or mediates transcription of the nucleic acid.

Also provided are "conservative sequence modifications" in the sequences set forth in the sequence listings described herein, i.e. nucleotide and amino acid sequence modifications that do not eliminate binding of an antibody encoded by or containing an amino acid sequence to an antigen. These conservative sequence modifications include conservative nucleotide and amino acid substitutions, and nucleotide and amino acid additions and deletions. For example, modifications can be introduced into the sequence listings described herein by standard techniques known in the art, such as site-directed mutagenesis and PCR-mediated mutagenesis. Conservative sequence modifications include conservative amino acid substitutions in which an amino acid residue is replaced with an amino acid residue having a similar side chain. Families of amino acid residues having similar side chains have been defined in the art. These families include amino acids with basic side chains (e.g. lysine, arginine, histidine), amino acids with acidic side chains (e.g. aspartic acid, glutamic acid), amino acids with uncharged polar side chains (e.g. glycine, asparagine, glutamine, serine, threonine, tyrosine, cysteine, tryptophan), amino acids with nonpolar side chains (e.g. alanine, valine, leucine, isoleucine, proline, phenylalanine, methionine), amino acids with P-branched side chains (e.g. threonine, valine, isoleucine) and amino acids with aromatic side chains (e.g. tyrosine, phenylalanine, tryptophan, histidine). Thus, a predicted nonessential amino acid residue in an anti-CD20, BCMA or GPC3 antibody is preferably replaced with another amino acid residue from the same side chain family. Methods for identifying conservative substitutions of nucleotides and amino acids that do not eliminate antigen-binding are well known in the art (see, e.g. Brummell et al. Biochem. 32: 1180-1187 (1993); Kobayashi et al. Protein Eng. 12(10): 879-884 (1999); Burks et al. Proc. Natl. Acad. Sci. USA 94: 412-417 (1997)).

Alternatively, in another embodiment, mutations can be randomly introduced along all or a portion of the anti-GCD20, BCMA or PC3 antibody coding sequence by, for example, saturation mutagenesis, and the resulting modified anti-CD20, BCMA or GPC3 antibodies can be screened for improved binding activity.

As used herein, "expression" refers to a process of producing a polypeptide by transcription and translation of a polynucleotide. The level of expression of a polypeptide can be assessed using any method known in the art, including, for example, methods of determining the amount of polypeptide produced from a host cell. Such methods may include, but are not limited to, quantitation of polypeptides in cell lysates by ELISA, gel electrophoresis followed by Coomassie blue staining, Lowry protein assay, and Bradford protein assay.

As used herein, a "host cell" is a cell for receiving, maintaining, replicating and expanding a vector. Host cells may also be used to express the polypeptide encoded by the vector. when the host cell divides, the nucleic acid contained in the vector replicates, thereby amplifying the nucleic acid. The host cell may be a eukaryotic cell or a prokaryotic cell. Suitable host cells include, but are not limited to, CHO cells, various COS cells, HeLa cells, HEK cells such as HEK 293 cells.

As used herein, a "vector" is a replicable nucleic acid from which one or more heterologous proteins can be expressed when the vector is transformed into an appropriate host cell. With respect to vectors, vectors include those vectors into which a nucleic acid encoding a polypeptide or fragment thereof may be introduced typically by restriction digestion and ligation. Vectors also include those comprising a nucleic acid encoding a polypeptide. Vectors are used to introduce a nucleic acid encoding a polypeptide into a host cell, to amplify the nucleic acid, or to express/display the polypeptide encoded by the nucleic acid. The vector usually remains episomal, but can be designed such that the gene or part thereof is integrated into the chromosome of the genome. Also contemplated are vectors for artificial chromosomes, such as yeast artificial vectors and mammalian artificial chromosomes. The selection and use of such vehicles are well known to those skilled in the art.

As used herein, a vector also includes a "virus vector" or a "viral vector". A viral vector is an engineered virus operably linked to a foreign gene to transfer (as a vehicle or shuttle) the foreign gene into a cell.

As used herein, an "expression vector" includes a vector capable of expressing a DNA, the DNA is operably linked to regulatory sequences such as a promoter region, and is capable of affecting the expression of such a DNA fragment. Such additional segments may include promoter and terminator sequences, and optionally may include one or more origins of replication, one or more selectable markers, enhancers, polyadenylation signals, and the like. Expression vectors are typically derived from plasmid or viral DNA, or may contain elements of both. Thus, an expression vector refers to a recombinant DNA or RNA construct, such as a plasmid, phage, recombinant virus or other vectors, when introduced into an appropriate host cell, it results in expression of a cloned DNA. Suitable expression vectors are well known to those skilled in the art and include expression vectors that are replicable in eukaryotic and/or prokaryotic cells and expression vectors that remain episomal or that are integrated into the host cell genome.

As used herein, "treating" a subject with a disease or condition means that the subject's symptoms are partially or completely alleviated or remain unchanged after treatments. Thus, the treatment includes prophylaxis, treatment and/or cure. Prevention refers to preventing the underlying disease and/or preventing the worsening of symptoms or the progression of the disease. Treatment also includes any antibody or antigen-binding fragment thereof provided and any pharmaceutical use of the compositions provided herein.

As used herein, "therapeutic effect" refers to an effect resulted from treatment of a subject that alters, typically ameliorates or ameliorates a symptom of a disease or condition, or cures a disease or condition.

As used herein, a "therapeutically effective amount" or "therapeutically effective dose" refers to an amount of a substance, compound, material, or composition comprising a compound that is at least sufficient to produce a therapeutic effect after administration to a subject. Thus, it is an amount necessary to prevent, cure, ameliorate, block, or partially block the symptoms of a disease or condition.

As used herein, a "prophylactically effective amount" or "prophylactically effective dose" refers to an amount of a substance, compound, material, or composition comprising a compound that, when administered to a subject, it has a desired prophylactic effect, e.g. preventing or delaying the occurrence or recurrence of a disease or condition, and reduces the likelihood of the occurrence or recurrence of a disease or condition. A fully prophylactically effective dose does not necessarily occur by administration of one dose, and may occur only after administration of a series of doses.

Thus, a prophylactically effective amount can be administered in one or more administrations.

As used herein, the term "patient" refers to a mammal, such as a human.

II. Detailed Description

In one aspect, the present disclosure provides a bispecific antibody or antigen-binding fragment thereof, comprising:

(a) a first antigen-binding portion or antigen-binding fragment thereof, the first antigen-binding portion comprises a first light chain and a first heavy chain, the first light chain is a κ light chain, the first antigen-binding portion comprises a first binding domain that binds to a first antigen; and (b) a second antigen-binding portion or antigen-binding fragment thereof, the second antigen-binding portion comprises a second light chain and a second heavy chain, the second light chain is a λ light chain, the second antigen-binding portion comprises a second binding domain that binds to a second antigen.

In some embodiments, the second antigen is a CD3 antigen.

In some embodiments, a second light chain variable region of the second antigen-binding portion has a $Gln_{40}Glu$ mutation ($V\lambda_{CD3}$: $Gln_{40}Glu$); and a second heavy chain variable region of the second antigen-binding portion has a $Gln_{39}Lys$ mutation ($VH_{CD3}$: $Gln_{39}Lys$).

In some embodiments, the second binding domain comprises second light chain CDRs selected from amino acid sequences of SEQ ID NOs: 7-9, 14, 15, 20, 21 or any variant thereof; and/or second heavy chain CDRs selected from amino acid sequences of SEQ ID NOs: 26-28, 31, 34, 40, 43, 46, 47 or any variant thereof.

In some embodiments, the second binding domain comprises a second light chain CDR1 selected from any of amino acid sequences of SEQ ID NOs: 7, 14 or any variant thereof, a second light chain CDR2 selected from any of amino acid sequences of SEQ ID NOs: 8, 15, 20 or any variant thereof, a second light chain CDR3 selected from any of amino acid sequences of SEQ ID NOs: 9, 21 or any variant thereof; and/or a second heavy chain CDR1 selected from any of amino acid sequences of SEQ ID NOs: 26, 31, 46 or any variant thereof, a second heavy chain CDR2 selected from any of amino acid sequences of SEQ ID NOs: 27, 47 or any variant thereof, a second heavy chain CDR3 selected from any of amino acid sequences of SEQ ID NOs: 28, 34, 37, 40, 43 of or any variant thereof.

In some embodiments, the second light chain CDRs of the second binding domain are selected from: the second light chain CDR1, CDR2 and CDR3 respectively comprising the amino acid sequences of SEQ ID NOs: 7, 8, 9; the second light chain CDR1, CDR2 and CDR3 respectively comprising the amino acid sequences of SEQ ID NOs: 14, 15, 9; the second light chain CDR1, CDR2 and CDR3 respectively comprising the amino acid sequences of SEQ ID NOs: 7, 8, 21; the second light chain CDR1, CDR2 and CDR3 respectively comprising the amino acid sequences of SEQ ID NOs: 7, 20, 21; and/or the heavy chain CDRs of the second binding domain are selected from: the second heavy chain CDR1, CDR2 and CDR3 respectively comprising the amino acid sequences of SEQ ID NOs: 26, 27, 28; the second heavy chain CDR1, CDR2 and CDR3 respectively comprising the amino acid sequences of SEQ ID NOs: 31, 27, 28; the second heavy chain CDR1, CDR2 and CDR3 respectively comprising the amino acid sequences of SEQ ID NOs: 31, 27, 34; the second heavy chain CDR1, CDR2 and CDR3 respectively comprising the amino acid sequences of SEQ ID NOs: 31, 27, 37; the second heavy chain CDR1, CDR2 and CDR3 respectively comprising the amino acid sequences of SEQ ID NOs: 31, 27, 40; the second heavy chain CDR1, CDR2 and CDR3 respectively comprising the amino acid sequences of SEQ ID NOs: 31, 27, 43; the second heavy chain CDR1, CDR2 and CDR3 respectively comprising the amino acid sequences of SEQ ID NOs: 46, 47, 28.

In some embodiments, the second binding domain comprises a second light chain variable region selected from any of amino acid sequences of SEQ ID NOs: 5, 10, 12, 16, 18, 22 or any variant thereof; and/or a second heavy chain variable region selected from any of amino acid sequences of SEQ ID NOs: 24, 29, 32, 35, 38, 41, 44, 48, 50, 52 or any variant thereof.

In some embodiments, the second binding domain comprises a second light chain variable region of the amino acid sequence of SEQ ID NO: 18 or any variant thereof; and a second heavy chain variable region of the amino acid sequence of SEQ ID NO: 24 or any variant thereof.

In some embodiments, the second binding domain comprises a second light chain variable region of the amino acid sequence of SEQ ID NO: 5 or any variant thereof; and a second heavy chain variable region of the amino acid sequence of SEQ ID NO: 48 or any variant thereof.

In some embodiments, the second binding domain comprises a second light chain variable region of the amino acid sequence of SEQ ID NO: 18 or any variant thereof; and a second heavy chain variable region of the amino acid sequence of SEQ ID NO: 48 or any variant thereof.

In some embodiments, the second binding domain comprises a second light chain variable region of the amino acid sequence of SEQ ID NO: 5 or any variant thereof; and a second heavy chain variable region of the amino acid sequence of SEQ ID NO: 50 or any variant thereof.

In some embodiments, the second binding domain comprises a second light chain variable region of the amino acid sequence of SEQ ID NO: 10 or any variant thereof; and a second heavy chain variable region of the amino acid sequence of SEQ ID NO: 50 or any variant thereof.

In some embodiments, the second binding domain comprises a second light chain variable region of the amino acid sequence of SEQ ID NO: 12 or any variant thereof; and a second heavy chain variable region of the amino acid sequence of SEQ ID NO: 50 or any variant thereof.

In some embodiments, the second binding domain comprises a second light chain variable region of the amino acid sequence of SEQ ID NO: 18 or any variant thereof; and a second heavy chain variable region of the amino acid sequence of SEQ ID NO: 50 or any variant thereof.

In some embodiments, the second light chain of the second antigen-binding portion is selected from any of amino acid sequences of SEQ ID NOs: 58 and 66; and/or the second heavy chain of the second antigen-binding portion is selected from any of amino acid sequences of SEQ ID NOs: 60 and 68. In some preferred embodiments, the second light chain of the second antigen-binding portion is the amino acid sequence of SEQ ID NO: 58; and the second heavy chain of the second antigen-binding portion is the amino acid sequence of SEQ ID NO: 60. In some preferred embodiments, the second light chain of the second antigen-binding portion is the amino acid sequence of SEQ ID NO: 66; and the second heavy chain of the second antigen-binding portion is the amino acid sequence of SEQ ID NO: 68.

In some embodiments, the first antigen is a tumor antigen.

In some preferred embodiments, the tumor antigen is selected from the group consisting of: CD19, CD20, CD22, CD30, CD38, CD72, CD180, CD171 (L1 CAM), CD123, CD133, CD138, CD37, CD70, CD79a, CD79b, CD56, CD74, CD166, CD71, CLL-1/CLECK12A, ROR1, BCMA, GPC3, mesothelin, CD33/IL3Ra, c-Met, PSCA, PSMA, glycolipid F77, EGFRvIII, GD-2, MY-ESO-1, Her2, Her3, MUC1, MUC17, Claudin18 or MAGEA3.

In a particular embodiment, the tumor-related antigen is selected from CD20, BCMA and GPC3.

In some embodiments, the first antigen is a CD20 antigen.

In some preferred embodiments, the first light chain variable region of the first antigen-binding portion has a $Gln_{38}Lys$ mutation ($V\kappa_{CD20}$: $Gln_{38}Lys$). In some preferred embodiments, the first heavy chain variable region of the first antigen-binding portion has a $Gln_{39}Glu$ mutation ($VH_{CD20}$: $Gln_{39}Glu$).

In some preferred embodiments, the first light chain variable region of the first antigen-binding portion has a $Gln_{38}Lys$ mutation ($V\kappa_{CD20}$: $Gln_{38}Lys$), and the first light chain constant region has $Glu_{123}Lys$ and $Gln_{124}Lys$ mutations ($V\kappa$-$Ck_{CD20}$: $Gln_{38}Lys\backslash Glu_{123}Lys\backslash Gln_{124}Lys$). In some preferred embodiments, the first heavy chain variable region of the first antigen-binding portion has a $Gln_{39}Glu$ mutation ($VH_{CD20}$: $Gln_{39}Glu$), and the first heavy chain constant region has $Lys_{152}Glu$ and $Lys_{218}Glu$ mutations ($V_{H}$-$C_{H}1_{CD20}$: $Gln_{39}Glu\backslash Lys_{152}Glu\backslash Lys_{218}Glu$).

In some preferred embodiments, the first light chain of the first antigen-binding portion is selected from any of amino acid sequences of SEQ ID NOs: 54, 62, and 70; and/or the first heavy chain of the first antigen-binding portion is selected from any of amino acid sequences of SEQ ID NOs: 56, 64, and 72.

In some preferred embodiments, the first light chain of the first antigen-binding portion is the amino acid sequence of SEQ ID NO: 54, and the first heavy chain of the first antigen-binding portion is the amino acid sequence of SEQ ID NO: 56.

In some preferred embodiments, the first light chain of the first antigen-binding portion is the amino acid sequence of SEQ ID NO: 62, and the first heavy chain of the first antigen-binding portion is the amino acid sequence of SEQ ID NO: 64.

In some preferred embodiments, the first light chain of the first antigen-binding portion is the amino acid sequence of SEQ ID NO: 70, and the first heavy chain of the first antigen-binding portion is the amino acid sequence of SEQ ID NO: 72.

In some preferred embodiments, the first light chain of the first antigen-binding portion is the amino acid sequence of SEQ ID NO: 54, and the first heavy chain of the first antigen-binding portion is the amino acid sequence of SEQ ID NO: 56, the second light chain of the second antigen-binding portion is the amino acid sequence of SEQ ID NO: 58; and the second heavy chain of the second antigen-binding portion is the amino acid sequence of SEQ ID NO: 60.

In some preferred embodiments, the first light chain of the first antigen-binding portion is the amino acid sequence of SEQ ID NO: 62, and the first heavy chain of the first antigen-binding portion is the amino acid sequence of SEQ ID NO: 64, the second light chain of the second antigen-binding portion is the amino acid sequence of SEQ ID NO: 66; and the second heavy chain of the second antigen-binding portion is the amino acid sequence of SEQ ID NO: 68, the second light chain of the second antigen-binding portion is the amino acid sequence of SEQ ID NO: 58; and the second heavy chain of the second antigen-binding portion is the amino acid sequence of SEQ ID NO: 60.

In some preferred embodiments, the first light chain of the first antigen-binding portion is the amino acid sequence of SEQ ID NO: 70, and the first heavy chain of the first antigen-binding portion is the amino acid sequence of SEQ ID NO: 72, the second light chain of the second antigen-binding portion is the amino acid sequence of SEQ ID NO:

66; and the second heavy chain of the second antigen-binding portion is the amino acid sequence of SEQ ID NO: 68.

In some preferred embodiments, the first light chain of the first antigen-binding portion is the amino acid sequence of SEQ ID NO: 62, and the first heavy chain of the first antigen-binding portion is the amino acid sequence of SEQ ID NO: 64, the second light chain of the second antigen-binding portion is the amino acid sequence of SEQ ID NO: 58; and the second heavy chain of the second antigen-binding portion is the amino acid sequence of SEQ ID NO: 60.

In some preferred embodiments, the first light chain of the first antigen-binding portion is the amino acid sequence of SEQ ID NO: 54, and the first heavy chain of the first antigen-binding portion is the amino acid sequence of SEQ ID NO: 56, the second light chain of the second antigen-binding portion is the amino acid sequence of SEQ ID NO: 66; and the second heavy chain of the second antigen-binding portion is the amino acid sequence of SEQ ID NO: 68.

In some embodiments, the first antigen is a BCMA antigen.

In some preferred embodiments, the first light chain variable region of the first antigen-binding portion has a $Gln_{42}Lys$ mutation ($V\kappa_{BCMA}$: $Gln_{42}Lys$). In some preferred embodiments, the first heavy chain variable region of the first antigen-binding portion has a $Gln_{39}Glu$ mutation ($VH_{BCMA}$: $Gln_{39}Glu$).

In some preferred embodiments, the first light chain of the first antigen-binding portion is selected from the amino acid sequences of SEQ ID NOs: 80, and 84; and/or the first heavy chain of the first antigen-binding portion is selected from the amino acid sequences of SEQ ID NOs: 82 and 86.

In some preferred embodiments, the first light chain of the first antigen-binding portion is the amino acid sequence of SEQ ID NO: 80; and the first heavy chain of the first antigen-binding portion is the amino acid sequence of SEQ ID NO: 82.

In some preferred embodiments, the first light chain of the first antigen-binding portion is the amino acid sequence of SEQ ID NO: 84; and the first heavy chain of the first antigen-binding portion is the amino acid sequence of SEQ ID NO: 82.

In some preferred embodiments, the first light chain of the first antigen-binding portion is the amino acid sequence of SEQ ID NO: 80; and the first heavy chain of the first antigen-binding portion is the amino acid sequence of SEQ ID NO: 86.

In some preferred embodiments, the first light chain of the first antigen-binding portion is the amino acid sequence of SEQ ID NO: 84; and the first heavy chain of the first antigen-binding portion is the amino acid sequence of SEQ ID NO: 86.

In some preferred embodiments, the first light chain of the first antigen-binding portion is the amino acid sequence of SEQ ID NO: 80, and the first heavy chain of the first antigen-binding portion is the amino acid sequence of SEQ ID NO: 82, the second light chain of the second antigen-binding portion is the amino acid sequence of SEQ ID NO: 66; and the second heavy chain of the second antigen-binding portion is the amino acid sequence of SEQ ID NO: 68.

In some preferred embodiments, the first light chain of the first antigen-binding portion is the amino acid sequence of SEQ ID NO: 84, and the first heavy chain of the first antigen-binding portion is the amino acid sequence of SEQ ID NO: 82, the second light chain of the second antigen-binding portion is the amino acid sequence of SEQ ID NO: 66; and the second heavy chain of the second antigen-binding portion is the amino acid sequence of SEQ ID NO: 68.

In some preferred embodiments, the first light chain of the first antigen-binding portion is the amino acid sequence of SEQ ID NO: 80, and the first heavy chain of the first antigen-binding portion is the amino acid sequence of SEQ ID NO: 86, the second light chain of the second antigen-binding portion is the amino acid sequence of amino acid sequence of SEQ ID NO: 66; and the second heavy chain of the second antigen-binding portion is the amino acid sequence of amino acid sequence of SEQ ID NO: 68.

In some preferred embodiments, the first light chain of the first antigen-binding portion is the amino acid sequence of SEQ ID NO: 84, and the first heavy chain of the first antigen-binding portion is the amino acid sequence of SEQ ID NO: 86, the second light chain of the second antigen-binding portion is the amino acid sequence of SEQ ID NO: 66; and the second heavy chain of the second antigen-binding portion is the amino acid sequence of SEQ ID NO: 68.

In some embodiments, the first antigen is a GPC3 antigen.

In some preferred embodiments, the first light chain variable region of the first antigen-binding portion has $Gln_{43}Lys$ and $Gln_{39}Glu$ mutations ($V\kappa_{GPC3}$: $Gln_{43}Lys$; $VH_{GPC3}$: $Gln_{39}Glu$).

In some preferred embodiments, the first light chain of the first antigen-binding portion is selected from the amino acid sequences of SEQ ID NOs: 88 and 92; and/or the first heavy chain of the first antigen-binding portion is selected from the amino acid sequences of SEQ ID NOs: 90 and 94.

In some preferred embodiments, the first light chain of the first antigen-binding portion is the amino acid sequence of SEQ ID NO: 88, and the first heavy chain of the first antigen-binding portion is the amino acid sequence of SEQ ID NO: 90.

In some preferred embodiments, the first light chain of the first antigen-binding portion is the amino acid sequence of SEQ ID NO: 92, and the first heavy chain of the first antigen-binding portion is the amino acid sequence of SEQ ID NO: 94.

In some preferred embodiments, the first light chain of the first antigen-binding portion is the amino acid sequence of SEQ ID NO: 88, and the first heavy chain of the first antigen-binding portion is the amino acid sequence of SEQ ID NO: 90, the second light chain of the second antigen-binding portion is the amino acid sequence of SEQ ID NO: 66; and the second heavy chain of the second antigen-binding portion is the amino acid sequence of SEQ ID NO: 68.

In some preferred embodiments, the first light chain of the first antigen-binding portion is the amino acid sequence of SEQ ID NO: 92, and the first heavy chain of the first antigen-binding portion is the amino acid sequence of SEQ ID NO: 94, the second light chain of the second antigen-binding portion is the amino acid sequence of SEQ ID NO: 66; and the second heavy chain of the second antigen-binding portion is the amino acid sequence of SEQ ID NO: 68.

In some embodiments, the Fc portion of the first antigen-binding portion and/or the second antigen-binding portion of the bispecific antibody adopts a knob-into-hole structure. In some preferred embodiments, the human IgG4 knob-into-hole structure is used.

In some preferred embodiments, the first antigen-binding portion and/or the second antigen-binding portion of the bispecific antibody further has a $Ser_{228}Pro$ mutation, $Leu_{235}Glu$ mutation and/or Pro329Ala mutation.

In one aspect, the present disclosure provides a nucleic acid encoding the bispecific antibody or antigen-binding portion thereof described in the above.

In some preferred embodiments, the second antigen-binding portion binds to a CD3 antigen, the nucleic acid encoding the second light chain variable region of the second antigen-binding portion is selected from any of nucleotide sequences of SEQ ID NOs: 6, 11, 13, 17, 19 and 23; and/or the nucleic acid encoding the second heavy chain variable region of the second antigen-binding portion is selected from any of nucleotide sequences of SEQ ID NOs: 25, 30, 33, 36, 39, 42, 45, 49, 51 and 53. In some preferred embodiments, the nucleic acid encoding the second light chain of the second antigen-binding portion is selected from any of nucleotide sequences of SEQ ID NOs: 59 and 67; and/or the nucleic acid encoding the second heavy chain of the second antigen-binding portion is selected from any of nucleotide sequences of SEQ ID NOs: 61 and 69. In some preferred embodiments, the nucleic acid encoding the second light chain of the second antigen-binding portion is selected from the nucleotide sequence of SEQ ID NO: 59, and the nucleic acid encoding the second heavy chain of the second antigen-binding portion is selected from the nucleotide sequence of SEQ ID NO: 61. In some preferred embodiments, the nucleic acid encoding the second light chain of the second antigen-binding portion is selected from the nucleotide sequence of SEQ ID NO: 67, and the nucleic acid encoding the second heavy chain of the second antigen-binding portion is selected from the nucleotide sequence of SEQ ID NO: 69.

In some preferred embodiments, the first antigen-binding portion binds to a CD20 antigen, the nucleic acid encoding the first light chain variable region of the first antigen-binding portion is selected from any of nucleotide sequences of SEQ ID NOs: 55, 63 and 71; and/or the nucleic acid encoding the first heavy chain of the first antigen-binding portion is selected from any of nucleotide sequences of SEQ ID NOs: 57, 65, and 73. In some preferred embodiments, the nucleic acid encoding the first light chain of the first antigen-binding portion is selected from the nucleotide sequence of SEQ ID NO: 55, and the nucleic acid encoding the first heavy chain of the first antigen-binding portion is selected from the nucleotide sequence of SEQ ID NO: 57. In some preferred embodiments, the nucleic acid encoding the first light chain of the first antigen-binding portion is selected from the nucleotide sequence of SEQ ID NO: 63, and the nucleic acid encoding the first heavy chain of the first antigen-binding portion is selected from the nucleotide sequence of SEQ ID NO: 65. In some preferred embodiments, the nucleic acid encoding the first light chain of the first antigen-binding portion is selected from the nucleotide sequence of SEQ ID NO: 71, and the nucleic acid encoding the first heavy chain of the first antigen-binding portion is selected from a nucleotide sequence of SEQ ID NO: 73.

In some preferred embodiments, the first antigen-binding portion binds to a BCMA antigen, the nucleic acid encoding the first light chain variable region of the first antigen-binding portion is selected from any of nucleotide sequences of SEQ ID NOs: 81 and 85; and/or the nucleic acid encoding the first heavy chain of the first antigen-binding portion is selected from any of nucleotide sequences of SEQ ID NOs: 83 and 87. In some preferred embodiments, the nucleic acid encoding the first light chain of the first antigen-binding portion is selected from the nucleotide sequence of SEQ ID NO: 81, and the nucleic acid encoding the first heavy chain of the first antigen-binding portion is selected from the nucleotide sequence of SEQ ID NO: 83. In some preferred embodiments, the nucleic acid encoding the first light chain of the first antigen-binding portion is selected from the nucleotide sequence of SEQ ID NO: 85, and the nucleic acid encoding the first heavy chain of the first antigen-binding portion is selected from the nucleotide sequence of SEQ ID NO: 83. In some preferred embodiments, the nucleic acid encoding the first light chain of the first antigen-binding portion is selected from the nucleotide sequence of SEQ ID NO: 81, and the nucleic acid encoding the first heavy chain of the first antigen-binding portion is selected from the nucleotide sequence of SEQ ID NO: 87. In some preferred embodiments, the nucleic acid encoding the first light chain of the first antigen-binding portion is selected from the nucleotide sequence of SEQ ID NO: 85, and the nucleic acid encoding the first heavy chain of the first antigen-binding portion is selected from the nucleotide sequence of SEQ ID NO: 87.

In some preferred embodiments, the first antigen-binding portion binds to a GPC3 antigen, the nucleic acid encoding the first light chain variable region of the first antigen-binding portion is selected from any of nucleotide sequences of SEQ ID NOs: 89 and 93; and/or the nucleic acid encoding the first heavy chain of the first antigen-binding portion is selected from any of nucleotide sequences of SEQ ID NOs: 91 and 95. In some preferred embodiments, the nucleic acid encoding the first light chain of the first antigen-binding portion is selected from the nucleotide sequence of SEQ ID NO: 89, and the nucleic acid encoding the first heavy chain of the first antigen-binding portion is selected from the nucleotide sequence of SEQ ID NO: 91. In some preferred embodiments, the nucleic acid encoding the first light chain of the first antigen-binding portion is selected from the nucleotide sequence of SEQ ID NO: 93, and the nucleic acid encoding the first heavy chain of the first antigen-binding portion is selected from the nucleotide sequence of SEQ ID NO: 95.

In some preferred embodiments, the first antigen-binding portion of the bispecific antibody binds to the CD20 antigen, the second antigen binds to the CD3 antigen, the nucleic acid encoding the first light chain of the first antigen-binding portion is selected from the nucleotide sequence of SEQ ID NO: 55, and the nucleic acid encoding the first heavy chain of the first antigen-binding portion is selected from the nucleotide sequence of SEQ ID NO: 57, the nucleic acid encoding the second light chain of the second antigen-binding portion is selected from the nucleotide sequence of SEQ ID NO: 59, and the nucleic acid encoding the second heavy chain of the second antigen-binding portion is selected from the nucleotide sequence of SEQ ID NO: 61. In some preferred embodiments, the nucleic acid encoding the first light chain of the first antigen-binding portion is selected from the nucleotide sequence of SEQ ID NO: 63, and the nucleic acid encoding the first heavy chain of the first antigen-binding portion is selected from the nucleotide sequence of SEQ ID NO: 65, the nucleic acid encoding the second light chain of the second antigen-binding portion is selected from the nucleotide sequence of SEQ ID NO: 67, and the nucleic acid encoding the second heavy chain of the second antigen-binding portion is selected from the nucleotide sequence of SEQ ID NO: 69, the nucleic acid encoding the second light chain of the second antigen-binding portion is selected from the nucleotide sequence of SEQ ID NO: 59, and the nucleic acid encoding the second heavy chain of the second antigen-binding portion is selected from the nucleotide sequence of SEQ ID NO: 61. In some preferred embodiments, the nucleic acid encoding the first light chain of the first antigen-binding portion is selected from the nucleotide sequence of SEQ ID NO: 71, and the nucleic acid encoding the first heavy chain of the first antigen-binding portion is selected from the nucleotide sequence of SEQ ID NO: 73, the nucleic acid encoding the second light chain of the second antigen-binding portion is selected from the nucleotide sequence of SEQ ID NO: 67, and the nucleic acid encoding the second heavy chain of the second antigen-binding portion is selected from the nucleotide sequence of SEQ ID NO: 69. In some preferred embodiments, the nucleic acid encoding the first light chain of the first antigen-binding portion is selected from the nucleotide sequence of SEQ ID NO: 63, and the nucleic acid encoding the first heavy chain of the first antigen-binding portion is selected from the nucleotide sequence of SEQ ID NO: 65, the nucleic acid encoding the second light chain of the second antigen-binding portion is selected from the nucleotide sequence of SEQ ID NO: 59, and the nucleic acid encoding the second heavy chain of the second antigen-binding portion is selected from the nucleotide sequence of SEQ ID NO: 61. In some preferred embodiments, the nucleic acid encoding the first light chain of the first antigen-binding portion is selected from the nucleotide sequence of SEQ ID NO: 55, and the nucleic acid encoding the first heavy chain of the first antigen-binding portion is selected from the nucleotide sequence of SEQ ID NO: 57, the nucleic acid encoding the second light chain of the second antigen-binding portion is selected from the nucleotide sequence of SEQ ID NO: 67, and the nucleic acid encoding the second heavy chain of the second antigen-binding portion is selected from the nucleotide sequence of SEQ ID NO: 69.

In some preferred embodiments, the first antigen-binding portion of the bispecific antibody binds to the BCMA antigen, the second antigen binds to the CD3 antigen, the nucleic acid encoding the first light chain of the first antigen-binding portion is selected from the nucleotide sequence of SEQ ID NO: 81, and the nucleic acid encoding the first heavy chain of the first antigen-binding portion is selected from the nucleotide sequence of SEQ ID NO: 83, the nucleic acid encoding the second light chain of the second antigen-binding portion is selected from the nucleotide sequence of SEQ ID NO: 67, and the nucleic acid encoding the second heavy chain of the second antigen-binding portion is selected from the nucleotide sequence of SEQ ID NO: 69. In some preferred embodiments, the nucleic acid encoding the first light chain of the first antigen-binding portion is selected from the nucleotide sequence of SEQ ID NO: 85, and the nucleic acid encoding the first heavy chain of the first antigen-binding portion is selected from the nucleotide sequence of SEQ ID NO: 83, the nucleic acid encoding the second light chain of the second antigen-binding portion is selected from the nucleotide sequence of SEQ ID NO: 67, and the nucleic acid encoding the second heavy chain of the second antigen-binding portion is selected from the nucleotide sequence of SEQ ID NO: 69. In some preferred embodiments, the nucleic acid encoding the first light chain of the first antigen-binding portion is selected from the nucleotide sequence of SEQ ID NO: 81, and the nucleic acid encoding the first heavy chain of the first antigen-binding portion is selected from the nucleotide sequence of SEQ ID NO: 87, the nucleic acid encoding the second light chain of the second antigen-binding portion is selected from the nucleotide sequence of SEQ ID NO: 67, and the nucleic acid encoding the second heavy chain of the second antigen-binding portion is selected from the nucleotide sequence of SEQ ID NO: 69. In some preferred embodiments, the nucleic acid encoding the first light chain of the first antigen-binding portion is selected from the nucleotide sequence of SEQ ID NO: 85, and the nucleic acid encoding the first heavy chain of the first antigen-binding portion is selected from the nucleotide sequence of SEQ ID NO: 87, the nucleic acid encoding the second light chain of the second antigen-binding portion is selected from the nucleotide sequence of SEQ ID NO: 67, and the nucleic acid encoding the second heavy chain of the second antigen-binding portion is selected from the nucleotide sequence of SEQ ID NO: 69.

In some preferred embodiments, the first antigen-binding portion of the bispecific antibody binds to the GPC3 antigen, the second antigen binds to the CD3 antigen, the nucleic acid encoding the first light chain of the first antigen-binding portion is selected from the nucleotide sequence of SEQ ID NO: 89, and the nucleic acid encoding the first heavy chain of the first antigen-binding portion is selected from the nucleotide sequence of SEQ ID NO: 91, the nucleic acid encoding the second light chain of the second antigen-binding portion is selected from the nucleotide sequence of SEQ ID NO: 67, and the nucleic acid encoding the second heavy chain of the second antigen-binding portion is selected from the nucleotide sequence of SEQ ID NO: 69. In some preferred embodiments, the nucleic acid encoding the first light chain of the first antigen-binding portion is selected from the nucleotide sequence of SEQ ID NO: 93, and the nucleic acid encoding the first heavy chain of the first antigen-binding portion is selected from the nucleotide sequence of SEQ ID NO: 95, the nucleic acid encoding the second light chain of the second antigen-binding portion is selected from the nucleotide sequence of SEQ ID NO: 67, and the nucleic acid encoding the second heavy chain of the second antigen-binding portion is selected from the nucleotide sequence of SEQ ID NO: 69.

In one aspect, the present disclosure provides a vector comprising the nucleic acid described in the above.

In one aspect, the present disclosure provides a cell comprising the nucleic acid or vector described in the above.

In one aspect, the present disclosure provides a composition comprising the bispecific antibody or antigen-binding portion thereof, the nucleic acid, the vector and/or the cell described in the above.

In one aspect, the present disclosure provides an antibody-drug conjugate comprising the bispecific antibody or antigen-binding portions thereof covalently attached to a therapeutic moiety described in the above.

In one embodiment, the therapeutic moiety is selected from a cytotoxic moiety, a chemotherapeutic agent, a cytokine, an immunosuppressant, an immunostimulant, a lytic peptide, or a radioisotope; The antibody of the present disclosure is used as a therapeutic or diagnostic tool in diseases in which various tumor antigens are adversely expressed or found.

In one embodiment of the diseases associated with a tumor antigen, the expression of the tumor antigen in cells of the diseased tissue or organ is increased compared to the state in a healthy tissue or organ. An increase means an increase of at least 10%, in particular at least 20%, at least 50%, at least 100%, at least 200%, at least 500%, at least 1000%, at least 10000% or even more. In one embodiment, the expression is found only in diseased tissues, whereas the expression in corresponding healthy tissues is suppressed. According to the present disclosure, the diseases associated with tumor antigens include tumors.

In some embodiments, the disease associated with a tumor antigen is a CD20-related disease. In some preferred embodiments, the CD20-related disease comprises a B-cell disease, for example, a B cell proliferative disorder, in particular a CD20-positive B-cell disorder; preferably, the disease is selected from non-Hodgkin's lymphoma (NHL), acute lymphocytic leukemia (ALL), chronic lymphocytic leukemia (CLL), diffuse large B-cell lymphoma (DLBCL), follicular lymphoma (FL), mantle cell lymphoma (MCL), marginal zone lymphoma (MZL), and multiple myeloma (MM) and Hodgkin's lymphoma (HL).

In some embodiments, the tumor antigen-related disease is a BCMA-related disease; preferably, the BCMA-related disease includes B-cell disease; preferably, the disease is a cancer; more preferably, the cancer is a B-cell related cancer selected from multiple myeloma, malignant plasmacytoma, hodgkin's lymphoma, nodular lymphocyte-predominant Hodgkin's lymphoma, Kahler's disease and myeloid leukemia, plasma cell leukemia, plasmacytoma, B-cell prolymphocytic leukemia, hairy cell leukemia, B-cell non-Hodgkin's lymphoma (NHL), acute myelogenous leukemia (AML), chronic lymphocytic leukemia (CLL), acute lymphocytic leukemia (ALL), chronic myelogenous leukemia (CML), follicular lymphoma, burkitt lymphoma, marginal zone lymphoma, mantle cell lymphoma, large cell lymphoma, precursor B-lymphocyte lymphoma, myeloid leukemia, waldenstrom's macroglobulinemia, diffuse large B cell lymphoma, follicular lymphoma, marginal zone lymphoma, mucosa-related lymphoid tissue lymphoma, small cell lymphocytic lymphoma, mantle cell lymphoma, burkitt lymphoma, primary mediastinal (thymic) large B cell lymphoma, lymphoplasmacytic lymphoma, waldenstrom's macroglobulinemia, lymph node marginal zone B cell lymphoma, splenic marginal zone lymphoma, intravascular large B-cell lymphoma, primary effusion lymphoma, lymphomatoid granulomatosis, large B-cell lymphoma rich in T-cells/histiocytes, primary central nervous system lymphoma, primary cutaneous diffuse large B-cell lymphoma (leg type), elderly EBV-positive diffuse large B-cell lymphoma, inflammation-related diffuse large B-cell lymphoma, intravascular large B-cell lymphoma, ALK-positive large B-cell lymphoma, plasmablast-cell lymphoma, large B-cell lymphoma arising in HHV8-related multicenter Castleman's disease, unclassified B-cell lymphoma with intermediate features between diffuse large B-cell lymphoma and Burkitt's lymphoma, unclassified B-cell lymphoma with intermediate features between diffuse large B-cell lymphoma and classic Hodgkin's lymphoma, and other B-cell-related lymphomas; more preferably, the B-cell disease is a B-cell disorder; preferably, the plasma cell disorder is selected from: multiple myeloma, plasmacytoma, plasma cell leukemia, macroglobulinemia, amyloidosis, waldenstrom's macroglobulinemia, solitary plasmacytoma of the bone, extramedullary plasmacytoma, osteosclerotic myeloma, heavy chain disease, monoclonal gammopathy of unclear significance, and multiple myeloma of stasis type; preferably, the disease is an autoimmune disease such as systemic lupus erythematosus or rheumatoid arthritis.

In some embodiments, the therapeutic agent comprises an antibody that specifically binds to an activated T-cell antigen.

In one embodiment, the therapeutic agent comprises an antibody that specifically binds CD3, particularly CD3 epsilon.

A method of treating diseases and conditions by using bispecific antibodies of the present disclosure include the steps of: administering to the mammal a therapeutically effective amount of the antibody or antigen-binding fragment thereof or the nucleic acid molecule or vector or cell or pharmaceutical composition according to any of the preceding aspects.

In some embodiments, the disclosure provides a method of treating or preventing a cancer disease comprising administering to a patient an antibody capable of binding to GPC3, wherein the antibody is administered to provide a serum level of at least 40 g/ml. In various embodiments, the antibody is administered to provide a serum level of at least 50 gg/ml, at least 150 g/ml, at least 300 g/ml, at least 400 g/ml, or at least 500 gg/ml. In various embodiments, the antibody is administered to provide a serum level of no more than 800 gg/ml, 700 g/ml, 600 g/ml, 550 g/ml, or 500 g/ml. In one embodiment, the serum level provided is from 40 µg/ml to 700 g/ml, preferably from 40 g/ml to 600 gg/ml, preferably from 50 g/ml to 500 gg/ml, such as from 150 g/ml to 500 µg/ml or from 300 µg/ml to 500 g/ml. The term "serum level" as used in the present description means the concentration of the discussed substance in serum. In one embodiment, serum levels are provided for at least 7 days or at least 14 days. In one embodiment, the method comprises administering a dose of antibody of at least 300 mg/m$^2$, for example, at least 600 mg/m$^2$, and preferably at most 1500 mg/m$^2$, at most 1200 mg/m$^2$ or at most 1000 mg/m$^2$.

In some embodiments, the disclosure provides a method of treating or preventing a cancer disease comprising administering to a patient an antibody capable of binding to GPC3, wherein the antibody is administered at a dose of at least 300 mg/m$^2$, such as at least 600 mg/m$^2$, and preferably at most 1500 mg/m$^2$, at most 1200 mg/m$^2$, or at most 1000 mg/m$^2$.

In some embodiments, the disclosure provides a method of treating or preventing a cancer disease comprising administering to a patient an antibody capable of binding to GPC3, wherein at least 50%, preferably 60%, 70%, 80% or 90% of the cancer cells of the patient are positive for GPC3, and/or at least 40%, preferably 50% or 60% of the cancer cells of the patient are positive for surface expression of GPC3. In this aspect, the present disclosure also provides a method of treating or preventing a cancer disease, the method comprising: a. identifying patients showing at least 50%, preferably 60%, 70%, 80% or 90% of GPC3-positive cancer cells and/or at least 40%, preferably 50% or 60% of cancer cells that are positive for surface expression of GPC3; and b. administering to the patient an antibody capable of binding GPC3. In one embodiment, at least 95% or at least 98% of the cancer cells of the patient are GPC3-positive. In one embodiment, at least 70%, at least 80%, or at least 90% of the cancer cells of the patient are positive for surface expression of GPC3.

In one embodiment of the methods of any of the aspects herein, the therapeutic outcome of the cancer disease is to achieve stable disease conditions. In one embodiment, stable disease condition is achieved for at least 2 months, at least 3 months, or at least 6 months.

In some embodiments, the present disclosure provides methods of achieving stable disease condition in a cancer patient comprising administering to the patient an antibody capable of binding GPC3. In one embodiment, stable disease condition is achieved for at least 2 months, at least 3 months, or at least 6 months.

In one embodiment of the methods of any aspect herein, the antibody is administered in a single dose or multiple doses.

In some embodiments, the disclosure provides a method of treating or preventing a cancer disease comprising administering to a patient an antibody capable of binding to GPC3, wherein the antibody is administered in multiple doses.

If the antibody is administered in multiple doses according to the present disclosure, the antibody is preferably administered in at least 3 doses, at least 4 doses, at least 5 doses, at least 6 doses, at least 7 doses, at least 8 doses, at least 9 doses, or at least 10 doses and preferably at most 30 doses, 25 doses, 20 doses, 15 doses, or 10 doses. Preferably, the dose of antibody is administered at intervals of at least 7 days, at least 10 days, at least 14 days, or at least 20 days. The dose of antibody is preferably administered at intervals of from 7 to 30 days, from 10 to 20 days and preferably about 14 days.

In one embodiment, the antibody is administered so as to provide a serum level of at least 40 gg/ml. In various embodiments, the antibody is administered to provide a serum level of at least 50 gg/ml, at least 150 gg/ml, at least 300 gg/ml, at least 400 gg/ml, or at least 500 gg/ml. In various embodiments, the antibody is administered to provide a serum level of no more than 800 gg/ml, 700 gg/ml, 600 gg/ml, 550 gg/ml, or 500 gg/ml. In one embodiment, the serum level provided is from 40 gg/ml to 700 gg/ml, preferably from 40 μg/ml to 600 gg/ml, preferably from 50 μg/ml to 500 gg/ml, such as from 150 μg/ml to 500 gg/ml or from 300 gg/ml to 500 gg/ml. In one embodiment, serum levels are provided for at least 7 days or at least 14 days. In one embodiment, the method comprises administering a dose of at least 300 mg/m², such as at least 600 mg/m² and preferably at most 1500 mg/m², at most 1200 mg/m² or at most 1000 mg/m² of the antibody.

Use of the antibody or antigen-binding fragment thereof or the nucleic acid molecule or the vector or the cell or the pharmaceutical composition according to any of the preceding aspects in the manufacture of a medicament for the treatment of a GPC3-related disease in a mammal.

According to any of the preceding aspects, optionally, the antibody is conjugated to other drugs, such as a labeled or cytotoxic conjugate.

In one aspect, the disclosure also includes kits, e.g. kits comprising the antibodies, fragments thereof, homologues, derivatives thereof, nucleic acids, vectors, cells, compositions, etc. of the disclosure, e.g. a labeled or cytotoxic conjugate, as well as instructions for use of the antibody, a conjugate that kills a particular type of cell, etc. The instructions can include directions for using the antibody, conjugate, etc. in vitro, in vivo, or ex vivo. The antibody may be in liquid form or in solid form, usually lyophilized. The kit may contain other suitable reagents, such as buffers, reconstitution solutions and other necessary components for the intended uses. Combinations of reagents packaged in predetermined amounts with instructions for their use, e.g. for therapeutic use or for conducting diagnostic assays, are contemplated. When the antibody is labeled, e.g. with an enzyme, then the kit can include a substrate and cofactors required for the enzyme (e.g. a substrate precursor providing a detectable chromophore or fluorophore). In addition, other additives such as stabilizers, buffers (e.g. blocking buffers or lysis buffers), and the like may also be included. The relative amounts of the various reagents can be varied to provide a concentrate of a reagent solution, which provides user flexibility, space savings, reagent savings, etc. These reagents may also be provided in dry powder form, usually in lyophilized form, including excipients which, when dissolved, provide a reagent solution having the appropriate concentration.

Use of the antibody or functional fragment thereof or the nucleic acid molecule or the vector or the cell or the pharmaceutical composition or the kit according to any of the preceding aspects for the preparation of an agent for inhibiting GPC3 binding.

In addition, the antibodies of the present disclosure can be used in immunoassays, purification methods, and other methods using immunoglobulins or fragments thereof. Such uses are well known in the art.

Accordingly, the present disclosure also provides compositions comprising the anti-GPC3 antibodies of the present disclosure, or fragments thereof, conveniently combined with a pharmaceutically acceptable carrier, diluent or excipient, as is conventional in the art.

As used in this disclosure, the term "pharmaceutical composition" refers to formulations of various preparations. Formulations containing therapeutically effective amounts of multivalent antibodies are in sterile liquid solution, liquid suspension, or lyophilized form, optionally containing stabilizers or excipients.

The antibodies of the present disclosure can be used as a composition administered alone, or can be used in combination with other active agents.

In some embodiments, the humanized antibodies of the disclosure are conjugated to a therapeutic moiety (i.e. a drug). The therapeutic moiety can be, for example, a cytotoxin, a chemotherapeutic agent, a cytokine, an immunosuppressant, an immunostimulant, a lytic peptide, or a radioisotope.

Such conjugates are referred to herein as "antibody-drug conjugates" or "ADC".

In some embodiments, the antibody is conjugated to a cytotoxic moiety. The cytotoxic moiety may for example be selected from: paclitaxel; cytochalasin B; gramicidin D; ethidium bromide; emetine; mitomycin; etoposide; teniposide; vincristine; vinblastine; colchicine; doxorubicin; daunorubicin; dihydroxy anthracenedione; tubulin inhibitors such as maytansine or analogs or derivatives thereof; antimitotic agents such as monomethyl auristatin E or F or analogues or derivatives thereof; hareotoxin 10 or 15 or an analogue thereof; irinotecan or an analog thereof; mitoxantrone; mithramycin; actinomycin D; 1-dehydrotestosterone; glucocorticoids; procaine; tetracaine; lidocaine; propranolol; puromycin; calicheamicin or an analogue or derivative thereof; antimetabolites such as methotrexate, 6 mercaptopurine, 6 thioguanine, cytarabine, fludarabine, 5 fluorouracil, decadiazine, hydroxyurea, asparaginase, gemcitabine or cladribine; alkylating agents such as mechlorethamine, thiopurine, chlorambucil, melphalan, BSNU, CCNU, cyclophosphamide, busulfan, dibromomannitol, streptozotocin, DTIC, procarbazine, mitomycin C; platinum derivatives such as cisplatin or carboplatin; duocarmycin A, duocarmycin SA, rapamycin (CC-1065) or analogs or derivatives thereof; antibiotics such as actinomycin, bleomycin, daunorubicin, doxorubicin, idarubicin, mithramycin, mitomycin, mitoxantrone, plicomycin, AMC; pyrrolo [2, 1-c][1, 4]-benzodiazepine (PDB); diphtheria toxins and related molecules such as diphtheria A chain and active fragments and hybrid molecules thereof, ricin toxins such as ricin A or deglycosylated ricin A chain toxins, cholera toxins, shiga-like toxins such as SLT I, SLT II, SLT IIV, LT toxins, C3 toxins, shiga toxins, pertussis toxins, tetanus toxins, soybean Bowman-Birk protease inhibitors, *pseudomonas* exotoxin, arolin, saporin, modeccin, gelsolin, abrin A chain, modeccin A chain, a-sarcin, *Aleurites fordii* proteins, caryophyllin proteins, pokeweed proteins such as PAPI, PAPII and PAP-S, *Momordica charantia* inhibitors, curcin, crotin, *Sapaonaria officinalis* inhibitors, gelonin, mitomycin, restrictocin, phenomycin and enomycin toxins;

RNase; DNase I, staphylococcal endotoxin A; pokeweed antiviral protein; diphtheria toxin and *pseudomonas* endotoxin.

In some embodiments, the antibody is conjugated to auristatin or a peptide analog, derivative or prodrug thereof. It has been shown that auristatin interferes with microtubule dynamics, GTP hydrolysis and nuclear and cell division and has anti-cancer and anti-fungal activity. For example, auristatin E can be reacted with p-acetylbenzoic acid or benzoylpentanoic acid to produce AEB and AEVB, respectively. Other typical auristatin derivatives include AFP, MMAF (monomethyl auristatin F) and MMAE (monomethyl auristatin E). Suitable auristatins and analogs, derivatives, and prodrugs of auristatins, as well as suitable linkers for conjugating auristatins to Ab, are described, for example, in U.S. Pat. Nos. 5,635,483, 5,780,588, and 6,214,345, and International Patent Application Publication Nos. WO02088172, WO2004010957, WO2005081711, WO2005084390, WO2006132670, WO03026577, WO200700860, WO207011968, and WO205082023.

In some embodiments, the antibody is conjugated to a pyrrolo [2, 1-c][1, 4]-benzodiazepine (PDB) or a peptide analog, derivative or prodrug thereof. Suitable PDB and PDB derivatives and related art are described, for example, in Hartley J. A. et al. Cancer Res 2010; 70(17): 6849-6858; antonow D. et al. Cancer J 2008; 14(3): 154-169; howard P. W. et al. Bioorg Med Chem Lett 2009; 19: 6463-6466 and Sagnou et al. Bioorg MedChem Lett 2000; 10(18): 2083-2086.

In some embodiments, the antibody is conjugated to a cytotoxic moiety selected from: anthracyclines, maytansinoids, calicheamicins, duocarmycins, rapamycin (CC-1065), dolastatin 10, dolastatin 15, irinotecan, monomethyl auristatin E, monomethyl auristatin F, PDB, or any analog, derivative or prodrug thereof.

In some embodiments, the antibody is conjugated to an anthracycline or an analog, derivative or prodrug thereof. In some embodiments, the antibody is conjugated to maytansine or an analog, derivative or prodrug thereof. In some embodiments, the antibody is conjugated to a calicheamicin or an analog, derivative or prodrug thereof. In some embodiments, the antibody is conjugated to a duocarmycin or an analog, derivative or prodrug thereof. In some embodiments, the antibody is conjugated to rapamycin (CC-1065) or an analog, derivative or prodrug thereof. In some embodiments, the antibody is conjugated to haremomycin 10 or an analog, derivative or prodrug thereof. In some embodiments, the antibody is conjugated to haremomycin 15 or an analog, derivative or prodrug thereof. In some embodiments, the antibody is conjugated to monomethyl auristatin E or an analog, derivative or prodrug thereof. In some embodiments, the antibody is conjugated to monomethyl auristatin F or an analog, derivative or prodrug thereof. In some embodiments, the antibody is conjugated to a pyrrolo [2, 1-c][1, 4]-benzodiazepine or an analog, derivative or prodrug thereof. In some embodiments, the antibody is conjugated to irinotecan or an analog, derivative or prodrug thereof.

In some embodiments, the antibody is conjugated to a cytokine (e.g. IL-2, IL-4, IL-6, IL-7, IL-10, IL-12, IL-13, IL-15, IL-18, IL-23, IL-24, IL-27, IL-28a, IL-28b, IL-29, KGF, IFNa, IFN3, IFNy, GM-CSF, CD40L, Flt3 ligand, stem cell factor, ancestine, and TNFa).

In some embodiments, the antibody is conjugated to a radioisotope or a chelate containing a radioisotope. For example, the antibody can be conjugated to a chelator linker (e.g. DOTA, DTPA, or tixistan) that allows the antibody to complex with the radioisotope. The antibody may also or alternatively comprise or be conjugated to one or more radiolabeled amino acids or other radiolabeled molecules. Non-limiting examples of radioisotopes include $^3$H, $^{14}$C, $^{15}$N, $^{35}$S, $^{90}$Y $^{99}$Tc, $^{125}$I, $^{131}$I, $^{186}$Re, $^{213}$Bi, $^{225}$Ac, and $^{227}$Th. For therapeutic purposes, radioisotopes emitting D or a particle radiation may be used, such as $^{131}$I, $^{90}$Y, $^{211}$At, $^{212}$Bi, $^{67}$Cu, $^{186}$Re, $^{188}$Re and $^{212}$Pb.

Techniques for conjugating molecules to antibodies are well known in the art. Typically, the nucleic acid molecule is covalently linked to a lysine or cysteine on the antibody via an N-hydroxysuccinimide ester or maleimide functional group, respectively. Conjugation methods using engineered cysteines or incorporating unnatural amino acids have been reported to improve homogeneity of conjugates. In particular, one skilled in the art may also contemplate generating reactive endogenous glutamine-engineered Fc-containing polypeptides with acyl donor glutamine-containing tags (e.g. Gin peptide-containing tags or Q-tags) or by polypeptide engineering (e.g. by amino acid deletions, insertions, substitutions, or mutations in the polypeptide). Transglutaminase can then be covalently cross-linked with an amine donor agent (e.g. a small molecule comprising or linked to a reactive amine) to form a stable and homogeneous population of engineered Fc-containing polypeptide conjugates, wherein the amine donor agent is site-specifically conjugated to the Fc-containing polypeptide through an acyl-donor glutamine-containing tag or an accessible/exposed/reactive endogenous glutamine (WO2012059882).

It will be appreciated that the therapeutic agents according to the foregoing embodiments will be administered with suitable pharmaceutically acceptable carriers, excipients, and other agents incorporated into the formulation to provide improved transfer, delivery, tolerability, etc. These formulations include, for example, powders, pastes, ointments, gels, waxes, oils, lipids, lipid-containing (cationic or anionic) carriers (e.g. Lipofectin™), DNA conjugates, anhydrous syrups, oil-in-water and water-in-oil emulsions, emulsion polyethylene glycols (polyethylene glycols of various molecular weights), semi-solid gels, and semi-solid mixtures containing polyethylene glycol. Any of the foregoing mixtures may be suitable for treatment or therapy according to the present disclosure, provided that the active ingredients in the formulation are not inactivated by the formulation and that the formulation is physiologically compatible and tolerates the route of administration.

In one embodiment, the antibodies described above can be used as therapeutic agents. Such agents will generally be used to treat, alleviate and/or prevent a disease or pathology associated with abnormal tumor antigen expression, activity and/or signaling in a subject. A treatment regimen can be performed using standard methods by identifying a subject, e.g. a human patient, having (or at risk of or developing) a disease or disorder associated with aberrant tumor antigen expression, activity, and/or signaling, e.g. a tumor antigen-related disorder. An antibody preparation, preferably one with high specificity and affinity for its target antigen, is administered to a subject and will generally have an effect due to its binding to the target. The administered antibody can eliminate or inhibit or interfere with the expression, activity and/or signaling function of the target (e.g. tumor antigen). The administered antibody can eliminate or inhibit or interfere with the binding of the target (e.g. tumor antigen) to its endogenous ligand to which it naturally binds. For example, an antibody binds to a target and modulates, blocks, inhibits, reduces, antagonizes, neutralizes, and/or otherwise interferes with tumor antigen expression, activity, and/or signaling.

In some embodiments, to treat a disease or disorder associated with aberrant tumor antigen expression, antibodies having heavy and light chain CDR can be administered to a subject.

In another embodiment, antibodies directed against tumor antigens can be used in methods known in the art to correlate tumor antigen localization and/or quantitation (e.g. for determining tumor antigen and/or levels of tumor antigen in an appropriate physiological sample, for diagnostic methods, for protein imaging, etc.). In a given embodiment, an antibody having specificity for a tumor antigen or a derivative, fragment, analog and comprising an antigen-binding domain derived from the antigen, is used as a pharmaceutically active compound (hereinafter referred to as "therapeutic agent").

In another embodiment, antibodies specific for tumor antigens can be used to isolate tumor antigen polypeptides by standard techniques such as immunoaffinity, chromatography or immunoprecipitation. Antibodies (or fragments thereof) directed against a tumor antigen protein can be used to detect the protein in a biological sample. In some embodiments, tumor antigens can be detected in a biological sample as part of a clinical testing procedure, for example, to determine the efficacy of a given treatment regimen. Detection may be facilitated by conjugating (i.e. physically linking) the antibody to a detectable substance. Examples of detectable substances include various enzymes, prosthetic groups, fluorescent materials, luminescent materials, bioluminescent materials and radioactive materials. Examples of suitable enzymes include horseradish peroxidase, alkaline phosphatase, D-galactosidase or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazine aminofluorescein, dansyl chloride, or phycoerythrin; one example of a luminescent material includes luminol; examples of bioluminescent materials include luciferase, luciferin and aequorin, and examples of suitable radioactive materials include $^{125}$I, $^{131}$I, $^{3}$S or $^{3}$H. In another embodiment, antibodies according to the present disclosure can be used as reagents for detecting the presence of tumor antigens or protein fragments thereof in a sample. In some embodiments, the antibody comprises a detectable label. The antibody is a polyclonal antibody, or more preferably a monoclonal antibody. Whole antibodies or fragments thereof (e.g. Fab, scFv or F(ab')$_2$) are used. The term "labeling" in reference to an antibody is intended to encompass direct labeling of the antibody by conjugating (i.e. physically linking) a detectable substance to the antibody, as well as indirect labeling of the antibody by reaction with another reagent that is directly labeled. Examples of indirect labeling include detection of the first antibody using a fluorescently labeled second antibody, and end-labeling of the antibody with biotin to enable detection with fluorescently labeled streptavidin. The term "biological sample" is intended to include tissues, cells and biological fluids isolated from a subject, as well as tissues, cells and fluids present in a subject. Thus, the term "biological sample" as used includes blood and fractions or components of blood, including serum, plasma, or lymph. In other words, the detection method of the foregoing embodiments can be used to detect the analyte mRNA, protein or genomic DNA in a biological sample in vitro as well as in vivo. For example, analyte mRNA in vitro detection techniques include Northern hybridization and in situ hybridization. In vitro techniques for detection of analyte proteins include enzyme-linked immunosorbent assays (ELISA), Western blots, immunoprecipitations, and immunofluorescence. Analyte genomic DNA in vitro detection techniques include Southern hybridization. Procedures for performing immunoassays are described, for example, in "ELISA: Theory and Practice: Methods in Molecular Biology, vol. 42, J. R. Crowther (ed.) Human Press, totowa, N. J. 1995. In addition, in vivo techniques for detection of an analyte protein include introducing into a subject a labeled anti-analyte protein antibody. For example, an antibody can be labeled with a radiolabel, and the presence and location of the radiolabel in the subject can then be detected by standard imaging techniques.

The antibodies described herein and derivatives, fragments, analogs, and homologs thereof can be incorporated into pharmaceutical compositions suitable for administration. The principles and considerations involved in preparing such compositions and guidelines for selecting components are well known in the art.

Such compositions typically comprise the antibody and a pharmaceutically acceptable carrier.

When antibody fragments are used, minimal inhibitory fragments that specifically bind to the target protein binding domain may be preferred. For example, based on the variable region sequence of an antibody, peptide molecules can be designed that retain the ability to bind to a target protein sequence. Such peptides can be chemically synthesized and/or produced by recombinant DNA techniques (see, e.g. Marasco et al. Proc. Natl. Acad. Sci. USA, 90: 7889-7893 (1993)).

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable pharmaceutically acceptable carriers are described in the latest edition of Remington's Pharmaceutical Sciences, a standard reference text in the art, which is incorporated herein by reference. Preferred examples of such carriers or diluents include, but are not limited to, water, saline, ringer's solution, dextrose solution, and 5% human serum albumin. Liposomes and non-aqueous vehicles such as fixed oils can also be used. The use of such media and agents for pharmaceutically active substances is well known in the art. Except insofar as any conventional media or agent is incompatible with the antibody, its use in the compositions is contemplated.

The pharmaceutical compositions of the foregoing embodiments are formulated to be compatible with their intended route of administration. Examples of routes of administration include parenteral, e.g. intravenous, intradermal, subcutaneous, oral (e.g. inhalation), transdermal (i.e. topical), transmucosal, and rectal administration. Solutions or suspensions for parenteral, intradermal or subcutaneous administration may include the following components: sterile diluents for injection such as water, saline solutions, fixed oils, polyethylene glycols, glycerol, propylene glycol or other synthetic solvents; antibacterial agents such as benzyl alcohol or methyl paraben; antioxidants such as ascorbic acid or sodium bisulfite; chelating agents such as Ethylene Diamine Tetraacetic Acid (EDTA); buffers, such as acetates, citrates or phosphates, and agents to adjust the osmotic pressure, such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable pharmaceutically acceptable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, such as parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the antibody in the required amount in an appropriate solvent with one or a combination of ingredients enumerated above, as required, followed by filtered sterilization. Generally, dispersions are prepared by incorporating the antibody into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution of such ingredients.

For administration by inhalation, the compounds are delivered in the form of an aerosol spray from pressurized container or dispenser that contains a suitable propellant, such as a gas, for example carbon dioxide, or a nebulizer.

Systemic administration may also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, one or more of the antibodies can be formulated into ointments, salves, gels, or creams as generally known in the art.

The compounds may also be prepared in the form of suppositories (e.g. with conventional suppository bases such as cocoa butter or other glycerides) or retention enemas for rectal delivery.

In one embodiment, the antibody may be prepared with carriers that prevent rapid elimination from the body, such as sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparing such formulations will be apparent to those skilled in the art.

It is especially advantageous to formulate parenteral compositions in dosage unit form for ease of administration and uniformity of dosage. Dosage unit form, as used herein, refers to physically discrete units suited as unitary dosages for the subject to be treated; each unit contains a predetermined quantity of one or more antibodies calculated to produce the desired therapeutic effect in association with the required pharmaceutical carrier. The specification for the dosage unit forms of the foregoing embodiments are dictated by and directly dependent on: the unique characteristics of antibodies and the specific therapeutic effects to be achieved, and the limitations inherent in the art of formulating such antibodies for treating individuals.

The pharmaceutical compositions can be presented in a container, pack, or dispenser together with instructions for administration.

The formulations described herein may also contain more than one antibody depending on the particular situation to be treated, preferably those which have complementary activities but do not adversely affect each other. Alternatively or additionally, the composition may, for example, comprise an agent that enhances its function, such as a cytotoxic agent, a cytokine, a chemotherapeutic agent, or a growth inhibitor. Such molecules are suitably present in combination in amounts effective for the intended purpose. For example, they may be present in combination in a kit or in combination for use.

In one embodiment, one or more antibodies can be administered in combination therapy, i.e. in combination with other agents such as therapeutic agents that can be used to treat pathological conditions or disorders, such as various forms of cancer, autoimmune disorders, and inflammatory diseases. The term "in combination" means herein that the agents are administered substantially synchronously, simultaneously or sequentially. If administered sequentially, the first of the two compounds is still preferably detected at an effective concentration at the treatment site when the second compound is initially administered. In one instance, a "combination" can also include both an antibody of the present disclosure and another therapeutic agent in a kit.

For example, combination therapy can comprise coformulation and/or coadministration of one or more antibodies described herein with one or more additional therapeutic agents (e.g. one or more cytokine and growth factor inhibitors, immunosuppressants, anti-inflammatory agents, metabolic inhibitors, enzyme inhibitors, and/or cytotoxic or cytostatic agents, as described in more detail below). Such combination therapy may advantageously utilize lower dosages of the administered therapeutic agents, thus avoiding possible toxicities or complications associated with each monotherapy.

In one embodiment, the treatment regimen is effective to reduce cytokine release associated with administration of the T-cell activating therapeutic agent in the subject as compared to a corresponding treatment regimen without administration of an anti-tumor antigen antibody.

For purposes of clarity and conciseness, features are described herein as part of the same or separate embodiments. However, it will be understood that the scope of the disclosure may include some embodiments having a combination of all or some of the features described.

FIG. 1 shows the structure of a novel primary antigen× CD3 κλ bispecific antibody.

The experiments of the present disclosure demonstrate that in the case of free combination, the λ light chain of the humanized CD3 arm tends to pair with the homologous heavy chain at a lower pairing ratio with the heterologous heavy chain; similarly, the κ light chain of the humanized antigen arm also tends to pair with the homologous heavy chain, with a very low pairing ratio with the humanized CD3 heavy chain; at the same time, the introduction of complementary charge variants in the Fv further reduces the potential for light chain mismatches. The Fc portion of the anti-CD20×CD3 κλ bispecific antibody adopts the human IgG4 knob-into-hole structure, and stabilizes the hinge region and reduces interaction with Fcγ receptors as well as C1q by mutating $Ser_{228}Pro$, $Leu_{235}Glu$ and Pro329Ala.

EXAMPLES

Example 1: Optimization of Anti-CD3 Antibody and Activation of T-Cells

1. Synthesis of Recombinant Proteins

The nucleotide sequences of the extracellular regions of human CD3γ (UniProt P09693, gln23-Asn116) and CD3ε (UniProt P07766, gln23-Asp126) were synthesized, fused with human IgG Fc hole or Fc knob respectively at the C-terminus, and expressed to form a human CD3εγ-Fc heterodimer (the amino acid sequence of human CD3γ IgG Fc (hole) is shown in SEQ ID NO. 1, and the amino acid sequence of human CD3ε IgG Fc (knob) is shown in SEQ ID NO. 2); cynomolgus monkey CD3γ (UniProt Q 95LI7, gln23-Asn110) and CD3ε (UniProt Q 95LI5, gln22-Asp117) were also synthesized, C-terminally fused to Cynomolgus monkey IgG Fc hole or Fc knob, respectively, and expressed to form a Cynomolgus monkey CD3εγ-Fc heterodimer (the amino acid sequence of Cynomolgus monkey CD3γ IgG Fc (hole) is shown in SEQ ID NO. 3, and the amino acid sequence of Cynomolgus monkey CD3γ IgG Fc (knob) is shown in SEQ ID NO. 4). Recombinant plasmids expressing CD3γ-Fc and CD3ε-Fc were mixed with 3 mg/mL PEI (Polysciences, #24765-2) and co-transfected into HEK 293E cells (culture medium OPM-293 CD03 DPM). After 7 days at 37° C. in 120 rpm 5% $CO_2$, the supernatant of culture medium was collected and purified by Protein A affinity chromatography to obtain recombinant CD3εγ-Fc protein of human or cynomolgus monkeys.

2. Humanization of CD3 Antibody

Mouse hybridoma CD3 antibody (EMBO J. 1985.4 (2): 337-344; J. Immunol. 1986, 137(4): 1097-100; J. Exp. Med. 1991, 174: 319-326; J. Immunol. 1991, 147(9): 3047-52) recognizes the human and cynomolgus monkey CD3 receptor, the sequence of which is as follows. The amino acid sequence of the light chain of anti-CD3 murine monoclonal antibody_(SEQ ID NO. 96):

QAVVTQESALTTSPGETVTLTCRSTGAVTTSNYANWVQQKPDHLFTG

LIGGTNKRAPGVPARFSGSLIGDKAALTITGAQTEDEAIYFCALWYSN

LWVFGGGTKLTVL

The amino acid sequence of the heavy chain of anti-CD3 murine monoclonal antibody (SEQ ID NO. 97):

EVQLVESGGGLVQPKGSLKLSCAASGFTFNTYAMNWVRQAPGKGLEWV

ARIRSKYNNYATYYADSVKDRFTISRDDSQSILYLQMNNLKTEDTAMY

YCVRHGNFGNSYVSWFAYWGQGTLVTVSS

The anti-CD3 murine monoclonal antibody was humanized, the human germline gene IMGT_hVL7-43 with the highest homology was selected for light chain CDR transplantation, and human IGLJ3*02 was selected for FM4; human IMGT hVH3-73 was selected for heavy chain CDR grafting and human IGHJ4*01 for FM4. Different heavy and light chain variants were designed (Table 1).

TABLE 1

| Variable region sequences of humanized anti-CD3 antibodies | | | | | |
|---|---|---|---|---|---|
| | SEQ ID Nos. 5-23 | | | | |
| Light chain variable | LCVR | | LCDR1 | LCDR2 | LCDR3 |
| region of CD3 humanized antibody | Amino acid sequence | Nucleotide sequence | Amino acid sequence | Amino acid Sequence | Amino acid Sequence |
| hVL1 | 5 | 6 | 7 | 8 | 9 |
| hVL2 | 10 | 11 | 7 | 8 | 9 |
| hVL3 | 12 | 13 | 14 | 15 | 9 |
| hVL4 | 16 | 17 | 14 | 15 | 9 |
| hVL5 | 18 | 19 | 7 | 8 | 21 |
| hVL6 | 22 | 23 | 7 | 20 | 21 |
| | SEQ ID Nos. 24-53 | | | | |
| Heavy chain variable | HCVR | | HCDR1 | HCDR2 | HCDR3 |
| region of CD3 humanized antibody | Amino acid sequence | Nucleotide sequence | Amino acid Sequence | Amino acid Sequence | Amino acid Sequence |
| hVH1 | 24 | 25 | 26 | 27 | 28 |
| hVH2 | 29 | 30 | 31 | 27 | 28 |
| hVH3 | 32 | 33 | 31 | 27 | 34 |
| hVH4 | 35 | 36 | 31 | 27 | 37 |
| hVH5 | 38 | 39 | 31 | 27 | 40 |
| hVH6 | 41 | 42 | 31 | 27 | 43 |
| hVH7 | 44 | 45 | 46 | 47 | 28 |

TABLE 1-continued

| Variable region sequences of humanized anti-CD3 antibodies | | | | | |
|---|---|---|---|---|---|
| hVH8 | 48 | 49 | 26 | 27 | 28 |
| hVH9 | 50 | 51 | 26 | 27 | 28 |
| hVH10 | 52 | 53 | 26 | 27 | 28 |

The amino acid sequence of hVL1 is shown in SEQ ID NO. 5, nucleic acid encoding the same is shown in SEQ ID NO. 6, and LCDR1, LCDR2 and LCDR3 thereof are shown in SEQ ID NOs. 7 (RSSTGAVTTSNYAN), 8 (GGTNK-RAP) and 9 (ALWYSNLWV), respectively.

(SEQ ID NO: 5)
QAVVTQEPSLTVSPGGTVTLTCRSSTGAVTTSNYANWVQQKPGQAPRG

LIGGTNKRAPWTPARFSGSLLGGKAALTLSGAQPEDEAEYYCALWYSN

LWVFGGGTKLTVL

Nucleic Acid Sequence (SEQ ID NO: 6)
CAGGCTGTGGTCACACAAGAGCCTAGCCTGACAGTGTCTCCTGGCGGC

ACAGTGACCCTGACCTGTAGATCTTCTACAGGCGCCGTGACCACCAGC

AACTACGCTAATTGGGTGCAGCAGAAGCCCGGCCAGGCTCCTAGAGGA

CTGATCGGCGGAACAAACAAGAGAGCCCCTTGGACACCCGCCAGATTC

TCTGGATCTCTGCTCGGCGGAAAGGCCGCTCTGACACTTTCTGGTGCT

CAGCCTGAGGACGAGGCCGAGTACTATTGTGCCCTGTGGTACAGCAAC

CTGTGGGTGTTCGGCGGAGGCACCAAACTGACAGTTCTG

The amino acid sequence of hVL2 is shown in SEQ ID NO. 10, nucleic acid encoding the same is shown in SEQ ID NO. 11, and LCDR1, LCDR2 and LCDR3 thereof are shown in SEQ ID NOs. 7 (RSSTGAVTTSNYAN), 8 (GGTNKRAP) and 9 (ALWYSNLWV), respectively.

(SEQ ID NO: 10)
QAVVTQEPSLTVSPGGTVTLTCRSSTGAVTTSNYANWVQEKPGQAPRG

LIGGTNKRAPWTPARFSGSLLGGKAALTLSGAQPEDEAEYYCALWYSN

LWVFGGGTKLTVL

Nucleic Acid Sequence (SEQ ID NO: 11)
CAGGCTGTGGTCACACAAGAGCCTAGCCTGACAGTGTCTCCTGGCGGC

ACAGTGACCCTGACCTGTAGATCTTCTACAGGCGCCGTGACCACCAGC

AACTACGCTAATTGGGTGCAGgAGAAGCCCGGCCAGGCTCCTAGAGGA

CTGATCGGCGGAACAAACAAGAGAGCCCCTTGGACACCCGCCAGATTC

TCTGGATCTCTGCTCGGCGGAAAGGCCGCTCTGACACTTTCTGGTGCT

CAGCCTGAGGACGAGGCCGAGTACTATTGTGCCCTGTGGTACAGCAAC

CTGTGGGTGTTCGGCGGAGGCACCAAACTGACAGTTCTG

The amino acid sequence of hVL3 is shown in SEQ ID NO. 12, its encoding nucleic acid is shown in SEQ ID NO. 13, and its LCDR1, LCDR2 and LCDR3 are shown in SEQ ID NOs. 14 (ESSDGAVTTSNYAN), 15 (GGTNKEAP) and 9 (ALWYSNLWV), respectively.

(SEQ ID NO. 12)
EAVVTQEPSLTVSPGGTVTLTCESSDGAVTTSNYANWVQEKPGQAPRG

LIGGTNKEAPWTPARFSGSLLGGKAALTLSGAQPEDEAEYYCALWYSN

LWVFGGGTKLTVL

Nucleic Acid Sequence (SEQ ID NO. 13)
GAGGCTGTGGTCACACAAGAGCCTAGCCTGACAGTGTCTCCTGGCGGC

ACAGTGACCCTGACCTGTGAGTCTTCTGACGGCGCCGTGACCACCAGC

AACTACGCTAATTGGGTGCAGGAGAAGCCCGGCCAGGCTCCTAGAGGA

CTGATCGGCGGAACAAACAAGGAGGCCCCTTGGACACCCGCCAGATTC

TCTGGATCTCTGCTCGGCGGAAAGGCCGCTCTGACACTTTCTGGTGCT

CAGCCTGAGGACGAGGCCGAGTACTATTGTGCCCTGTGGTACAGCAAC

CTGTGGGTGTTCGGCGGAGGCACCAAACTGACAGTTCTG

The amino acid sequence of hVL4 is shown in SEQ ID NO. 16, nucleic acid encoding the same is shown in SEQ ID NO. 17, and LCDR1, LCDR2 and LCDR3 thereof are shown in SEQ ID NOs. 14 (ESSDGAVTTSNYAN), 15 (GGTNKEAP) and 9 (ALWYSNLWV), respectively.

(SEQ ID NO. 16)
QAVVTQEPSLTVSPGGTVTLTCESSDGAVTTSNYANWVQEKPGQAPRG

LIGGTNKEAPWTPARFSGSLLGGKAALTLSGAQPEDEAEYYCALWYSN

LWVFGGGTKLTVL

Nucleic Acid Sequence (SEQ ID NO. 17)
CAGGCTGTGGTCACACAAGAGCCTAGCCTGACAGTGTCTCCTGGCGGCA

CAGTGACCCTGACCTGTGAGTCTTCTGACGGCGCCGTGACCACCAGCAA

CTACGCTAATTGGGTGCAGGAGAAGCCCGGCCAGGCTCCTAGAGGACTG

ATCGGCGGAACAAACAAGGAGGCCCCTTGGACACCCGCCAGATTCTCTG

GATCTCTGCTCGGCGGAAAGGCCGCTCTGACACTTTCTGGTGCTCAGCC

TGAGGACGAGGCCGAGTACTATTGTGCCCTGTGGTACAGCAACCTGTGG

GTGTTCGGCGGAGGCACCAAACTGACAGTTCTG

The amino acid sequence of hVL5 is shown in SEQ ID NO. 18, nucleic acid encoding the same is shown in SEQ ID NO. 19, and LCDR1, LCDR2 and LCDR3 thereof are shown in SEQ ID NOs. 7 (RSSTGAVTTSNYAN), 8 (GGTNKRAP) and 21 (VLWYSNLWV), respectively.

(SEQ ID NO. 18)
QAVVTQEPSLTVSPGGTVTLTCRSSTGAVTTSNYANWVQEKPGQAPRGL

IGGTNKRAPWTPARFSGSLLGGKAALTITGAQAEDEAEYYCVLWYSNLW

VFGGGTKLTVL

Nucleic Acid Sequence (SEQ ID NO. 19)
CAGGCTGTGGTCACACAAGAGCCTAGCCTGACAGTGTCTCCTGGCGGCA

CAGTGACCCTGACCTGTAGATCTTCTACAGGCGCCGTGACCACCAGCAA

CTACGCTAATTGGGTGCAGgAGAAGCCCGGCCAGGCTCCTAGAGGACTG

ATCGGCGGAACAAACAAGAGAGCCCCTTGGACACCCGCCAGATTCTCTG

GATCTCTGCTCGGCGGAAAGGCCGCTCTGACAATCACTGGTGCTCAGGC

TGAGGACGAGGCCGAGTACTATTGTGTGCTGTGGTACAGCAACCTGTGG

GTGTTCGGCGGAGGCACCAAACTGACAGTTCTG

The amino acid sequence of hVL6 is shown in SEQ ID NO. 22, nucleic acid encoding the same is shown in SEQ ID NO. 23, and LCDR1, LCDR2 and LCDR3 thereof are shown in SEQ ID NOs. 7 (RSSTGAVTTSNYAN), 20 (YGTNKRAP) and 21 (VLWYSNLWV), respectively.

(SEQ ID NO. 22)
QAVVTQEPSLTVSPGGTVTLTCRSSTGAVTTSNYANWFQEKPGQAPRGL

IYGTNKRAPWTPARFSGSLLGGKAALTLSGAQAEDEAEYYCVLWYSNLW

VFGGGTKLTVL

Nucleic Acid Sequence (SEQ ID NO. 23)
CAGGCTGTGGTCACACAAGAGCCTAGCCTGACAGTGTCTCCTGGCGGCA

CAGTGACCCTGACCTGTAGATCTTCTACAGGCGCCGTGACCACCAGCAA

CTACGCTAATTGGTTCCAGGAGAAGCCCGGCCAGGCTCCTAGAGGACTG

ATCTACGGAACAAACAAGAGAGCCCCTTGGACACCCGCCAGATTCTCTG

GATCTCTGCTCGGCGGAAAGGCCGCTCTGACACTTTCTGGTGCTCAGGC

TGAGGACGAGGCCGAGTACTATTGTGTCCTGTGGTACAGCAACCTGTGG

GTGTTCGGCGGAGGCACCAAACTGACAGTTCTG

The amino acid sequence of hVH1 is shown in SEQ ID NO. 24, nucleic acid encoding the same is shown in SEQ ID NO. 25, and HCDR1, HCDR2 and HCDR3 thereof are shown in SEQ ID NOs. 26 (NTYAMN), 27 (IRSKYN-NYATYYADSVKD) and 28 (HGNFGNSYVSWFAY), respectively.

(SEQ ID NO. 24)
EVQLVESGGGLVQPGGSLRLSCAASGFTFNTYAMNWVRQAPGKGLEWVS

RIRSKYNNYATYYADSVKDRFTISRDDSKNTLYLQMNSLRAEDTAVYYC

VRHGNFGNSYVSWFAYWGQGTLVTVSS

Nucleic Acid Sequence (SEQ ID NO. 25)
GAGGTGCAGCTGGTTGAATCTGGCGGAGGACTGGTTCAGCCTGGCGGAT

CTCTGAGACTGTCTTGTGCCGCCAGCGGCTTCACCTTCAACACCTACGC

TATGAACTGGGTCCGACAGGCCCCTGGCAAAGGACTGGAATGGGTGTCC

AGAATCAGGTCCAAGTACAACAACTACGCCACCTACTACGCCGACAGCG

TGAAGGACAGATTCACCATCAGCAGGGACGACAGCAAGAACACCCTGTA

CCTGCAGATGAACAGCCTGAGAGCCGAGGACACCGCCGTGTACTACTGT

GTCAGACACGGCAACTTCGGCAACAGCTATGTGTCTTGGTTTGCCTACT

GGGGCCAGGGCACACTGGTCACAGTTAGCTCT

The amino acid sequence of hVH2 is shown in SEQ ID NO. 29, nucleic acid encoding the same is shown in SEQ ID NO. 30, and HCDR1, HCDR2 and HCDR3 thereof are shown in SEQ ID NOs. 31 (STYAMN), 27 (IRSKYN-NYATYYADSVKD) and 28 (HGNFGNSYVSWFAY), respectively.

(SEQ ID NO. 29)
EVQLVESGGGLVQPGGSLRLSCAASGFTFSTYAMNWVRKAPGKGLEWVS

RIRSKYNNYATYYADSVKDRFTISRDDSKNTLYLQMNSLRAEDTAVYYC

VRHGNFGNSYVSWFAYWGQGTLVTVSS

Nucleic Acid Sequence (SEQ ID NO. 30)
GAGGTGCAGCTGGTTGAATCTGGCGGAGGACTGGTTCAGCCTGGCGGAT CTCTGAGACTGTCTTGTGCCGCCAGCGGCTTCACCTTCtcCACCTACGC TATGAACTGGGTCCGAaagGCCCCTGGCAAAGGACTGGAATGGGTGTCC

AGAATCAGGTCCAAGTACAACAACTACGCCACCTACTACGCCGACAGCG

TGAAGGACAGATTCACCATCAGCAGGGACGACAGCAAGAACACCCTGTA

CCTGCAGATGAACAGCCTGAGAGCCGAGGACACCGCCGTGTACTACTGT

GTCAGACACGGCAACTTCGGCAACAGCTATGTGTCTTGGTTTGCCTACT

GGGGCCAGGGCACACTGGTCACAGTTAGCTCT

The amino acid sequence of hVH3 is shown in SEQ ID NO. 32, nucleic acid encoding the same is shown in SEQ ID NO. 33, and HCDR1, HCDR2 and HCDR3 thereof are shown in SEQ ID NOs. 31 (STYAMN), 27 (IRSKYN-NYATYYADSVKD) and 34 (HGNFGESYVSWFAY), respectively.

(SEQ ID NO. 32)
EVQLVESGGGLVQPGGSLRLSCAASGFTFSTYAMNWVRKAPGKGLEWVS

RIRSKYNNYATYYADSVKDRFTISRDDSKNTLYLQMNSLRAEDTAVYYC

VRHGNFGESYVSWFAYWGQGTLVTVSS

Nucleic Acid Sequence (SEQ ID NO. 33)
GAGGTGCAGCTGGTTGAATCTGGCGGAGGACTGGTTCAGCCTGGCGGAT

CTCTGAGACTGTCTTGTGCCGCCAGCGGCTTCACCTTCTCCACCTACGC

TATGAACTGGGTCCGAAAGGCCCCTGGCAAAGGACTGGAATGGGTGTCC

AGAATCAGGTCCAAGTACAACAACTACGCCACCTACTACGCCGACAGCG

TGAAGGACAGATTCACCATCAGCAGGGACGACAGCAAGAACACCCTGTA

CCTGCAGATGAACAGCCTGAGAGCCGAGGACACCGCCGTGTACTACTGT

GTCAGACACGGCAACTTCGGCGAGAGCTATGTGTCTTGGTTTGCCTACT

GGGGCCAGGGCACACTGGTCACAGTTAGCTCT

The amino acid sequence of hVH4 is shown in SEQ ID NO. 35, nucleic acid encoding the same is shown in SEQ ID NO. 36, and HCDR1, HCDR2 and HCDR3 thereof are shown in SEQ ID NOs. 31 (STYAMN), 27 (IRSKYN-NYATYYADSVKD) and 37 (HGNFGQSYVSWFAY), respectively.

(SEQ ID NO. 35)
EVQLVESGGGLVQPGGSLRLSCAASGFTFSTYAMNWVRKAPGKGLEWVS

RIRSKYNNYATYYADSVKDRFTISRDDSKNTLYLQMNSLRAEDTAVYYC

VRHGNFGDSYVSWFAYWGQGTLVTVSS

Nucleic Acid Sequence (SEQ ID NO. 36)
GAGGTGCAGCTGGTTGAATCTGGCGGAGGACTGGTTCAGCCTGGCGGAT

CTCTGAGACTGTCTTGTGCCGCCAGCGGCTTCACCTTCTCCACCTACGC

TATGAACTGGGTCCGAAAGGCCCCTGGCAAAGGACTGGAATGGGTGTCC

AGAATCAGGTCCAAGTACAACAACTACGCCACCTACTACGCCGACAGCG

TGAAGGACAGATTCACCATCAGCAGGGACGACAGCAAGAACACCCTGTA

CCTGCAGATGAACAGCCTGAGAGCCGAGGACACCGCCGTGTACTACTGT

GTCAGACACGGCAACTTCGGCCAGAGCTATGTGTCTTGGTTTGCCTACT

GGGGCCAGGGCACACTGGTCACAGTTAGCTCT

The amino acid sequence of hVH5 is shown in SEQ ID NO. 38, nucleic acid encoding the same is shown in SEQ ID NO. 39, and HCDR1, HCDR2 and HCDR3 thereof are shown in SEQ ID NOs. 31 (STYAMN), 27 (IRSKYN-NYATYYADSVKD and 40 (HGNFGDSYVSWFAY), respectively.

(SEQ ID NO. 38)
EVQLVESGGGLVQPGGSLRLSCAASGFTFSTYAMNWVRKAPGKGLEWVS

RIRSKYNNYATYYADSVKDRFTISRDDSKNTLYLQMNSLRAEDTAVYYC

VRHGNFGDSYVSWFAYWGQGTLVTVSS

Nucleic Acid Sequence (SEQ ID NO. 39)
GAGGTGCAGCTGGTTGAATCTGGCGGAGGACTGGTTCAGCCTGGCGGAT

CTCTGAGACTGTCTTGTGCCGCCAGCGGCTTCACCTTCTCCACCTACGC

TATGAACTGGGTCCGAAAGGCCCCTGGCAAAGGACTGGAATGGGTGTCC

AGAATCAGGTCCAAGTACAACAACTACGCCACCTACTACGCCGACAGCG

TGAAGGACAGATTCACCATCAGCAGGGACGACAGCAAGAACACCCTGTA

CCTGCAGATGAACAGCCTGAGAGCCGAGGACACCGCCGTGTACTACTGT

GTCAGACACGGCAACTTCGGCGACAGCTATGTGTCTTGGTTTGCCTACT

GGGGCCAGGGCACACTGGTCACAGTTAGCTCT

The amino acid sequence of hVH6 is shown in SEQ ID NO. 41, nucleic acid encoding the same is shown in SEQ ID NO. 42, and HCDR1, HCDR2 and HCDR3 thereof are shown in SEQ ID NOs. 31 (STYAMN), 27 (IRSKYN-NYATYYADSVKD) and 43 (HGNFGTSYVSWFAY), respectively.

(SEQ ID NO. 41)
EVQLVESGGGLVQPGGSLRLSCAASGFTFSTYAMNWVRKAPGKGLEWV

SRIRSKYNNYATYYADSVKDRFTISRDDSKNTLYLQMNSLRAEDTAVY

YCVRHGNFGTSYVSWFAYWGQGTLVTVSS

Nucleic Acid Sequence (SEQ ID NO. 42)
GAGGTGCAGCTGGTTGAATCTGGCGGAGGACTGGTTCAGCCTGGCGGAT

CTCTGAGACTGTCTTGTGCCGCCAGCGGCTTCACCTTCTCCACCTACGC

TATGAACTGGGTCCGAAAGGCCCCTGGCAAAGGACTGGAATGGGTGTCC

AGAATCAGGTCCAAGTACAACAACTACGCCACCTACTACGCCGACAGCG

TGAAGGACAGATTCACCATCAGCAGGGACGACAGCAAGAACACCCTGTA

CCTGCAGATGAACAGCCTGAGAGCCGAGGACACCGCCGTGTACTACTGT

GTCAGACACGGCAACTTCGGCACCAGCTATGTGTCTTGGTTTGCCTACT

GGGGCCAGGGCACACTGGTCACAGTTAGCTCT

The amino acid sequence of hVH7 is shown in SEQ ID NO. 44, nucleic acid encoding the same is shown in SEQ ID NO. 45, and HCDR1, HCDR2 and HCDR3 thereof are shown in SEQ ID NOs. 46 (SDYAMN), 47 (IRSKYN-NYATYYADSVED) and 28 (HGNFGNSYVSWFAY), respectively.

(SEQ ID NO. 44)
EVQLVESGGGLVQPGGSLRLSCAASGFTFSDYAMNWVRKAPGKGLEWVS

RIRSKYNNYATYYADSVEDRFTISRDDSKNTLYLQMNSLRAEDTAVYYC

VRHGNFGNSYVSWFAYWGQGTLVTVSS

Nucleic Acid Sequence (SEQ ID NO: 45)
GAGGTGCAGCTGGTTGAATCTGGCGGAGGACTGGTTCAGCCTGGCGGAT

CTCTGAGACTGTCTTGTGCCGCCAGCGGCTTCACCTTCTCCGACTACGC

TATGAACTGGGTCCGAAAGGCCCCTGGCAAAGGACTGGAATGGGTGTCC

AGAATCAGGTCCAAGTACAACAACTACGCCACCTACTACGCCGACAGCG

TGGAGGACAGATTCACCATCAGCAGGGACGACAGCAAGAACACCCTGTA

CCTGCAGATGAACAGCCTGAGAGCCGAGGACACCGCCGTGTACTACTGT

GTCAGACACGGCAACTTCGGCAACAGCTATGTGTCTTGGTTTGCCTACT

GGGGCCAGGGCACACTGGTCACAGTTAGCTCT

The amino acid sequence of hVH8 is shown in SEQ ID NO. 48, nucleic acid encoding the same is shown in SEQ ID NO. 49, and HCDR1, HCDR2 and HCDR3 thereof are shown in SEQ ID NOs. 26 (NTYAMN), 27 (IRSKYN-NYATYYADSVKD) and 28 (HGNFGNSYVSWFAY), respectively.

```
                                      (SEQ ID NO. 48)
EVQLVESGGGLVQPGGSLRLSCAASGFTFNTYAMNWVRKAPGKGLEWVG

RIRSKYNNYATYYADSVKDRFTISRDDSKNSLYLQMNSLKTEDTAVYYC

ARHGNFGNSYVSWFAYWGQGTLVTVSS
```

Nucleic Acid Sequence

```
                                      (SEQ ID NO. 49)
GAGGTGCAGCTGGTTGAATCTGGCGGAGGACTGGTTCAGCCTGGCGGAT

CTCTGAGACTGTCTTGTGCCGCCAGCGGCTTCACCTTCAACACCTACGC

TATGAACTGGGTCCGAAAGGCCCCTGGCAAAGGACTGGAATGGGTGGGA

AGAATCAGGTCCAAGTACAACAACTACGCCACCTACTACGCCGACAGCG

TGAAGGACAGATTCACCATCAGCAGGGACGACAGCAAGAACAGCCTGTA

CCTGCAGATGAACAGCCTGAAAACCGAGGACACCGCCGTGTACTACTGT

GCCAGACACGGCAACTTCGGCAACAGCTATGTGTCTTGGTTTGCCTACT

GGGGCCAGGGCACACTGGTCACAGTTAGCTCT
```

The amino acid sequence of hVH9 is shown in SEQ ID NO. 50, nucleic acid encoding the same is shown in SEQ ID NO. 51, and HCDR1, HCDR2 and HCDR3 thereof are shown in SEQ ID NOs. 26 (NTYAMN), 27 (IRSKYN-NYATYYADSVKD) and 28 (HGNFGNSYVSWFAY), respectively.

```
                                      (SEQ ID NO. 50)
EVQLVESGGGLVQPGGSLRLSCAASGFTFNTYAMNWVRKAPGKGLEWVG

RIRSKYNNYATYYADSVKDRFTISRDDSKNSLYLQMNSLKTEDTAVYYC

VRHGNFGNSYVSWFAYWGQGTLVTVSS
```

Nucleic Acid Sequence

```
                                      (SEQ ID NO. 51)
GAGGTGCAGCTGGTTGAATCTGGCGGAGGACTGGTTCAGCCTGGCGGAT

CTCTGAGACTGTCTTGTGCCGCCAGCGGCTTCACCTTCAACACCTACGC

TATGAACTGGGTCCGAAAGGCCCCTGGCAAAGGACTGGAATGGGTGGGA

AGAATCAGGTCCAAGTACAACAACTACGCCACCTACTACGCCGACAGCG

TGAAGGACAGATTCACCATCAGCAGGGACGACAGCAAGAACAGCCTGTA

CCTGCAGATGAACAGCCTGAAAACCGAGGACACCGCCGTGTACTACTGT

GTCAGACACGGCAACTTCGGCAACAGCTATGTGTCTTGGTTTGCCTACT

GGGGCCAGGGCACACTGGTCACAGTTAGCTCT
```

The amino acid sequence of hVH10 is shown in SEQ ID NO. 52, nucleic acid encoding the same is shown in SEQ ID NO. 53, and HCDR1, HCDR2 and HCDR3 thereof are shown in SEQ ID NOs. 26 (NTYAMN), 27 (IRSKYN-NYATYYADSVKD) and 28 (HGNFGNSYVSWFAY), respectively.

```
                                      (SEQ ID NO. 52)
EVQLVESGGGLVQPGGSLRLSCAASGFTFNTYAMNWVRKAPGKGLEWVA

RIRSKYNNYATYYADSVKDRFTISRDDSKNSLYLQMNSLKTEDTAVYYC

VRHGNFGNSYVSWFAYWGQGTLVTVSS
```

Nucleic Acid Sequence

```
                                      (SEQ ID NO. 53)
GAGGTGCAGCTGGTTGAATCTGGCGGAGGACTGGTTCAGCCTGGCGGAT

CTCTGAGACTGTCTTGTGCCGCCAGCGGCTTCACCTTCAACACCTACGC

TATGAACTGGGTCCGAAAGGCCCCTGGCAAAGGACTGGAATGGGTGGCC

AGAATCAGGTCCAAGTACAACAACTACGCCACCTACTACGCCGACAGCG

TGAAGGACAGATTCACCATCAGCAGGGACGACAGCAAGAACAGCCTGTA

CCTGCAGATGAACAGCCTGAAAACCGAGGACACCGCCGTGTACTACTGT

GTCAGACACGGCAACTTCGGCAACAGCTATGTGTCTTGGTTTGCCTACT

GGGGCCAGGGCACACTGGTCACAGTTAGCTCT
```

After the humanized variants of light and heavy chain have been respectively subjected to full sequence synthesis, they are cloned into the eukaryotic expression vector containing the constant region of light chain of antibody λ or the constant region CH1-CH3 of heavy chain of human IgG4, co-transfected into HEK 293E cells, and cultured at 37° C. under 120 rpm of 5% $CO_2$ for 5-6 days, and then the culture supernatant is collected and purified by Protein A chromatography column.

3. Affinity of Humanized CD3 Antibody

Figure 2:
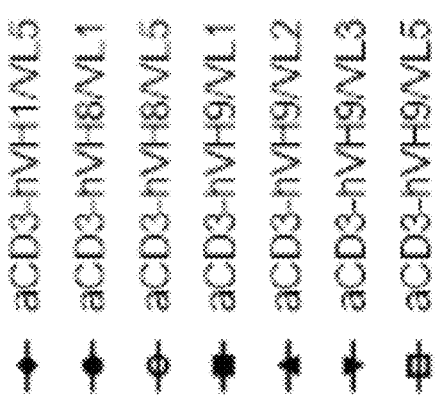
FIG. 2 shows binding of the humanized anti-CD3 antibody to human CD3εγ protein.
Figure 2:
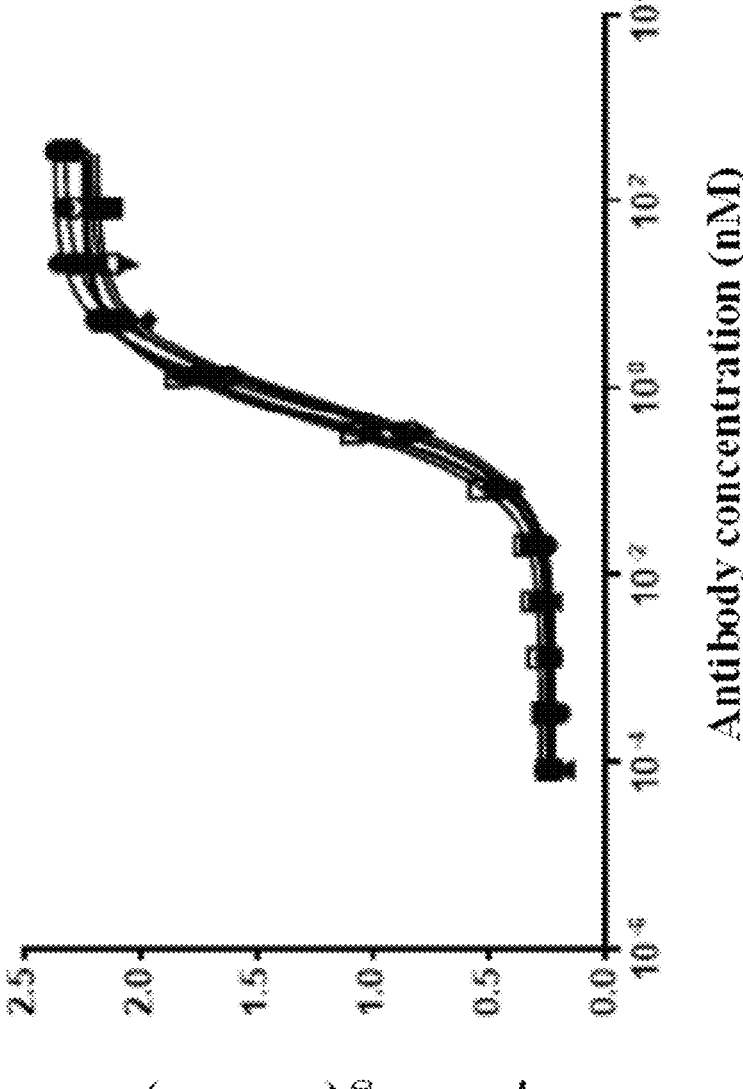

Human CD3εγ recombinant protein was coated overnight at 4° C. After blocking with 2% skim milk, different dilutions of CD3 antibody were added to each well and incubated for 1 hour. After the secondary antibody was developed by adding HPR-labeled goat anti-human IgG Fc and TMB solution, the reaction was stopped with concentrated sulfuric acid and the absorbance was read at 450 nm. FIG. 2 shows the binding of humanized anti-CD3 antibodies (including aCD3-hVH1/VL5, aCD3-hVH8/VL1, aCD3-hVH8/VL5, aCD3-hVH9/VL1, aCD3-hVH9/VL2, aCD3-hVH9/VL3, aCD3-hVH9/VL5) to human CD3εγ protein, where humanized CD3 antibodies bind with high affinity to CD3εγ recombinant protein.

Figure 3:
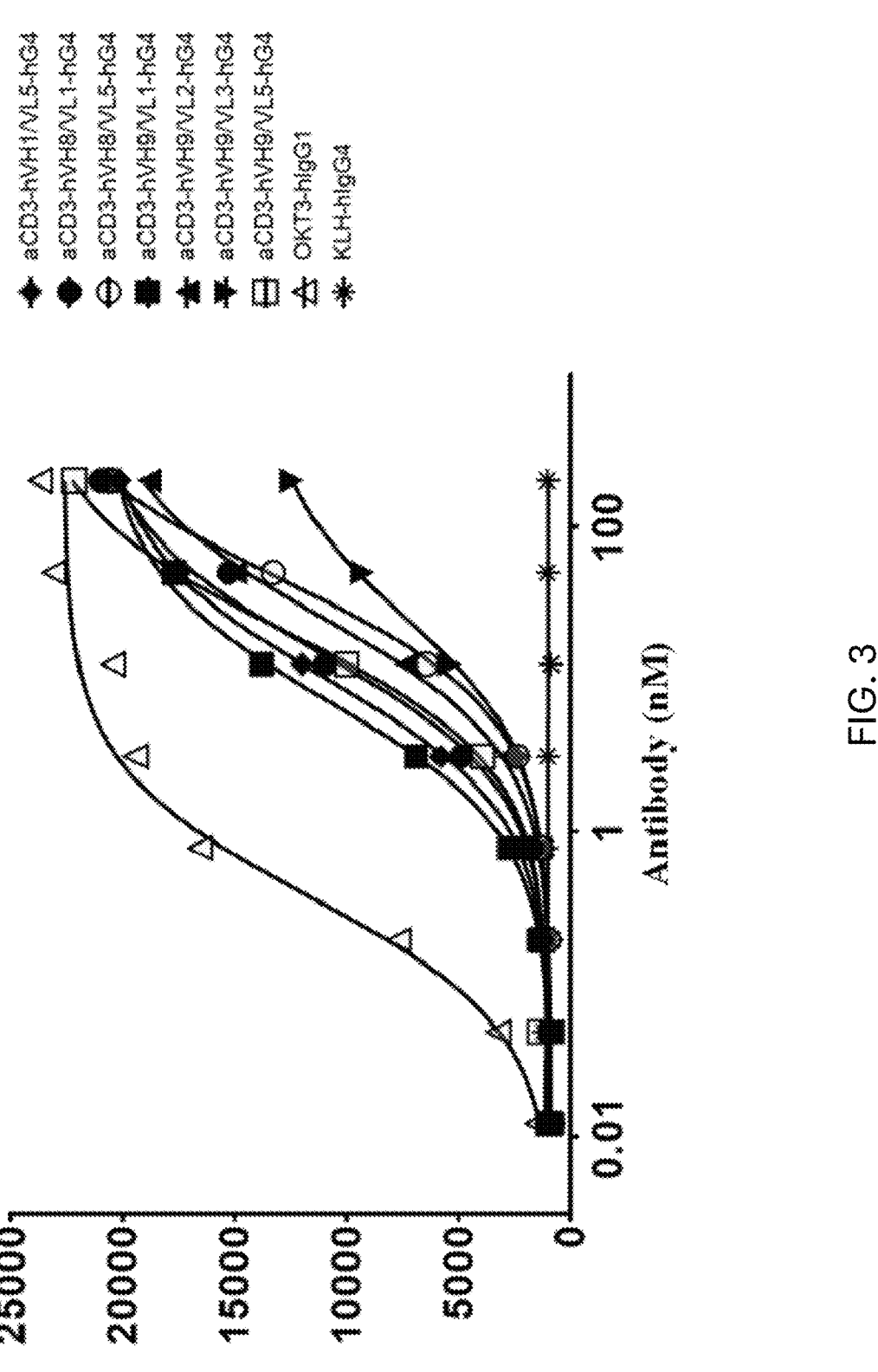
FIG. 3 shows binding of the humanized anti-CD3 antibody to a Jurkat cell.

Jurkat cells in logarithmic growth phase were blocked with 3% BSA for 30 min, added to 96-well U-plate at 5×104 cells per well, centrifuged to discard the supernatant, and added with 50 μL of gradient diluted antibody (antibody concentration: from 30 μg/mL, with 3-fold dilution for 5 gradients) per well, and incubated at 4° C. for 1 hour. After washing off the primary antibody, a 1: 300 dilution of Alexa Fluro647 labeled goat anti-human IgG Fc (Jackson Immu-noResearch, 109-606-170) was added to the secondary antibody, incubated for 45 min at 4° C., and, after washing, resuspended in 50 μL of PBS per well for FACS (iQue, intellicyt) detection. As a result, as shown in FIG. 3, the humanized anti-CD3 antibody bound to Jurkat cells, wherein both humanized anti-CD3 antibodies hVH9/VL5 (aCD3-hVH9/VL5) and hVH9/VL2 (aCD3-hVH9/VL2) were significantly weaker than the control antibody OKT3, and bound to Jurkat cells with moderate affinity.

Table 2 shows the affinity of the humanized CD3 antibody to CD3 recombinant protein and Jurkat cells.

TABLE 2

| | ELISA (CD3εγ) | FACS (Jurkat) |
|---|---|---|
| | Affinities of humanized anti-CD3 antibodies | |
| aCD3-hVH1/VL5 | 0.60 nM | 10 nM |
| aCD3-hVH8/VL1 | 0.65 nM | 15 nM |
| aCD3-hVH8/VL5 | 0.74 nM | Weak |
| aCD3-hVH9/VL1 | 0.49 nM | 7 nM |
| aCD3-hVH9/VL2 | 0.44 nM | 25 nM |
| aCD3-hVH9/VL3 | 0.70 nM | Weak |
| aCD3-hVH9/VL5 | 0.42 nM | 20 nM |
| OKT3-hIgG1 | ND | 0.27 nM |
| KLH-hIgG4 | — | — |

ND: not detected.

—: not combined with

Figure 4:
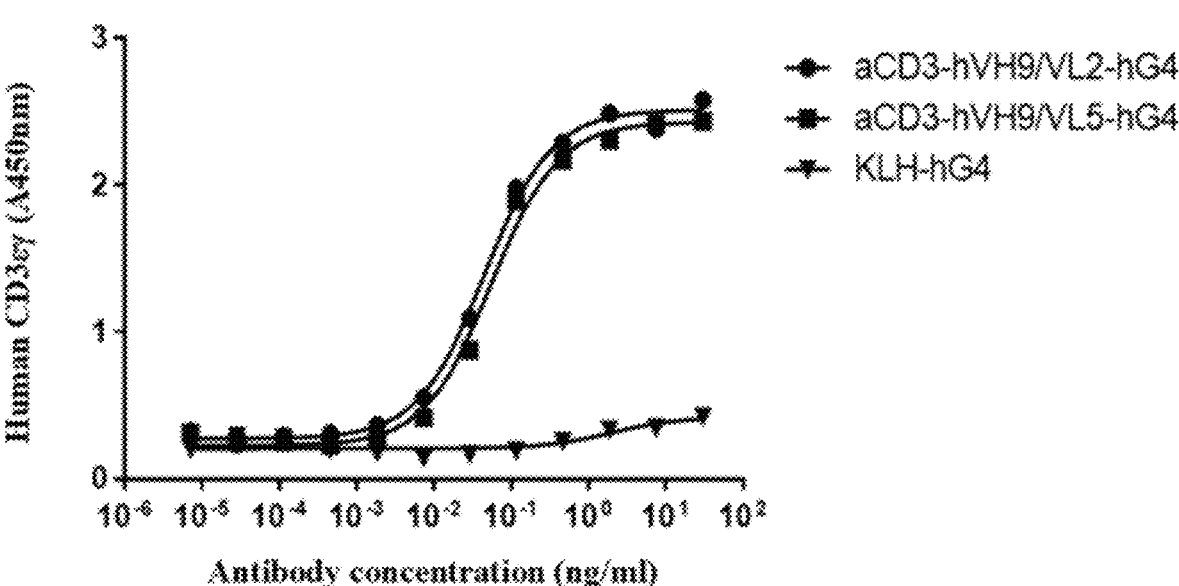
FIG. 4 shows binding of the humanized anti-CD3 humanized antibody to human CD3εγ and cynomolgus monkey CD3εγ proteins.
Figure 4:
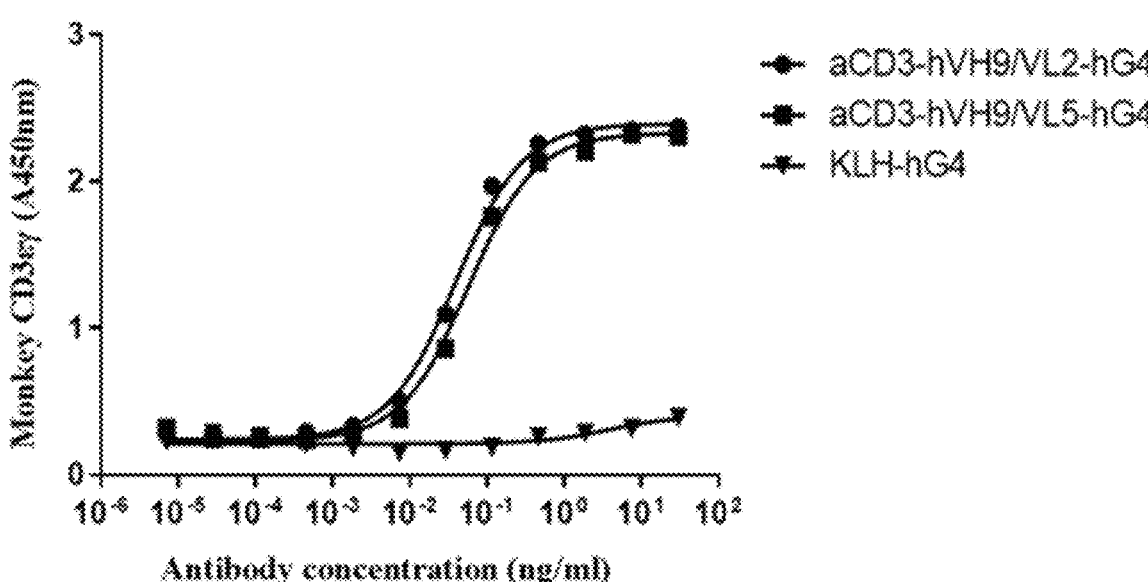

4. Cross-Recognition of Humanized Anti-CD3 Antibody with Human and Cynomolgus Monkey CD3 Antigens Human CD3εγ protein and cynomolgus monkey CD3εγ protein were coated separately overnight at 4° C. After blocking with 2% skim milk, different dilutions of CD3 antibody were added to each well and incubated for 1 hour. After the secondary antibody was developed by adding HPR-labeled goat anti-human IgG Fc and TMB solution, the reaction was stopped with concentrated sulfuric acid, and the absorbance was read at 450 nm. FIG. 4 shows that both humanized anti-CD3 antibodies hVH9/VL5 (aCD3-hVH9/VL5) and hVH9/VL2 (aCD3-hVH9/VL2) can bind both human CD3εγ and cynomolgus monkey CD3εγ proteins.

Example 2: Construction of Anti-CD20×CD3 KX Bispecific Antibodies Formed by Different Types of Light Chains

1. Construction of Anti-CD20×CD3 KX Bispecific Antibody

A novel T-cell κλ bispecific antibody with the native IgG configuration was constructed with the humanized CD3 antibody hVH9/VL5 (λ light chain and paired heavy chain) and the humanized CD20 antibody (κ light chain and paired heavy chain).

Figure 5:
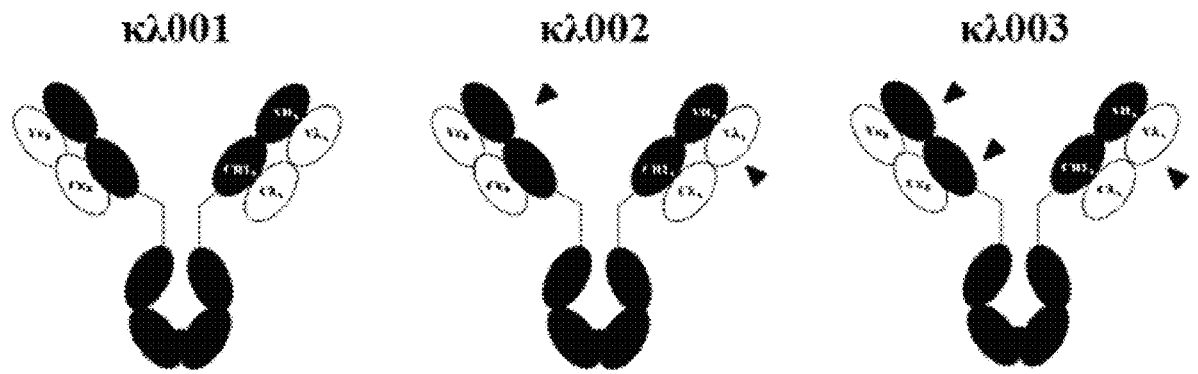
FIG. 5 shows the structures of κλ001, κλ002, κλ003, κλ004, κλ005 of the present disclosure.
Figure 5:
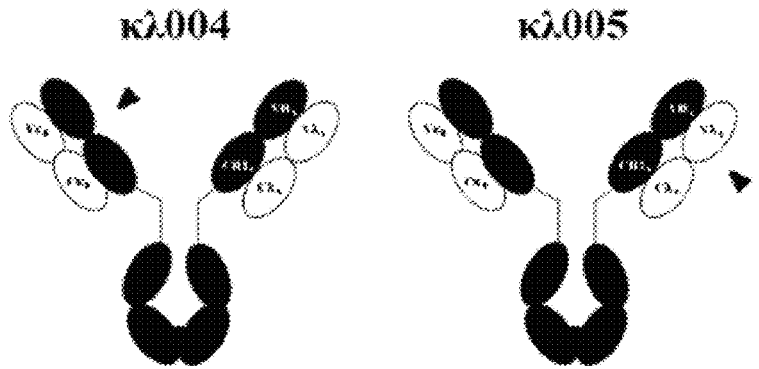

As shown in FIG. 5, the following five CD20×CD3 bispecific antibodies were designed and constructed:

1) CD20×CD3 κλ001: retaining the native sequences of the CD3 arm and the CD20 antigen arm;

2) CD20×CD3 κλ002: a charge variant ($V\kappa_{CD20}$: $Gln_{38}Lys$; $VH_{CD20}$: $Gln_{39}Glu$; $VH_{CD3}$: $Gln_{40}Glu$; $V_{HCD3}$: $Gln_{39}Lys$);

3) CD20×CD3 κλ003: based on CD20×CD3 κλ002, adding between $CH1/C_{KS}$ complementary charge pairs ($V\kappa$-$Ck_{CD2}0$: $Gln_{38}Lys\backslash Glu_{123}Lys\backslash Gln_{124}Lys$; $V_H$-$C_H]_{CD20}$: $Gln_{39}Glu\backslash Lys_{152}Glu\backslash Lys_{218}Glu$; $VH_{CD3}$: $Gln_{40}Glu$; $VH_{CD30}$: $Gln_{39}Lys$);

4) CD20×CD3 κλ004: introducing, only in the CD20 antigen arm, charge variants ($V\kappa_{CD20}$: $Gln_{38}Lys$; $VH_{CD20}$: $Gln_{39}Glu$);

5) CD20×CD3 κλ005: introducing, only in the CD3 arm, charge variants ($V\lambda_{CD3}$: $Gln_{40}Glu$; $V_{HCD3}$: $Gln_{39}Lys$).

The corresponding sequences are shown in Table 3. The control antibody CD20×CD3-crossFab was constructed by reference to the CrossFab method (Schaefer W et al. PNAS 2011).

TABLE 3

| | light chain of CD20 arm | heavy chain of CD20 arm | light chain of CD3 arm | heavy chain of CD3 arm |
|---|---|---|---|---|
| Sequences of anti-CD20 x CD3 κλ bispecific antibodies | | | | |
| CD20 x CD3 κλ001 | SEQ ID NO.54 | SEQ ID NO.56 | SEQ ID NO.58 | SEQ ID NO.60 |
| CD20 x CD3 κλ002 | SEQ ID NO.62 | SEQ ID NO.64 | SEQ ID NO.66 | SEQ ID NO.68 |
| CD20 x CD3 κλ003 | SEQ ID NO.70 | SEQ ID NO.72 | SEQ ID NO.66 | SEQ ID NO.68 |
| CD20 x CD3 κλ004 | SEQ ID NO.62 | SEQ ID NO.64 | SEQ ID NO.58 | SEQ ID NO.60 |
| CD20 x CD3 κλ005 | SEQ ID NO.54 | SEQ ID NO.56 | SEQ ID NO.66 | SEQ ID NO.68 |
| CD20 x CD3-crossFab | SEQ ID NO.70 | SEQ ID NO.74 | SEQ ID NO.76 | SEQ ID NO.78 |

CD20×CD3 κλ001:

κ light chain of CD20 arm:

SEQ ID NO. 54

EIVLTQSPGTLSLSPGERATLSCRASQSVSSYLAWYQQKPGQAPRLLIYDASNRATGIPDRF

SGSGSGTDFTLTISRLEPEDFAVYYCQQRSNWPITFGQGTKLEIKRTVAAPSVFIFPPSDEQL

KSGTASVVCLLNNFYPREAKVQWKVDNALQSGNSQESVTEQDSKDSTYSLSSTLTLSKA

DYEKHKVYACEVTHQGLSSPVTKSFNRGEC

Nucleotide sequence:

SEQ ID NO. 55

GAGATCGTGCTGACACAGAGCCCTGGCACACTGTCACTGTCTCCAGGCGAGAGAGCC

ACACTGAGCTGTAGAGCCAGCCAGAGCGTGTCCTCTTACCTGGCCTGGTATCAGCAGA

AGCCTGGACAGGCTCCCAGACTGCTGATCTACGACGCCAGCAACAGAGCCACAGGCA

-continued

TCCCCGATAGATTCAGCGGCTCTGGCTCTGGCACCGACTTCACCCTGACAATCAGCAG

ACTGGAACCCGAGGACTTCGCCGTGTACTACTGCCAGCAGAGAAGCAACTGGCCCAT

CACATTCGGCCAGGGCACCAAGCTGGAAATCAAGCGAACTGTGGCTGCACCATCTGTC

TTCATCTTCCCGCCATCTGATGAGCAGTTGAAATCTGGAACTGCCTCTGTTGTGTGCCT

GCTGAATAACTTCTATCCCAGAGAGGCCAAAGTACAGTGGAAGGTGGATAACGCCCTC

CAATCGGGTAACTCCCAGGAGAGTGTCACAGAGCAGGACAGCAAGGACAGCACCTAC

AGCCTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAACAGG

GGAGAGTGT

Heavy chain (heavy chain 1) of CD20 arm:

SEQ ID NO. 56

EVQLLESGGGVVQPGGSLRLSCAASGFTFNDYAMHWVRQAPGKGLEWVSTISWNSGSIG

YADSVKGRFTISRDNSKNTLYLQMNSLRAEDTAVYYCAKDIQYGNYYYGMDYWGQGTL

VTVSSASTKGPSVFPLAPCSRSTSESTAALGCLVKDYFPEPVTVSWNSGALTSGVHTFPAVL

QSSGLYSLSSVVTVPSSSLGTKTYTCNVDHKPSNTKVDKRVESKYGPPCPPCPAPEFEGGP

SVFLFPPKPKDTLMISRTPEVTCVVVDVSQEDPEVQFNWYVDGVEVHNAKTKPREEQFNS

TYRVVSVLTVLHQDWLNGKEYKCKVSNKGLASSIEKTISKAKGQPREPQVCTLPPSQEEM

TKNQVSLSCAVKGFYPSDIAVEWESNGQPENNYKTTPPVLDSDGSFFLVSKLTVDKSRWQ

EGNVFSCSVMHEALHNHYTQKSLSLSLGK

Nucleotide sequence:

SEQ ID NO. 57

GAAGTGCAGCTGCTGGAATCTGGTGGCGGAGTTGTTCAGCCTGGCGGCTCTCTGAGAC

TGTCTTGTGCTGCCAGCGGCTTCACCTTCAACGACTACGCTATGCACTGGGTCCGACA

GGCCCCTGGCAAAGGACTTGAATGGGTGTCCACCATCAGCTGGAACAGCGGCTCTATC

GGCTACGCCGATTCCGTGAAGGGCAGATTCACCATCTCCAGAGACAACAGCAAGAAC

ACCCTGTACCTGCAGATGAACAGCCTGAGAGCCGAGGACACCGCCGTGTACTACTGTG

CCAAGGACATCCAGTACGGCAACTACTACTACGGCATGGACTACTGGGGCCAGGGAAC

ACTGGTTACCGTTAGCTCTGCTAGCACCAAGGGCCCCAGCGTGTTCCCCCTGGCCCCTT

GCAGCAGAAGCACCAGCGAGAGCACAGCCGCCCTGGGCTGCCTGGTGAAGGACTACT

TCCCCGAGCCCGTGACCGTGTCCTGGAACAGCGGCGCTCTGACCAGCGGCGTGCATAC

CTTCCCCGCCGTGCTCCAGAGCAGCGGACTGTACTCCCTGAGCAGCGTGGTGACCGTG

CCTTCCAGCAGCCTGGGCACCAAGACCTACACCTGCAACGTGGACCACAAGCCCAGC

AACACCAAGGTGGACAAGAGAGTGGAGAGCAAGTACGGCCCTCCCTGCCCCCCTTGC

CCTGCCCCCGAGTTCGAGGGCGGACCTAGCGTGTTCCTGTTCCCCCCCAAGCCCAAGG

ACACCCTGATGATCAGCAGAACCCCCGAGGTGACCTGCGTGGTGGTGGACGTGTCCC

AGGAGGACCCCGAGGTCCAGTTTAATTGGTACGTGGACGGCGTGGAAGTGCATAACGC

CAAGACCAAGCCCAGAGAGGAGCAGTTCAACAGCACCTACAGAGTGGTGTCCGTGCT

GACCGTGCTGCACCAGGACTGGCTGAACGGCAAGGAATACAAGTGCAAGGTCTCCAA

CAAGGGCCTGGCCAGCAGCATCGAGAAGACCATCAGCAAGGCCAAGGGCCAGCCAC

GGGAGCCCCAGGTCTGCACCCTGCCACCTAGCCAAGAGGAGATGACCAAGAACCAGG

TGTCCCTGAGCTGTGCCGTGAAAGGCTTCTATCCCAGCGATATCGCCGTGGAGTGGGA

GAGCAACGGCCAGCCCGAGAACAACTACAAGACCACCCCCCCTGTGCTGGACAGCGA

CGGCAGCTTCTTCCTGGTTTCCAAGCTGACCGTGGACAAGTCCAGATGGCAGGAGGG

-continued

CAACGTCTTCAGCTGCTCCGTGATGCACGAGGCCCTGCACAACCACTACACCCAGAAG

TCCCTGAGCCTGAGCCTGGGCAAG

λ light chain of CD3 arm:

SEQ ID NO. 58

QAVVTQEPSLTVSPGGTVTLTCRSSTGAVTTSNYANWVQQKPGQAPRGLIGGTNKRAPWT

PARFSGSLLGGKAALTITGAQAEDEAEYYCVLWYSNLWVFGGGTKLTVLGQPKAAPSVT

LFPPSSEELQANKATLVCLISDFYPGAVTVAWKADSSPVKAGVETTTPSKQSNNKYAASSY

LSLTPEQWKSHRSYSCQVTHEGSTVEKTVAPTECS

Nucleotide sequence:

SEQ ID NO. 59

CAGGCTGTGGTCACACAAGAGCCTAGCCTGACAGTGTCTCCTGGCGGCACAGTGACC

CTGACCTGTAGATCTTCTACAGGCGCCGTGACCACCAGCAACTACGCTAATTGGGTGC

AGCAGAAGCCCGGCCAGGCTCCTAGAGGACTGATCGGCGGAACAAACAAGAGAGCC

CCTTGGACACCCGCCAGATTCTCTGGATCTCTGCTCGGCGGAAAGGCCGCTCTGACAA

TCACTGGTGCTCAGGCTGAGGACGAGGCCGAGTACTATTGTGTGCTGTGGTACAGCAA

CCTGTGGGTGTTCGGCGGAGGCACCAAACTGACAGTTCTGGGTCAGCCCAAGGCGGC

GCCCTCGGTCACTCTGTTCCCGCCCTCCTCTGAGGAGCTTCAAGCCAACAAGGCCACA

CTGGTGTGTCTCATAAGTGACTTCTATCCGGGAGCCGTGACAGTGGCCTGGAAGGCAG

ATAGCAGCCCCGTCAAGGCGGGAGTGGAGACCACCACACCCTCCAAACAAAGCAACA

ACAAGTACGCGGCCAGCAGCTACCTGAGCCTGACGCCTGAGCAGTGGAAGTCCCACA

GAAGCTACAGCTGCCAGGTCACGCATGAAGGGAGCACCGTGGAGAAGACAGTGGCCC

CTACAGAATGTTCA

Heavy chain (heavy chain 2) of CD3 arm:

SEQ ID NO. 60

EVQLVESGGGLVQPGGSLRLSCAASGFTFNTYAMNWVRQAPGKGLEWVGRIRSKYNNYA

TYYADSVKDRFTISRDDSKNSLYLQMNSLKTEDTAVYYCVRHGNFGNSYVSWFAYWGQG

TLVTVSSASTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRVESKYGPPCPPCPAPEFEG

GPSVFLFPPKPKDTLMISRTPEVTCVVVDVSQEDPEVQFNWYVDGVEVHNAKTKPREEQF

NSTYRVVSVLTVLHQDWLNGKEYKCKVSNKGLASSIEKTISKAKGQPREPQVYTLPPCQE

EMTKNQVSLWCLVKGFYPSDIAVEWESNGQPENNYKTTPPVLDSDGSFFLYSKLTVDKSR

WQEGNVFSCSVMHEALHNHYTQKSLSLSLGK

Nucleotide sequence:

SEQ ID NO. 61

GAGGTGCAGCTGGTTGAATCTGGCGGAGGACTGGTTCAGCCTGGCGGATCTCTGAGA

CTGTCTTGTGCCGCCAGCGGCTTCACCTTCAACACCTACGCTATGAACTGGGTCCGAC

AGGCCCCTGGCAAAGGACTGGAATGGGTGGGAAGAATCAGGTCCAAGTACAACAACT

ACGCCACCTACTACGCCGACAGCGTGAAGGACAGATTCACCATCAGCAGGGACGACA

GCAAGAACAGCCTGTACCTGCAGATGAACAGCCTGAAAACCGAGGACACCGCCGTGT

ACTACTGTGTCAGACACGGCAACTTCGGCAACAGCTATGTGTCTTGGTTTGCCTACTGG

GGCCAGGGCACACTGGTCACAGTTAGCTCTGCTAGCACCAAGGGCCCCAGCGTGTTCC

CCCTGGCCCCTTGCAGCAGAAGCACCAGCGAGAGCACAGCCGCCCTGGGCTGCCTGG

TGAAGGACTACTTCCCCGAGCCCGTGACCGTGTCCTGGAACAGCGGCGCTCTGACCA

GCGGCGTGCATACCTTCCCCGCCGTGCTCCAGAGCAGCGGACTGTACTCCCTGAGCAG

-continued

CGTGGTGACCGTGCCTTCCAGCAGCCTGGGCACCAAGACCTACACCTGCAACGTGGA

CCACAAGCCCAGCAACACCAAGGTGGACAAGAGAGTGGAGAGCAAGTACGGCCCTC

CCTGCCCCCCTTGCCCTGCCCCCGAGTTCGAGGGCGGACCTAGCGTGTTCCTGTTCCC

CCCCAAGCCCAAGGACACCCTGATGATCAGCAGAACCCCCGAGGTGACCTGCGTGGT

GGTGGACGTGTCCCAGGAGGACCCCGAGGTCCAGTTTAATTGGTACGTGGACGGCGT

GGAAGTGCATAACGCCAAGACCAAGCCCAGAGAGGAGCAGTTCAACAGCACCTACAG

AGTGGTGTCCGTGCTGACCGTGCTGCACCAGGACTGGCTGAACGGCAAGGAATACAA

GTGCAAGGTCTCCAACAAGGGCCTGGCCAGCAGCATCGAGAAGACCATCAGCAAGGC

CAAGGGCCAGCCACGGGAGCCCCAGGTCTACACCCTGCCACCTTGTCAAGAGGAGAT

GACCAAGAACCAGGTGTCCCTGTGGTGTCTGGTGAAAGGCTTCTATCCCAGCGATATC

GCCGTGGAGTGGGAGAGCAACGGCCAGCCCGAGAACAACTACAAGACCACCCCCCCT

GTGCTGGACAGCGACGGCAGCTTCTTCCTGTACTCCAAGCTGACCGTGGACAAGTCCA

GATGGCAGGAGGGCAACGTCTTCAGCTGCTCCGTGATGCACGAGGCCCTGCACAACC

ACTACACCCAGAAGTCCCTGAGCCTGAGCCTGGGCAAG

CD20×CD3 κλ002:

κ light chain of CD20 arm:
                                                SEQ ID NO. 62
EIVLTQSPGTLSLSPGERATLSCRASQSVSSYLAWYQKKPGQAPRLLIYDASNRATGIPDRF

SGSGSGTDFTLTISRLEPEDFAVYYCQQRSNWPITFGQGTKLEIKRTVAAPSVFIFPPSDEQL

KSGTASVVCLLNNFYPREAKVQWKVDNALQSGNSQESVTEQDSKDSTYSLSSTLTLSKA

DYEKHKVYACEVTHQGLSSPVTKSFNRGEC

Nucleotide sequence:
                                                SEQ ID NO. 63
GAGATCGTGCTGACACAGAGCCCTGGCACACTGTCACTGTCTCCAGGCGAGAGAGCC

ACACTGAGCTGTAGAGCCAGCCAGAGCGTGTCCTCTTACCTGGCCTGGTATCAGAAGA

AGCCTGGACAGGCTCCCAGACTGCTGATCTACGACGCCAGCAACAGAGCCACAGGCA

TCCCCGATAGATTCAGCGGCTCTGGCTCTGGCACCGACTTCACCCTGACAATCAGCAG

ACTGGAACCCGAGGACTTCGCCGTGTACTACTGCCAGCAGAGAAGCAACTGGCCCAT

CACATTCGGCCAGGGCACCAAGCTGGAAATCAAGCGAACTGTGGCTGCACCATCTGTC

TTCATCTTCCCGCCATCTGATGAGCAGTTGAAATCTGGAACTGCCTCTGTTGTGTGCCT

GCTGAATAACTTCTATCCCAGAGAGGCCAAAGTACAGTGGAAGGTGGATAACGCCCTC

CAATCGGGTAACTCCCAGGAGAGTGTCACAGAGCAGGACAGCAAGGACAGCACCTAC

AGCCTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAACAGG

GGAGAGTGT

Heavy chain (heavy chain 1) of CD20 arm:
                                                SEQ ID NO. 64
EVQLLESGGGVVQPGGSLRLSCAASGFTFNDYAMHWVREAPGKGLEWVSTISWNSGSIG

YADSVKGRFTISRDNSKNTLYLQMNSLRAEDTAVYYCAKDIQYGNYYYGMDYWGQGTL

VTVSSASTKGPSVFPLAPCSRSTSESTAALGCLVKDYFPEPVTVSWNSGALTSGVHTFPAVL

QSSGLYSLSSVVTVPSSSLGTKTYTCNVDHKPSNTKVDKRVESKYGPPCPPCPAPEFEGGP

SVFLFPPKPKDTLMISRTPEVTCVVVDVSQEDPEVQFNWYVDGVEVHNAKTKPREEQFNS

TYRVVSVLTVLHQDWLNGKEYKCKVSNKGLASSIEKTISKAKGQPREPQVCTLPPSQEEM

-continued

TKNQVSLSCAVKGFYPSDIAVEWESNGQPENNYKTTPPVLDSDGSFFLVSKLTVDKSRWQ

EGNVFSCSVMHEALHNHYTQKSLSLSLGK

Nucleotide sequence:

SEQ ID NO. 65

GAAGTGCAGCTGCTGGAATCTGGTGGCGGAGTTGTTCAGCCTGGCGGCTCTCTGAGAC

TGTCTTGTGCTGCCAGCGGCTTCACCTTCAACGACTACGCTATGCACTGGGTCCGAGA

GGCCCCTGGCAAAGGACTTGAATGGGTGTCCACCATCAGCTGGAACAGCGGCTCTATC

GGCTACGCCGATTCCGTGAAGGGCAGATTCACCATCTCCAGAGACAACAGCAAGAAC

ACCCTGTACCTGCAGATGAACAGCCTGAGAGCCGAGGACACCGCCGTGTACTACTGTG

CCAAGGACATCCAGTACGGCAACTACTACTACGGCATGGACTACTGGGGCCAGGGAAC

ACTGGTTACCGTTAGCTCTGCTAGCACCAAGGGCCCCAGCGTGTTCCCCCTGGCCCCTT

GCAGCAGAAGCACCAGCGAGAGCACAGCCGCCCTGGGCTGCCTGGTGAAGGACTACT

TCCCCGAGCCCGTGACCGTGTCCTGGAACAGCGGCGCTCTGACCAGCGGCGTGCATAC

CTTCCCCGCCGTGCTCCAGAGCAGCGGACTGTACTCCCTGAGCAGCGTGGTGACCGTG

CCTTCCAGCAGCCTGGGCACCAAGACCTACACCTGCAACGTGGACCACAAGCCCAGC

AACACCAAGGTGGACAAGAGAGTGGAGAGCAAGTACGGCCCTCCCTGCCCCCCTTGC

CCTGCCCCCGAGTTCGAGGGCGGACCTAGCGTGTTCCTGTTCCCCCCCAAGCCCAAGG

ACACCCTGATGATCAGCAGAACCCCCGAGGTGACCTGCGTGGTGGTGGACGTGTCCC

AGGAGGACCCCGAGGTCCAGTTTAATTGGTACGTGGACGGCGTGGAAGTGCATAACGC

CAAGACCAAGCCCAGAGAGGAGCAGTTCAACAGCACCTACAGAGTGGTGTCCGTGCT

GACCGTGCTGCACCAGGACTGGCTGAACGGCAAGGAATACAAGTGCAAGGTCTCCAA

CAAGGGCCTGGCCAGCAGCATCGAGAAGACCATCAGCAAGGCCAAGGGCCAGCCAC

GGGAGCCCCAGGTCTGCACCCTGCCACCTAGCCAAGAGGAGATGACCAAGAACCAGG

TGTCCCTGAGCTGTGCCGTGAAAGGCTTCTATCCCAGCGATATCGCCGTGGAGTGGGA

GAGCAACGGCCAGCCCGAGAACAACTACAAGACCACCCCCCCTGTGCTGGACAGCGA

CGGCAGCTTCTTCCTGGTTTCCAAGCTGACCGTGGACAAGTCCAGATGGCAGGAGGG

CAACGTCTTCAGCTGCTCCGTGATGCACGAGGCCCTGCACAACCACTACACCCAGAAG

TCCCTGAGCCTGAGCCTGGGCAAG

λ light chain of CD3 arm:

SEQ ID NO. 66

QAVVTQEPSLTVSPGGTVTLTCRSSTGAVTTSNYANWVQEKPGQAPRGLIGGTNKRAPWT

PARFSGSLLGGKAALTITGAQAEDEAEYYCVLWYSNLWVFGGGTKLTVLGQPKAAPSVT

LFPPSSEELQANKATLVCLISDFYPGAVTVAWKADSSPVKAGVETTTPSKQSNNKYAASSY

LSLTPEQWKSHRSYSCQVTHEGSTVEKTVAPTECS

Nucleotide sequence:

SEQ ID NO. 67

CAGGCTGTGGTCACACAAGAGCCTAGCCTGACAGTGTCTCCTGGCGGCACAGTGACC

CTGACCTGTAGATCTTCTACAGGCGCCGTGACCACCAGCAACTACGCTAATTGGGTGC

AGGAGAAGCCCGGCCAGGCTCCTAGAGGACTGATCGGCGGAACAAACAAGAGAGCC

CCTTGGACACCCGCCAGATTCTCTGGATCTCTGCTCGGCGGAAAGGCCGCTCTGACAA

TCACTGGTGCTCAGGCTGAGGACGAGGCCGAGTACTATTGTGTGCTGTGGTACAGCAA

CCTGTGGGTGTTCGGCGGAGGCACCAAACTGACAGTTCTGGGTCAGCCCAAGGCGGC

GCCCTCGGTCACTCTGTTCCCGCCCTCCTCTGAGGAGCTTCAAGCCAACAAGGCCACA

-continued

CTGGTGTGTCTCATAAGTGACTTCTATCCGGGAGCCGTGACAGTGGCCTGGAAGGCAG

ATAGCAGCCCCGTCAAGGCGGGAGTGGAGACCACCACACCCTCCAAACAAAGCAACA

ACAAGTACGCGGCCAGCAGCTACCTGAGCCTGACGCCTGAGCAGTGGAAGTCCCACA

GAAGCTACAGCTGCCAGGTCACGCATGAAGGGAGCACCGTGGAGAAGACAGTGGCCC

CTACAGAATGTTCA

Heavy chain (heavy chain 2) of CD3 arm:

SEQ ID NO. 68

EVQLVESGGGLVQPGGSLRLSCAASGFTFNTYAMNWVRKAPGKGLEWVGRIRSKYNNYA

TYYADSVKDRFTISRDDSKNSLYLQMNSLKTEDTAVYYCVRHGNFGNSYVSWFAYWGQG

TLVTVSSASTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRVESKYGPPCPPCPAPEFEG

GPSVFLFPPKPKDTLMISRTPEVTCVVVDVSQEDPEVQFNWYVDGVEVHNAKTKPREEQF

NSTYRVVSVLTVLHQDWLNGKEYKCKVSNKGLASSIEKTISKAKGQPREPQVYTLPPCQE

EMTKNQVSLWCLVKGFYPSDIAVEWESNGQPENNYKTTPPVLDSDGSFFLYSKLTVDKSR

WQEGNVFSCSVMHEALHNHYTQKSLSLSLGK

Nucleotide sequence:

SEQ ID NO. 69

GAGGTGCAGCTGGTTGAATCTGGCGGAGGACTGGTTCAGCCTGGCGGATCTCTGAGA

CTGTCTTGTGCCGCCAGCGGCTTCACCTTCAACACCTACGCTATGAACTGGGTCCGAA

AGGCCCCTGGCAAAGGACTGGAATGGGTGGGAAGAATCAGGTCCAAGTACAACAACT

ACGCCACCTACTACGCCGACAGCGTGAAGGACAGATTCACCATCAGCAGGGACGACA

GCAAGAACAGCCTGTACCTGCAGATGAACAGCCTGAAAACCGAGGACACCGCCGTGT

ACTACTGTGTCAGACACGGCAACTTCGGCAACAGCTATGTGTCTTGGTTTGCCTACTGG

GGCCAGGGCACACTGGTCACAGTTAGCTCTGCTAGCACCAAGGGCCCCAGCGTGTTCC

CCCTGGCCCCTTGCAGCAGAAGCACCAGCGAGAGCACAGCCGCCCTGGGCTGCCTGG

TGAAGGACTACTTCCCCGAGCCCGTGACCGTGTCCTGGAACAGCGGCGCTCTGACCA

GCGGCGTGCATACCTTCCCCGCCGTGCTCCAGAGCAGCGGACTGTACTCCCTGAGCAG

CGTGGTGACCGTGCCTTCCAGCAGCCTGGGCACCAAGACCTACACCTGCAACGTGGA

CCACAAGCCCAGCAACACCAAGGTGGACAAGAGAGTGGAGAGCAAGTACGGCCCTC

CCTGCCCCCCTTGCCCTGCCCCCGAGTTCGAGGGCGGACCTAGCGTGTTCCTGTTCCC

CCCCAAGCCCAAGGACACCCTGATGATCAGCAGAACCCCCGAGGTGACCTGCGTGGT

GGTGGACGTGTCCCAGGAGGACCCCGAGGTCCAGTTTAATTGGTACGTGGACGGCGT

GGAAGTGCATAACGCCAAGACCAAGCCCAGAGAGGAGCAGTTCAACAGCACCTACAG

AGTGGTGTCCGTGCTGACCGTGCTGCACCAGGACTGGCTGAACGGCAAGGAATACAA

GTGCAAGGTCTCCAACAAGGGCCTGGCCAGCAGCATCGAGAAGACCATCAGCAAGGC

CAAGGGCCAGCCACGGGAGCCCCAGGTCTACACCCTGCCACCTTGTCAAGAGGAGAT

GACCAAGAACCAGGTGTCCCTGTGGTGTCTGGTGAAAGGCTTCTATCCCAGCGATATC

GCCGTGGAGTGGGAGAGCAACGGCCAGCCCGAGAACAACTACAAGACCACCCCCCCT

GTGCTGGACAGCGACGGCAGCTTCTTCCTGTACTCCAAGCTGACCGTGGACAAGTCCA

GATGGCAGGAGGGCAACGTCTTCAGCTGCTCCGTGATGCACGAGGCCCTGCACAACC

ACTACACCCAGAAGTCCCTGAGCCTGAGCCTGGGCAAG

CD20×CD3 κλ.003:

κ light chain of CD20 arm:
```
                                           SEQ ID NO. 70
EIVLTQSPGTLSLSPGERATLSCRASQSVSSYLAWYQKKPGQAPRLLIYDASNRATGIPDRF

SGSGSGTDFTLTISRLEPEDFAVYYCQQRSNWPITFGQGTKLEIKRTVAAPSVFIFPPSDKKL

KSGTASVVCLLNNFYPREAKVQWKVDNALQSGNSQESVTEQDSKDSTYSLSSTLTLSKA

DYEKHKVYACEVTHQGLSSPVTKSFNRGEC
```

Nucleotide sequence:
```
                                           SEQ ID NO. 71
GAGATCGTGCTGACACAGAGCCCTGGCACACTGTCACTGTCTCCAGGCGAGAGAGCC

ACACTGAGCTGTAGAGCCAGCCAGAGCGTGTCCTCTTACCTGGCCTGGTATCAGAAGA

AGCCTGGACAGGCTCCCAGACTGCTGATCTACGACGCCAGCAACAGAGCCACAGGCA

TCCCCGATAGATTCAGCGGCTCTGGCTCTGGCACCGACTTCACCCTGACAATCAGCAG

ACTGGAACCCGAGGACTTCGCCGTGTACTACTGCCAGCAGAGAAGCAACTGGCCCAT

CACATTCGGCCAGGGCACCAAGCTGGAAATCAAGCGAACTGTGGCTGCACCATCTGTC

TTCATCTTCCCGCCATCTGATAAGAAATTGAAATCTGGAACTGCCTCTGTTGTGTGCCT

GCTGAATAACTTCTATCCCAGAGAGGCCAAAGTACAGTGGAAGGTGGATAACGCCCTC

CAATCGGGTAACTCCCAGGAGAGTGTCACAGAGCAGGACAGCAAGGACAGCACCTAC

AGCCTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAACAGG

GGAGAGTGT
```

Heavy chain (heavy chain 1) of CD20 arm:
```
                                           SEQ ID NO. 72
EVQLLESGGGVVQPGGSLRLSCAASGFTFNDYAMHWVREAPGKGLEWVSTISWNSGSIG

YADSVKGRFTISRDNSKNTLYLQMNSLRAEDTAVYYCAKDIQYGNYYYGMDYWGQGTL

VTVSSASTKGPSVFPLAPCSRSTSESTAALGCLVEDYFPEPVTVSWNSGALTSGVHTFPAVL

QSSGLYSLSSVVTVPSSSLGTKTYTCNVDHKPSNTKVDERVESKYGPPCPPCPAPEFEGGPS

VFLFPPKPKDTLMISRTPEVTCVVVDVSQEDPEVQFNWYVDGVEVHNAKTKPREEQFNST

YRVVSVLTVLHQDWLNGKEYKCKVSNKGLASSIEKTISKAKGQPREPQVCTLPPSQEEMT

KNQVSLSCAVKGFYPSDIAVEWESNGQPENNYKTTPPVLDSDGSFFLVSKLTVDKSRWQE

GNVFSCSVMHEALHNHYTQKSLSLSLGK
```

Nucleotide sequence:
```
                                           SEQ ID NO. 73
GAAGTGCAGCTGCTGGAATCTGGTGGCGGAGTTGTTCAGCCTGGCGGCTCTCTGAGAC

TGTCTTGTGCTGCCAGCGGCTTCACCTTCAACGACTACGCTATGCACTGGGTCCGAGA

GGCCCCTGGCAAAGGACTTGAATGGGTGTCCACCATCAGCTGGAACAGCGGCTCTATC

GGCTACGCCGATTCCGTGAAGGGCAGATTCACCATCTCCAGAGACAACAGCAAGAAC

ACCCTGTACCTGCAGATGAACAGCCTGAGAGCCGAGGACACCGCCGTGTACTACTGTG

CCAAGGACATCCAGTACGGCAACTACTACTACGGCATGGACTACTGGGGCCAGGGAAC

ACTGGTTACCGTTAGCTCTGCTAGCACCAAGGGCCCCAGCGTGTTCCCCCTGGCCCCTT

GCAGCAGAAGCACCAGCGAGAGCACAGCCGCCCTGGGCTGCCTGGTGGAGGACTACT

TCCCCGAGCCCGTGACCGTGTCCTGGAACAGCGGCGCTCTGACCAGCGGCGTGCATAC

CTTCCCCGCCGTGCTCCAGAGCAGCGGACTGTACTCCCTGAGCAGCGTGGTGACCGTG

CCTTCCAGCAGCCTGGGCACCAAGACCTACACCTGCAACGTGGACCACAAGCCCAGC

AACACCAAGGTGGACGAGAGAGTGGAGAGCAAGTACGGCCCCTCCCTGCCCCCCTTGC
```

CCTGCCCCCGAGTTCGAAGGCGGACCTAGCGTGTTCCTGTTCCCCCCCAAGCCCAAGG

ACACCCTGATGATCAGCAGAACCCCCGAGGTGACCTGCGTGGTGGTGGACGTGTCCC

AGGAGGACCCCGAGGTCCAGTTTAATTGGTACGTGGACGGCGTGGAAGTGCATAACGC

CAAGACCAAGCCCAGAGAGGAGCAGTTCAACAGCACCTACAGAGTGGTGTCCGTGCT

GACCGTGCTGCACCAGGACTGGCTGAACGGCAAGGAATACAAGTGCAAGGTCTCCAA

CAAGGGCCTGGCCAGCAGCATCGAGAAGACCATCAGCAAGGCCAAGGGCCAGCCAC

GGGAGCCCCAGGTCTGCACCCTGCCACCTAGCCAAGAGGAGATGACCAAGAACCAGG

TGTCCCTGAGCTGTGCCGTGAAAGGCTTCTATCCCAGCGATATCGCCGTGGAGTGGGA

GAGCAACGGCCAGCCCGAGAACAACTACAAGACCACCCCCCCTGTGCTGGACAGCGA

CGGCAGCTTCTTCCTGGTTTCCAAGCTGACCGTGGACAAGTCCAGATGGCAGGAGGG

CAACGTCTTCAGCTGCTCCGTGATGCACGAGGCCCTGCACAACCACTACACCCAGAAG

TCCCTGAGCCTGAGCCTGGGCAAG

λ light chain of CD3 arm:

SEQ ID NO. 66

QAVVTQEPSLTVSPGGTVTLTCRSSTGAVTTSNYANWVQEKPGQAPRGLIGGTNKRAPWT

PARFSGSLLGGKAALTITGAQAEDEAEYYCVLWYSNLWVFGGGTKLTVLGQPKAAPSVT

LFPPSSEELQANKATLVCLISDFYPGAVTVAWKADSSPVKAGVETTTPSKQSNNKYAASSY

LSLTPEQWKSHRSYSCQVTHEGSTVEKTVAPTECS

Nucleotide sequence:

SEQ ID NO. 67

CAGGCTGTGGTCACACAAGAGCCTAGCCTGACAGTGTCTCCTGGCGGCACAGTGACC

CTGACCTGTAGATCTTCTACAGGCGCCGTGACCACCAGCAACTACGCTAATTGGGTGC

AGGAGAAGCCCGGCCAGGCTCCTAGAGGACTGATCGGCGGAACAAACAAGAGAGCC

CCTTGGACACCCGCCAGATTCTCTGGATCTCTGCTCGGCGGAAAGGCCGCTCTGACAA

TCACTGGTGCTCAGGCTGAGGACGAGGCCGAGTACTATTGTGTGCTGTGGTACAGCAA

CCTGTGGGTGTTCGGCGGAGGCACCAAACTGACAGTTCTGGGTCAGCCCAAGGCGGC

GCCCTCGGTCACTCTGTTCCCGCCCTCCTCTGAGGAGCTTCAAGCCAACAAGGCCACA

CTGGTGTGTCTCATAAGTGACTTCTATCCGGGAGCCGTGACAGTGGCCTGGAAGGCAG

ATAGCAGCCCCGTCAAGGCGGGAGTGGAGACCACCACACCCTCCAAACAAAGCAACA

ACAAGTACGCGGCCAGCAGCTACCTGAGCCTGACGCCTGAGCAGTGGAAGTCCCACA

GAAGCTACAGCTGCCAGGTCACGCATGAAGGGAGCACCGTGGAGAAGACAGTGGCCC

CTACAGAATGTTCA

Heavy chain (heavy chain 2) of CD3 arm:

SEQ ID NO. 68

EVQLVESGGGLVQPGGSLRLSCAASGFTFNTYAMNWVRKAPGKGLEWVGRIRSKYNNYA

TYYADSVKDRFTISRDDSKNSLYLQMNSLKTEDTAVYYCVRHGNFGNSYVSWFAYWGQG

TLVTVSSASTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRVESKYGPPCPPCPAPEFEG

GPSVFLFPPKPKDTLMISRTPEVTCVVVDVSQEDPEVQFNWYVDGVEVHNAKTKPREEQF

NSTYRVVSVLTVLHQDWLNGKEYKCKVSNKGLASSIEKTISKAKGQPREPQVYTLPPCQE

EMTKNQVSLWCLVKGFYPSDIAVEWESNGQPENNYKTTPPVLDSDGSFFLYSKLTVDKSR

WQEGNVFSCSVMHEALHNHYTQKSLSLSLGK

-continued

Nucleotide sequence:

SEQ ID NO. 69

GAGGTGCAGCTGGTTGAATCTGGCGGAGGACTGGTTCAGCCTGGCGGATCTCTGAGA

CTGTCTTGTGCCGCCAGCGGCTTCACCTTCAACACCTACGCTATGAACTGGGTCCGAA

AGGCCCCTGGCAAAGGACTGGAATGGGTGGGAAGAATCAGGTCCAAGTACAACAACT

ACGCCACCTACTACGCCGACAGCGTGAAGGACAGATTCACCATCAGCAGGGACGACA

GCAAGAACAGCCTGTACCTGCAGATGAACAGCCTGAAAACCGAGGACACCGCCGTGT

ACTACTGTGTCAGACACGGCAACTTCGGCAACAGCTATGTGTCTTGGTTTGCCTACTGG

GGCCAGGGCACACTGGTCACAGTTAGCTCTGCTAGCACCAAGGGCCCCAGCGTGTTCC

CCCTGGCCCCTTGCAGCAGAAGCACCAGCGAGAGCACAGCCGCCCTGGGCTGCCTGG

TGAAGGACTACTTCCCCGAGCCCGTGACCGTGTCCTGGAACAGCGGCGCTCTGACCA

GCGGCGTGCATACCTTCCCCGCCGTGCTCCAGAGCAGCGGACTGTACTCCCTGAGCAG

CGTGGTGACCGTGCCTTCCAGCAGCCTGGGCACCAAGACCTACACCTGCAACGTGGA

CCACAAGCCCAGCAACACCAAGGTGGACAAGAGAGTGGAGAGCAAGTACGGCCCTC

CCTGCCCCCCTTGCCCTGCCCCCGAGTTCGAGGGCGGACCTAGCGTGTTCCTGTTCCC

CCCCAAGCCCAAGGACACCCTGATGATCAGCAGAACCCCCGAGGTGACCTGCGTGGT

GGTGGACGTGTCCCAGGAGGACCCCGAGGTCCAGTTTAATTGGTACGTGGACGGCGT

GGAAGTGCATAACGCCAAGACCAAGCCCAGAGAGGAGCAGTTCAACAGCACCTACAG

AGTGGTGTCCGTGCTGACCGTGCTGCACCAGGACTGGCTGAACGGCAAGGAATACAA

GTGCAAGGTCTCCAACAAGGGCCTGGCCAGCAGCATCGAGAAGACCATCAGCAAGGC

CAAGGGCCAGCCACGGGAGCCCCAGGTCTACACCCTGCCACCTTGTCAAGAGGAGAT

GACCAAGAACCAGGTGTCCCTGTGGTGTCTGGTGAAAGGCTTCTATCCCAGCGATATC

GCCGTGGAGTGGGAGAGCAACGGCCAGCCCGAGAACAACTACAAGACCACCCCCCCT

GTGCTGGACAGCGACGGCAGCTTCTTCCTGTACTCCAAGCTGACCGTGGACAAGTCCA

GATGGCAGGAGGGCAACGTCTTCAGCTGCTCCGTGATGCACGAGGCCCTGCACAACC

ACTACACCCAGAAGTCCCTGAGCCTGAGCCTGGGCAAG

CD20×CD3 κλ004:

κ light chain of CD20 arm:

SEQ ID NO. 62

EIVLTQSPGTLSLSPGERATLSCRASQSVSSYLAWYQKKPGQAPRLLIYDASNRATGIPDRF

SGSGSGTDFTLTISRLEPEDFAVYYCQQRSNWPITFGQGTKLEIKRTVAAPSVFIFPPSDEQL

KSGTASVVCLLNNFYPREAKVQWKVDNALQSGNSQESVTEQDSKDSTYSLSSTLTLSKA

DYEKHKVYACEVTHQGLSSPVTKSFNRGEC

Nucleotide sequence:

SEQ ID NO. 63

GAGATCGTGCTGACACAGAGCCCTGGCACACTGTCACTGTCTCCAGGCGAGAGAGCC

ACACTGAGCTGTAGAGCCAGCCAGAGCGTGTCCTCTTACCTGGCCTGGTATCAGAAGA

AGCCTGGACAGGCTCCCAGACTGCTGATCTACGACGCCAGCAACAGAGCCACAGGCA

TCCCCGATAGATTCAGCGGCTCTGGCTCTGGCACCGACTTCACCCTGACAATCAGCAG

ACTGGAACCCGAGGACTTCGCCGTGTACTACTGCCAGCAGAGAAGCAACTGGCCCAT

CACATTCGGCCAGGGCACCAAGCTGGAAATCAAGCGAACTGTGGCTGCACCATCTGTC

TTCATCTTCCCCGCCATCTGATGAGCAGTTGAAATCTGGAACTGCCTCTGTTGTGTGCCT

GCTGAATAACTTCTATCCCAGAGAGGCCAAAGTACAGTGGAAGGTGGATAACGCCCTC

-continued

CAATCGGGTAACTCCCAGGAGAGTGTCACAGAGCAGGACAGCAAGGACAGCACCTAC

AGCCTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAACAGG

GGAGAGTGT

Heavy chain (heavy chain 1) of CD20 arm:
                                                        SEQ ID NO. 64
EVQLLESGGGVVQPGGSLRLSCAASGFTFNDYAMHWVREAPGKGLEWVSTISWNSGSIG

YADSVKGRFTISRDNSKNTLYLQMNSLRAEDTAVYYCAKDIQYGNYYYGMDYWGQGTL

VTVSSASTKGPSVFPLAPCSRSTSESTAALGCLVKDYFPEPVTVSWNSGALTSGVHTFPAVL

QSSGLYSLSSVVTVPSSSLGTKTYTCNVDHKPSNTKVDKRVESKYGPPCPPCPAPEFEGGP

SVFLFPPKPKDTLMISRTPEVTCVVVDVSQEDPEVQFNWYVDGVEVHNAKTKPREEQFNS

TYRVVSVLTVLHQDWLNGKEYKCKVSNKGLASSIEKTISKAKGQPREPQVCTLPPSQEEM

TKNQVSLSCAVKGFYPSDIAVEWESNGQPENNYKTTPPVLDSDGSFFLVSKLTVDKSRWQ

EGNVFSCSVMHEALHNHYTQKSLSLSLGK

Nucleotide sequence:
                                                        SEQ ID NO. 65
GAAGTGCAGCTGCTGGAATCTGGTGGCGGAGTTGTTCAGCCTGGCGGCTCTCTGAGAC

TGTCTTGTGCTGCCAGCGGCTTCACCTTCAACGACTACGCTATGCACTGGGTCCGAGA

GGCCCCTGGCAAAGGACTTGAATGGGTGTCCACCATCAGCTGGAACAGCGGCTCTATC

GGCTACGCCGATTCCGTGAAGGGCAGATTCACCATCTCCAGAGACAACAGCAAGAAC

ACCCTGTACCTGCAGATGAACAGCCTGAGAGCCGAGGACACCGCCGTGTACTACTGTG

CCAAGGACATCCAGTACGGCAACTACTACTACGGCATGGACTACTGGGGCCAGGGAAC

ACTGGTTACCGTTAGCTCTGCTAGCACCAAGGGCCCCAGCGTGTTCCCCCTGGCCCCTT

GCAGCAGAAGCACCAGCGAGAGCACAGCCGCCCTGGGCTGCCTGGTGAAGGACTACT

TCCCCGAGCCCGTGACCGTGTCCTGGAACAGCGGCGCTCTGACCAGCGGCGTGCATAC

CTTCCCCGCCGTGCTCCAGAGCAGCGGACTGTACTCCCTGAGCAGCGTGGTGACCGTG

CCTTCCAGCAGCCTGGGCACCAAGACCTACACCTGCAACGTGGACCACAAGCCCAGC

AACACCAAGGTGGACAAGAGAGTGGAGAGCAAGTACGGCCCTCCCTGCCCCCCCTTGC

CCTGCCCCCGAGTTCGAGGGCGGACCTAGCGTGTTCCTGTTCCCCCCCAAGCCCAAGG

ACACCCTGATGATCAGCAGAACCCCCGAGGTGACCTGCGTGGTGGTGGACGTGTCCC

AGGAGGACCCCGAGGTCCAGTTTAATTGGTACGTGGACGGCGTGGAAGTGCATAACGC

CAAGACCAAGCCCAGAGAGGAGCAGTTCAACAGCACCTACAGAGTGGTGTCCGTGCT

GACCGTGCTGCACCAGGACTGGCTGAACGGCAAGGAATACAAGTGCAAGGTCTCCAA

CAAGGGCCTGGCCAGCAGCATCGAGAAGACCATCAGCAAGGCCAAGGGCCAGCCAC

GGGAGCCCCAGGTCTGCACCCTGCCACCTAGCCAAGAGGAGATGACCAAGAACCAGG

TGTCCCTGAGCTGTGCCGTGAAAGGCTTCTATCCCAGCGATATCGCCGTGGAGTGGGA

GAGCAACGGCCAGCCCGAGAACAACTACAAGACCACCCCCCCTGTGCTGGACAGCGA

CGGCAGCTTCTTCCTGGTTTCCAAGCTGACCGTGGACAAGTCCAGATGGCAGGAGGG

CAACGTCTTCAGCTGCTCCGTGATGCACGAGGCCCTGCACAACCACTACACCCAGAAG

TCCCTGAGCCTGAGCCTGGGCAAG

-continued

λ light chain of CD3 arm:

```
                                                  SEQ ID NO. 58
QAVVTQEPSLTVSPGGTVTLTCRSSTGAVTTSNYANWVQQKPGQAPRGLIGGTNKRAPWT

PARFSGSLLGGKAALTITGAQAEDEAEYYCVLWYSNLWVFGGGTKLTVLGQPKAAPSVT

LFPPSSEELQANKATLVCLISDFYPGAVTVAWKADSSPVKAGVETTTPSKQSNNKYAASSY

LSLTPEQWKSHRSYSCQVTHEGSTVEKTVAPTECS
```

Nucleotide sequence:

```
                                                  SEQ ID NO. 59
CAGGCTGTGGTCACACAAGAGCCTAGCCTGACAGTGTCTCCTGGCGGCACAGTGACC

CTGACCTGTAGATCTTCTACAGGCGCCGTGACCACCAGCAACTACGCTAATTGGGTGC

AGCAGAAGCCCGGCCAGGCTCCTAGAGGACTGATCGGCGGAACAAACAAGAGAGCC

CCTTGGACACCCGCCAGATTCTCTGGATCTCTGCTCGGCGGAAAGGCCGCTCTGACAA

TCACTGGTGCTCAGGCTGAGGACGAGGCCGAGTACTATTGTGTGCTGTGGTACAGCAA

CCTGTGGGTGTTCGGCGGAGGCACCAAACTGACAGTTCTGGGTCAGCCCAAGGCGGC

GCCCTCGGTCACTCTGTTCCCGCCCTCCTCTGAGGAGCTTCAAGCCAACAAGGCCACA

CTGGTGTGTCTCATAAGTGACTTCTATCCGGGAGCCGTGACAGTGGCCTGGAAGGCAG

ATAGCAGCCCCGTCAAGGCGGGAGTGGAGACCACCACACCCTCCAAACAAAGCAACA

ACAAGTACGCGGCCAGCAGCTACCTGAGCCTGACGCCTGAGCAGTGGAAGTCCCACA

GAAGCTACAGCTGCCAGGTCACGCATGAAGGGAGCACCGTGGAGAAGACAGTGGCCC

CTACAGAATGTTCA
```

Heavy chain (heavy chain 2) of CD3 arm:

```
                                                  SEQ ID NO. 60
EVQLVESGGGLVQPGGSLRLSCAASGFTFNTYAMNWVRQAPGKGLEWVGRIRSKYNNYA

TYYADSVKDRFTISRDDSKNSLYLQMNSLKTEDTAVYYCVRHGNFGNSYVSWFAYWGQG

TLVTVSSASTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRVESKYGPPCPPCPAPEFEG

GPSVFLFPPKPKDTLMISRTPEVTCVVVDVSQEDPEVQFNWYVDGVEVHNAKTKPREEQF

NSTYRVVSVLTVLHQDWLNGKEYKCKVSNKGLASSIEKTISKAKGQPREPQVYTLPPCQE

EMTKNQVSLWCLVKGFYPSDIAVEWESNGQPENNYKTTPPVLDSDGSFFLYSKLTVDKSR

WQEGNVFSCSVMHEALHNHYTQKSLSLSLGK
```

Nucleotide sequence:

```
                                                  SEQ ID NO. 61
GAGGTGCAGCTGGTTGAATCTGGCGGAGGACTGGTTCAGCCTGGCGGATCTCTGAGA

CTGTCTTGTGCCGCCAGCGGCTTCACCTTCAACACCTACGCTATGAACTGGGTCCGAC

AGGCCCCTGGCAAAGGACTGGAATGGGTGGGAAGAATCAGGTCCAAGTACAACAACT

ACGCCACCTACTACGCCGACAGCGTGAAGGACAGATTCACCATCAGCAGGGACGACA

GCAAGAACAGCCTGTACCTGCAGATGAACAGCCTGAAAACCGAGGACACCGCCGTGT

ACTACTGTGTCAGACACGGCAACTTCGGCAACAGCTATGTGTCTTGGTTTGCCTACTGG

GGCCAGGGCACACTGGTCACAGTTAGCTCTGCTAGCACCAAGGGCCCCAGCGTGTTCC

CCCTGGCCCCTTGCAGCAGAAGCACCAGCGAGAGCACAGCCGCCCTGGGCTGCCTGG

TGAAGGACTACTTCCCCGAGCCCGTGACCGTGTCCTGGAACAGCGGCGCTCTGACCA

GCGGCGTGCATACCTTCCCCGCCGTGCTCCAGAGCAGCGGACTGTACTCCCTGAGCAG

CGTGGTGACCGTGCCTTCCAGCAGCCTGGGCACCAAGACCTACACCTGCAACGTGGA

CCACAAGCCCAGCAACACCAAGGTGGACAAGAGAGTGGAGAGCAAGTACGGCCCTC

CCTGCCCCCCTTGCCCTGCCCCCGAGTTCGAGGGCGGACCTAGCGTGTTCCTGTTCCC
```

-continued

CCCCAAGCCCAAGGACACCCTGATGATCAGCAGAACCCCCGAGGTGACCTGCGTGGT

GGTGGACGTGTCCCAGGAGGACCCCGAGGTCCAGTTTAATTGGTACGTGGACGGCGT

GGAAGTGCATAACGCCAAGACCAAGCCCAGAGAGGAGCAGTTCAACAGCACCTACAG

AGTGGTGTCCGTGCTGACCGTGCTGCACCAGGACTGGCTGAACGGCAAGGAATACAA

GTGCAAGGTCTCCAACAAGGGCCTGGCCAGCAGCATCGAGAAGACCATCAGCAAGGC

CAAGGGCCAGCCACGGGAGCCCCAGGTCTACACCCTGCCACCTTGTCAAGAGGAGAT

GACCAAGAACCAGGTGTCCCTGTGGTGTCTGGTGAAAGGCTTCTATCCCAGCGATATC

GCCGTGGAGTGGGAGAGCAACGGCCAGCCCGAGAACAACTACAAGACCACCCCCCCT

GTGCTGGACAGCGACGGCAGCTTCTTCCTGTACTCCAAGCTGACCGTGGACAAGTCCA

GATGGCAGGAGGGCAACGTCTTCAGCTGCTCCGTGATGCACGAGGCCCTGCACAACC

ACTACACCCAGAAGTCCCTGAGCCTGAGCCTGGGCAAG

20

CD20×CD3 κλ005:

κ light chain of CD20 arm:
                                              SEQ ID NO. 54
EIVLTQSPGTLSLSPGERATLSCRASQSVSSYLAWYQQKPGQAPRLLIYDASNRATGIPDRF

SGSGSGTDFTLTISRLEPEDFAVYYCQQRSNWPITFGQGTKLEIKRTVAAPSVFIFPPSDEQL

KSGTASVVCLLNNFYPREAKVQWKVDNALQSGNSQESVTEQDSKDSTYSLSSTLTLSKA

DYEKHKVYACEVTHQGLSSPVTKSFNRGEC

Nucleotide sequence:
                                              SEQ ID NO. 55
GAGATCGTGCTGACACAGAGCCCTGGCACACTGTCACTGTCTCCAGGCGAGAGAGCC

ACACTGAGCTGTAGAGCCAGCCAGAGCGTGTCCTCTTACCTGGCCTGGTATCAGCAGA

AGCCTGGACAGGCTCCCAGACTGCTGATCTACGACGCCAGCAACAGAGCCACAGGCA

TCCCCGATAGATTCAGCGGCTCTGGCTCTGGCACCGACTTCACCCTGACAATCAGCAG

ACTGGAACCCGAGGACTTCGCCGTGTACTACTGCCAGCAGAGAAGCAACTGGCCCAT

CACATTCGGCCAGGGCACCAAGCTGGAAATCAAGCGAACTGTGGCTGCACCATCTGTC

TTCATCTTCCCGCCATCTGATGAGCAGTTGAAATCTGGAACTGCCTCTGTTGTGTGCCT

GCTGAATAACTTCTATCCCAGAGAGGCCAAAGTACAGTGGAAGGTGGATAACGCCCTC

CAATCGGGTAACTCCCAGGAGAGTGTCACAGAGCAGGACAGCAAGGACAGCACCTAC

AGCCTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAACAGG

GGAGAGTGT

Heavy chain (heavy chain 1) of CD20 arm:
                                              SEQ ID NO. 56
EVQLLESGGGVVQPGGSLRLSCAASGFTFNDYAMHWVRQAPGKGLEWVSTISWNSGSIG

YADSVKGRFTISRDNSKNTLYLQMNSLRAEDTAVYYCAKDIQYGNYYYGMDYWGQGTL

VTVSSASTKGPSVFPLAPCSRSTSESTAALGCLVKDYFPEPVTVSWNSGALTSGVHTFPAVL

QSSGLYSLSSVVTVPSSSLGTKTYTCNVDHKPSNTKVDKRVESKYGPPCPPCPAPEFEGGP

SVFLFPPKPKDTLMISRTPEVTCVVVDVSQEDPEVQFNWYVDGVEVHNAKTKPREEQENS

TYRVVSVLTVLHQDWLNGKEYKCKVSNKGLASSIEKTISKAKGQPREPQVCTLPPSQEEM

TKNQVSLSCAVKGFYPSDIAVEWESNGQPENNYKTTPPVLDSDGSFFLVSKLTVDKSRWQ

EGNVFSCSVMHEALHNHYTQKSLSLSLGK

-continued

Nucleotide sequence:

SEQ ID NO. 57

GAAGTGCAGCTGCTGGAATCTGGTGGCGGAGTTGTTCAGCCTGGCGGCTCTCTGAGAC

TGTCTTGTGCTGCCAGCGGCTTCACCTTCAACGACTACGCTATGCACTGGGTCCGACA

GGCCCCTGGCAAAGGACTTGAATGGGTGTCCACCATCAGCTGGAACAGCGGCTCTATC

GGCTACGCCGATTCCGTGAAGGGCAGATTCACCATCTCCAGAGACAACAGCAAGAAC

ACCCTGTACCTGCAGATGAACAGCCTGAGAGCCGAGGACACCGCCGTGTACTACTGTG

CCAAGGACATCCAGTACGGCAACTACTACTACGGCATGGACTACTGGGGCCAGGGAAC

ACTGGTTACCGTTAGCTCTGCTAGCACCAAGGGCCCCAGCGTGTTCCCCCTGGCCCCTT

GCAGCAGAAGCACCAGCGAGAGCACAGCCGCCCTGGGCTGCCTGGTGAAGGACTACT

TCCCCGAGCCCGTGACCGTGTCCTGGAACAGCGGCGCTCTGACCAGCGGCGTGCATAC

CTTCCCCGCCGTGCTCCAGAGCAGCGGACTGTACTCCCTGAGCAGCGTGGTGACCGTG

CCTTCCAGCAGCCTGGGCACCAAGACCTACACCTGCAACGTGGACCACAAGCCCAGC

AACACCAAGGTGGACAAGAGAGTGGAGAGCAAGTACGGCCCTCCCTGCCCCCCTTGC

CCTGCCCCCGAGTTCGAGGGCGGACCTAGCGTGTTCCTGTTCCCCCCCAAGCCCAAGG

ACACCCTGATGATCAGCAGAACCCCCGAGGTGACCTGCGTGGTGGTGGACGTGTCCC

AGGAGGACCCCGAGGTCCAGTTTAATTGGTACGTGGACGGCGTGGAAGTGCATAACGC

CAAGACCAAGCCCAGAGAGGAGCAGTTCAACAGCACCTACAGAGTGGTGTCCGTGCT

GACCGTGCTGCACCAGGACTGGCTGAACGGCAAGGAATACAAGTGCAAGGTCTCCAA

CAAGGGCCTGGCCAGCAGCATCGAGAAGACCATCAGCAAGGCCAAGGGCCAGCCAC

GGGAGCCCCAGGTCTGCACCCTGCCACCTAGCCAAGAGGAGATGACCAAGAACCAGG

TGTCCCTGAGCTGTGCCGTGAAAGGCTTCTATCCCAGCGATATCGCCGTGGAGTGGGA

GAGCAACGGCCAGCCCGAGAACAACTACAAGACCACCCCCCCTGTGCTGGACAGCGA

CGGCAGCTTCTTCCTGGTTTCCAAGCTGACCGTGGACAAGTCCAGATGGCAGGAGGG

CAACGTCTTCAGCTGCTCCGTGATGCACGAGGCCCTGCACAACCACTACACCCAGAAG

TCCCTGAGCCTGAGCCTGGGCAAG

λ light chain of CD3 arm:

SEQ ID NO. 66

QAVVTQEPSLTVSPGGTVTLTCRSSTGAVTTSNYANWVQEKPGQAPRGLIGGTNKRAPWT

PARFSGSLLGGKAALTITGAQAEDEAEYYCVLWYSNLWVFGGGTKLTVLGQPKAAPSVT

LFPPSSEELQANKATLVCLISDFYPGAVTVAWKADSSPVKAGVETTTPSKQSNNKYAASSY

LSLTPEQWKSHRSYSCQVTHEGSTVEKTVAPTECS

Nucleotide sequence:

SEQ ID NO. 67

CAGGCTGTGGTCACACAAGAGCCTAGCCTGACAGTGTCTCCTGGCGGCACAGTGACC

CTGACCTGTAGATCTTCTACAGGCGCCGTGACCACCAGCAACTACGCTAATTGGGTGC

AGGAGAAGCCCGGCCAGGCTCCTAGAGGACTGATCGGCGGAACAAACAAGAGAGCC

CCTTGGACACCCGCCAGATTCTCTGGATCTCTGCTCGGCGGAAAGGCCGCTCTGACAA

TCACTGGTGCTCAGGCTGAGGACGAGGCCGAGTACTATTGTGTGCTGTGGTACAGCAA

CCTGTGGGTGTTCGGCGGAGGCACCAAACTGACAGTTCTGGGTCAGCCCAAGGCGGC

GCCCTCGGTCACTCTGTTCCCGCCCTCCTCTGAGGAGCTTCAAGCCAACAAGGCCACA

CTGGTGTGTCTCATAAGTGACTTCTATCCGGGAGCCGTGACAGTGGCCTGGAAGGCAG

ATAGCAGCCCCGTCAAGGCGGGAGTGGAGACCACCACACCCTCCAAACAAAGCAACA

ACAAGTACGCGGCCAGCAGCTACCTGAGCCTGACGCCTGAGCAGTGGAAGTCCCACA

-continued

GAAGCTACAGCTGCCAGGTCACGCATGAAGGGAGCACCGTGGAGAAGACAGTGGCCC

CTACAGAATGTTCA

Heavy chain (heavy chain 2) of CD3 arm:

SEQ ID NO. 68

EVQLVESGGGLVQPGGSLRLSCAASGFTFNTYAMNWVRKAPGKGLEWVGRIRSKYNNYA

TYYADSVKDRFTISRDDSKNSLYLQMNSLKTEDTAVYYCVRHGNFGNSYVSWFAYWGQG

TLVTVSSASTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRVESKYGPPCPPCPAPEFEG

GPSVFLFPPKPKDTLMISRTPEVTCVVVDVSQEDPEVQFNWYVDGVEVHNAKTKPREEQF

NSTYRVVSVLTVLHQDWLNGKEYKCKVSNKGLASSIEKTISKAKGQPREPQVYTLPPCQE

EMTKNQVSLWCLVKGFYPSDIAVEWESNGQPENNYKTTPPVLDSDGSFFLYSKLTVDKSR

WQEGNVFSCSVMHEALHNHYTQKSLSLSLGK

Nucleotide sequence:

SEQ ID NO. 69

GAGGTGCAGCTGGTTGAATCTGGCGGAGGACTGGTTCAGCCTGGCGGATCTCTGAGA

CTGTCTTGTGCCGCCAGCGGCTTCACCTTCAACACCTACGCTATGAACTGGGTCCGAA

AGGCCCCTGGCAAAGGACTGGAATGGGTGGGAAGAATCAGGTCCAAGTACAACAACT

ACGCCACCTACTACGCCGACAGCGTGAAGGACAGATTCACCATCAGCAGGGACGACA

GCAAGAACAGCCTGTACCTGCAGATGAACAGCCTGAAAACCGAGGACACCGCCGTGT

ACTACTGTGTCAGACACGGCAACTTCGGCAACAGCTATGTGTCTTGGTTTGCCTACTGG

GGCCAGGGCACACTGGTCACAGTTAGCTCTGCTAGCACCAAGGGCCCCAGCGTGTTCC

CCCTGGCCCCTTGCAGCAGAAGCACCAGCGAGAGCACAGCCGCCCTGGGCTGCCTGG

TGAAGGACTACTTCCCCGAGCCCGTGACCGTGTCCTGGAACAGCGGCGCTCTGACCA

GCGGCGTGCATACCTTCCCCGCCGTGCTCCAGAGCAGCGGACTGTACTCCCTGAGCAG

CGTGGTGACCGTGCCTTCCAGCAGCCTGGGCACCAAGACCTACACCTGCAACGTGGA

CCACAAGCCCAGCAACACCAAGGTGGACAAGAGAGTGGAGAGCAAGTACGGCCCTC

CCTGCCCCCCTTGCCCTGCCCCCGAGTTCGAGGGCGGACCTAGCGTGTTCCTGTTCCC

CCCCAAGCCCAAGGACACCCTGATGATCAGCAGAACCCCCGAGGTGACCTGCGTGGT

GGTGGACGTGTCCCAGGAGGACCCCGAGGTCCAGTTTAATTGGTACGTGGACGGCGT

GGAAGTGCATAACGCCAAGACCAAGCCCAGAGAGGAGCAGTTCAACAGCACCTACAG

AGTGGTGTCCGTGCTGACCGTGCTGCACCAGGACTGGCTGAACGGCAAGGAATACAA

GTGCAAGGTCTCCAACAAGGGCCTGGCCAGCAGCATCGAGAAGACCATCAGCAAGGC

CAAGGGCCAGCCACGGGAGCCCCAGGTCTACACCCTGCCACCTTGTCAAGAGGAGAT

GACCAAGAACCAGGTGTCCCTGTGGTGTCTGGTGAAAGGCTTCTATCCCAGCGATATC

GCCGTGGAGTGGGAGAGCAACGGCCAGCCCGAGAACAACTACAAGACCACCCCCCCT

GTGCTGGACAGCGACGGCAGCTTCTTCCTGTACTCCAAGCTGACCGTGGACAAGTCCA

GATGGCAGGAGGGCAACGTCTTCAGCTGCTCCGTGATGCACGAGGCCCTGCACAACC

ACTACACCCAGAAGTCCCTGAGCCTGAGCCTGGGCAAG

CD20×CD3-crossFab

κ light chain of CD20 arm:

SEQ ID NO. 70

EIVLTQSPGTLSLSPGERATLSCRASQSVSSYLAWYQKKPGQAPRLLIYDASNRATGIPDRF

SGSGSGTDFTLTISRLEPEDFAVYYCQQRSNWPITFGQGTKLEIKRTVAAPSVFIFPPSDKKL

KSGTASVVCLLNNFYPREAKVQWKVDNALQSGNSQESVTEQDSKDSTYSLSSTLTLSKA

DYEKHKVYACEVTHQGLSSPVTKSFNRGEC

Nucleotide sequence:

SEQ ID NO. 71

GAGATCGTGCTGACACAGAGCCCTGGCACACTGTCACTGTCTCCAGGCGAGAGAGCC

ACACTGAGCTGTAGAGCCAGCCAGAGCGTGTCCTCTTACCTGGCCTGGTATCAGAAGA

AGCCTGGACAGGCTCCCAGACTGCTGATCTACGACGCCAGCAACAGAGCCACAGGCA

TCCCCGATAGATTCAGCGGCTCTGGCTCTGGCACCGACTTCACCCTGACAATCAGCAG

ACTGGAACCCGAGGACTTCGCCGTGTACTACTGCCAGCAGAGAAGCAACTGGCCCAT

CACATTCGGCCAGGGCACCAAGCTGGAAATCAAGCGAACTGTGGCTGCACCATCTGTC

TTCATCTTCCCGCCATCTGATAAGAAATTGAAATCTGGAACTGCCTCTGTTGTGTGCCT

GCTGAATAACTTCTATCCCAGAGAGGCCAAAGTACAGTGGAAGGTGGATAACGCCCTC

CAATCGGGTAACTCCCAGGAGAGTGTCACAGAGCAGGACAGCAAGGACAGCACCTAC

AGCCTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAACAGG

GGAGAGTGT

Heavy chain (heavy chain 1) of CD20 arm:

SEQ ID NO. 74

EVQLLESGGGVVQPGGSLRLSCAASGFTFNDYAMHWVREAPGKGLEWVSTISWNSGSIG

YADSVKGRFTISRDNSKNTLYLQMNSLRAEDTAVYYCAKDIQYGNYYYGMDYWGQGTL

VTVSSASTKGPSVFPLAPCSRSTSESTAALGCLVEDYFPEPVTVSWNSGALTSGVHTFPAVL

QSSGLYSLSSVVTVPSSSLGTKTYTCNVDHKPSNTKVDERVESKYGPPCPPCPAPEFEGGPS

VFLFPPKPKDTLMISRTPEVTCVVVDVSQEDPEVQFNWYVDGVEVHNAKTKPREEQFAST

YRVVSVLTVLHQDWLNGKEYKCKVSNKGLPSSIEKTISKAKGQPREPQVCTLPPSQEEMT

KNQVSLSCAVKGFYPSDIAVEWESNGQPENNYKTTPPVLDSDGSFFLVSKLTVDKSRWQE

GNVFSCSVMHEALHNHYTQKSLSLSLGK

Nucleotide sequence:

SEQ ID NO. 75

GAAGTGCAGCTGCTGGAATCTGGTGGCGGAGTTGTTCAGCCTGGCGGCTCTCTGAGAC

TGTCTTGTGCTGCCAGCGGCTTCACCTTCAACGACTACGCTATGCACTGGGTCCGAGA

GGCCCCTGGCAAAGGACTTGAATGGGTGTCCACCATCAGCTGGAACAGCGGCTCTATC

GGCTACGCCGATTCCGTGAAGGGCAGATTCACCATCTCCAGAGACAACAGCAAGAAC

ACCCTGTACCTGCAGATGAACAGCCTGAGAGCCGAGGACACCGCCGTGTACTACTGTG

CCAAGGACATCCAGTACGGCAACTACTACTACGGCATGGACTACTGGGGCCAGGGAAC

ACTGGTTACCGTTAGCTCTGCTAGCACCAAGGGCCCCAGCGTGTTCCCCCTGGCCCCTT

GCAGCAGAAGCACCAGCGAGAGCACAGCCGCCCTGGGCTGCCTGGTGGAGGACTACT

TCCCCGAGCCCGTGACCGTGTCCTGGAACAGCGGCGCTCTGACCAGCGGCGTGCATAC

CTTCCCCGCCGTGCTCCAGAGCAGCGGACTGTACTCCCTGAGCAGCGTGGTGACCGTG

CCTTCCAGCAGCCTGGGCACCAAGACCTACACCTGCAACGTGGACCACAAGCCCAGC

AACACCAAGGTGGACGAGAGAGTGGAGAGCAAGTACGGCCCTCCCTGCCCCCCTTGC

-continued

CCTGCCCCCGAGTTCGAAGGCGGACCTAGCGTGTTCCTGTTCCCCCCCAAGCCCAAGG

ACACCCTGATGATCAGCAGAACCCCCGAGGTGACCTGCGTGGTGGTGGACGTGTCCC

AGGAGGACCCCGAGGTCCAGTTTAATTGGTACGTGGACGGCGTGGAAGTGCATAACGC

CAAGACCAAGCCCAGAGAGGAGCAGTTCGCCAGCACCTACAGAGTGGTGTCCGTGCT

GACCGTGCTGCACCAGGACTGGCTGAACGGCAAGGAATACAAGTGCAAGGTCTCCAA

CAAGGGCCTGCCTAGCAGCATCGAGAAGACCATCAGCAAGGCCAAGGGCCAGCCACG

GGAGCCCCAGGTCTGCACCCTGCCACCTAGCCAAGAGGAGATGACCAAGAACCAGGT

GTCCCTGAGCTGTGCCGTGAAAGGCTTCTATCCCAGCGATATCGCCGTGGAGTGGGAG

AGCAACGGCCAGCCCGAGAACAACTACAAGACCACCCCCCCTGTGCTGGACAGCGAC

GGCAGCTTCTTCCTGGTTTCCAAGCTGACCGTGGACAAGTCCAGATGGCAGGAGGGC

AACGTCTTCAGCTGCTCCGTGATGCACGAGGCCCTGCACAACCACTACACCCAGAAGT

CCCTGAGCCTGAGCCTGGGCAAG

λ light chain of CD3 arm:

SEQ ID NO. 76

EVQLVESGGGLVQPGGSLRLSCAASGFTFNTYAMNWVRKAPGKGLEWVGRIRSKYNNYA

TYYADSVKDRFTISRDDSKNSLYLQMNSLKTEDTAVYYCVRHGNFGNSYVSWFAYWGQG

TLVTVSSASTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRV

Nucleotide sequence:

SEQ ID NO. 77

GAGGTGCAGCTGGTTGAATCTGGCGGAGGACTGGTTCAGCCTGGCGGATCTCTGAGA

CTGTCTTGTGCCGCCAGCGGCTTCACCTTCAACACCTACGCTATGAACTGGGTCCGAA

AGGCCCCTGGCAAAGGACTGGAATGGGTGGGAAGAATCAGGTCCAAGTACAACAACT

ACGCCACCTACTACGCCGACAGCGTGAAGGACAGATTCACCATCAGCAGGGACGACA

GCAAGAACAGCCTGTACCTGCAGATGAACAGCCTGAAAACCGAGGACACCGCCGTGT

ACTACTGTGTCAGACACGGCAACTTCGGCAACAGCTATGTGTCTTGGTTTGCCTACTGG

GGCCAGGGCACACTGGTCACAGTTAGCTCTGCTAGCACCAAGGGCCCCAGCGTGTTCC

CCCTGGCCCCTTGCAGCAGAAGCACCAGCGAGAGCACAGCCGCCCTGGGCTGCCTGG

TGAAGGACTACTTCCCCGAGCCCGTGACCGTGTCCTGGAACAGCGGCGCTCTGACCA

GCGGCGTGCATACCTTCCCCGCCGTGCTCCAGAGCAGCGGACTGTACTCCCTGAGCAG

CGTGGTGACCGTGCCTTCCAGCAGCCTGGGCACCAAGACCTACACCTGCAACGTGGA

CCACAAGCCCAGCAACACCAAGGTGGACAAGAGAGTG

Heavy chain (heavy chain 2) of CD3 arm:

SEQ ID NO. 78

QAVVTQEPSLTVSPGGTVTLTCRSSTGAVTTSNYANWVQEKPGQAPRGLIGGTNKRAPWT

PARFSGSLLGGKAALTITGAQAEDEAEYYCVLWYSNLWVFGGGTKLTVLGQPKAAPSVT

LFPPSSEELQANKATLVCLISDFYPGAVTVAWKADSSPVKAGVETTTPSKQSNNKYAASSY

LSLTPEQWKSHRSYSCQVTHEGSTVEKTVAPTECSESKYGPPCPPCPAPEFEGGPSVFLFPP

KPKDTLMISRTPEVTCVVVDVSQEDPEVQFNWYVDGVEVHNAKTKPREEQFASTYRVVS

VLTVLHQDWLNGKEYKCKVSNKGLPSSIEKTISKAKGQPREPQVYTLPPCQEEMTKNQVS

-continued

LWCLVKGFYPSDIAVEWESNGQPENNYKTTPPVLDSDGSFFLYSKLTVDKSRWQEGNVFS

CSVMHEALHNHYTQKSLSLSLGK

Nucleotide sequence:

SEQ ID NO. 79

CAGGCTGTGGTCACACAAGAGCCTAGCCTGACAGTGTCTCCTGGCGGCACAGTGACC

CTGACCTGTAGATCTTCTACAGGCGCCGTGACCACCAGCAACTACGCTAATTGGGTGC

AGGAGAAGCCCGGCCAGGCTCCTAGAGGACTGATCGGCGGAACAAACAAGAGAGCC

CCTTGGACACCCGCCAGATTCTCTGGATCTCTGCTCGGCGGAAAGGCCGCTCTGACAA

TCACTGGTGCTCAGGCTGAGGACGAGGCCGAGTACTATTGTGTGCTGTGGTACAGCAA

CCTGTGGGTGTTCGGCGGAGGCACCAAACTGACAGTTCTGGGTCAGCCCAAGGCGGC

GCCCTCGGTCACTCTGTTCCCGCCCTCCTCTGAGGAGCTTCAAGCCAACAAGGCCACA

CTGGTGTGTCTCATAAGTGACTTCTATCCGGGAGCCGTGACAGTGGCCTGGAAGGCAG

ATAGCAGCCCCGTCAAGGCGGGAGTGGAGACCACCACACCCTCCAAACAAAGCAACA

ACAAGTACGCGGCCAGCAGCTACCTGAGCCTGACGCCTGAGCAGTGGAAGTCCCACA

GAAGCTACAGCTGCCAGGTCACGCATGAAGGGAGCACCGTGGAGAAGACAGTGGCCC

CTACAGAATGTTCAGAGAGCAAGTACGGCCCTCCCTGCCCCCCTTGCCCTGCCCCCGA

GTTCGAGGGCGGACCTAGCGTGTTCCTGTTCCCCCCCAAGCCCAAGGACACCCTGATG

ATCAGCAGAACCCCCGAGGTGACCTGCGTGGTGGTGGACGTGTCCCAGGAGGACCCC

GAGGTCCAGTTTAATTGGTACGTGGACGGCGTGGAAGTGCATAACGCCAAGACCAAGC

CCAGAGAGGAGCAGTTCGCCAGCACCTACAGAGTGGTGTCCGTGCTGACCGTGCTGC

ACCAGGACTGGCTGAACGGCAAGGAATACAAGTGCAAGGTCTCCAACAAGGGCCTGC

CTAGCAGCATCGAGAAGACCATCAGCAAGGCCAAGGGCCAGCCACGGGAGCCCCAGG

TCTACACCCTGCCACCTTGTCAAGAGGAGATGACCAAGAACCAGGTGTCCCTGTGGTG

TCTGGTGAAAGGCTTCTATCCCAGCGATATCGCCGTGGAGTGGGAGAGCAACGGCCAG

CCCGAGAACAACTACAAGACCACCCCCCCTGTGCTGGACAGCGACGGCAGCTTCTTC

CTGTACTCCAAGCTGACCGTGGACAAGTCCAGATGGCAGGAGGGCAACGTCTTCAGC

TGCTCCGTGATGCACGAGGCCCTGCACAACCACTACACCCAGAAGTCCCTGAGCCTGA

GCCTGGGCAAG

2. Expression and Purification of Anti-CD20×CD3 κλ Bispecific Antibodies

Figure 6:
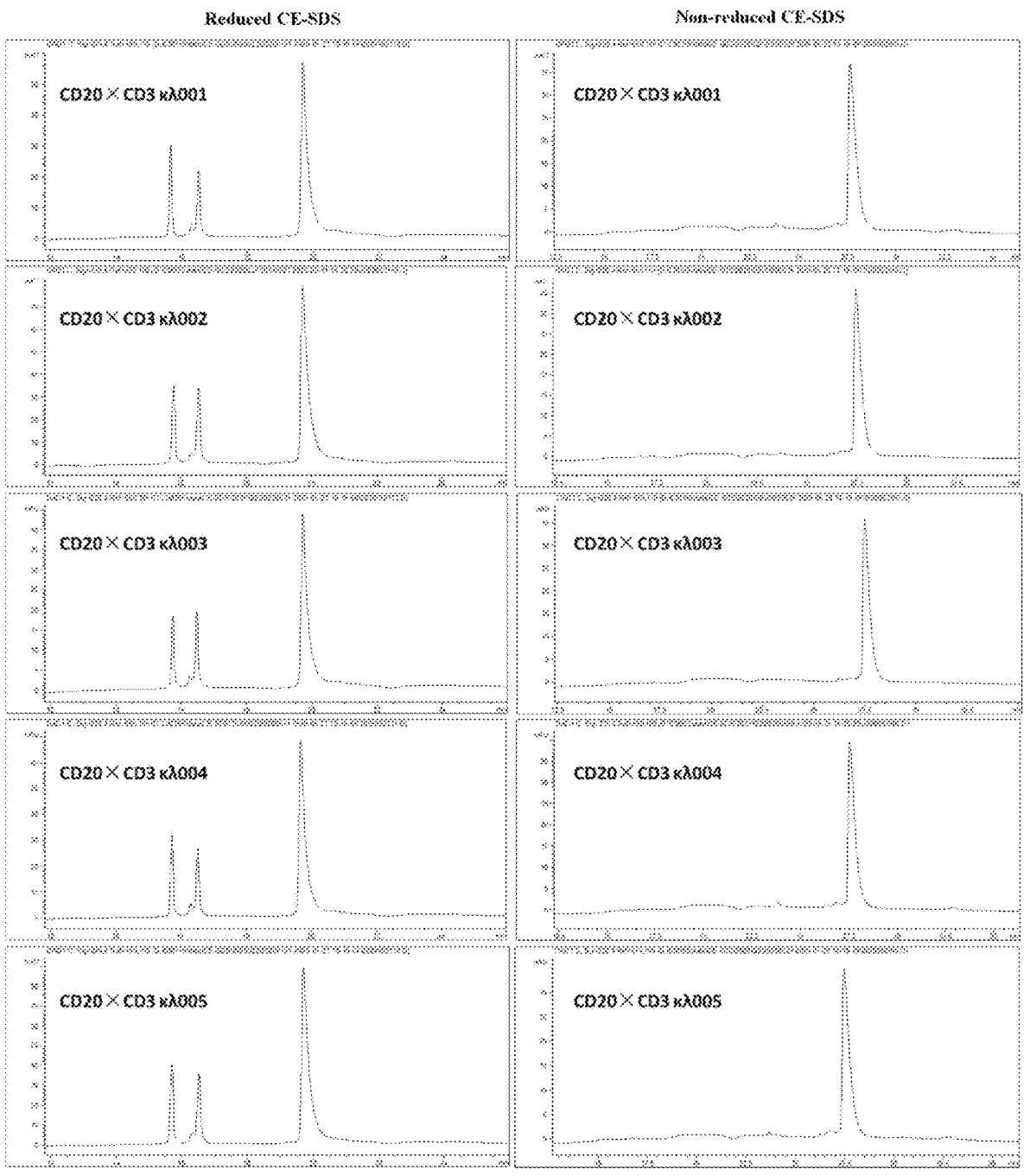
FIG. 6 shows the result of purification of Protein A of the anti-CD20×CD3 κλ bispecific antibody.

The plasmids encoding the corresponding antibody fragments were mixed with CD20 arm light chain: CD3 arm light chain: CD20 arm heavy chain (heavy chain 1): CD3 arm heavy chain (heavy chain 2)=2:2:1:1 ratio. After mixing with 3 mg/mL PEI, CHO-S cells were performed with co-transfect, culture in 500 mL CD CHO AGT medium (Gibco #12490-001) at 37° C., 5% C02, 150 rpm, and addition of 4% CHO Feed C+supplement (Gibco #A25031-05) at transient day 2, 4 and 6, respectively. When the cell viability decreased to about 85%, the fermentation broth was harvested, filtered and purified by Protein A affinity chromatography. With the anti-CD20×CD3 κλ bispecific antibody constructed on the basis of different light chain types, the monomer purity after one-step purification of Protein A was close to or higher than 90%, while the monomer purity of the control antibody CD20×CD3-crossFab was lower than 80% (Table 4), and the ratio of da, light chains was close to 1:1 (FIG. 6).

TABLE 4

Purity of anti-CD20 × CD3 κλ bispecific antibodies (SEC-HPLC)

| Bispecific antibody | SEC-HPLC(%) | | |
| --- | --- | --- | --- |
| | Mer | Monomer | Fragment |
| CD20 × CD3 κλ001 | 4.1 | 92.5 | 3.5 |
| CD20 × CD3 κλ002 | 4.6 | 90.8 | 4.5 |
| CD20 × CD3 κλ003 | 3.1 | 88.3 | 8.6 |
| CD20 × CD3 κλ004 | 4.8 | 91.1 | 4.0 |
| CD20 × CD3 κλ005 | 6.0 | 90.5 | 3.5 |
| CD20 × CD3-crossFab | 7.6 | 76.0 | 16.4 |

Figure 7:
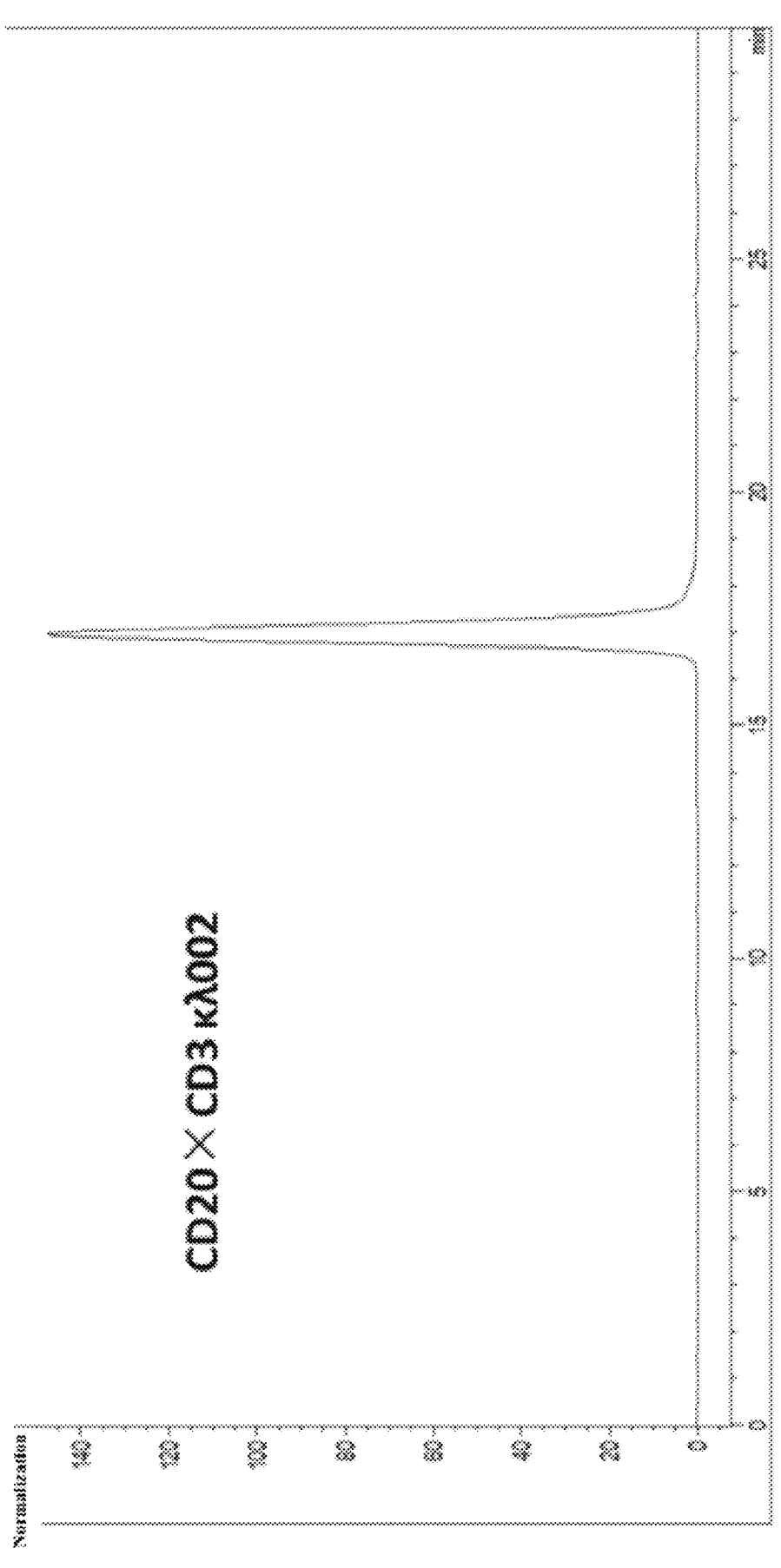
FIG. 7 shows the result of SEC-HPLC detection of the anti-CD20×CD3 κλ bispecific antibody.
Figure 8:
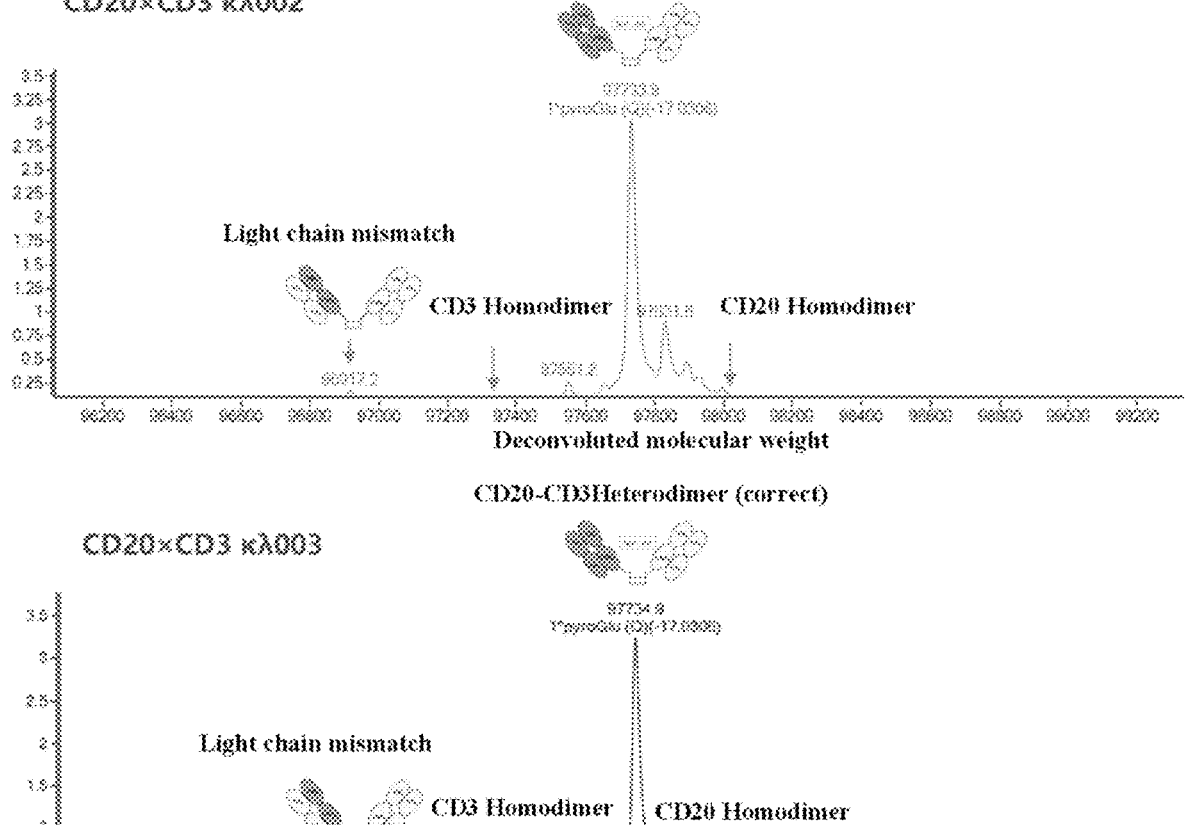
FIG. 8 shows detection results of homodimers of anti-CD20×CD3 κλ bispecific antibody.

The anti-CD20×CD3 κλ bispecific antibody was further purified by purification using Capto S ImpAct ion exchange chromatography, eluting through a 50-300 mM NaCl, 50 mM phosphate, pH6.4 gradient, pooling the elution peaks and showing greater than 99% SEC-HPLC monomer content (FIG. 7). In the purified samples of CD20×CD3 κλ002 and CD20×CD3 κλ003, the light chain mismatch ratio was very low (≤1%) and no CD3 homodimers or CD20 homodimers were detected (FIG. 8).

3. Binding Activity of Anti-CD20×CD3 κλ Bispecific Antibodies

The affinity of the bispecific antibody CD20 antigen arm was determined by measuring binding to CD20 over-expressing stably transfected cells or CD20+tumor cells, respectively, and the affinity of the bispecific antibody CD3 arm was determined by measuring binding to CD3 recombinant antigen, Jurkat cells, or freshly isolated peripheral blood T-cells. The results showed that the affinity of the novel anti-CD20×CD3×bispecific antibody to tumor cells was about 3-5 times higher than that to T-cells. The positive control antibody bsAB1 was synthesized and expressed as described in US20170174781.

Figure 9:
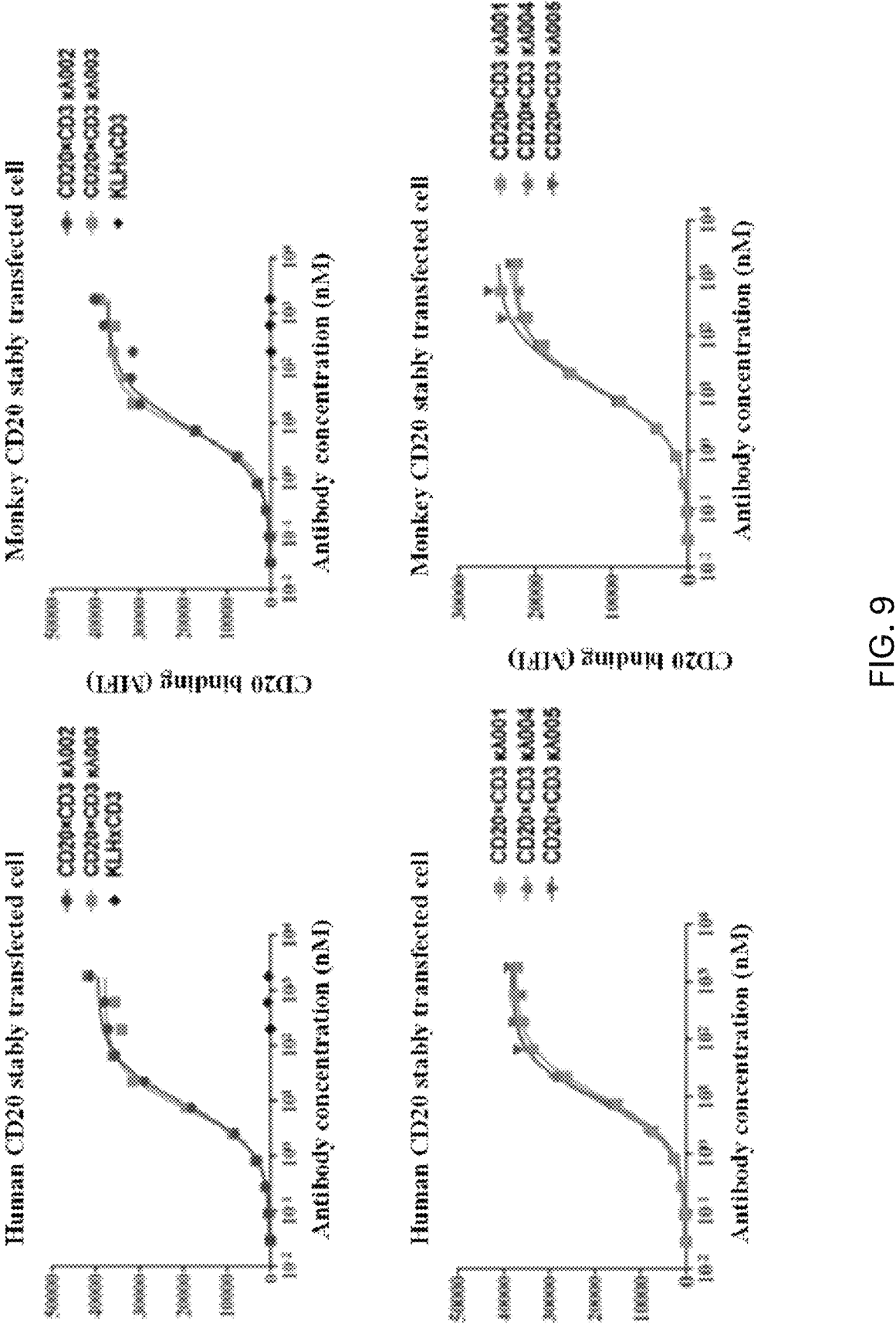
FIG. 9 shows binding of the anti-CD20×CD3 κλ bispecific antibody to a CD20 stably transfected cell.
Figure 10:
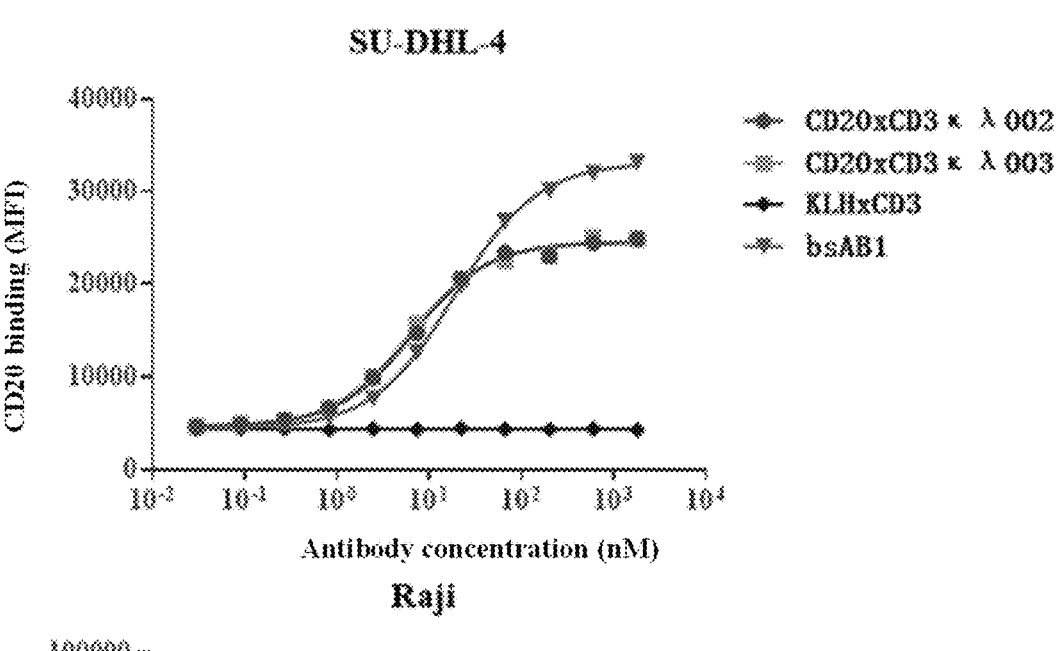
FIG. 10 shows binding of the anti-CD20×CD3 κλ bispecific antibody to tumor cells SU-DHL-4, Raji and NALM-6.
Figure 10:
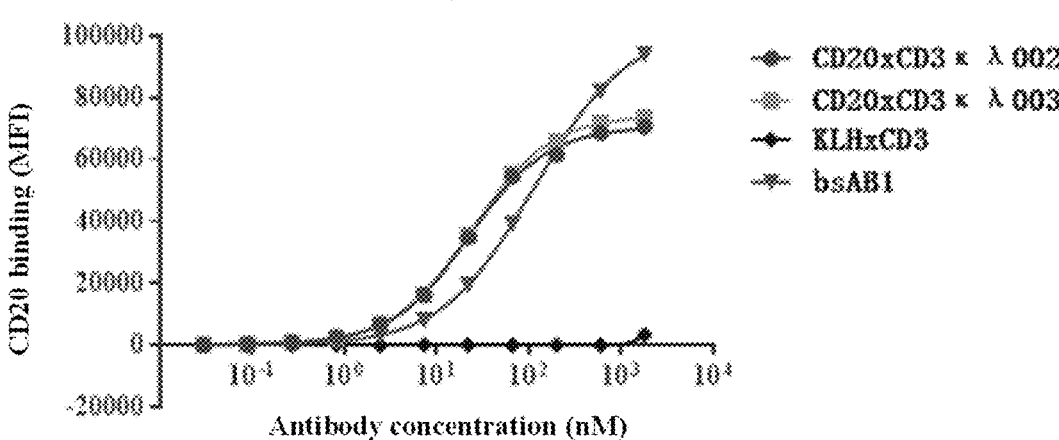
Figure 10:
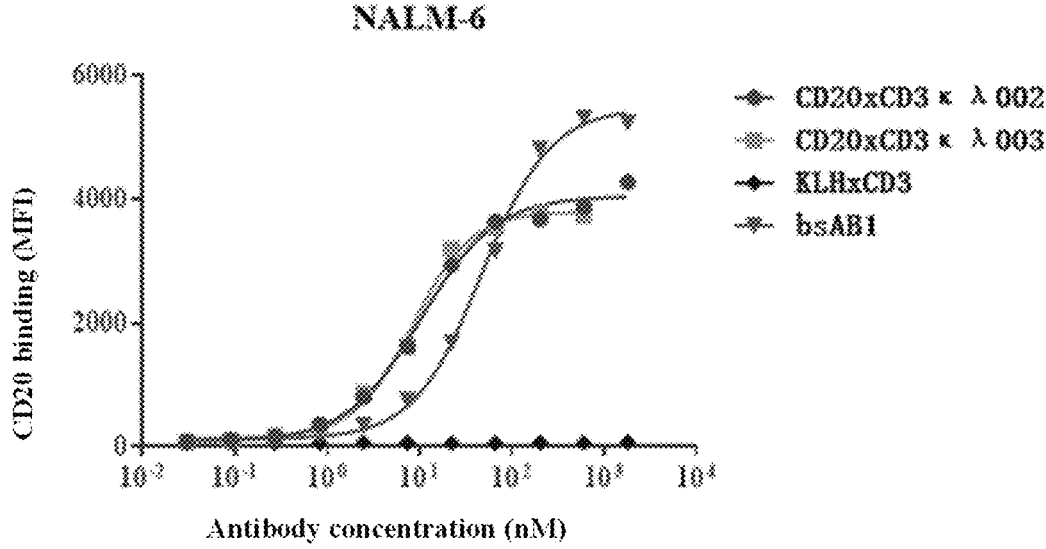

(1) Binding of Anti-CD20×CD3 κλ Bispecific Antibodies to Human and Cynomolgus Monkey CD20 Stably Transfected Cells CHO-human CD20 and CHO-cynomolgus monkey CD20 stably transfected cells prepared in Example 1 in logarithmic growth phase were adjusted to $5 \times 10^5$ cells/ml with 4% calf serum (Hyclone, SH30626.06), 100 W/well cell suspension was added to 96-well U-plate, 300 g thereof was centrifuged for 5 min, the supernatant was discarded, and 100 μL of gradient diluted antibody (with starting concentration of 1800 nM, 3-fold dilution, 10 gradients) was added to each well and incubated at 4° C. for 60 min. 50 μL/well Alexa Fluro647 labeled goat anti-human IgG Fc (1: 300 dilution) was added to the secondary antibody and incubated on ice for 20 min. After washing once, 50 μL/well propidium iodide (PI) solution (1: 300) was added, incubated for 5 min, and performed with detection by flow cytometry. FIG. 9 and Table 5 show that the anti-CD20×CD3 κλ bispecific antibody binds with high affinity to the cellular CD20 receptor with comparable affinity on human and cynomolgus monkey CD20 stably transfected cells.

TABLE 5

| Binding of anti-CD20 × CD3 κλ bispecific antibodies to CD20 stably transfected cells. | | |
| --- | --- | --- |
| $EC_{50}$ | Human CD20-CHO | Cynomolgus monkey CD20-CHO |
| CD20 × CD3 κλ001 | 10 nM | 12 nM |
| CD20 × CD3 κλ002 | 9 nM | 8 nM |
| CD20 × CD3 κλ003 | 7 nM | 8 nM |
| CD20 × CD3 κλ004 | 8 nM | 10 nM |
| CD20 × CD3 κλ005 | 9 nM | 14 nM |
| KLH × CD3 | — | — |

"—": not combined with (2) Binding of Anti-CD20×CD3 κλ Bispecific Antibody to Human CD20+Tumor Cells The SU-DHL-4, Raji and NALM-6 cells were taken in logarithmic growth phase, added with 200 g/mL murine IgG (Jackson ImmunoResearch, 115-005-03) to ice bath for blocking for 30 min, the cells were adjusted to $5 \times 105$ cells/mL with 4% calf serum, and 100 μL/well was added to 96-well U-plate, 300 g was centrifuged for 5 min, discarding the supernatant. 100 μL/well of gradient diluted antibody (initial concentration: 1800 nM, 3-fold dilution, 10 gradients) was added, and incubated at 4° C. for 60 min. The primary antibody was washed off, 50 μL/well Alexa Fluro647-labeled goat anti-human IgG Fc (1: 300 dilution) was added and incubated on ice for 20 min. 50 μL/well PI was added after washing once, incubated for 5 min, and detected with flow cytometer. The results are shown in FIG.

10 and Table 6. The anti-CD20×CD3 κλ bispecific antibody binds with high affinity to CD20+tumor cells SU-DHL-4, Raji and NALM-6.

(3) Binding of Anti-CD20×CD3 κλ Bispecific Antibody to Jurkat Cells

Figure 11:
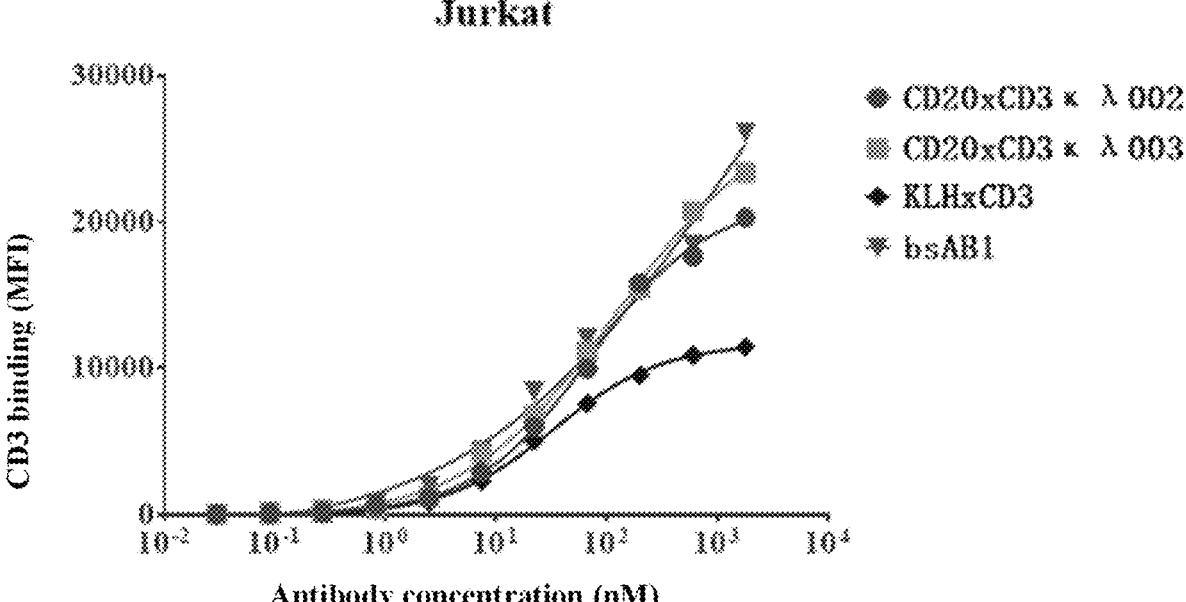
FIG. 11 shows binding of the anti-CD20×CD3 κλ bispecific antibody to a Jurkat cell.

Jurkat cells in logarithmic growth phase were added with 200 μg/mL murine IgG (Jackson ImmunoResearch, 115-005-03) and incubated on ice for 30 minutes. The cells were adjusted to $5 \times 105$ cells/mL with 4% calf serum, 100 μL/well was added to 96-well U-plate, 300 g was centrifuged to removed the supernatant, 100 μL/well of gradient diluted antibody (initial concentration: 1800 nM, 3-fold dilution, 10 gradients) was added and incubated at 4° C. for 60 min. 50 μL/well Alexa Fluro647-labeled goat anti-human IgG Fc (1: 300 dilution) was added to the secondary antibody and incubated on ice for 20 min. 50 μL/well PI was added after washing once, incubated for 5 min, and detected with flow cytometer (BD C6). As shown in FIG. 11 and Table 6, the anti-CD20×CD3 κλ bispecific antibody binds with moderate affinity to human leukemia T-cell line Jurkat cells with an $EC_{50}$ of about 71-120 nM, which is about 10-fold lower than the binding of the CD20 antigen arm to the CD20 receptor.

Figure 12:
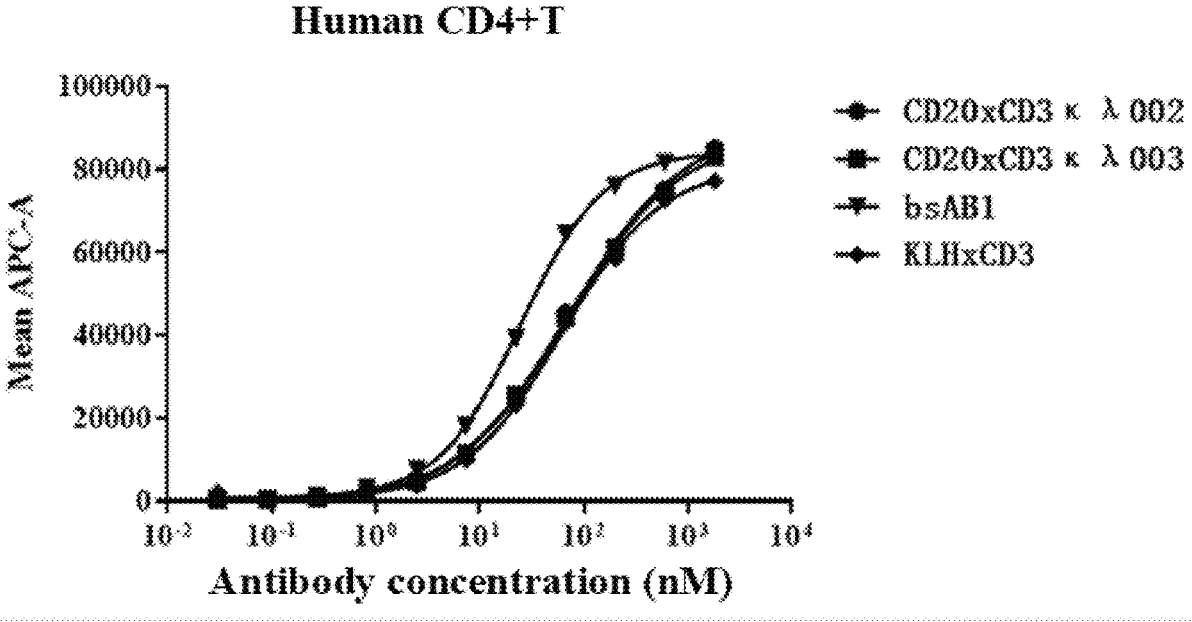
FIG. 12 shows binding of the anti-CD20×CD3 κλ bispecific antibody to a T-cell in peripheral blood.
Figure 12:
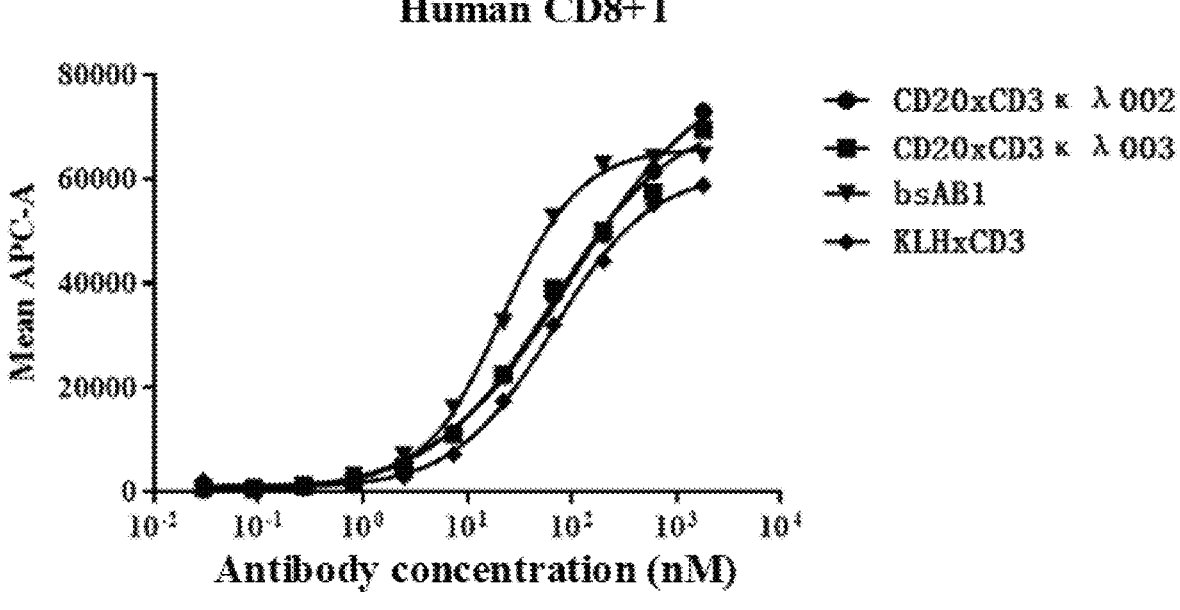

(4) Binding of Anti-CD20×CD3 lck Bispecific Antibody to Human Peripheral Blood T-Cells Human fresh peripheral blood was taken and PBMC was isolated by Ficoll.Paque Plu (GE, 17-1440-03). PBMC was adjusted to $5 \times 10^5$ cells/mL with 4% calf serum (Hyclone, SH30626.06), 100 μL/well was added to a 96-well U-plate, the supernatant was centrifuged off and 100 μL of gradient diluted antibody (with starting concentration of 1800 nM, 3-fold dilution, 10 gradients) was added to each well and incubated for 60 min at 4° C. 50 μL/well of Alexa Fluro647 labeled goat anti-human IgG Fc (1: 300 dilution) was added to the secondary antibody, with ice bath for 20 min, and 50 μL/well PI added after washing once, incubated for 5 min, and flow cytometer (BD C6) was used for detection. The detection results are shown in FIG. 12 and Table 6. The anti-CD20×CD3 κλ bispecific antibody recognizes human peripheral blood CD4+T and CD8+T-cells, has an affinity of about 65-98 nM with human T-cells, is weaker than the binding force of CD20 antigen arm with CD20 receptor by about 10 times, and favors the preferential enrichment of the bispecific antibody to tumor cells.

TABLE 6

| Binding capacity (nM) of anti-CD20 × CD3 κλ bispecific antibodies to human cells | | | | | |
| --- | --- | --- | --- | --- | --- |
| $EC_{50}$ (nM) | SU-DHL-4 | Raji | NALM-6 | Jurkat | CD4T | CD8T |
| CD20 × CD3 κλ002 | 7 | 23 | 10 | 71 | 73 | 98 |
| CD20 × CD3 κλ003 | 6 | 25 | 8 | 120 | 69 | 65 |
| bsAB1 | 19 | 115 | 48 | ND | 25 | 22 |
| KLH × CD3 | — | — | — | 33 | 62 | 65 |

ND: not saturated at high concentration

4. TDCC Mediated by Anti-CD20×CD3 κλ Bispecific Antibody

Figure 13A:
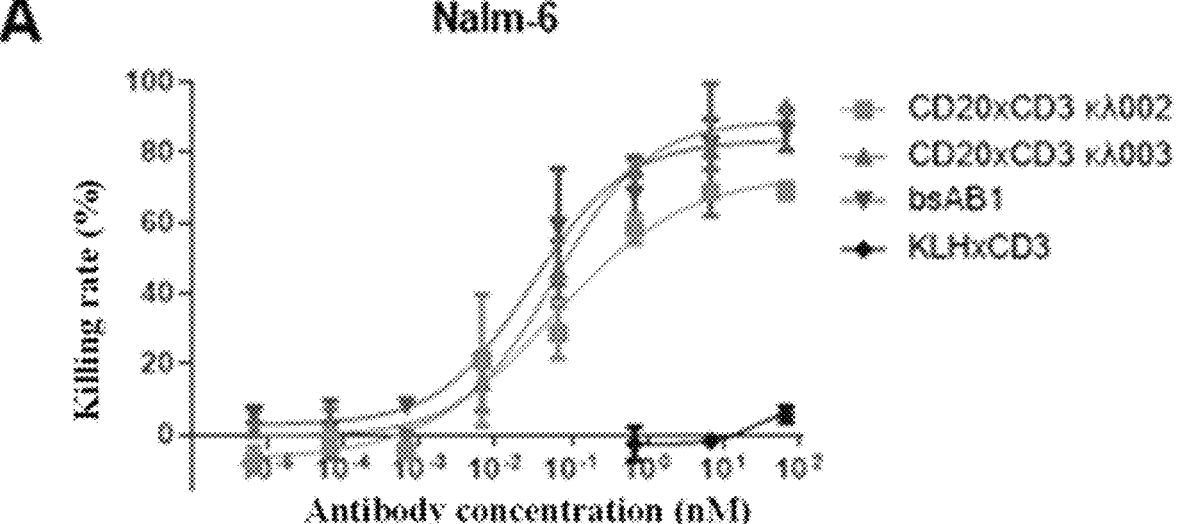
FIG. 13A and FIG. 13B show T-cell dependent cellular cytotoxicity (TDCC) mediated by anti-CD20×CD3 κλ bispecific antibody.
Figure 13B:
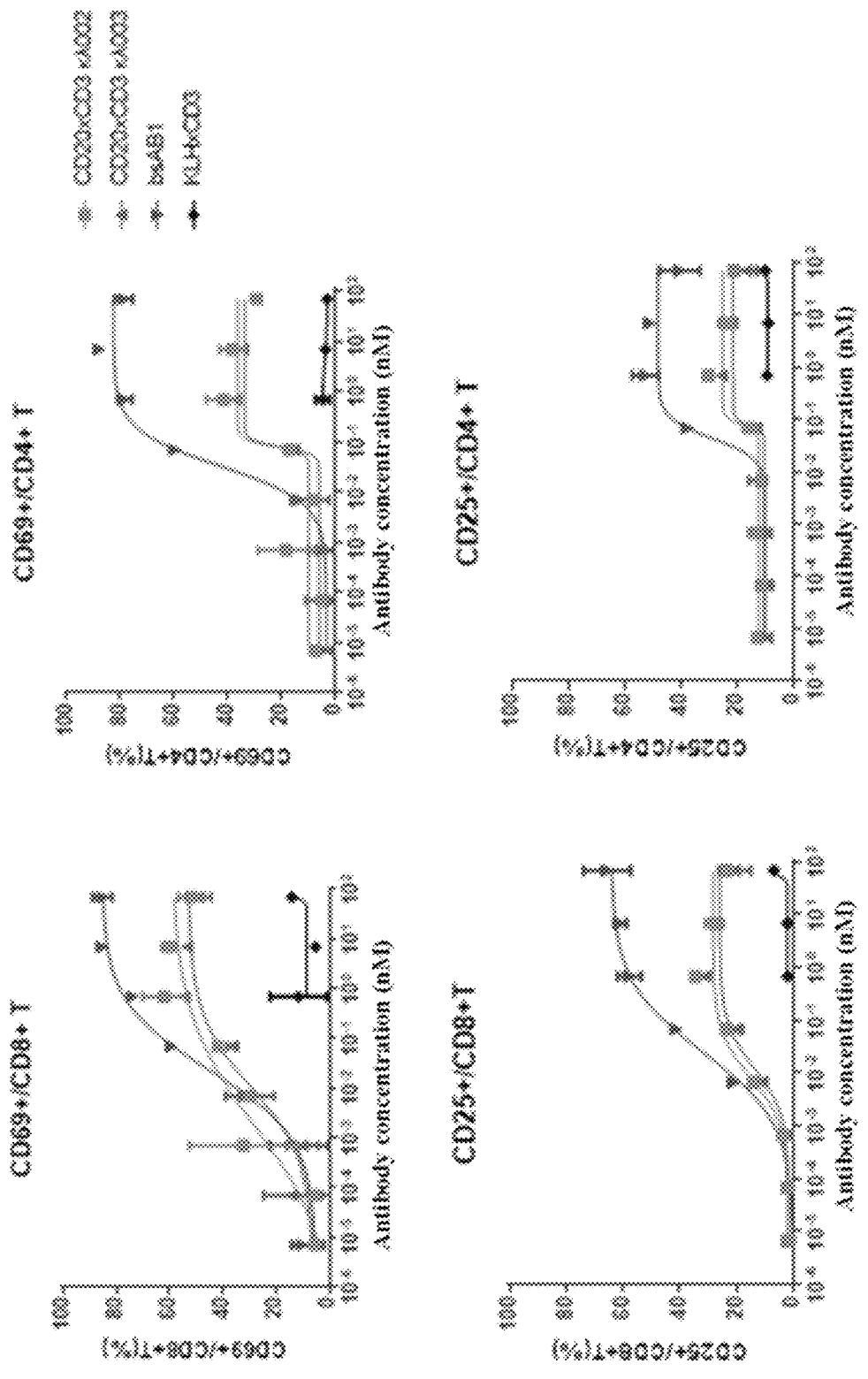
Figure 14A:
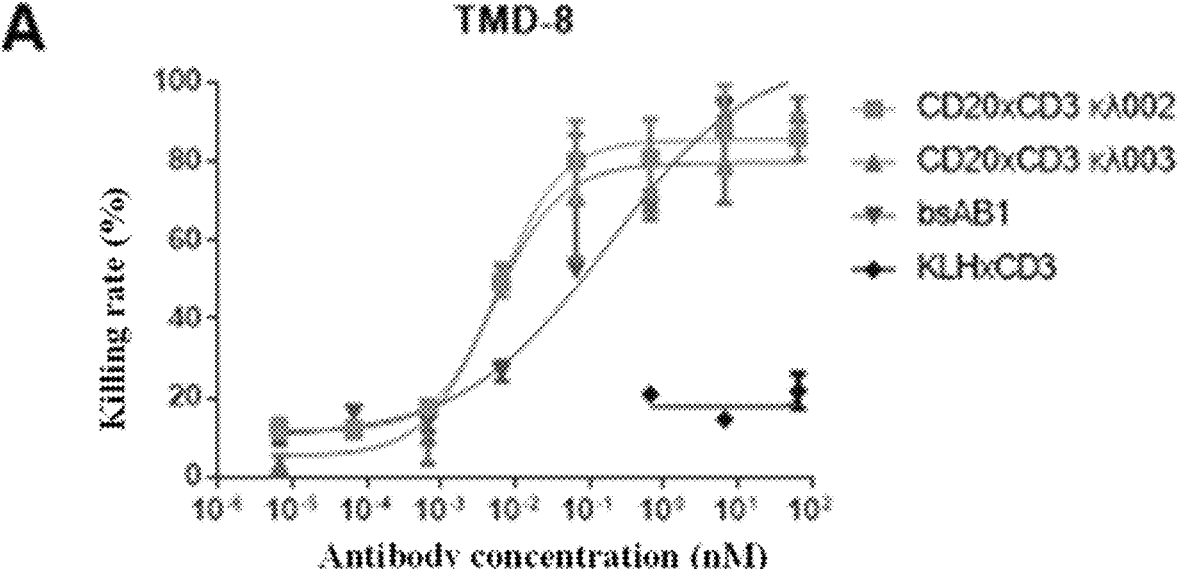
FIG. 14A and FIG. 14B show TDCC mediated by anti-CD20×CD3 κλ bispecific antibody.
Figure 14B:
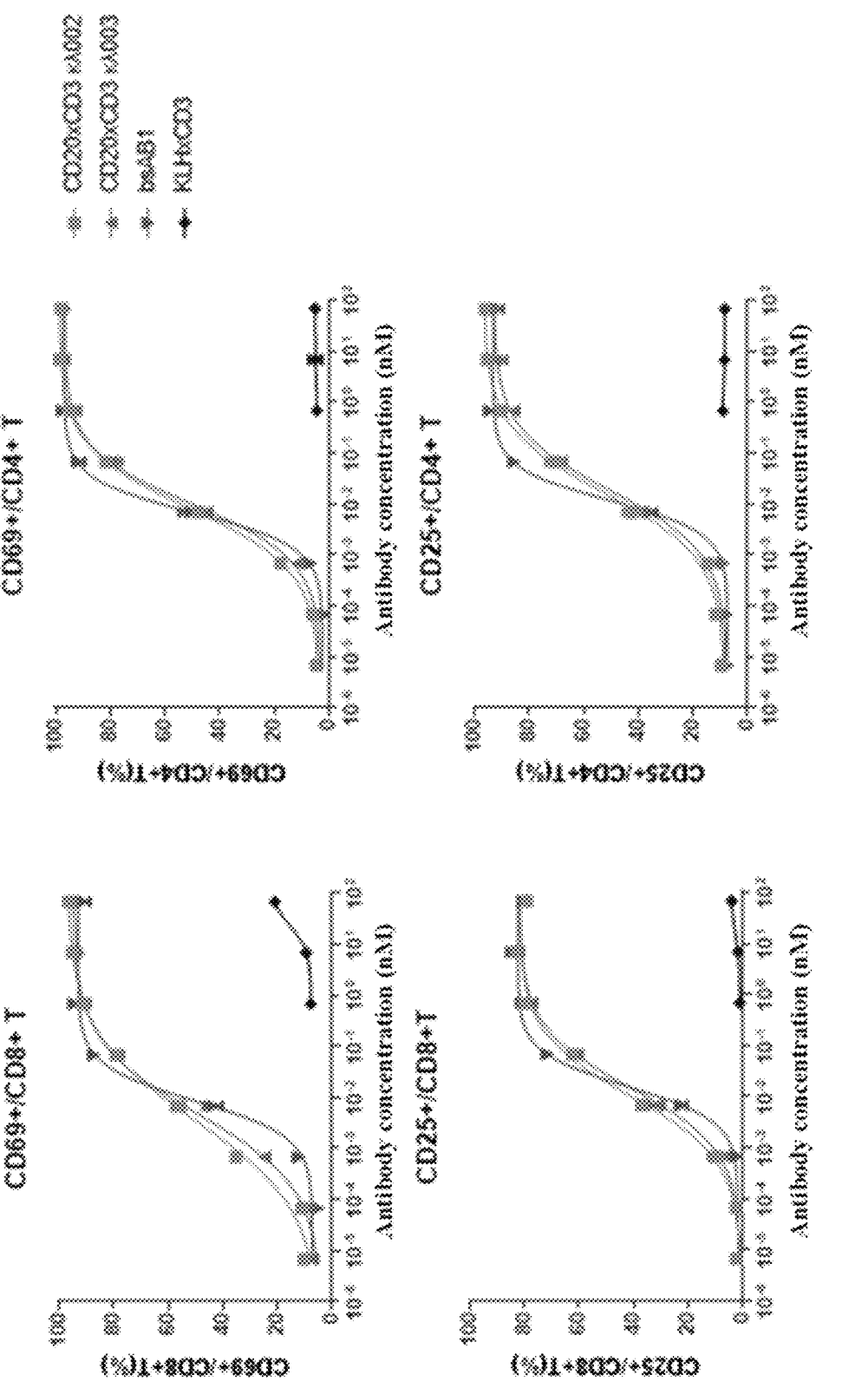
Figure 15A:
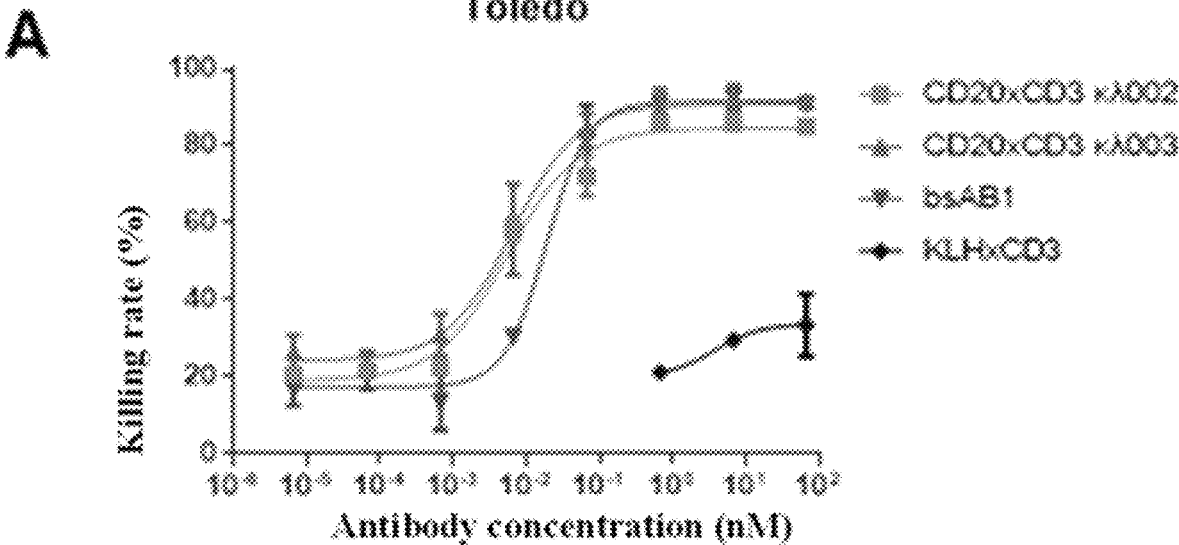
FIG. 15A and FIG. 15B show TDCC mediated by anti-CD20×CD3 κλ bispecific antibody.
Figure 15B:
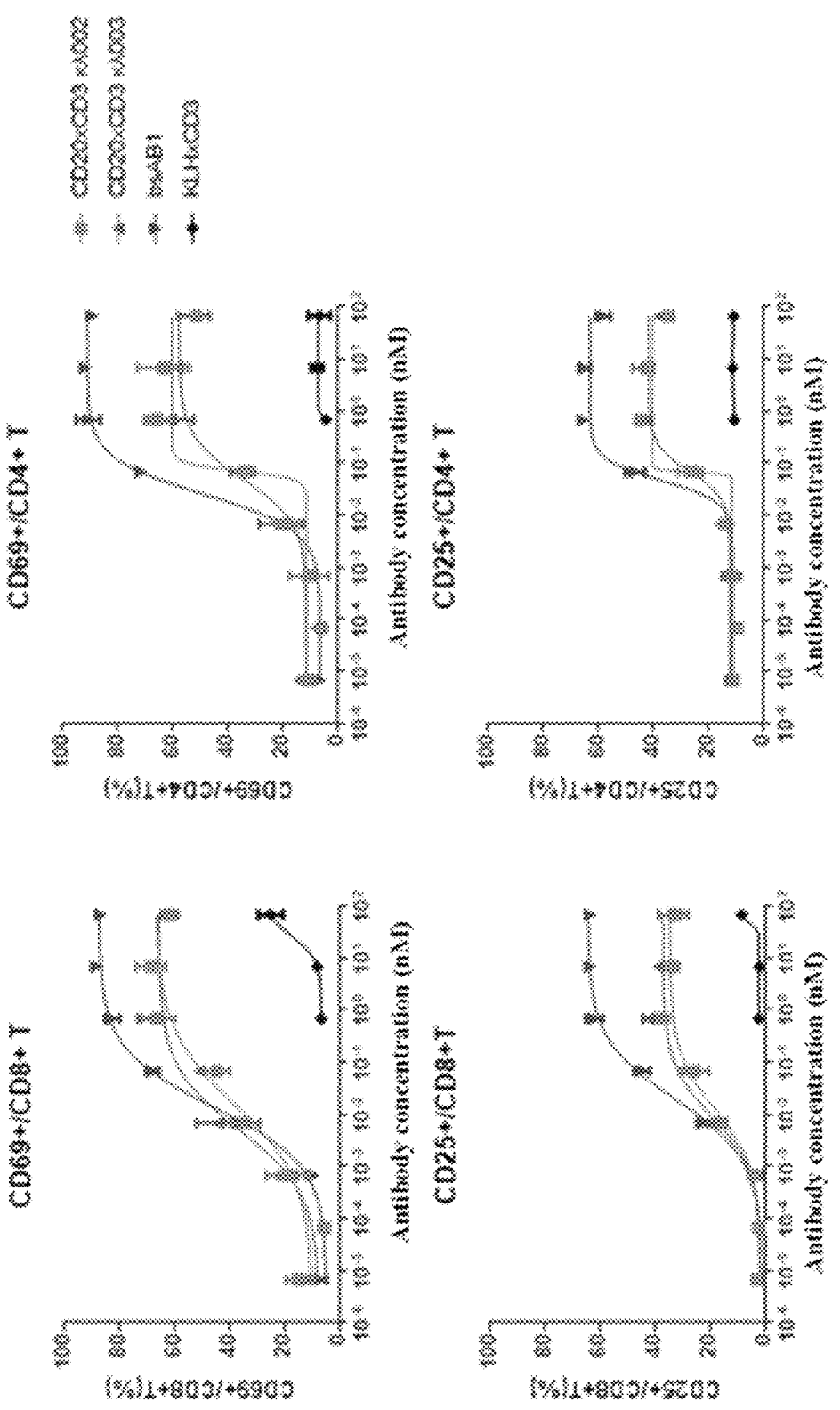
Figure 16:
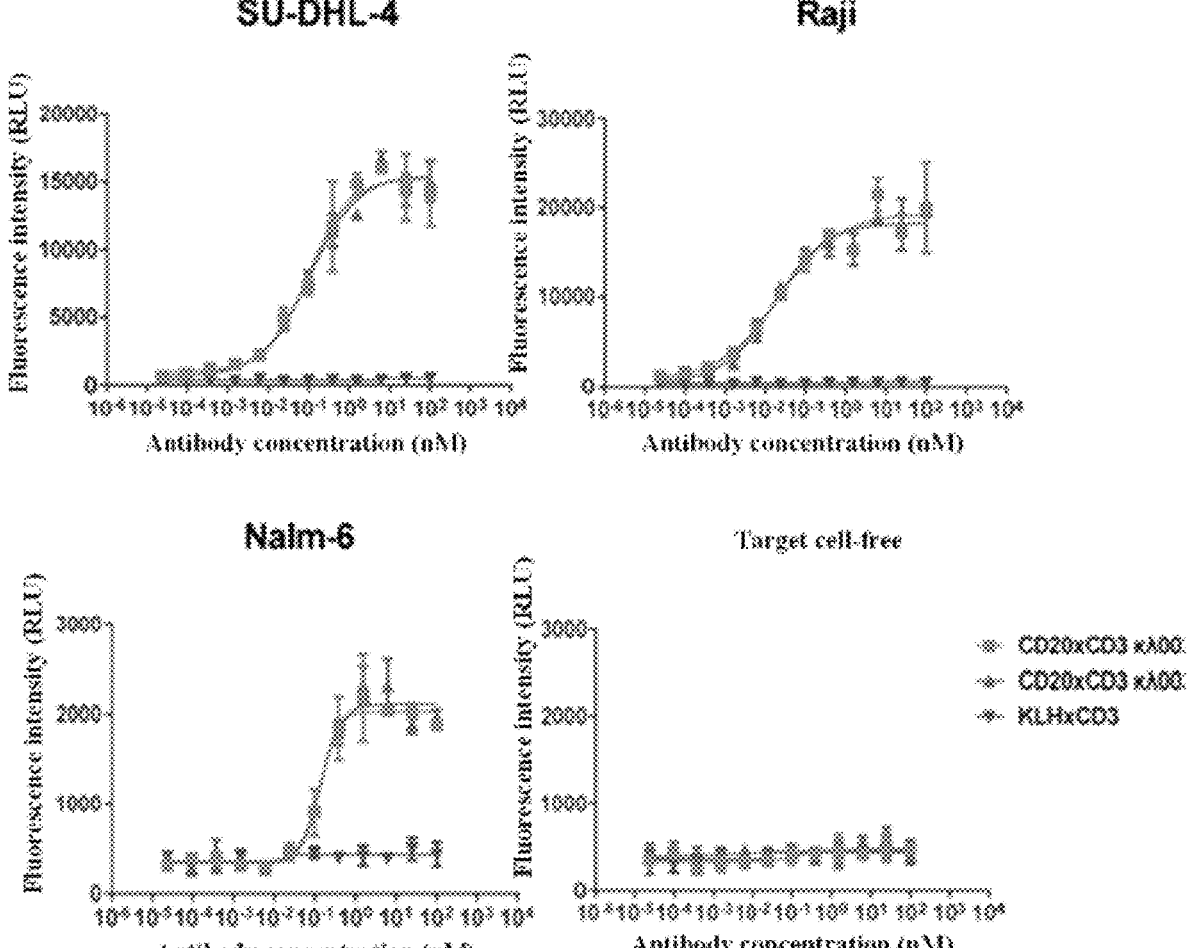
FIG. 16 shows effect of anti-CD20×CD3 κλ bispecific antibody on the T-cell NFAT signaling pathway.

Freshly isolated PBMC was mixed with target cells NALM-6, TMD-8 and Toledo cells in logarithmic growth phase, with effect/target cell=8: 1, respectively. 50 μL of gradient diluted antibody (antibody concentration from 66.7 nM, 10-fold dilution, 7 gradients) was added to each well, and incubated for 24 h at 37° C. in 5% $CO_2$. At the end of the incubation, 50 μL of the supernatant was transferred to a new black elisa plate, 50 μL/well of LDH detection substrate was added, the reaction was stopped after 10 minutes and LDH release was detected. The remaining cells in the wells were washed twice with 4% calf blood, incubated with 100 μg/mL human IgG for 10 minutes, followed by T-cell activation detection antibodies (CD25-PE, CD4-APC, CD69-FITC and CD8-APC) and incubated on ice for 20 minutes. The supernatant was washed and discarded, 60 μL/well PI was added, incubated on ice for 5 minutes and detected by flow cytometry. FIGS. 13A, 13B show the killing of human B-lymphoblastic leukemia cells Nalm-6 by the anti-CD20×CD3 κλ bispecific antibody and the activation of T-cells, respectively. FIGS. 14A, 14B show killing of TMD-8 cells and activation of T-cells by the anti-CD20× CD3×bispecific antibody, respectively. FIGS. 15A, 15B show killing of Toledo cells and activation of T-cells by a CD20×CD3×bispecific antibody, respectively. For tumor cells Nalm-6, TMD-8 and Toledo with different CD20 expression levels, both CD20×CD3κλ.002 and CD20× CD3κλ.003 could mediate effective killing of T-cells, with killing activity comparable to or slightly stronger than that of control antibody bsAB1, and the activation of T-cells was milder than the latter. 5. Activation of T-cell activation pathway by anti-CD20×CD3 κλ bispecific antibody Logarithmically growing Jurkat-NFAT-luc reporter cells and CD20-positive target cells (SU-DHL-4, raji and NALM-6 cells) were taken, centrifuged, with the supernatant discarded and resuspended to $2\times10^6$ cells/ml. 50 μl/well of the target cells were inoculated into a 96-well plate, the supernatant was discarded by centrifugation at 300 g for 5 minutes, and 50 μl/well of the Jurkat-NFAT-luc reporter cells were inoculated into a 96-well plate, and 50 μl of gradient-diluted CD20×CD3×bispecific antibody or control antibody KLH×CD3 (initial concentration of 20 g/ml, 10-fold dilution, 10 gradients) was added to each well, and incubated at 37° C. for 6 hours in 5% $CO_2$. After the incubation, 100 μL of detection reagent was added to each well according to ONE-Glo Luciferase Assay System instructions, allowed to stand at room temperature for 3 minutes, and detected on a microplate reader (Biotek Synergy HT). The detection results are shown in FIG. 16 and Table 7. The CD20×CD3× bispecific antibody can activate the NFAT signaling pathway of T-cells when tumor cells with different CD20 expression levels are used as target cells.

TABLE 7

Activation of the T-cell NFAT pathway by
the anti-CD20 × CD3 κλ bispecific antibody.

| EC$_{50}$(nM) | SU-DHL-4 | Raji | NALM-6 |
|---|---|---|---|
| CD20 × CD3 κλ002 | 0.10 | 0.02 | 0.14 |
| CD20 × CD3 κλ003 | 0.11 | 0.02 | 0.14 |
| KLH × CD3 | — | — | — |

6. Binding of Anti-CD20×CD3 κλ Bispecific Antibodies to Fcγ Receptors

50Mg/ml of His-Tag antibody was amino-conjugated to a CM5 chip to capture the His-tagged FcγRI, FcγRIIA$_{H131}$ and FcγRIIIA$_{V158}$ recombinant proteins (Sino Biological, #10256-H08H/10374-H08H1/10389-H08H1), respectively, with a capture time of 40 seconds and a flow rate of 10 μL/min. After baseline plateau, the gradient diluted antibody (with starting concentration of 37.5 μg/mL, 2-fold dilution) was flowed through the chip at a flow rate of 30 μL/min, with an association time of 120 seconds and a dissociation time of 200 seconds, and affinity constants were obtained by fitting with Biacore evaluation software. As can be seen from Table 8, the CD20×CD3×bispecific antibody did not bind to FcγRI, FcγRIIA$_{H131}$ and FcγRIIIA$_{V158}$; the wild-type IgG4 control antibody bound FcγRI with high affinity and weakly bound to FcγRIIA$_{H131}$.

TABLE 8

Affinities of anti-CD20 × CD3 κλ bispecific antibodies to Fcγ receptors

| KD | FcγRI | FcγRIIA$_{H131}$ | FcγRIIIA$_{V158}$ |
|---|---|---|---|
| CD20 × CD3 κλ002 | Not combined | Not combined | Not combined |
| CD20 × CD3 κλ003 | Not combined | Not combined | Not combined |
| IgG4 isotype control | 14 nM | Weak | Not combined |

7. Immune Reconstitution of Subcutaneous Raji Tumor Model in Mice

Figure 17:
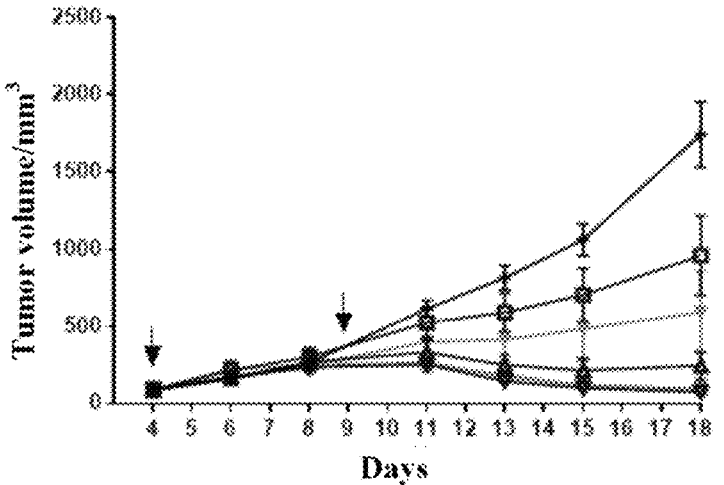
FIG. 17 shows inhibitory effect of the anti-CD20×CD3 κλ bispecific antibody in a xenograft model of mouse Raji with immune reconstitution.
Figure 17:
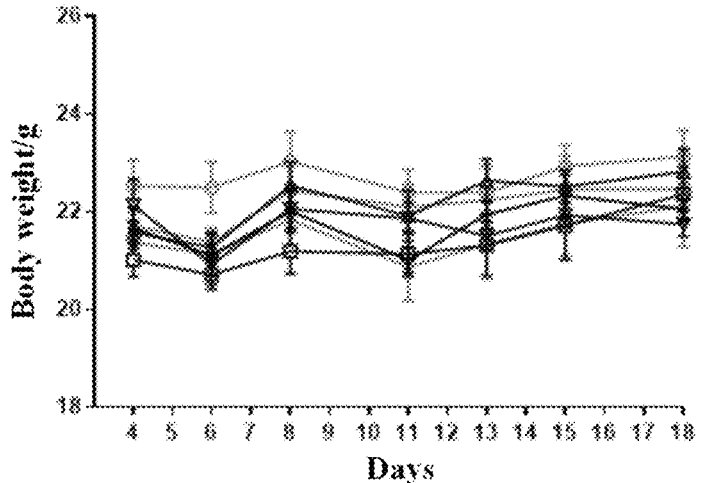

Six to eight-week-old female B-NGD mice (Bio-Tech Co. Ltd.) were subcutaneously inoculated with $3\times10^6$ Raji cells. When the tumors grew to 60 mm$^3$, they were randomly divided into treatment group 3.0 mg/kg, treatment group 0.6 mg/kg, treatment group 0.12 mg/kg and a negative control group with KLH×CD3 of 3 mg/kg. Each mouse received 1×107 PBMC cells via tail vein injection. Three days later, the first dose was administered to the mouse once every 5 days for a total of 3 doses. The tumor volume and body weight of the mice were monitored. At the end of the experiment, the mice were killed by cervical dislocation and the tumors were collected and weighed. The results are shown in FIG. 17. The in vivo efficacy of anti-CD20×CD3 κd. bispecific antibody was dose-related, with tumor inhibition rates of 82% and 89% at medium and high doses, respectively. The tumor-bearing mice tolerated the foregoing doses well, without weight loss and other adverse reactions.

Figure 18:
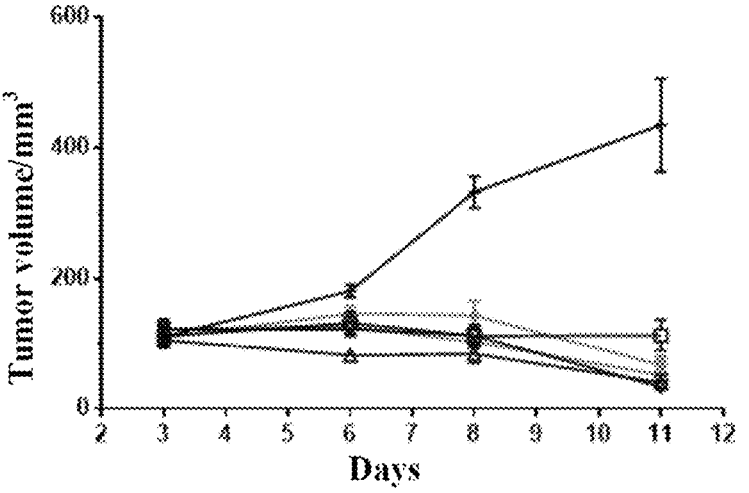
FIG. 18 shows inhibitory effect of the anti-CD20×CD3 κλ bispecific antibody in a subcutaneous tumor model grafted by a mixture of murine Raji and human PBMC in immunodeficient mice.
Figure 18:
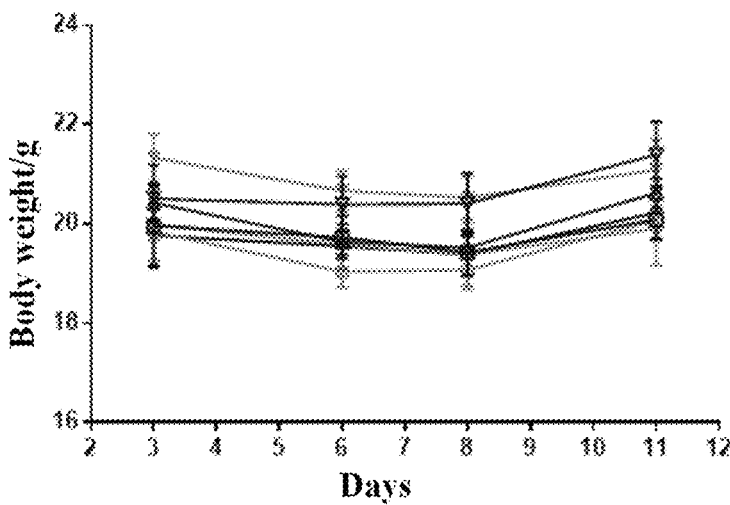

8. Subcutaneous Tumor Model Grafted by a Mixture of Murine Raji and Human PBMC in Immunodeficient Mice 6-8 week female B-NGD mice (Bio-Oracle Bio-Tech Co. Ltd.) were selected, Raji ($3\times10^6$) and human PBMC ($5\times10^6$) were mixed and inoculated subcutaneously. When the tumor volume reaches 60-100 mm$^3$, they were randomly divided into groups. The dose groups were respectively set as dose group of 3.0 mg/mL, dose group of 0.6 mg/mL, dose group of 0.12 mg/mL and negative control group of KLH x CD3 of 3 mg/kg. The dosing interval was once every 5 days for a total of 2 doses. The tumor volume and body weight of the mice were monitored. At the end of the experiment, the mice were killed by cervical dislocation and the tumors were collected and weighed. The results are shown in FIG. 18. The in vivo efficacy of anti-CD20×CD3 κλ. bispecific antibody was dose-related, with tumor inhibition rates of 65%, 98% and 162% at low, medium and high doses, respectively. The tumor was completely inhibited or subsided in high and medium dose groups.

9. Efficacy of Anti-CD20×CD3 κλ Bispecific Antibody in Cynomolgus Monkeys

Figure 19:
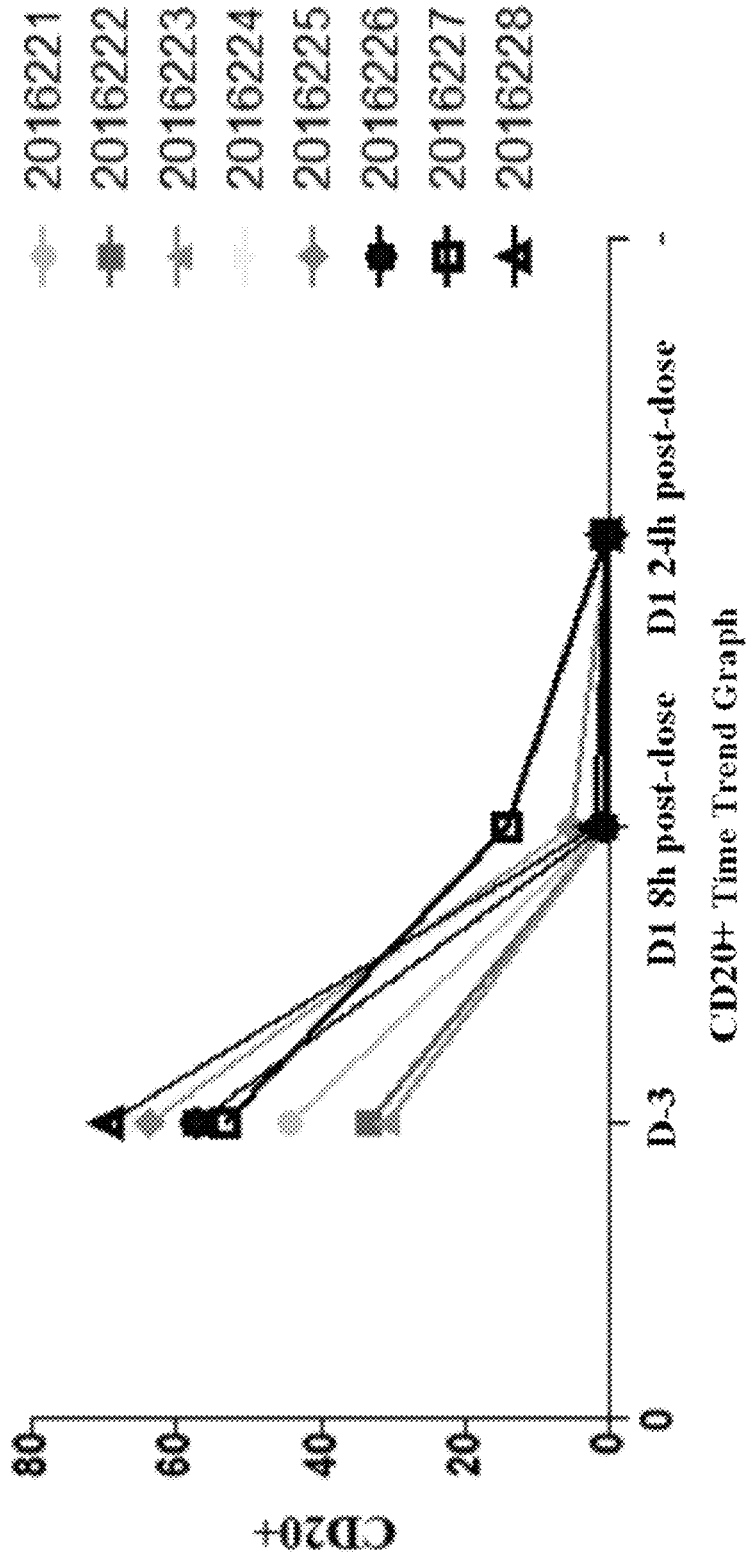
FIG. 19 shows efficacy of the anti-CD20×CD3 κλ bispecific antibody in a cynomolgus monkey.

Eight cynomolgus monkeys were assigned to 4 dose groups, each dose group consisted of 2 monkeys, half males and half females. Each dose group received doses of 0.3, 1 and 3 mg/kg (once a week for 3 weeks, a total of 4 doses) and 1 mg/kg (single dose) of CD20×CD3 κλ002 bispecific antibody. See Table 9 for dosing schedule. During the administration period and recovery period, all monkeys in each group were in good general condition, without toxic reaction or death or moribund. No significant abnormal change in body temperature was observed in each dose group, and lead II ECG waveform was normal. There was no significant abnormality in heart rate, R-R interval, P-R interval, QT interval, QRS time limit, systolic blood pressure and diastolic blood pressure. Changes in the number of B and T-cell populations in peripheral blood were analyzed by flow cytometry at various time points after administration, with B cells identified using the cell surface marker CD20 (CD20+cells) and T-cells identified using CD3 (CD3+ cells). B cells were rapidly cleared from peripheral blood at 8 hours post-dose and were below the lower detection limit at 24 hours (FIG. 19).

TABLE 9

CD20 × CD3 κλ bispecific antibody dosing regimen

| Group | Dose | Route and frequency of administration | Gender | Animal Number |
|---|---|---|---|---|
| Low dose group | 0.3 mg/kg | IV, one time per week/3 weeks, D1, D8, D15, D22 | Male<br>Female | 2016221<br>2016222 |
| Medium dose group | 1 mg/kg | IV, one time per week/3 weeks, D1, D8, D15, D22 | Male<br>Female | 2016223<br>2016224 |
| High dose group | 3 mg/kg | IV, one time per week/3 weeks, D1, D8, D15, D22 | Male<br>Female | 2016225<br>2016226 |
| Medium dose group | 1 mg/kg | IV, Single dose on D1 | Female<br>Male | 2016227<br>2016228 |

Example 3: Construction of BCMA×CD3 κλ Bispecific Antibodies Formed by Different Types of Light Chains 1. Construction of BCMA×CD3 κλ Bispecific Antibody A novel BCMA-CD3 κλ humanized bispecific antibody having the native IgG configuration was constructed with a κ light chain-containing BCMA humanized antibody, and a, light chain-containing humanized CD3 antibody, with reference to example 2, while charge variants are introduced in the BCMA antigen arm and the CD3 arm($V\kappa_{BCMA}$: $Gln_{42}Lys$; $V_{HBC}MA$: $Gln_{39}Glu$; $V/\lambda_{CD3}$: $Gln_{40}Glu$; $V_{HCD3}$: $Gln_{39}Lys$) (see Table 10 for sequence); the Fc portion of the bispecific antibody adopts the human IgG4 knob-into-hole structure to achieve heterodimer pairing, and through mutation of $Ser_{228}Pro$, $Leu_{235}Glu$ and $Pro_{329}Ala$, the hinge region remains stable and interaction with FcγR receptor and C1q is reduced.

TABLE 10

BCMA × CD3 κλ bispecific antibodies

| Protein sequence | light chain of BCMA arm | heavy chain of BCMA arm | light chain of CD3 arm | heavy chain of CD3 arm |
|---|---|---|---|---|
| BCMA × CD3 κλ003 | SEQ ID NO. 80 | SEQ ID NO. 82 | SEQ ID NO. 66 | SEQ ID NO. 68 |
| BCMA × CD3 κλ004 | SEQ ID NO. 84 | SEQ ID NO. 82 | SEQ ID NO. 66 | SEQ ID NO. 68 |
| BCMA × CD3 κλ005 | SEQ ID NO. 80 | SEQ ID NO. 86 | SEQ ID NO. 66 | SEQ ID NO. 68 |
| BCMA × CD3 κλ006 | SEQ ID NO. 84 | SEQ ID NO. 86 | SEQ ID NO. 66 | SEQ ID NO. 68 |

BCMA×CD3 κλ003

```
κ light chain of BCMA arm:
                                          SEQ ID NO. 80
DIVLTQSPASLAVSPGQRATITCRASKSVSTSGYSYMHWYQKKPGQPPKLLIYLASNLESG

VPARFSGSGSGTDFTLTINPVEAEDTANYYCQHSRELPWTFGQGTKVEIKRTVAAPSVFIFP

PSDEQLKSGTASVVCLLNNFYPREAKVQWKVDNALQSGNSQESVTEQDSKDSTYSLSSTL

TLSKADYEKHKVYACEVTHQGLSSPVTKSFNRGEC

Nucleotide sequence:
                                          SEQ ID NO. 81
GACATCGTGCTGACACAGAGCCCTGCTTCTCTGGCTGTGTCTCCTGGCCAGAGAGCCA

CCATCACCTGTAGAGCCAGCAAGAGCGTGTCCACCAGCGGCTACTCTTACATGCACTG

GTATCAGAAGAAGCCCGGCCAGCCTCCTAAGCTGCTGATCTACCTGGCTAGCAACCTC

GAAAGCGGAGTGCCTGCTAGATTTTCTGGCAGCGGCTCTGGCACCGACTTCACCCTGA

CAATCAACCCCGTGGAAGCCGAAGACACCGCCAACTACTACTGCCAGCACAGCAGAG

AGCTGCCCTGGACATTTGGCCAGGGCACCAAGGTGGAAATCAAGCGAACTGTGGCTG

CACCATCTGTCTTCATCTTCCCGCCATCTGATGAGCAGTTGAAATCTGGAACTGCCTCT

GTTGTGTGCCTGCTGAATAACTTCTATCCCAGAGAGGCCAAAGTACAGTGGAAGGTGG

ATAACGCCCTCCAATCGGGTAACTCCCAGGAGAGTGTCACAGAGCAGGACAGCAAGG

ACAGCACCTACAGCCTCAGCAGCACCCTGACGCTGAGCAAAGCAGACTACGAGAAAC

ACAAAGTCTACGCCTGCGAAGTCACCCATCAGGGCCTGAGCTCGCCCGTCACAAAGA

GCTTCAACAGGGGAGAGTGT
```

-continued

Heavy chain (heavy chain 1) of BCMA arm:

SEQ ID NO. 82

QVQLVQSGSELKKPGASVKVSCKASGYIFTNFGMNWVREAPGQGLEWMGWINTYTGEQ

IYADGFTGRFVFSLDTSASTAYLQISSLKAEDTAVYFCARGEIYYGYDVGFVYWGQGTLVT

VSSASTKGPSVFPLAPCSRSTSESTAALGCLVKDYFPEPVTVSWNSGALTSGVHTFPAVLQS

SGLYSLSSVVTVPSSSLGTKTYTCNVDHKPSNTKVDKRVESKYGPPCPPCPAPEFEGGPSV

FLFPPKPKDTLMISRTPEVTCVVVDVSQEDPEVQFNWYVDGVEVHNAKTKPREEQFNSTY

RVVSVLTVLHQDWLNGKEYKCKVSNKGLASSIEKTISKAKGQPREPQVCTLPPSQEEMTK

NQVSLSCAVKGFYPSDIAVEWESNGQPENNYKTTPPVLDSDGSFFLVSKLTVDKSRWQEG

NVFSCSVMHEALHNHYTQKSLSLSLGK

Nucleotide sequence:

SEQ ID NO. 83

CAGGTTCAGCTGGTGCAGTCTGGCAGCGAGCTGAAGAAACCTGGCGCCTCTGTGAAG

GTGTCCTGCAAGGCTAGCGGCTACATCTTCACCAACTTCGGCATGAACTGGGTCCGAG

AGGCTCCTGGACAGGGACTCGAATGGATGGGCTGGATCAACACCTACACCGGCGAGC

AGATCTACGCCGATGGCTTCACAGGCAGATTCGTGTTCAGCCTGGACACCAGCGCCAG

CACAGCTTACCTGCAGATCAGCTCTCTGAAGGCCGAGGATACCGCCGTGTACTTCTGT

GCCAGAGGCGAGATCTACTACGGCTACGACGTGGGCTTTGTGTACTGGGGCCAGGGAA

CACTGGTCACCGTTAGCTCTGCTAGCACCAAGGGCCCCAGCGTGTTCCCCCTGGCCCC

TTGCAGCAGAAGCACCAGCGAGAGCACAGCCGCCCTGGGCTGCCTGGTGAAGGACTA

CTTCCCCGAGCCCGTGACCGTGTCCTGGAACAGCGGCGCTCTGACCAGCGGCGTGCAT

ACCTTCCCCGCCGTGCTCCAGAGCAGCGGACTGTACTCCCTGAGCAGCGTGGTGACCG

TGCCTTCCAGCAGCCTGGGCACCAAGACCTACACCTGCAACGTGGACCACAAGCCCA

GCAACACCAAGGTGGACAAGAGAGTGGAGAGCAAGTACGGCCCTCCCTGCCCCCCTT

GCCCTGCCCCCGAGTTCGAGGGCGGACCTAGCGTGTTCCTGTTCCCCCCCAAGCCCAA

GGACACCCTGATGATCAGCAGAACCCCCGAGGTGACCTGCGTGGTGGTGGACGTGTC

CCAGGAGGACCCCGAGGTCCAGTTTAATTGGTACGTGGACGGCGTGGAAGTGCATAAC

GCCAAGACCAAGCCCAGAGAGGAGCAGTTCAACAGCACCTACAGAGTGGTGTCCGTG

CTGACCGTGCTGCACCAGGACTGGCTGAACGGCAAGGAATACAAGTGCAAGGTCTCC

AACAAGGGCCTGGCCAGCAGCATCGAGAAGACCATCAGCAAGGCCAAGGGCCAGCC

ACGGGAGCCCCAGGTCTGCACCCTGCCACCTAGCCAAGAGGAGATGACCAAGAACCA

GGTGTCCCTGAGCTGTGCCGTGAAAGGCTTCTATCCCAGCGATATCGCCGTGGAGTGG

GAGAGCAACGGCCAGCCCGAGAACAACTACAAGACCACCCCCCCTGTGCTGGACAGC

GACGGCAGCTTCTTCCTGGTTTCCAAGCTGACCGTGGACAAGTCCAGATGGCAGGAG

GGCAACGTCTTCAGCTGCTCCGTGATGCACGAGGCCCTGCACAACCACTACACCCAGA

AGTCCCTGAGCCTGAGCCTGGGCAAG

λ light chain of CD3 arm:

SEQ ID NO. 66

QAVVTQEPSLTVSPGGTVTLTCRSSTGAVTTSNYANWVQEKPGQAPRGLIGGTNKRAPWT

PARFSGSLLGGKAALTITGAQAEDEAEYYCVLWYSNLWVFGGGTKLTVLGQPKAAPSVT

LFPPSSEELQANKATLVCLISDFYPGAVTVAWKADSSPVKAGVETTTPSKQSNNKYAASSY

LSLTPEQWKSHRSYSCQVTHEGSTVEKTVAPTECS

-continued

Nucleotide sequence:

SEQ ID NO. 67

CAGGCTGTGGTCACACAAGAGCCTAGCCTGACAGTGTCTCCTGGCGGCACAGTGACC

CTGACCTGTAGATCTTCTACAGGCGCCGTGACCACCAGCAACTACGCTAATTGGGTGC

AGGAGAAGCCCGGCCAGGCTCCTAGAGGACTGATCGGCGGAACAAACAAGAGAGCC

CCTTGGACACCCGCCAGATTCTCTGGATCTCTGCTCGGCGGAAAGGCCGCTCTGACAA

TCACTGGTGCTCAGGCTGAGGACGAGGCCGAGTACTATTGTGTGCTGTGGTACAGCAA

CCTGTGGGTGTTCGGCGGAGGCACCAAACTGACAGTTCTGGGTCAGCCCAAGGCGGC

GCCCTCGGTCACTCTGTTCCCGCCCTCCTCTGAGGAGCTTCAAGCCAACAAGGCCACA

CTGGTGTGTCTCATAAGTGACTTCTATCCGGGAGCCGTGACAGTGGCCTGGAAGGCAG

ATAGCAGCCCCGTCAAGGCGGGAGTGGAGACCACCACACCCTCCAAACAAAGCAACA

ACAAGTACGCGGCCAGCAGCTACCTGAGCCTGACGCCTGAGCAGTGGAAGTCCCACA

GAAGCTACAGCTGCCAGGTCACGCATGAAGGGAGCACCGTGGAGAAGACAGTGGCCC

CTACAGAATGTTCA

Heavy chain (heavy chain 2) of CD3 arm:

SEQ ID NO. 68

EVQLVESGGGLVQPGGSLRLSCAASGFTFNTYAMNWVRKAPGKGLEWVGRIRSKYNNYA

TYYADSVKDRFTISRDDSKNSLYLQMNSLKTEDTAVYYCVRHGNFGNSYVSWFAYWGQG

TLVTVSSASTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRVESKYGPPCPPCPAPEFEG

GPSVFLFPPKPKDTLMISRTPEVTCVVVDVSQEDPEVQFNWYVDGVEVHNAKTKPREEQF

NSTYRVVSVLTVLHQDWLNGKEYKCKVSNKGLASSIEKTISKAKGQPREPQVYTLPPCQE

EMTKNQVSLWCLVKGFYPSDIAVEWESNGQPENNYKTTPPVLDSDGSFFLYSKLTVDKSR

WQEGNVFSCSVMHEALHNHYTQKSLSLSLGK

Nucleotide sequence:

SEQ ID NO. 69

GAGGTGCAGCTGGTTGAATCTGGCGGAGGACTGGTTCAGCCTGGCGGATCTCTGAGA

CTGTCTTGTGCCGCCAGCGGCTTCACCTTCAACACCTACGCTATGAACTGGGTCCGAA

AGGCCCCTGGCAAAGGACTGGAATGGGTGGGAAGAATCAGGTCCAAGTACAACAACT

ACGCCACCTACTACGCCGACAGCGTGAAGGACAGATTCACCATCAGCAGGGACGACA

GCAAGAACAGCCTGTACCTGCAGATGAACAGCCTGAAAACCGAGGACACCGCCGTGT

ACTACTGTGTCAGACACGGCAACTTCGGCAACAGCTATGTGTCTTGGTTTGCCTACTGG

GGCCAGGGCACACTGGTCACAGTTAGCTCTGCTAGCACCAAGGGCCCCAGCGTGTTCC

CCCTGGCCCCTTGCAGCAGAAGCACCAGCGAGAGCACAGCCGCCCTGGGCTGCCTGG

TGAAGGACTACTTCCCCGAGCCCGTGACCGTGTCCTGGAACAGCGGCGCTCTGACCA

GCGGCGTGCATACCTTCCCCGCCGTGCTCCAGAGCAGCGGACTGTACTCCCTGAGCAG

CGTGGTGACCGTGCCTTCCAGCAGCCTGGGCACCAAGACCTACACCTGCAACGTGGA

CCACAAGCCCAGCAACACCAAGGTGGACAAGAGAGTGGAGAGCAAGTACGGCCCTC

CCTGCCCCCCTTGCCCTGCCCCCGAGTTCGAGGGCGGACCTAGCGTGTTCCTGTTCCC

CCCCAAGCCCAAGGACACCCTGATGATCAGCAGAACCCCCGAGGTGACCTGCGTGGT

GGTGGACGTGTCCCAGGAGGACCCCGAGGTCCAGTTTAATTGGTACGTGGACGGCGT

GGAAGTGCATAACGCCAAGACCAAGCCCAGAGAGGAGCAGTTCAACAGCACCTACAG

AGTGGTGTCCGTGCTGACCGTGCTGCACCAGGACTGGCTGAACGGCAAGGAATACAA

GTGCAAGGTCTCCAACAAGGGCCTGGCCAGCAGCATCGAGAAGACCATCAGCAAGGC

CAAGGGCCAGCCACGGGAGCCCCAGGTCTACACCCTGCCACCTTGTCAAGAGGAGAT

GACCAAGAACCAGGTGTCCCTGTGGTGTCTGGTGAAAGGCTTCTATCCCAGCGATATC

GCCGTGGAGTGGGAGAGCAACGGCCAGCCCGAGAACAACTACAAGACCACCCCCCCT

GTGCTGGACAGCGACGGCAGCTTCTTCCTGTACTCCAAGCTGACCGTGGACAAGTCCA

GATGGCAGGAGGGCAACGTCTTCAGCTGCTCCGTGATGCACGAGGCCCTGCACAACC

ACTACACCCAGAAGTCCCTGAGCCTGAGCCTGGGCAAG

BCMA×CD3 κλ004

κ light chain of BCMA arm:

SEQ ID NO. 84

DIVLTQSPASLAVSPGQRATITCRASKSVTTSGYSYIHWYQKKPGQPPKLLIYLASDLEAGV

PARFSGSGSGTDFTLTINPVEAEDTANYYCQHSRELPWTFGQGTKVEIKRTVAAPSVFIFPP

SDEQLKSGTASVVCLLNNFYPREAKVQWKVDNALQSGNSQESVTEQDSKDSTYSLSSTLT

LSKADYEKHKVYACEVTHQGLSSPVTKSFNRGEC

Nucleotide sequence:

SEQ ID NO. 85

GACATCGTGCTGACACAGAGCCCTGCTTCTCTGGCTGTGTCTCCTGGCCAGAGAGCCA

CCATCACCTGTAGAGCCAGCAAGAGCGTGACCACCAGCGGCTACTCTTACATCCACTG

GTATCAGAAGAAGCCCGGCCAGCCTCCTAAGCTGCTGATCTACCTGGCCAGCGATCTG

GAAGCTGGCGTGCCAGCTAGATTTTCTGGCAGCGGCTCTGGCACCGACTTCACCCTGA

CAATCAACCCCGTGGAAGCCGAAGACACCGCCAACTACTACTGCCAGCACAGCAGAG

AGCTGCCCTGGACATTTGGCCAGGGCACCAAGGTGGAAATCAAGCGAACTGTGGCTG

CACCATCTGTCTTCATCTTCCCGCCATCTGATGAGCAGTTGAAATCTGGAACTGCCTCT

GTTGTGTGCCTGCTGAATAACTTCTATCCCAGAGAGGCCAAAGTACAGTGGAAGGTGG

ATAACGCCCTCCAATCGGGTAACTCCCAGGAGAGTGTCACAGAGCAGGACAGCAAGG

ACAGCACCTACAGCCTCAGCAGCACCCTGACGCTGAGCAAAGCAGACTACGAGAAAC

ACAAAGTCTACGCCTGCGAAGTCACCCATCAGGGCCTGAGCTCGCCCGTCACAAAGA

GCTTCAACAGGGGAGAGTGT

Heavy chain (heavy chain 1) of BCMA arm:

SEQ ID NO. 86

QVQLVQSGSELKKPGASVKVSCKASGYIFTNFGMNWVREAPGQGLEWMGWINTYTGEQ

IYADGFTGRFVFSLDTSASTAYLQISSLKAEDTAVYFCARGEIYYGYDVGFVYWGQGTLVT

VSSASTKGPSVFPLAPCSRSTSESTAALGCLVKDYFPEPVTVSWNSGALTSGVHTFPAVLQS

SGLYSLSSVVTVPSSSLGTKTYTCNVDHKPSNTKVDKRVESKYGPPCPPCPAPEFEGGPSV

FLFPPKPKDTLMISRTPEVTCVVVDVSQEDPEVQFNWYVDGVEVHNAKTKPREEQFNSTY

RVVSVLTVLHQDWLNGKEYKCKVSNKGLASSIEKTISKAKGQPREPQVCTLPPSQEEMTK

NQVSLSCAVKGFYPSDIAVEWESNGQPENNYKTTPPVLDSDGSFFLVSKLTVDKSRWQEG

NVFSCSVMHEALHNHYTQKSLSLSLGK

Nucleotide sequence:

SEQ ID NO. 87

CAGGTTCAGCTGGTGCAGTCTGGCAGCGAGCTGAAGAAACCTGGCGCCTCTGTGAAG

GTGTCCTGCAAGGCTAGCGGCTACATCTTCACCAACTTCGGCATGAACTGGGTCCGAG

AGGCTCCTGGACAGGGACTCGAATGGATGGGCTGGATCAACACCTACACCGGCGAGC

AGATCTACGCCGATGGCTTCACAGGCAGATTCGTGTTCAGCCTGGACACCAGCGCCAG

-continued

CACAGCTTACCTGCAGATCAGCTCTCTGAAGGCCGAGGATACCGCCGTGTACTTCTGT

GCCAGAGGCGAGATCTACTACGGCTACGACGTGGGCTTTGTGTACTGGGGCCAGGGAA

CACTGGTCACCGTTAGCTCTGCTAGCACCAAGGGCCCCAGCGTGTTCCCCCTGGCCCC

TTGCAGCAGAAGCACCAGCGAGAGCACAGCCGCCCTGGGCTGCCTGGTGAAGGACTA

CTTCCCCGAGCCCGTGACCGTGTCCTGGAACAGCGGCGCTCTGACCAGCGGCGTGCAT

ACCTTCCCCGCCGTGCTCCAGAGCAGCGGACTGTACTCCCTGAGCAGCGTGGTGACCG

TGCCTTCCAGCAGCCTGGGCACCAAGACCTACACCTGCAACGTGGACCACAAGCCCA

GCAACACCAAGGTGGACAAGAGAGTGGAGAGCAAGTACGGCCCTCCCTGCCCCCCTT

GCCCTGCCCCCGAGTTCGAGGGCGGACCTAGCGTGTTCCTGTTCCCCCCCAAGCCCAA

GGACACCCTGATGATCAGCAGAACCCCCGAGGTGACCTGCGTGGTGGTGGACGTGTC

CCAGGAGGACCCCGAGGTCCAGTTTAATTGGTACGTGGACGGCGTGGAAGTGCATAAC

GCCAAGACCAAGCCCAGAGAGGAGCAGTTCAACAGCACCTACAGAGTGGTGTCCGTG

CTGACCGTGCTGCACCAGGACTGGCTGAACGGCAAGGAATACAAGTGCAAGGTCTCC

AACAAGGGCCTGGCCAGCAGCATCGAGAAGACCATCAGCAAGGCCAAGGGCCAGCC

ACGGGAGCCCCAGGTCTGCACCCTGCCACCTAGCCAAGAGGAGATGACCAAGAACCA

GGTGTCCCTGAGCTGTGCCGTGAAAGGCTTCTATCCCAGCGATATCGCCGTGGAGTGG

GAGAGCAACGGCCAGCCCGAGAACAACTACAAGACCACCCCCCCTGTGCTGGACAGC

GACGGCAGCTTCTTCCTGGTTTCCAAGCTGACCGTGGACAAGTCCAGATGGCAGGAG

GGCAACGTCTTCAGCTGCTCCGTGATGCACGAGGCCCTGCACAACCACTACACCCAGA

AGTCCCTGAGCCTGAGCCTGGGCAAG

λ light chain of CD3 arm:
                                                SEQ ID NO. 66
QAVVTQEPSLTVSPGGTVTLTCRSSTGAVTTSNYANWVQEKPGQAPRGLIGGTNKRAPWT

PARFSGSLLGGKAALTITGAQAEDEAEYYCVLWYSNLWVFGGGTKLTVLGQPKAAPSVT

LFPPSSEELQANKATLVCLISDFYPGAVTVAWKADSSPVKAGVETTTPSKQSNNKYAASSY

LSLTPEQWKSHRSYSCQVTHEGSTVEKTVAPTECS

Nucleotide sequence:
                                                SEQ ID NO. 67
CAGGCTGTGGTCACACAAGAGCCTAGCCTGACAGTGTCTCCTGGCGGCACAGTGACC

CTGACCTGTAGATCTTCTACAGGCGCCGTGACCACCAGCAACTACGCTAATTGGGTGC

AGGAGAAGCCCGGCCAGGCTCCTAGAGGACTGATCGGCGGAACAAACAAGAGAGCC

CCTTGGACACCCGCCAGATTCTCTGGATCTCTGCTCGGCGGAAAGGCCGCTCTGACAA

TCACTGGTGCTCAGGCTGAGGACGAGGCCGAGTACTATTGTGTGCTGTGGTACAGCAA

CCTGTGGGTGTTCGGCGGAGGCACCAAACTGACAGTTCTGGGTCAGCCCAAGGCGGC

GCCCTCGGTCACTCTGTTCCCGCCCTCCTCTGAGGAGCTTCAAGCCAACAAGGCCACA

CTGGTGTGTCTCATAAGTGACTTCTATCCGGGAGCCGTGACAGTGGCCTGGAAGGCAG

ATAGCAGCCCCGTCAAGGCGGGAGTGGAGACCACCACACCCTCCAAACAAAGCAACA

ACAAGTACGCGGCCAGCAGCTACCTGAGCCTGACGCCTGAGCAGTGGAAGTCCCACA

GAAGCTACAGCTGCCAGGTCACGCATGAAGGGAGCACCGTGGAGAAGACAGTGGCCC

CTACAGAATGTTCA

Heavy chain (heavy chain 2) of CD3 arm:
                                                SEQ ID NO. 68
EVQLVESGGGLVQPGGSLRLSCAASGFTFNTYAMNWVRKAPGKGLEWVGRIRSKYNNYA

TYYADSVKDRFTISRDDSKNSLYLQMNSLKTEDTAVYYCVRHGNFGNSYVSWFAYWGQG

-continued

TLVTVSSASTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRVESKYGPPCPPCPAPEFEG

GPSVFLFPPKPKDTLMISRTPEVTCVVVDVSQEDPEVQFNWYVDGVEVHNAKTKPREEQF

NSTYRVVSVLTVLHQDWLNGKEYKCKVSNKGLASSIEKTISKAKGQPREPQVYTLPPCQE

EMTKNQVSLWCLVKGFYPSDIAVEWESNGQPENNYKTTPPVLDSDGSFFLYSKLTVDKSR

WQEGNVFSCSVMHEALHNHYTQKSLSLSLGK

Nucleotide sequence:

SEQ ID NO. 69

GAGGTGCAGCTGGTTGAATCTGGCGGAGGACTGGTTCAGCCTGGCGGATCTCTGAGA

CTGTCTTGTGCCGCCAGCGGCTTCACCTTCAACACCTACGCTATGAACTGGGTCCGAA

AGGCCCCTGGCAAAGGACTGGAATGGGTGGGAAGAATCAGGTCCAAGTACAACAACT

ACGCCACCTACTACGCCGACAGCGTGAAGGACAGATTCACCATCAGCAGGGACGACA

GCAAGAACAGCCTGTACCTGCAGATGAACAGCCTGAAAACCGAGGACACCGCCGTGT

ACTACTGTGTCAGACACGGCAACTTCGGCAACAGCTATGTGTCTTGGTTTGCCTACTGG

GGCCAGGGCACACTGGTCACAGTTAGCTCTGCTAGCACCAAGGGCCCCAGCGTGTTCC

CCCTGGCCCCTTGCAGCAGAAGCACCAGCGAGAGCACAGCCGCCCTGGGCTGCCTGG

TGAAGGACTACTTCCCCGAGCCCGTGACCGTGTCCTGGAACAGCGGCGCTCTGACCA

GCGGCGTGCATACCTTCCCCGCCGTGCTCCAGAGCAGCGGACTGTACTCCCTGAGCAG

CGTGGTGACCGTGCCTTCCAGCAGCCTGGGCACCAAGACCTACACCTGCAACGTGGA

CCACAAGCCCAGCAACACCAAGGTGGACAAGAGAGTGGAGAGCAAGTACGGCCCTC

CCTGCCCCCCTTGCCCTGCCCCCGAGTTCGAGGGCGGACCTAGCGTGTTCCTGTTCCC

CCCCAAGCCCAAGGACACCCTGATGATCAGCAGAACCCCCGAGGTGACCTGCGTGGT

GGTGGACGTGTCCCAGGAGGACCCCGAGGTCCAGTTTAATTGGTACGTGGACGGCGT

GGAAGTGCATAACGCCAAGACCAAGCCCAGAGAGGAGCAGTTCAACAGCACCTACAG

AGTGGTGTCCGTGCTGACCGTGCTGCACCAGGACTGGCTGAACGGCAAGGAATACAA

GTGCAAGGTCTCCAACAAGGGCCTGGCCAGCAGCATCGAGAAGACCATCAGCAAGGC

CAAGGGCCAGCCACGGGAGCCCCAGGTCTACACCCTGCCACCTTGTCAAGAGGAGAT

GACCAAGAACCAGGTGTCCCTGTGGTGTCTGGTGAAAGGCTTCTATCCCAGCGATATC

GCCGTGGAGTGGGAGAGCAACGGCCAGCCCGAGAACAACTACAAGACCACCCCCCCT

GTGCTGGACAGCGACGGCAGCTTCTTCCTGTACTCCAAGCTGACCGTGGACAAGTCCA

GATGGCAGGAGGGCAACGTCTTCAGCTGCTCCGTGATGCACGAGGCCCTGCACAACC

ACTACACCCAGAAGTCCCTGAGCCTGAGCCTGGGCAAG

BCMAxCD3 κλ005

κ light chain of BCMA arm:

SEQ ID NO. 80

DIVLTQSPASLAVSPGQRATITCRASKSVSTSGYSYMHWYQKKPGQPPKLLIYLASNLESG

VPARFSGSGSGTDFTLTINPVEAEDTANYYCQHSRELPWTFGQGTKVEIKRTVAAPSVFIFP

PSDEQLKSGTASVVCLLNNFYPREAKVQWKVDNALQSGNSQESVTEQDSKDSTYSLSSTL

TLSKADYEKHKVYACEVTHQGLSSPVTKSFNRGEC

-continued

Nucleotide sequence:

SEQ ID NO. 81

GACATCGTGCTGACACAGAGCCCTGCTTCTCTGGCTGTGTCTCCTGGCCAGAGAGCCA

CCATCACCTGTAGAGCCAGCAAGAGCGTGTCCACCAGCGGCTACTCTTACATGCACTG

GTATCAGAAGAAGCCCGGCCAGCCTCCTAAGCTGCTGATCTACCTGGCTAGCAACCTC

GAAAGCGGAGTGCCTGCTAGATTTTCTGGCAGCGGCTCTGGCACCGACTTCACCCTGA

CAATCAACCCCGTGGAAGCCGAAGACACCGCCAACTACTACTGCCAGCACAGCAGAG

AGCTGCCCTGGACATTTGGCCAGGGCACCAAGGTGGAAATCAAGCGAACTGTGGCTG

CACCATCTGTCTTCATCTTCCCGCCATCTGATGAGCAGTTGAAATCTGGAACTGCCTCT

GTTGTGTGCCTGCTGAATAACTTCTATCCCAGAGAGGCCAAAGTACAGTGGAAGGTGG

ATAACGCCCTCCAATCGGGTAACTCCCAGGAGAGTGTCACAGAGCAGGACAGCAAGG

ACAGCACCTACAGCCTCAGCAGCACCCTGACGCTGAGCAAAGCAGACTACGAGAAAC

ACAAAGTCTACGCCTGCGAAGTCACCCATCAGGGCCTGAGCTCGCCCGTCACAAAGA

GCTTCAACAGGGGAGAGTGT

Heavy chain (heavy chain 1) of BCMA arm:

SEQ ID NO. 86

QVQLVQSGSELKKPGASVKVSCKASGYIFTNFGMNWVREAPGQGLEWMGWINTYTGEQ

IYADGFTGRFVFSLDTSVSTAYLQISSLKAEDTAVYFCARGEIYYGYDVGFVYWGQGTLVT

VSSASTKGPSVFPLAPCSRSTSESTAALGCLVKDYFPEPVTVSWNSGALTSGVHTFPAVLQS

SGLYSLSSVVTVPSSSLGTKTYTCNVDHKPSNTKVDKRVESKYGPPCPPCPAPEFEGGPSV

FLFPPKPKDTLMISRTPEVTCVVVDVSQEDPEVQFNWYVDGVEVHNAKTKPREEQFNSTY

RVVSVLTVLHQDWLNGKEYKCKVSNKGLASSIEKTISKAKGQPREPQVCTLPPSQEEMTK

NQVSLSCAVKGFYPSDIAVEWESNGQPENNYKTTPPVLDSDGSFFLVSKLTVDKSRWQEG

NVFSCSVMHEALHNHYTQKSLSLSLGK

Nucleotide sequence:

SEQ ID NO. 87

CAGGTTCAGCTGGTGCAGTCTGGCAGCGAGCTGAAGAAACCTGGCGCCTCTGTGAAG

GTGTCCTGCAAGGCTAGCGGCTACATCTTCACCAACTTCGGCATGAACTGGGTCCGAG

AGGCTCCTGGACAGGGACTCGAATGGATGGGCTGGATCAACACCTACACCGGCGAGC

AGATCTACGCCGATGGCTTCACAGGCAGATTCGTGTTCAGCCTGGACACCAGCGTCAG

CACAGCTTACCTGCAGATCAGCTCTCTGAAGGCCGAGGATACCGCCGTGTACTTCTGT

GCCAGAGGCGAGATCTACTACGGCTACGACGTGGGCTTTGTGTACTGGGGCCAGGGAA

CACTGGTCACCGTTAGCTCTGCTAGCACCAAGGGCCCCAGCGTGTTCCCCCTGGCCCC

TTGCAGCAGAAGCACCAGCGAGAGCACAGCCGCCCTGGGCTGCCTGGTGAAGGACTA

CTTCCCCGAGCCCGTGACCGTGTCCTGGAACAGCGGCGCTCTGACCAGCGGCGTGCAT

ACCTTCCCCGCCGTGCTCCAGAGCAGCGGACTGTACTCCCTGAGCAGCGTGGTGACCG

TGCCTTCCAGCAGCCTGGGCACCAAGACCTACACCTGCAACGTGGACCACAAGCCCA

GCAACACCAAGGTGGACAAGAGAGTGGAGAGCAAGTACGGCCCTCCCTGCCCCCCTT

GCCCTGCCCCCGAGTTCGAGGGCGGACCTAGCGTGTTCCTGTTCCCCCCCAAGCCCAA

GGACACCCTGATGATCAGCAGAACCCCCGAGGTGACCTGCGTGGTGGTGGACGTGTC

CCAGGAGGACCCCGAGGTCCAGTTTAATTGGTACGTGGACGGCGTGGAAGTGCATAAC

GCCAAGACCAAGCCCAGAGAGGAGCAGTTCAACAGCACCTACAGAGTGGTGTCCGTG

CTGACCGTGCTGCACCAGGACTGGCTGAACGGCAAGGAATACAAGTGCAAGGTCTCC

AACAAGGGCCTGGCCAGCAGCATCGAGAAGACCATCAGCAAGGCCAAGGGCCAGCC

-continued

ACGGGAGCCCCAGGTCTGCACCCTGCCACCTAGCCAAGAGGAGATGACCAAGAACCA

GGTGTCCCTGAGCTGTGCCGTGAAAGGCTTCTATCCCAGCGATATCGCCGTGGAGTGG

GAGAGCAACGGCCAGCCCGAGAACAACTACAAGACCACCCCCCCTGTGCTGGACAGC

GACGGCAGCTTCTTCCTGGTTTCCAAGCTGACCGTGGACAAGTCCAGATGGCAGGAG

GGCAACGTCTTCAGCTGCTCCGTGATGCACGAGGCCCTGCACAACCACTACACCCAGA

AGTCCCTGAGCCTGAGCCTGGGCAAG

λ light chain of CD3 arm:
                                                    SEQ ID NO. 66
QAVVTQEPSLTVSPGGTVTLTCRSSTGAVTTSNYANWVQEKPGQAPRGLIGGTNKRAPWT

PARFSGSLLGGKAALTITGAQAEDEAEYYCVLWYSNLWVFGGGTKLTVLGQPKAAPSVT

LFPPSSEELQANKATLVCLISDFYPGAVTVAWKADSSPVKAGVETTTPSKQSNNKYAASSY

LSLTPEQWKSHRSYSCQVTHEGSTVEKTVAPTECS

Nucleotide sequence:
                                                    SEQ ID NO. 67
CAGGCTGTGGTCACACAAGAGCCTAGCCTGACAGTGTCTCCTGGCGGCACAGTGACC

CTGACCTGTAGATCTTCTACAGGCGCCGTGACCACCAGCAACTACGCTAATTGGGTGC

AGGAGAAGCCCGGCCAGGCTCCTAGAGGACTGATCGGCGGAACAAACAAGAGAGCC

CCTTGGACACCCGCCAGATTCTCTGGATCTCTGCTCGGCGGAAAGGCCGCTCTGACAA

TCACTGGTGCTCAGGCTGAGGACGAGGCCGAGTACTATTGTGTGCTGTGGTACAGCAA

CCTGTGGGTGTTCGGCGGAGGCACCAAACTGACAGTTCTGGGTCAGCCCAAGGCGGC

GCCCTCGGTCACTCTGTTCCCGCCCTCCTCTGAGGAGCTTCAAGCCAACAAGGCCACA

CTGGTGTGTCTCATAAGTGACTTCTATCCGGGAGCCGTGACAGTGGCCTGGAAGGCAG

ATAGCAGCCCCGTCAAGGCGGGAGTGGAGACCACCACACCCTCCAAACAAAGCAACA

ACAAGTACGCGGCCAGCAGCTACCTGAGCCTGACGCCTGAGCAGTGGAAGTCCCACA

GAAGCTACAGCTGCCAGGTCACGCATGAAGGGAGCACCGTGGAGAAGACAGTGGCCC

CTACAGAATGTTCA

Heavy chain (heavy chain 2) of CD3 arm:
                                                    SEQ ID NO. 68
EVQLVESGGGLVQPGGSLRLSCAASGFTFNTYAMNWVRKAPGKGLEWVGRIRSKYNNYA

TYYADSVKDRFTISRDDSKNSLYLQMNSLKTEDTAVYYCVRHGNFGNSYVSWFAYWGQG

TLVTVSSASTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRVESKYGPPCPPCPAPEFEG

GPSVFLFPPKPKDTLMISRTPEVTCVVVDVSQEDPEVQFNWYVDGVEVHNAKTKPREEQF

NSTYRVVSVLTVLHQDWLNGKEYKCKVSNKGLASSIEKTISKAKGQPREPQVYTLPPCQE

EMTKNQVSLWCLVKGFYPSDIAVEWESNGQPENNYKTTPPVLDSDGSFFLYSKLTVDKSR

WQEGNVFSCSVMHEALHNHYTQKSLSLSLGK

Nucleotide sequence:
                                                    SEQ ID NO. 69
GAGGTGCAGCTGGTTGAATCTGGCGGAGGACTGGTTCAGCCTGGCGGATCTCTGAGA

CTGTCTTGTGCCGCCAGCGGCTTCACCTTCAACACCTACGCTATGAACTGGGTCCGAA

AGGCCCCTGGCAAAGGACTGGAATGGGTGGGAAGAATCAGGTCCAAGTACAACAACT

ACGCCACCTACTACGCCGACAGCGTGAAGGACAGATTCACCATCAGCAGGGACGACA

GCAAGAACAGCCTGTACCTGCAGATGAACAGCCTGAAAACCGAGGACACCGCCGTGT

ACTACTGTGTCAGACACGGCAACTTCGGCAACAGCTATGTGTCTTGGTTTGCCTACTGG

-continued

```
GGCCAGGGCACACTGGTCACAGTTAGCTCTGCTAGCACCAAGGGCCCCAGCGTGTTCC

CCCTGGCCCCTTGCAGCAGAAGCACCAGCGAGAGCACAGCCGCCCTGGGCTGCCTGG

TGAAGGACTACTTCCCCGAGCCCGTGACCGTGTCCTGGAACAGCGGCGCTCTGACCA

GCGGCGTGCATACCTTCCCCGCCGTGCTCCAGAGCAGCGGACTGTACTCCCTGAGCAG

CGTGGTGACCGTGCCTTCCAGCAGCCTGGGCACCAAGACCTACACCTGCAACGTGGA

CCACAAGCCCAGCAACACCAAGGTGGACAAGAGAGTGGAGAGCAAGTACGGCCCTC

CCTGCCCCCCTTGCCCTGCCCCCGAGTTCGAGGGCGGACCTAGCGTGTTCCTGTTCCC

CCCCAAGCCCAAGGACACCCTGATGATCAGCAGAACCCCCGAGGTGACCTGCGTGGT

GGTGGACGTGTCCCAGGAGGACCCCGAGGTCCAGTTTAATTGGTACGTGGACGGCGT

GGAAGTGCATAACGCCAAGACCAAGCCCAGAGAGGAGCAGTTCAACAGCACCTACAG

AGTGGTGTCCGTGCTGACCGTGCTGCACCAGGACTGGCTGAACGGCAAGGAATACAA

GTGCAAGGTCTCCAACAAGGGCCTGGCCAGCAGCATCGAGAAGACCATCAGCAAGGC

CAAGGGCCAGCCACGGGAGCCCCAGGTCTACACCCTGCCACCTTGTCAAGAGGAGAT

GACCAAGAACCAGGTGTCCCTGTGGTGTCTGGTGAAAGGCTTCTATCCCAGCGATATC

GCCGTGGAGTGGGAGAGCAACGGCCAGCCCGAGAACAACTACAAGACCACCCCCCCT

GTGCTGGACAGCGACGGCAGCTTCTTCCTGTACTCCAAGCTGACCGTGGACAAGTCCA

GATGGCAGGAGGGCAACGTCTTCAGCTGCTCCGTGATGCACGAGGCCCTGCACAACC

ACTACACCCAGAAGTCCCTGAGCCTGAGCCTGGGCAAG
```

BCMA×CD3 κλ006 k light chain of BCMA arm:
                                            SEQ ID NO. 84

```
DIVLTQSPASLAVSPGQRATITCRASKSVTTSGYSYIHWYQKKPGQPPKLLIYLASDLEAGV

PARFSGSGSGTDFTLTINPVEAEDTANYYCQHSRELPWTFGQGTKVEIKRTVAAPSVFIFPP

SDEQLKSGTASVVCLLNNFYPREAKVQWKVDNALQSGNSQESVTEQDSKDSTYSLSSTLT

LSKADYEKHKVYACEVTHQGLSSPVTKSFNRGEC
```

Nucleotide sequence:
                                            SEQ ID NO. 85

```
GACATCGTGCTGACACAGAGCCCTGCTTCTCTGGCTGTGTCTCCTGGCCAGAGAGCCA

CCATCACCTGTAGAGCCAGCAAGAGCGTGACCACCAGCGGCTACTCTTACATCCACTG

GTATCAGAAGAAGCCCGGCCAGCCTCCTAAGCTGCTGATCTACCTGGCCAGCGATCTG

GAAGCTGGCGTGCCAGCTAGATTTTCTGGCAGCGGCTCTGGCACCGACTTCACCCTGA

CAATCAACCCCGTGGAAGCCGAAGACACCGCCAACTACTACTGCCAGCACAGCAGAG

AGCTGCCCTGGACATTTGGCCAGGGCACCAAGGTGGAAATCAAGCGAACTGTGGCTG

CACCATCTGTCTTCATCTTCCCGCCATCTGATGAGCAGTTGAAATCTGGAACTGCCTCT

GTTGTGTGCCTGCTGAATAACTTCTATCCCAGAGAGGCCAAAGTACAGTGGAAGGTGG

ATAACGCCCTCCAATCGGGTAACTCCCAGGAGAGTGTCACAGAGCAGGACAGCAAGG

ACAGCACCTACAGCCTCAGCAGCACCCTGACGCTGAGCAAAGCAGACTACGAGAAAC

ACAAAGTCTACGCCTGCGAAGTCACCCATCAGGGCCTGAGCTCGCCCGTCACAAAGA

GCTTCAACAGGGGAGAGTGT
```

Heavy chain (heavy chain 1) of BCMA arm:
                                            SEQ ID NO. 86

```
QVQLVQSGSELKKPGASVKVSCKASGYIFTNFGMNWVREAPGQGLEWMGWINTYTGEQ

IYADGFTGRFVFSLDTSVSTAYLQISSLKAEDTAVYFCARGEIYYGYDVGFVYWGQGTLVT
```

-continued

VSSASTKGPSVFPLAPCSRSTSESTAALGCLVKDYFPEPVTVSWNSGALTSGVHTFPAVLQS

SGLYSLSSVVTVPSSSLGTKTYTCNVDHKPSNTKVDKRVESKYGPPCPPCPAPEFEGGPSV

FLFPPKPKDTLMISRTPEVTCVVVDVSQEDPEVQFNWYVDGVEVHNAKTKPREEQFNSTY

RVVSVLTVLHQDWLNGKEYKCKVSNKGLASSIEKTISKAKGQPREPQVCTLPPSQEEMTK

NQVSLSCAVKGFYPSDIAVEWESNGQPENNYKTTPPVLDSDGSFFLVSKLTVDKSRWQEG

NVFSCSVMHEALHNHYTQKSLSLSLGK

Nucleotide sequence:

SEQ ID NO. 87

CAGGTTCAGCTGGTGCAGTCTGGCAGCGAGCTGAAGAAACCTGGCGCCTCTGTGAAG

GTGTCCTGCAAGGCTAGCGGCTACATCTTCACCAACTTCGGCATGAACTGGGTCCGAG

AGGCTCCTGGACAGGGACTCGAATGGATGGGCTGGATCAACACCTACACCGGCGAGC

AGATCTACGCCGATGGCTTCACAGGCAGATTCGTGTTCAGCCTGGACACCAGCGTCAG

CACAGCTTACCTGCAGATCAGCTCTCTGAAGGCCGAGGATACCGCCGTGTACTTCTGT

GCCAGAGGCGAGATCTACTACGGCTACGACGTGGGCTTTGTGTACTGGGGCCAGGGAA

CACTGGTCACCGTTAGCTCTGCTAGCACCAAGGGCCCCAGCGTGTTCCCCCTGGCCCC

TTGCAGCAGAAGCACCAGCGAGAGCACAGCCGCCCTGGGCTGCCTGGTGAAGGACTA

CTTCCCCGAGCCCGTGACCGTGTCCTGGAACAGCGGCGCTCTGACCAGCGGCGTGCAT

ACCTTCCCCGCCGTGCTCCAGAGCAGCGGACTGTACTCCCTGAGCAGCGTGGTGACCG

TGCCTTCCAGCAGCCTGGGCACCAAGACCTACACCTGCAACGTGGACCACAAGCCCA

GCAACACCAAGGTGGACAAGAGAGTGGAGAGCAAGTACGGCCCTCCCTGCCCCCCTT

GCCCTGCCCCCGAGTTCGAGGGCGGACCTAGCGTGTTCCTGTTCCCCCCCAAGCCCAA

GGACACCCTGATGATCAGCAGAACCCCCGAGGTGACCTGCGTGGTGGTGGACGTGTC

CCAGGAGGACCCCGAGGTCCAGTTTAATTGGTACGTGGACGGCGTGGAAGTGCATAAC

GCCAAGACCAAGCCCAGAGAGGAGCAGTTCAACAGCACCTACAGAGTGGTGTCCGTG

CTGACCGTGCTGCACCAGGACTGGCTGAACGGCAAGGAATACAAGTGCAAGGTCTCC

AACAAGGGCCTGGCCAGCAGCATCGAGAAGACCATCAGCAAGGCCAAGGGCCAGCC

ACGGGAGCCCCAGGTCTGCACCCTGCCACCTAGCCAAGAGGAGATGACCAAGAACCA

GGTGTCCCTGAGCTGTGCCGTGAAAGGCTTCTATCCCAGCGATATCGCCGTGGAGTGG

GAGAGCAACGGCCAGCCCGAGAACAACTACAAGACCACCCCCCCTGTGCTGGACAGC

GACGGCAGCTTCTTCCTGGTTTCCAAGCTGACCGTGGACAAGTCCAGATGGCAGGAG

GGCAACGTCTTCAGCTGCTCCGTGATGCACGAGGCCCTGCACAACCACTACACCCAGA

AGTCCCTGAGCCTGAGCCTGGGCAAG

λ light chain of CD3 arm:

SEQ ID NO. 66

QAVVTQEPSLTVSPGGTVTLTCRSSTGAVTTSNYANWVQEKPGQAPRGLIGGTNKRAPWT

PARFSGSLLGGKAALTITGAQAEDEAEYYCVLWYSNLWVFGGGTKLTVLGQPKAAPSVT

LFPPSSEELQANKATLVCLISDFYPGAVTVAWKADSSPVKAGVETTTPSKQSNNKYAASSY

LSLTPEQWKSHRSYSCQVTHEGSTVEKTVAPTECS

Nucleotide sequence:

SEQ ID NO. 67

CAGGCTGTGGTCACACAAGAGCCTAGCCTGACAGTGTCTCCTGGCGGCACAGTGACC

CTGACCTGTAGATCTTCTACAGGCGCCGTGACCACCAGCAACTACGCTAATTGGGTGC

AGGAGAAGCCCGGCCAGGCTCCTAGAGGACTGATCGGCGGAACAAACAAGAGAGCC

-continued

CCTTGGACACCCGCCAGATTCTCTGGATCTCTGCTCGGCGGAAAGGCCGCTCTGACAA

TCACTGGTGCTCAGGCTGAGGACGAGGCCGAGTACTATTGTGTGCTGTGGTACAGCAA

CCTGTGGGTGTTCGGCGGAGGCACCAAACTGACAGTTCTGGGTCAGCCCAAGGCGGC

GCCCTCGGTCACTCTGTTCCCGCCCTCCTCTGAGGAGCTTCAAGCCAACAAGGCCACA

CTGGTGTGTCTCATAAGTGACTTCTATCCGGGAGCCGTGACAGTGGCCTGGAAGGCAG

ATAGCAGCCCCGTCAAGGCGGGAGTGGAGACCACCACACCCTCCAAACAAAGCAACA

ACAAGTACGCGGCCAGCAGCTACCTGAGCCTGACGCCTGAGCAGTGGAAGTCCCACA

GAAGCTACAGCTGCCAGGTCACGCATGAAGGGAGCACCGTGGAGAAGACAGTGGCCC

CTACAGAATGTTCA

Heavy chain (heavy chain 2) of CD3 arm:
                                                                                    SEQ ID NO. 68
EVQLVESGGGLVQPGGSLRLSCAASGFTFNTYAMNWVRKAPGKGLEWVGRIRSKYNNYA

TYYADSVKDRFTISRDDSKNSLYLQMNSLKTEDTAVYYCVRHGNFGNSYVSWFAYWGQG

TLVTVSSASTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRVESKYGPPCPPCPAPEFEG

GPSVFLFPPKPKDTLMISRTPEVTCVVVDVSQEDPEVQFNWYVDGVEVHNAKTKPREEQF

NSTYRVVSVLTVLHQDWLNGKEYKCKVSNKGLASSIEKTISKAKGQPREPQVYTLPPCQE

EMTKNQVSLWCLVKGFYPSDIAVEWESNGQPENNYKTTPPVLDSDGSFFLYSKLTVDKSR

WQEGNVFSCSVMHEALHNHYTQKSLSLSLGK

Nucleotide sequence:
                                                                                    SEQ ID NO. 69
GAGGTGCAGCTGGTTGAATCTGGCGGAGGACTGGTTCAGCCTGGCGGATCTCTGAGA

CTGTCTTGTGCCGCCAGCGGCTTCACCTTCAACACCTACGCTATGAACTGGGTCCGAA

AGGCCCCTGGCAAAGGACTGGAATGGGTGGGAAGAATCAGGTCCAAGTACAACAACT

ACGCCACCTACTACGCCGACAGCGTGAAGGACAGATTCACCATCAGCAGGGACGACA

GCAAGAACAGCCTGTACCTGCAGATGAACAGCCTGAAAACCGAGGACACCGCCGTGT

ACTACTGTGTCAGACACGGCAACTTCGGCAACAGCTATGTGTCTTGGTTTGCCTACTGG

GGCCAGGGCACACTGGTCACAGTTAGCTCTGCTAGCACCAAGGGCCCCAGCGTGTTCC

CCCTGGCCCCTTGCAGCAGAAGCACCAGCGAGAGCACAGCCGCCCTGGGCTGCCTGG

TGAAGGACTACTTCCCCGAGCCCGTGACCGTGTCCTGGAACAGCGGCGCTCTGACCA

GCGGCGTGCATACCTTCCCCGCCGTGCTCCAGAGCAGCGGACTGTACTCCCTGAGCAG

CGTGGTGACCGTGCCTTCCAGCAGCCTGGGCACCAAGACCTACACCTGCAACGTGGA

CCACAAGCCCAGCAACACCAAGGTGGACAAGAGAGTGGAGAGCAAGTACGGCCCTC

CCTGCCCCCCTTGCCCTGCCCCCGAGTTCGAGGGCGGACCTAGCGTGTTCCTGTTCCC

CCCCAAGCCCAAGGACACCCTGATGATCAGCAGAACCCCCGAGGTGACCTGCGTGGT

GGTGGACGTGTCCCAGGAGGACCCCGAGGTCCAGTTTAATTGGTACGTGGACGGCGT

GGAAGTGCATAACGCCAAGACCAAGCCCAGAGAGGAGCAGTTCAACAGCACCTACAG

AGTGGTGTCCGTGCTGACCGTGCTGCACCAGGACTGGCTGAACGGCAAGGAATACAA

GTGCAAGGTCTCCAACAAGGGCCTGGCCAGCAGCATCGAGAAGACCATCAGCAAGGC

CAAGGGCCAGCCACGGGAGCCCCAGGTCTACACCCTGCCACCTTGTCAAGAGGAGAT

-continued

```
GACCAAGAACCAGGTGTCCCTGTGGTGTCTGGTGAAAGGCTTCTATCCCAGCGATATC

GCCGTGGAGTGGGAGAGCAACGGCCAGCCCGAGAACAACTACAAGACCACCCCCCCT

GTGCTGGACAGCGACGGCAGCTTCTTCCTGTACTCCAAGCTGACCGTGGACAAGTCCA

GATGGCAGGAGGGCAACGTCTTCAGCTGCTCCGTGATGCACGAGGCCCTGCACAACC

ACTACACCCAGAAGTCCCTGAGCCTGAGCCTGGGCAAG
```

2. Expression and Purification of Anti-BCMA×CD3 κλ Bispecific Antibodies

The plasmids encoding the corresponding antibody fragments were mixed according to light chain (κ light chain) of BCMA arm: light chain (Q light chain) of CD3 arm: heavy chain (heavy chain 1) of BCMA arm: heavy chain (heavy chain 2) of CD3 arm=2:2:1:1 ratio. After mixing with 3 mg/mL PEI, co-transfecting of CHO-S cells, and culture in 500 mL CD CHO AGT medium (Gibco #12490-001) at 37° C. 5% $CO_2$ at 150 rpm, 4% CHO Feed C+supplement (Gibco #A25031-05) was added at transient day 2, 4 and 6, respectively. When the cell viability decreased to about 85%, the fermentation broth was harvested, filtered and purified by Protein A affinity chromatography, and the SEC-HPLC monomer content was close to or higher than 92%. The monomer content was further increased to above 98-99% by Capto S ImpAct ion exchange chromatography (Table 11).

TABLE 11

Purity of BCMA × CD3 κλ bispecific antibody

| HPLC detection | HPLC-SEC (post Protein A) | | | HPLC-SEC (after cation exchange chromatography) | | |
| --- | --- | --- | --- | --- | --- | --- |
| | Mer | Monomer | Fragment | Mer | Monomer | Fragment |
| BCMA × CD3 κλ003 | 2.3% | 94.4% | 3.3% | 1.8% | 98.2% | 0.0% |
| BCMA × CD3 κλ004 | 1.4% | 95.2% | 3.4% | 1.0% | 99.0% | 0.0% |
| BCMA × CD3 κλ005 | 2.0% | 91.9% | 6.2% | 1.6% | 98.4% | 0.0% |
| BCMA × CD3 κλ006 | 0.5% | 96.4% | 3.1% | 0.6% | 99.4% | 0.0% |

3. Binding Activity of BCMA×CD3 κλ Bi-Specific Antibodies

(1) Determination of Affinity of BCMA×CD3 Ick Bispecific Antibody to Antigen 10 µg/mL human or cynomolgus monkey BCMA or CD3εγ recombinant antigen was bound to a CM5 chip (GE healthcare) by amino conjugating, while the amount of antigen bound was controlled to approximately 200RU. After baseline plateau, gradient diluted antibodies (7 gradients of 2-fold dilutions from 10 gg/mL) were flowed through the chip at a flow rate of 30 L/min for a binding time of 350 seconds and a dissociation time of 600 seconds. Kinetic constants were fitted using Biacore T200 evaluation software with a 1: 1 binding model. The results of the affinity determination are shown in Table 12.

TABLE 12

Affinities of BCMA × CD3 κλ bispecific antibodies to antigens

| KD(nM) | Human BCMA | Cynomolgus monkey BCMA | Human CD3εγ | Cynomolgus monkey CD3εγ |
| --- | --- | --- | --- | --- |
| BCMA × CD3 κλ003 | 1.3 | 0.16 | 31 | 43 |

TABLE 12-continued

Affinities of BCMA × CD3 κλ bispecific antibodies to antigens

| KD(nM) | Human BCMA | Cynomolgus monkey BCMA | Human CD3εγ | Cynomolgus monkey CD3εγ |
| --- | --- | --- | --- | --- |
| BCMA × CD3 κλ004 | 1.0 | 0.12 | 32 | 43 |
| BCMA × CD3 κλ005 | 1.1 | 0.09 | 28 | 20 |
| BCMA × CD3 κλ006 | 1.2 | 0.10 | 27 | 33 |

(2) Binding of BCMA×CD3 Ick Bispecific Antibody to BCMA+Cells

Figure 20:
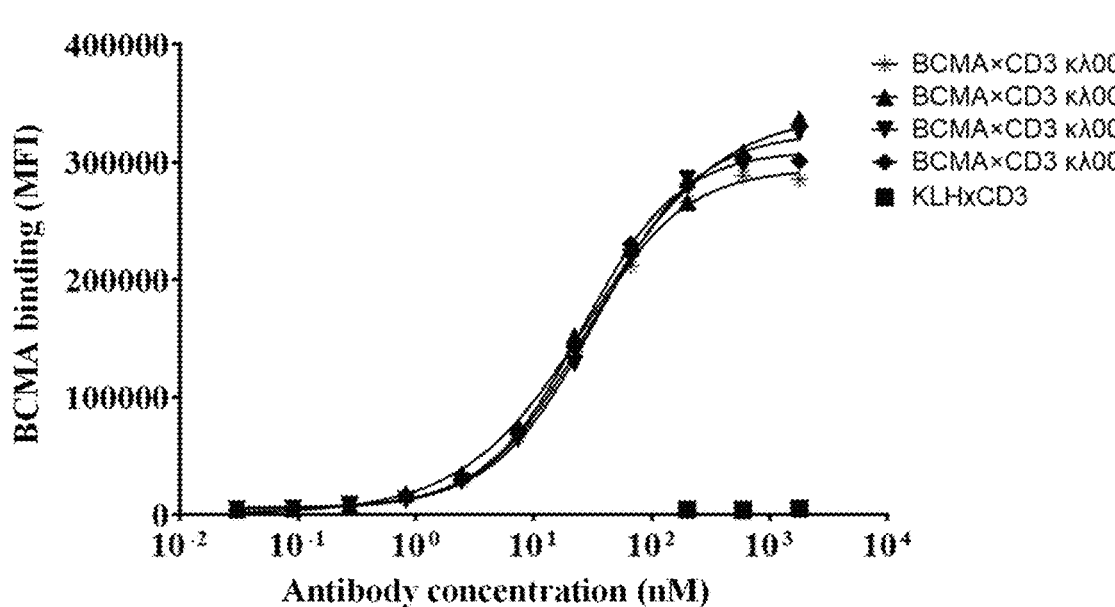
FIG. 20 shows binding of the anti-BCMA×CD3 κλ bispecific antibody to BCMA stably transfected cells.
Figure 20:
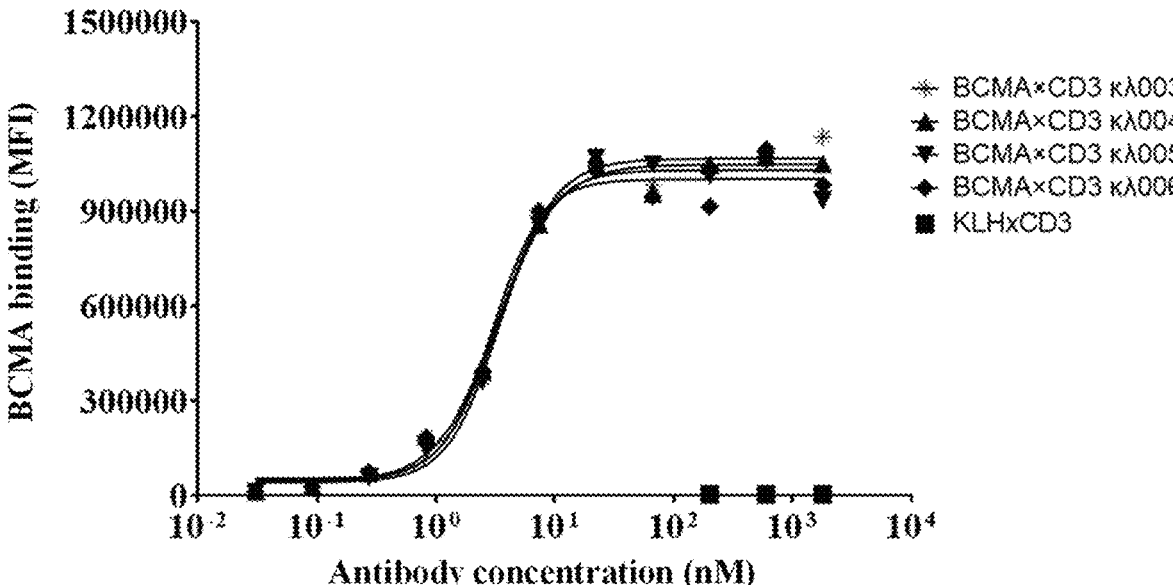
Figure 21:
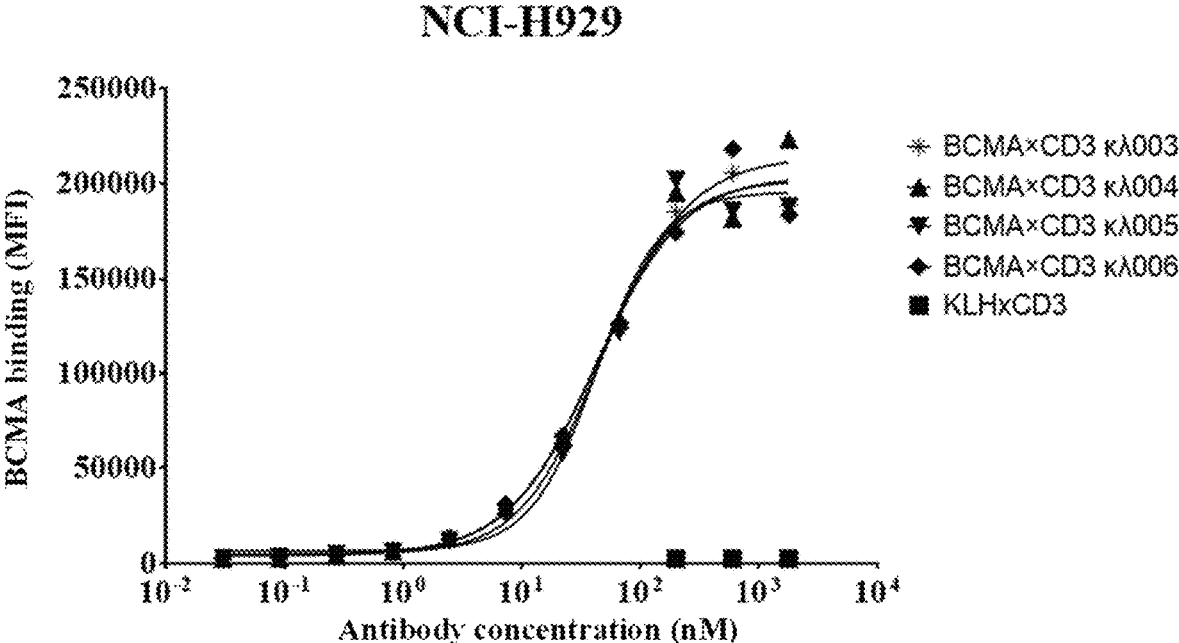
FIG. 21 shows binding of the anti-BCMA×CD3 κλ bispecific antibody to tumor cells NCI-H929 and RPMI-8226.
Figure 21:
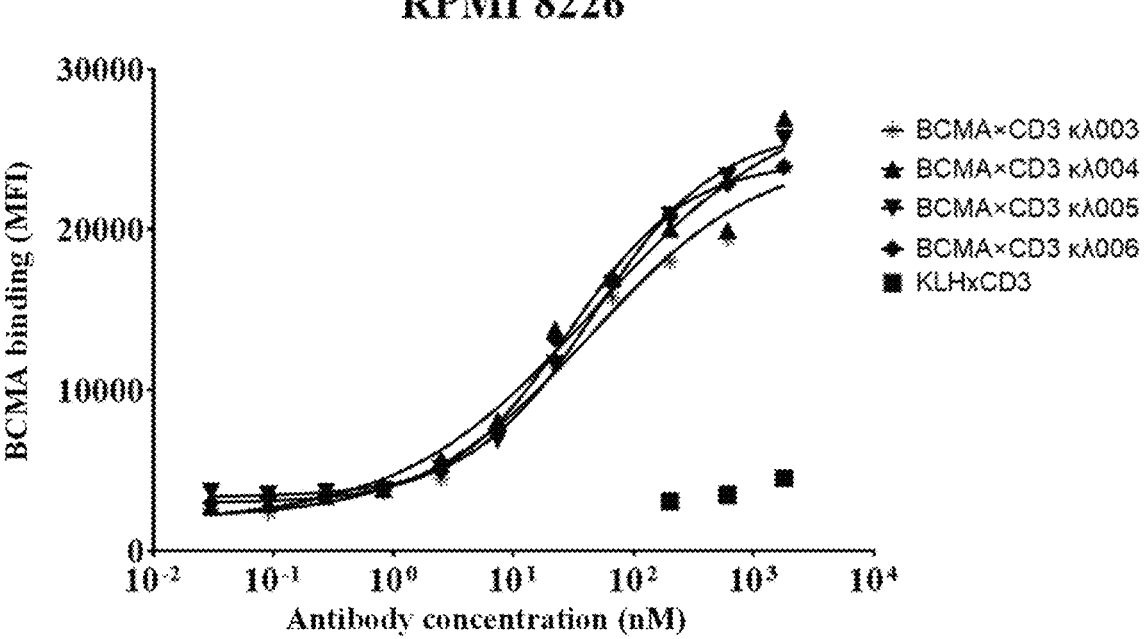

Logarithmically growing CHO-human BCMA stably transfected cells (CHO-hBCMA) and CHO-cynomolgus monkey BCMA stably transfected cells (CHO-cynoBCMA), and tumor cells NCI-H929 and RPMI-8226, respectively, were blocked and 100 µL of gradient diluted antibody (starting concentration 1800 nM, 3-fold dilution, 10 gradients) was added to each well and incubated for 60 min at 4° C. 50 µL/well Alexa Fluro647 labeled goat anti-human IgG Fc (1: 300 dilution) were added to the secondary antibody, incubated on ice for 20 min, added with 50 L/well PI solution (1: 300) after washing once, incubated for 5 min, and flow cytometer was used to make detection. FIG. 20 shows that the BCMA×CD3 κλ bispecific antibody binds with high affinity to human, cynomolgus monkey BCMA stably transfected cells. FIG. 21 shows that the BCMA×CD3 κλ bispecific antibody binds with high affinity to BCMA+ tumor cells NCI-H929 and RPMI-8226. The binding constants $EC_{50}$ of the BCMA×CD3 κλ bispecific antibody to cells are shown in Table 13.

TABLE 13

Binding of BCMA × CD3 κλ bispecific antibodies to BCMA stably transfected cells.

| $EC_{50}$(nM) | Human BCMA-CHO | Cynomolgus monkey BCMA-CHO | NCI-H929 | RPMI-8226 |
| --- | --- | --- | --- | --- |
| BCMA × CD3 κλ003 | 16 | 3 | 34 | 34 |

TABLE 13-continued

| | Human BCMA-CHO | Cynomolgus monkey BCMA-CHO | NCI-H929 | RPMI-8226 |
|---|---|---|---|---|
| EC_{50}(nM) | | | | |
| BCMA × CD3 κλ004 | 22 | 3 | 36 | 39 |
| BCMA × CD3 κλ005 | 24 | 3 | 33 | 38 |
| BCMA × CD3 κλ006 | 16 | 3 | 32 | 19 |
| KLH × CD3 | — | — | — | — |

Binding of BCMA × CD3 κλ bispecific antibodies to BCMA stably transfected cells.

(3) Binding of BCMA×CD3 κλ Bispecific Antibody to Jurkat Cells

Figure 22:
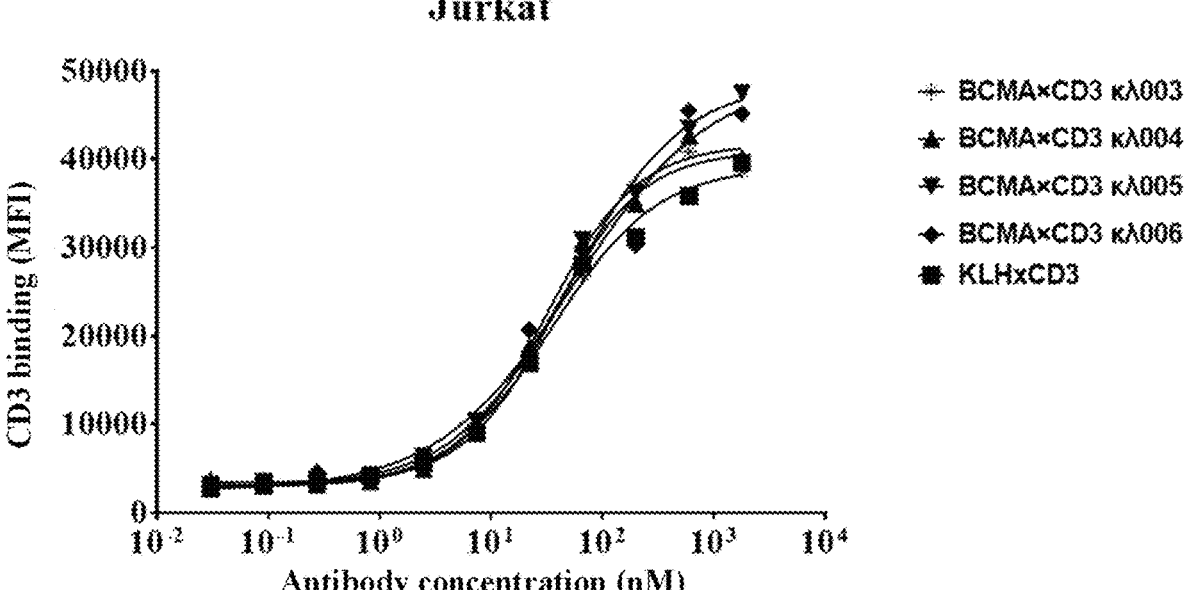
FIG. 22 shows binding of the anti-BCMA×CD3 κλ bispecific antibody to a Jurkat cell.

Jurkat cells in logarithmic growth phase were added with 200 μg/mL murine IgG (Jackson ImmunoResearch, 115-005-03) and incubated on ice for 30 minutes. The cells were adjusted to 5×105 cells/mL with 4% calf serum, 100 μL/well was added to 96-well U-plate, 300 g was centrifuged to removed the supernatant, 100 μL/well of gradient diluted antibody (initial concentration: 1800 nM, 3-fold dilution, 10 gradients) was added and incubated at 4° C. for 60 min. 50 μL/well Alexa Fluro647-labeled goat anti-human IgG Fc (1: 300 dilution) was added to the secondary antibody and incubated on ice for 20 min. 50 μL/well PI was added after washing once, incubated for 5 min, and detected with flow cytometer (BD C6). The results are shown in FIG. 22 and Table 14. The BCMA×CD3 κλ bispecific antibody binds human leukemia T-cell line Jurkat cells with moderate affinity.

(4) Binding of BCMA×CD3 κλ Bispecific Antibody to Peripheral Blood T-Cells

Figure 23:
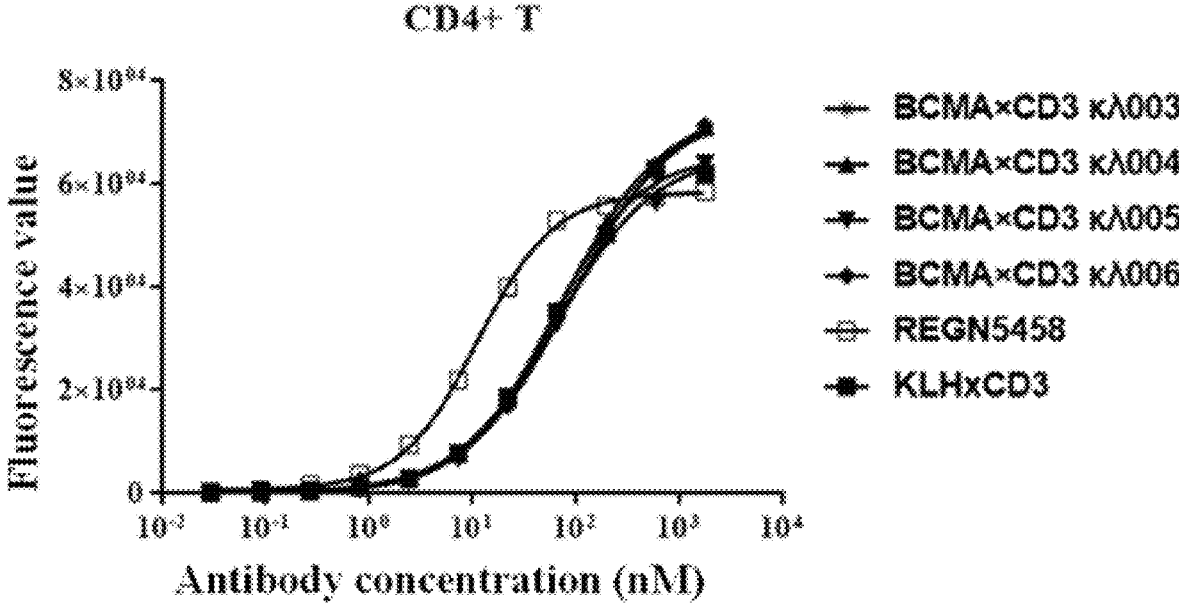
FIG. 23 shows binding of the anti-BCMA×CD3 κλ bispecific antibody to a T-cell in the peripheral blood.
Figure 23:
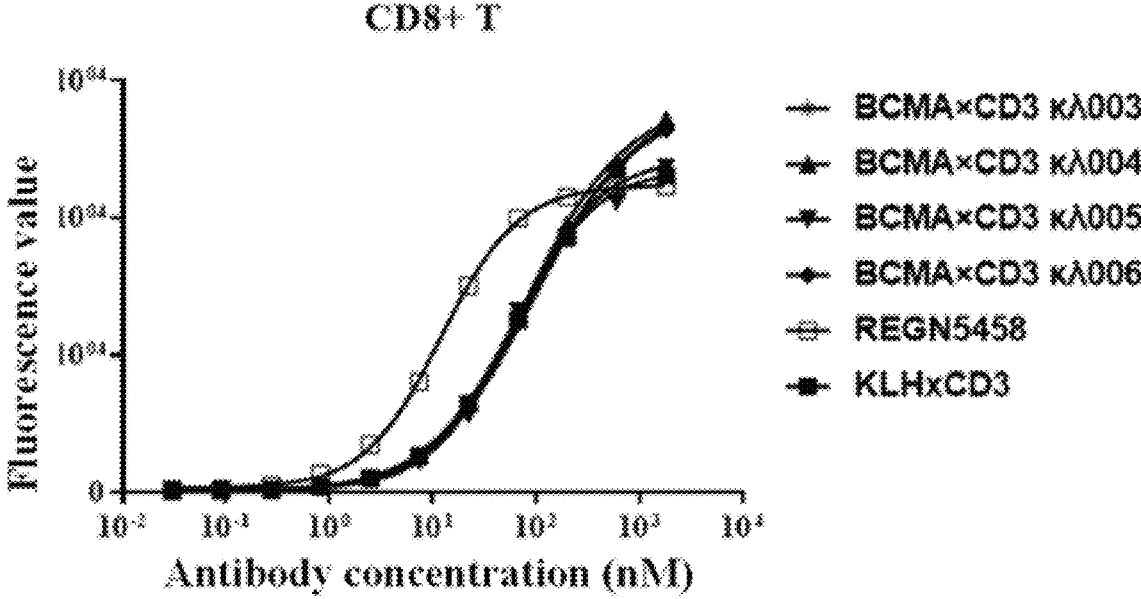

Fresh human peripheral blood was taken and PBMC was isolated by Ficoll. Paque Plu (GE, 17-1440-03). PBMC was adjusted to 5×105 cells/mL with 4% calf serum (Hyclone, SH30626.06), 100 μL/well was added to a 96-well U-plate, the supernatant was centrifuged off and 100 L of gradient diluted antibody (with starting concentration of 1800 nM, 3-fold dilution, 10 gradients) was added to each well and incubated for 60 min at 4° C. 50 μL/well of Alexa Fluro647 labeled goat anti-human IgG Fc (1: 300 dilution) was added to the secondary antibody, with ice bath for 20 min, and 50 μL/well PI added after washing once, incubated for 5 min, and flow cytometer (BD C6) was used for detection. The control antibody REGN5458 was synthesized and prepared according to US20200024356. As shown in FIG. 23 and Table 14. The BCMA x CD3×bispecific antibody recognizes human peripheral blood CD4+T and CD8+T-cells with an affinity of about 60-97 nM, which is weaker than the binding force of the BCMA antigen arm to the BCMA receptor, so that the bispecific antibody preferentially enriches into tumor cells.

TABLE 14

Binding of BCMA × CD3 κλ bispecific antibodies to Jurkat cells

| EC_{50}(nM) | Jurkat | CD4 + T | CD8 + T |
|---|---|---|---|
| BCMA × CD3 κλ003 | 66 | 89 | 97 |
| BCMA × CD3 κλ004 | 61 | 79 | 67 |
| BCMA × CD3 κλ005 | 51 | 66 | 60 |
| BCMA × CD3 κλ006 | 56 | 91 | 93 |
| KLH × CD3 | 76 | 57 | 62 |

4. TDCC Mediated by BCMA×CD3 κλ Bispecific Antibody

Figure 24A:
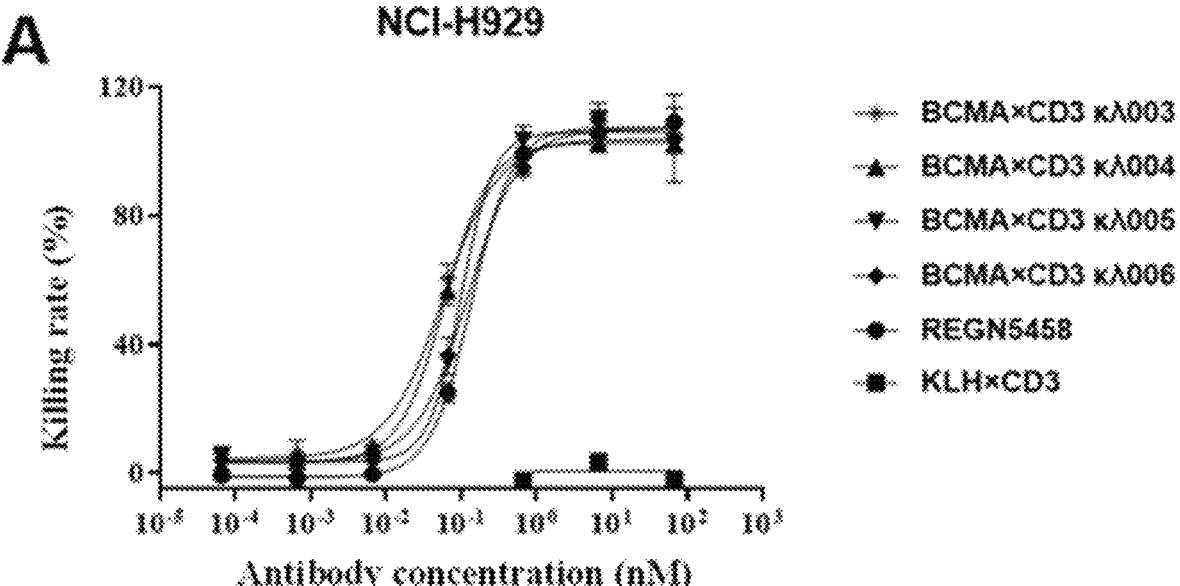
FIG. 24A and FIG. 24B show TDCC mediated by the anti-BCMA×CD3 κλ bispecific antibody.
Figure 24B:
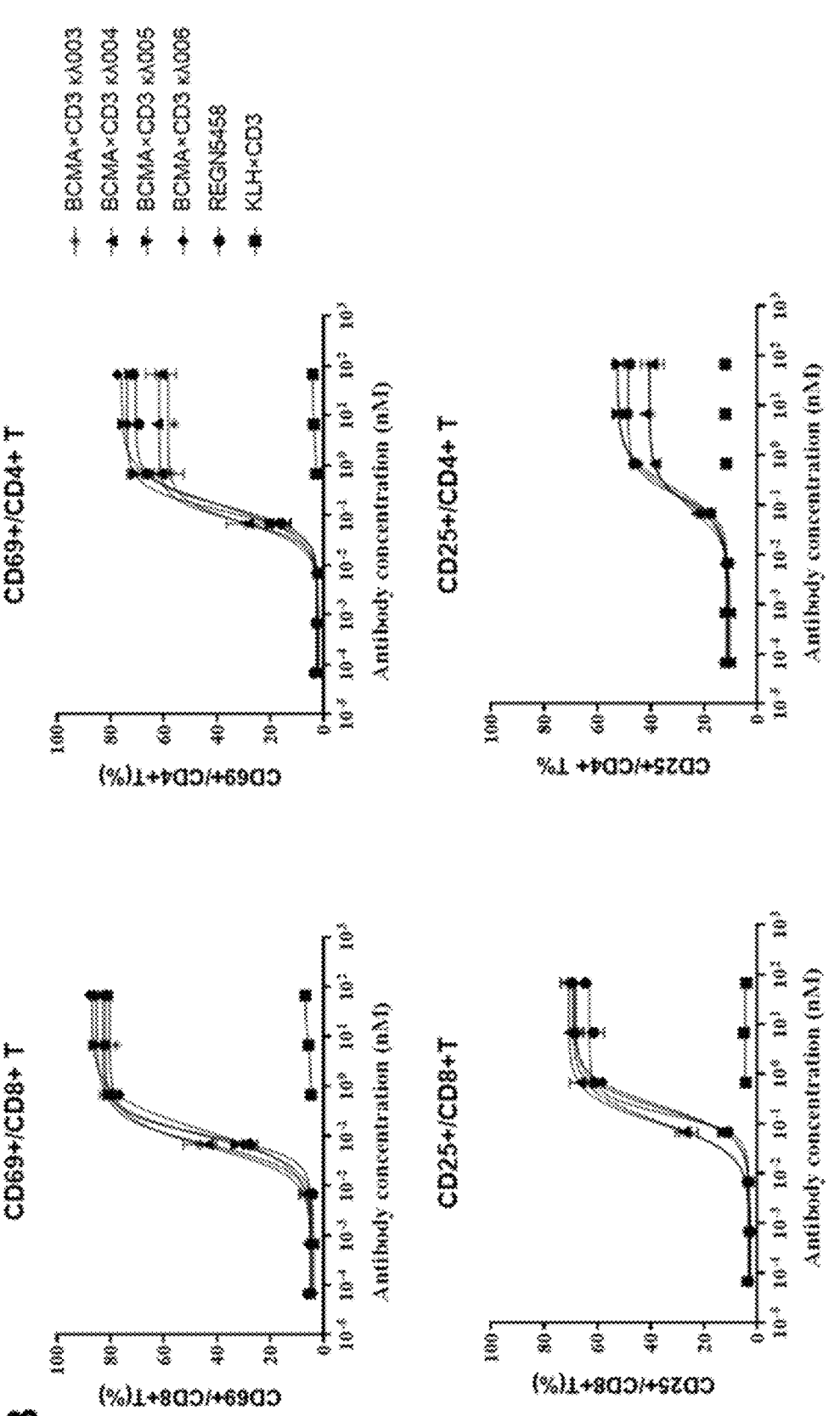
Figure 25A:
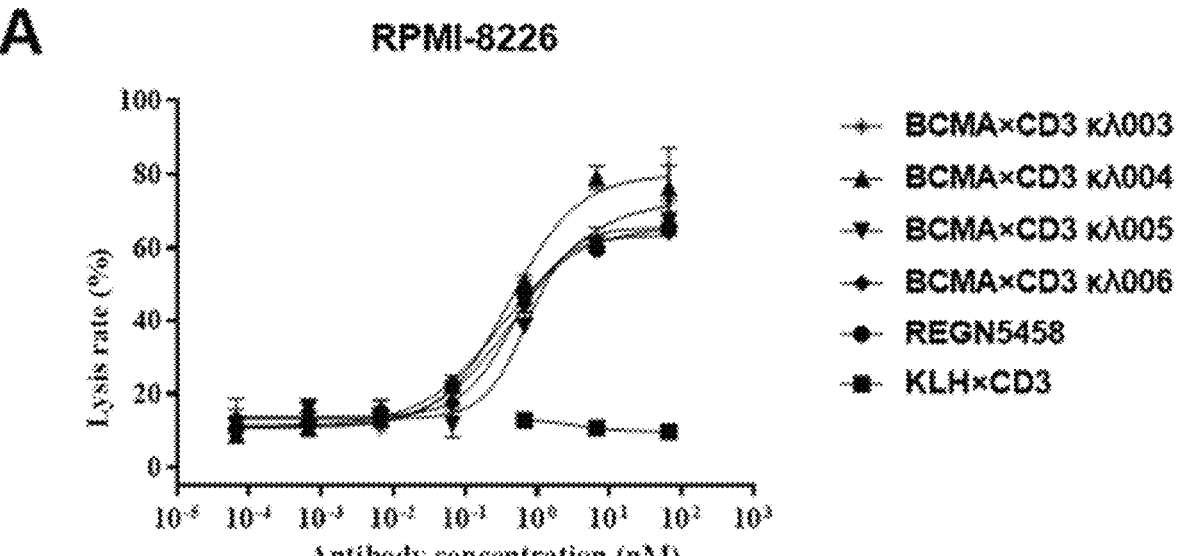
FIG. 25A and FIG. 25B show TDCC mediated by the anti-BCMA×CD3 κλ bispecific antibody.
Figure 25B:
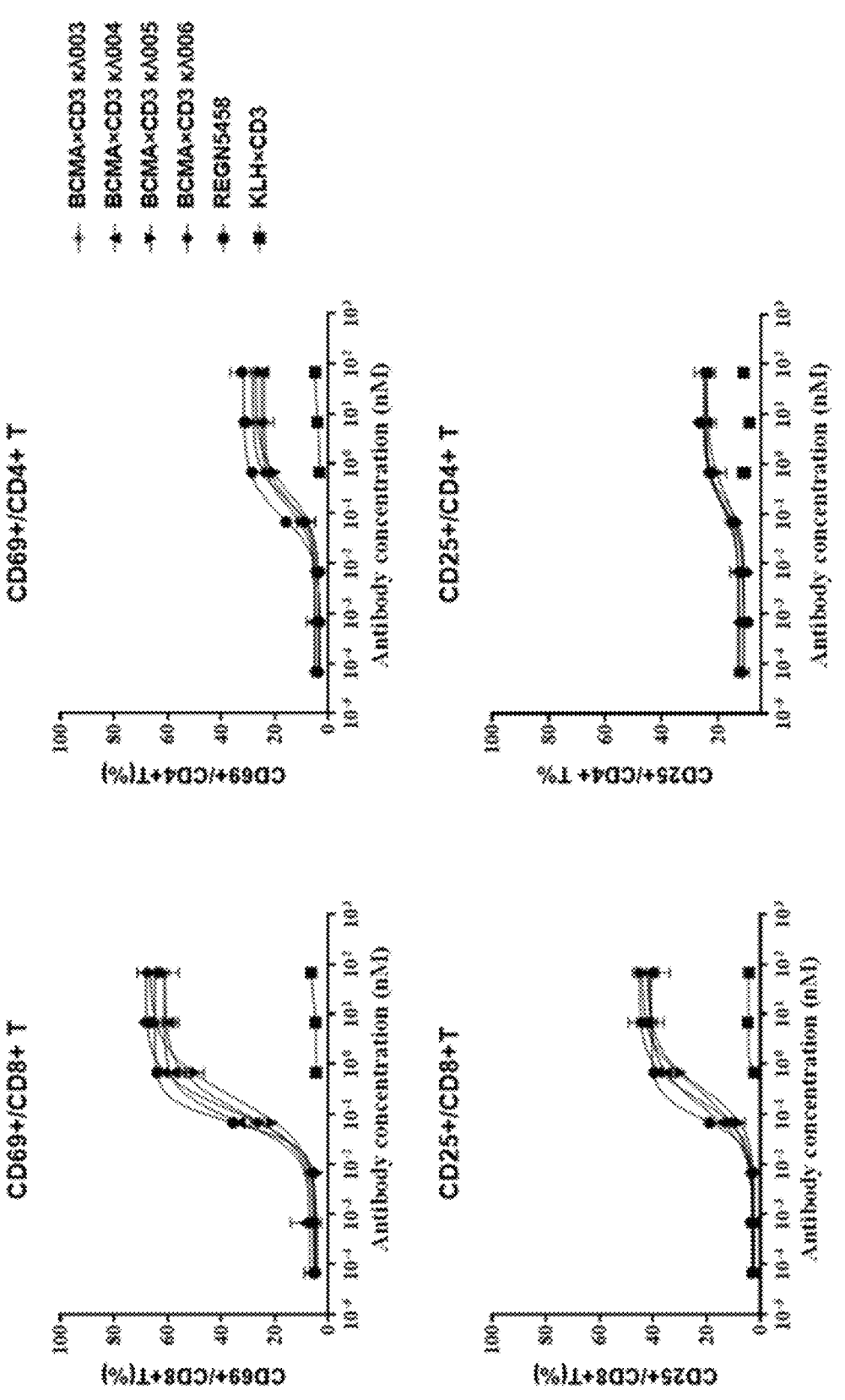

Freshly isolated PBMC was mixed with target cells in logarithmic growth phase, NCI-H929 and RPMI-8226 cells, respectively, with effect/target cell=8: 1. 50 L of gradient diluted antibody (antibody concentration from 66.7 nM, 10-fold dilution, 7 gradients) was added to each well and incubated for 24 h at 37° C. in 5% $CO_2$. At the end of the incubation, 50 μL of the supernatant was transferred to a new black elisa plate, 50 μL/well of LDH detection substrate was added, the reaction was stopped after 10 minutes and LDH release was detected. The remaining cells in the wells were washed twice with 4% calf blood, incubated with 100 μg/mL human IgG for 10 minutes, followed by T-cell activation detection antibodies (CD25-PE, CD4-APC, CD69-FITC and CD8-APC) and incubated on ice for 20 minutes. The supernatant was washed and discarded, 60 μL/well PI was added, incubated on ice for 5 minutes and detected by flow cytometry. FIGS. 24A, 24B show killing of NCI-H929 cells and activation of T-cells, respectively, by BCMA×CD3 κλ bispecific antibody. FIGS. 25A, 25B show killing of RPMI-8226 cells and activation of T-cells by CMA×CD3 κλ bispecific antibody, respectively. For tumor cells NCI-H929 and RPMI-8226 with different expression levels of BCMA, the BCMA×CD3 κλ bispecific antibody can mediate effective killing of T-cells, and the killing activity is equivalent to that of control antibody REGN5458.

5. Activation of T-Cell Activation Pathway by BCMA×CD3 κλ Bispecific Antibody

Figure 26:
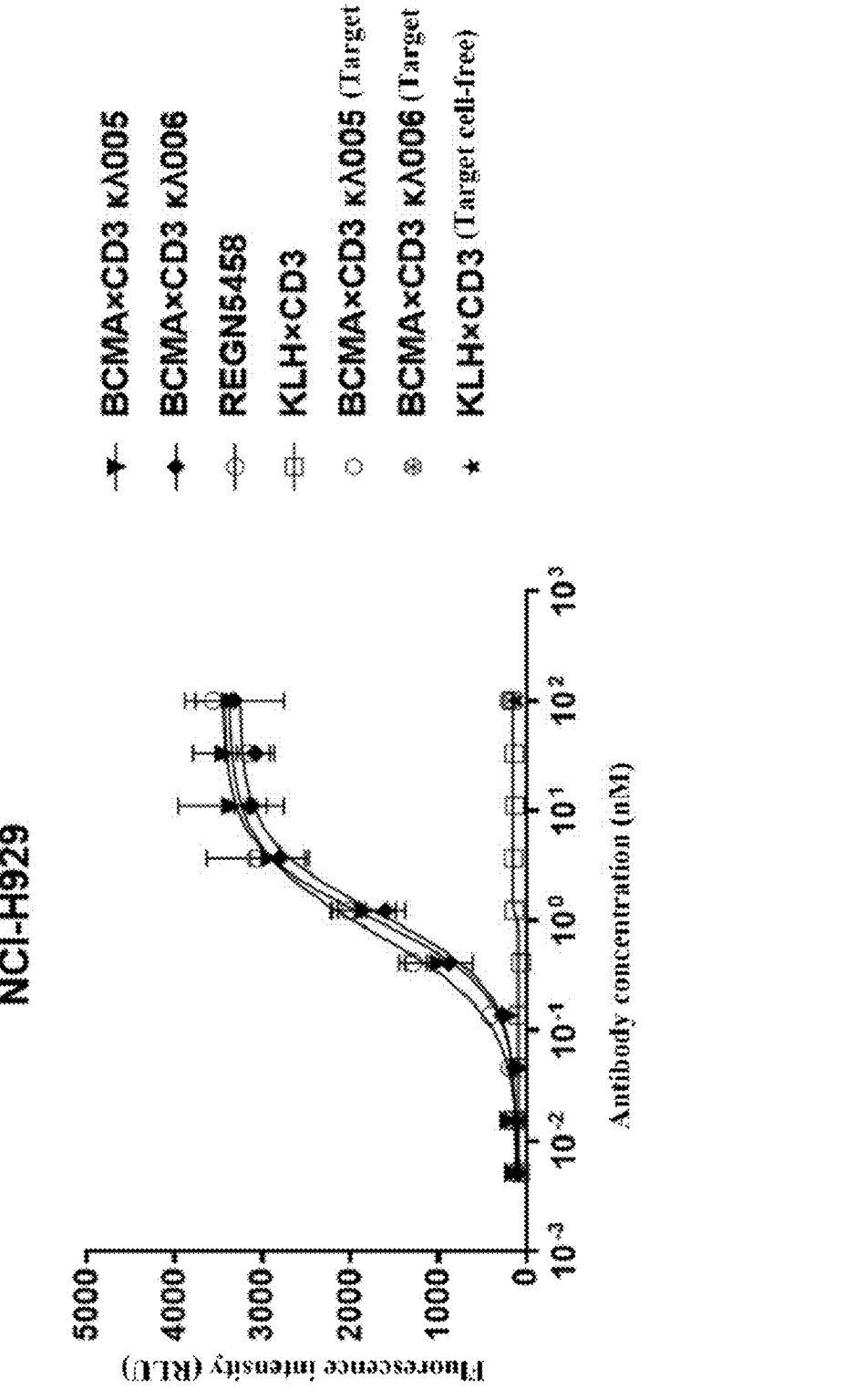
FIG. 26 shows the effect of the anti-BCMA×CD3 κλ bispecific antibody on the T-cell NFAT signaling pathway.

Logarithmically growing Jurkat-NFAT-luc reporter cells and BCMA-positive target cells RPMI-8226 were taken, centrifuged to discard the supernatant and resuspended to $2×10^6$ cells/ml. 50 μl/well of the target cells were inoculated into a 96-well plate, the supernatant was discarded by centrifugation at 300 g for 5 minutes, and 50 μl/well of the Jurkat-NFAT-luc reporter cells were inoculated into a 96-well plate, and 50 μl of gradient diluted BCMA×CD3 κλ bispecific antibody or control antibody KLH×CD3 (with a starting concentration of 20 g/ml, 10-fold dilution, 10 gradients) was added to each well, and incubated at 37° C. for 6 hours in 5% $CO_2$. After the incubation, 100 μL of detection reagent was added to each well according to ONE-Glo Luciferase Assay System instructions, allowed to stand at room temperature for 3 minutes, and detected on a microplate reader (Biotek Synergy HT). The detection results are shown in FIG. 26. The BCMA×CD3×bispecific antibody can activate the NFAT signaling pathway of T-cells when RPMI-8226 tumor cells are used as target cells. In the absence of target cells, the NFAT signaling pathway is not activated.

6. Non-Specific Activation of PBMC by BCMA×CD3 κλ Bispecific Antibody

Figure 27:
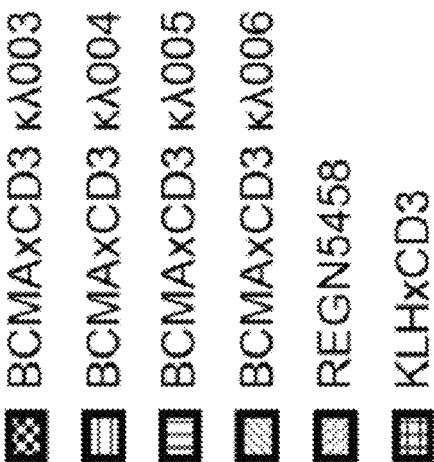
FIG. 27 shows non-specific activation of PBMC by the anti-BCMA×CD3 κλ bispecific antibody.
Figure 27:
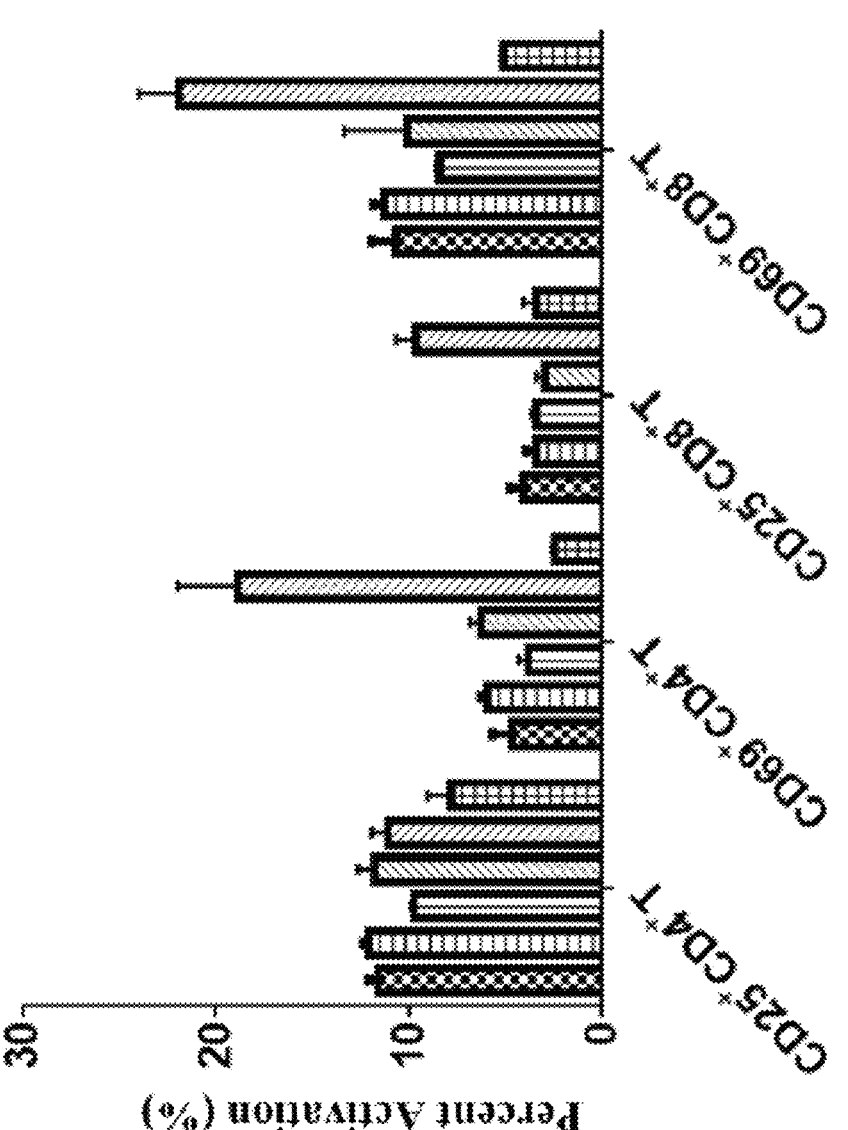

Freshly isolated PBMC was taken and 50 L of gradient diluted antibody (with antibody concentration from 66.7 nM, 10-fold dilution, 7 gradients) was added to each well and incubated at 37° C. in 5% $CO_2$ for 24 hours. At the end of the incubation, 50 L of the supernatant was transferred to a new black elisa plate, 50 μL/well of LDH detection substrate was added, the reaction was stopped after 10 minutes and LDH release was detected. The remaining cells in the wells were washed twice with 4% calf blood, incubated with 100 μg/mL human IgG for 10 minutes, followed by T-cell activation detection antibodies (CD25-PE, CD4-APC, CD69-FITC and CD8-APC) and incubated on ice for 20 minutes. The supernatant was washed and discarded, 60 μL/well PI was added, incubated on ice for 5 minutes and detected by flow cytometry. The results are shown in FIG. 27. In the absence of target cells, the BCMA×CD3 cd bispecific antibody had no activation of peripheral blood T-cells, comparable to the negative control KLH×CD3.

7. Binding of BCMA×CD3κλ Humanized Bispecific Antibody to Fc Receptor

Figure 28:
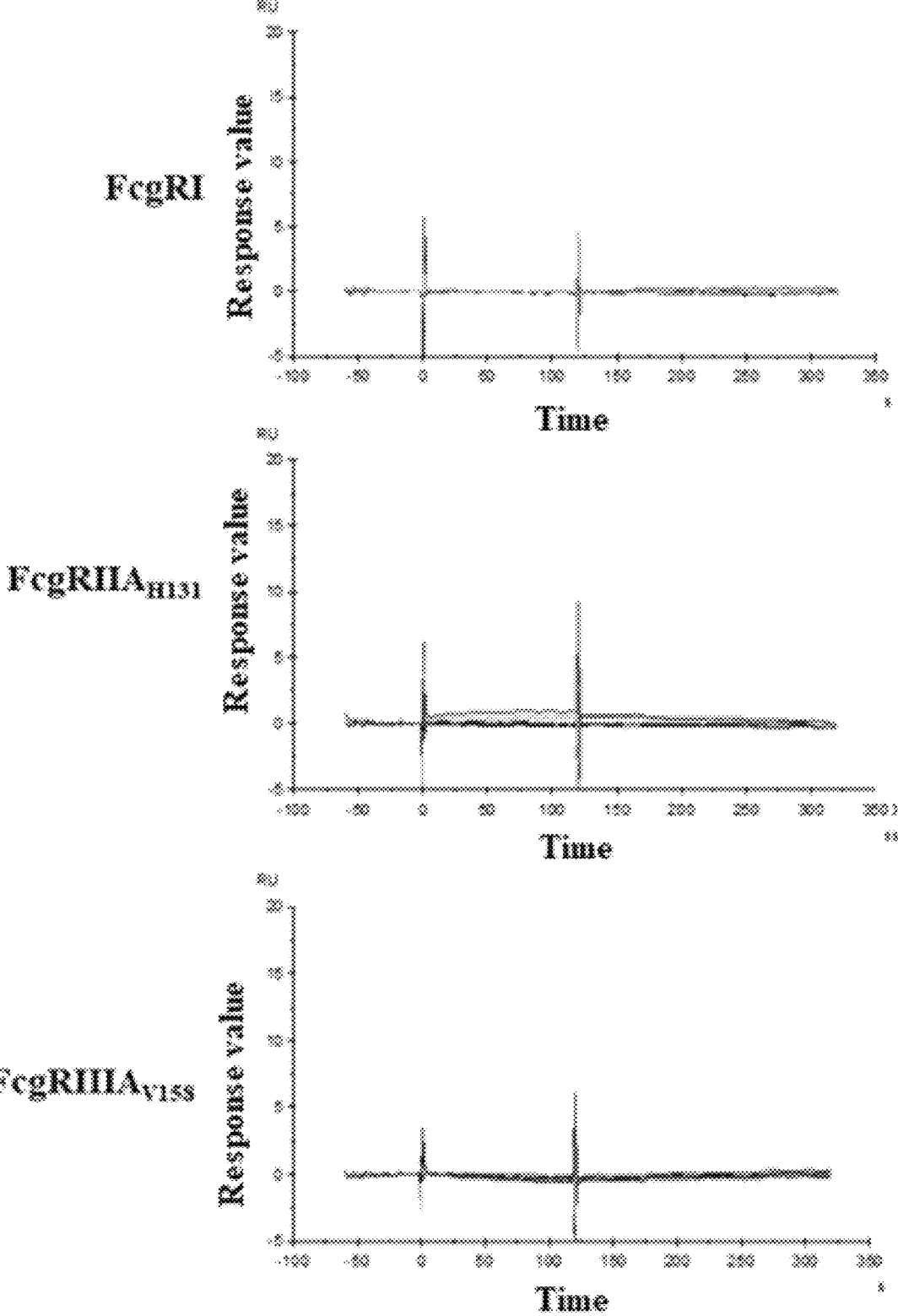
FIG. 28 shows binding of the anti-BCMA×CD3 κλ bispecific antibody to an Fc receptor.
Figure 28:
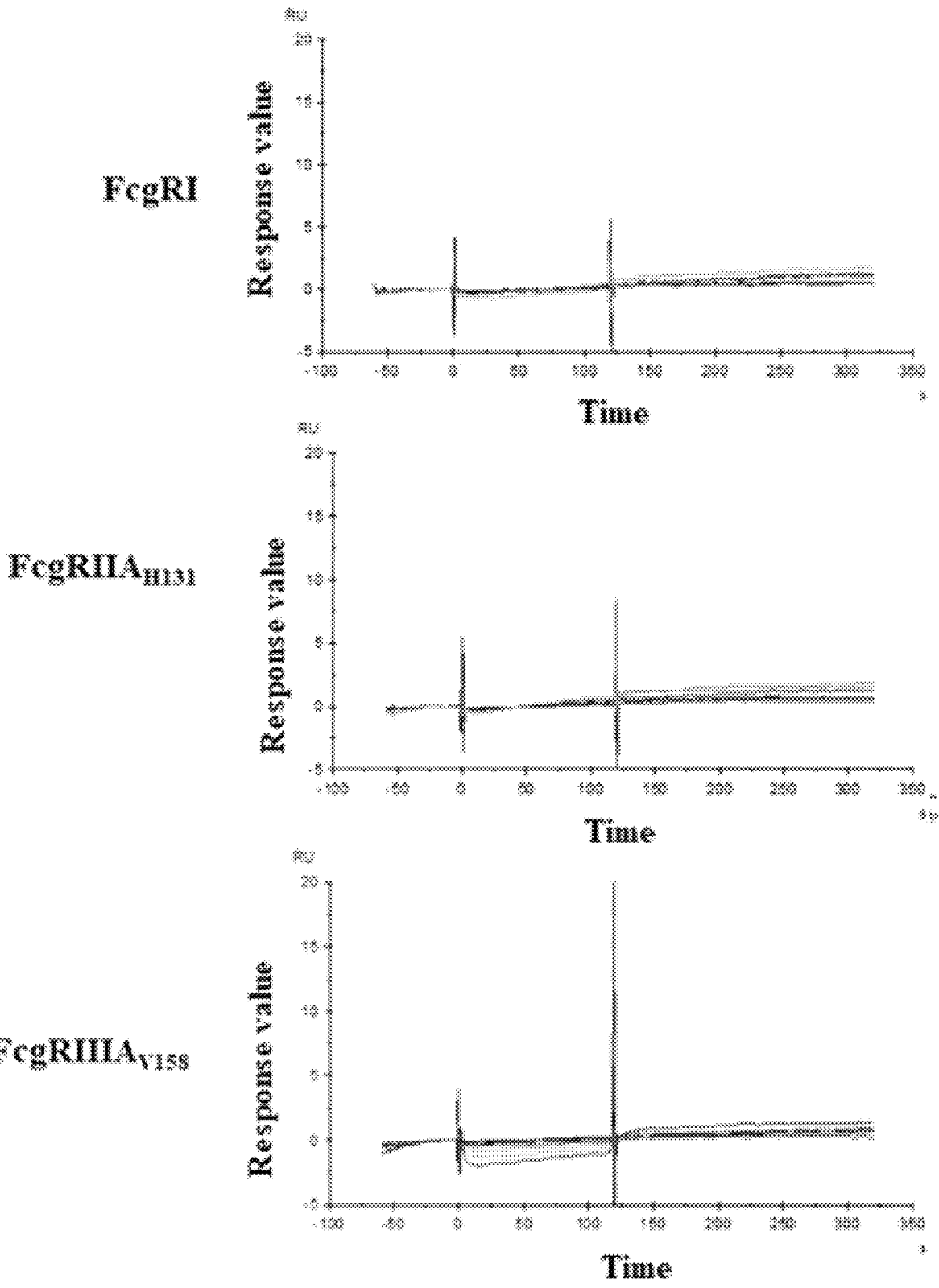
Figure 28:
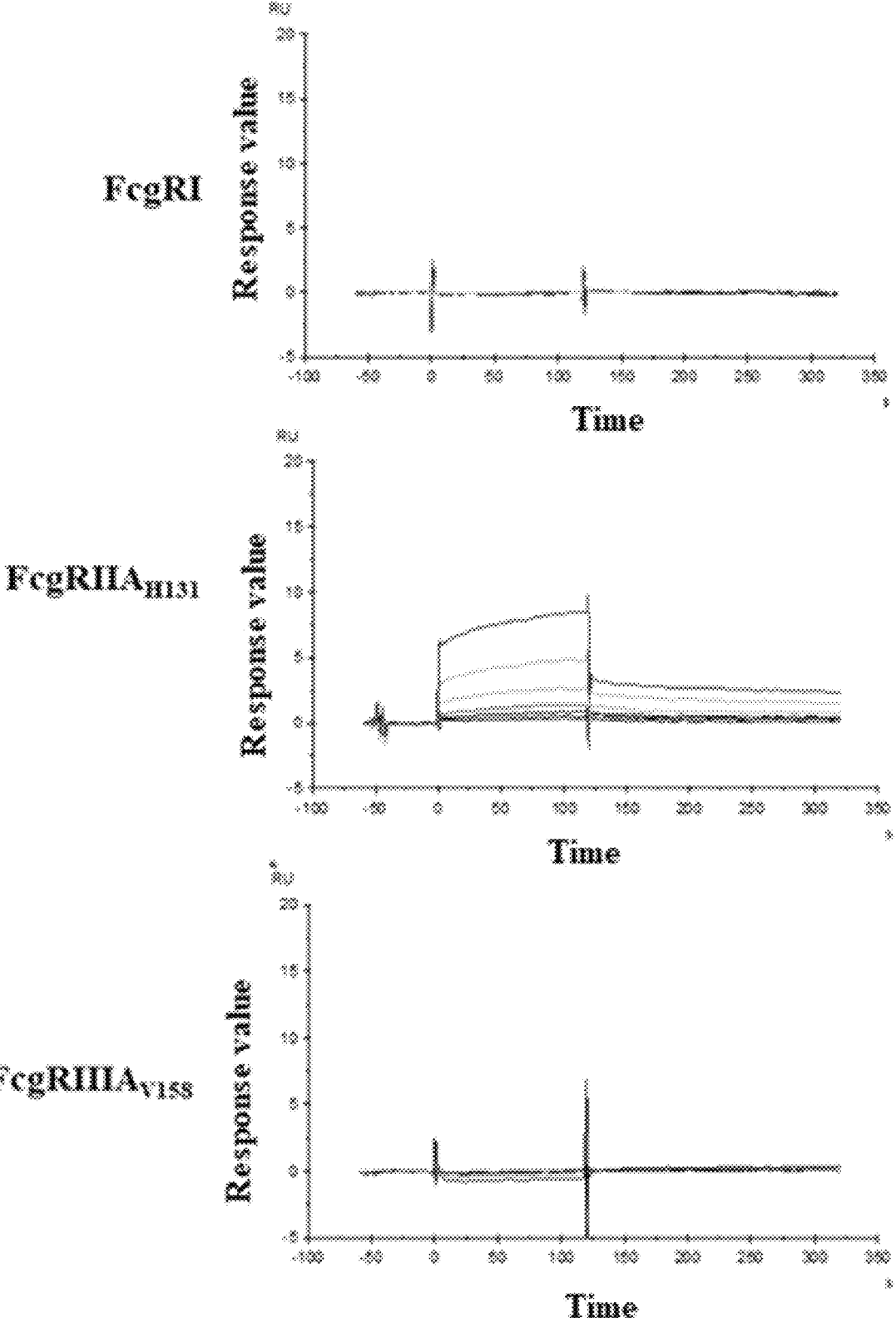
Figure 28:
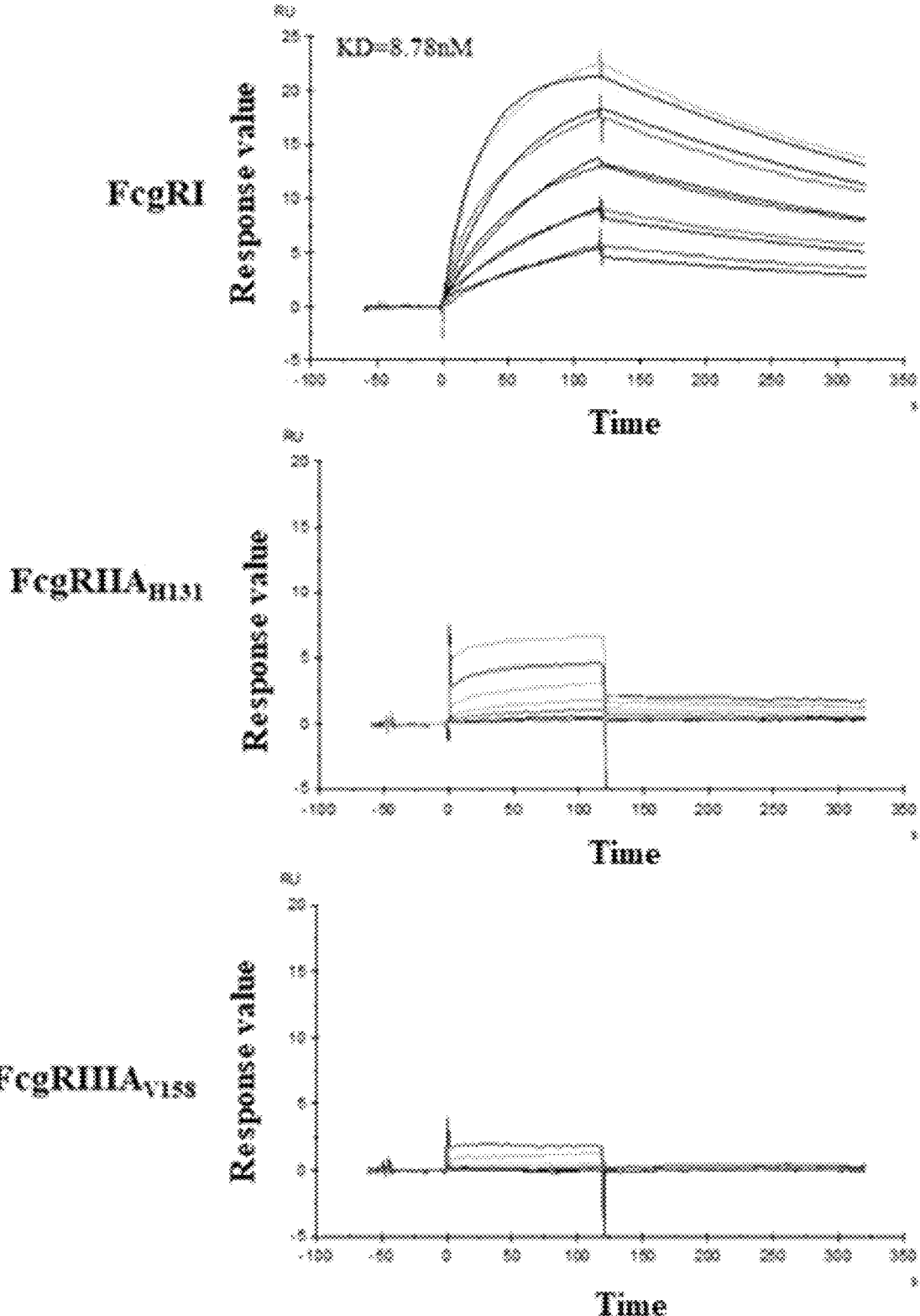

50Mg/ml of His-Tag antibody was amino-conjugated to a CM5 chip to capture the His6-tagged FcγRI, FcγRIIA$_{H131}$ and FcγRIIIA$_{V158}$ recombinant proteins, respectively, with a capture time of 40 seconds and a flow rate of 10 μL/min. After baseline plateau, the gradient diluted antibody (with starting concentration of 37.5 μg/mL, 2-fold dilution) was flowed through the chip at a flow rate of 30 μL/min, with an association time of 120 seconds and a dissociation time of 200 seconds, and affinity constants were obtained by fitting with Biacore evaluation software. As can be seen from FIG. 28, the BCMA x CD3×bispecific antibody did not bind to FcγRI, FcγRIIA$_{H131}$ and FcγRIIIA$_{V158}$; the wild-type IgG4 control antibody bound FcγRI with high affinity and weakly bound to FcγRIIA$_{H131}$.

8. Subcutaneous NCI-H929 Xenograft Tumor Model in Immunodeficient Mice

Figure 29:
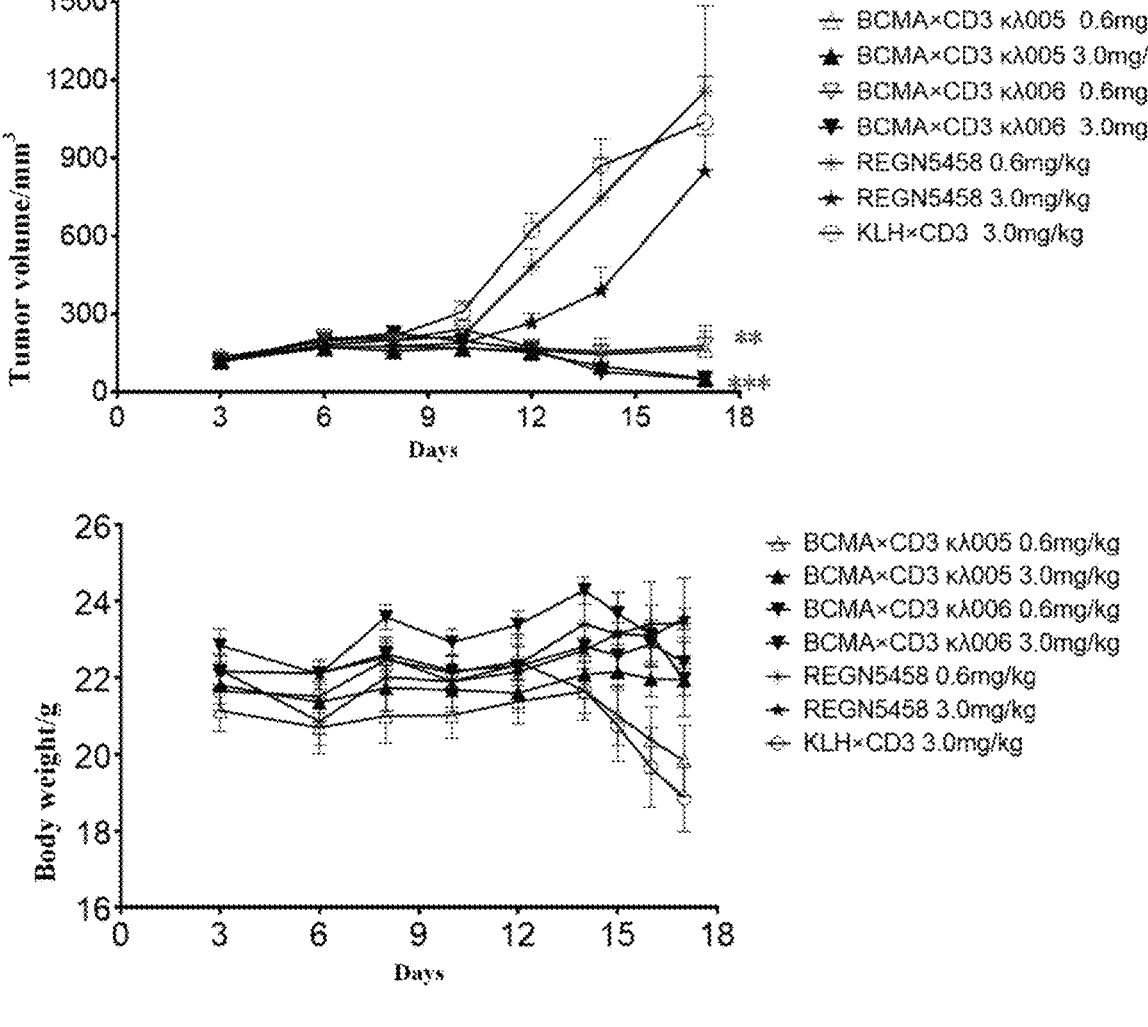
FIG. 29 shows inhibitory effect of the anti-BCMA×CD3 κλ bispecific antibody in the xenograft model of subcutaneous NCI-H929 in immunodeficient mice.

Six to eight-week-old female B-NGD mice (Bio-Tech Co. Ltd.) were subcutaneously inoculated with 2×10$^6$ NCI-H929 cells (mixed with Matrigel 1: 1). When the tumors grew to 60 mm$^3$, they were randomly divided into dose group (3.0 mg/kg), dose group (0.6 mg/kg) and negative control group (KLH×CD3 3 mg/kg). Each mouse received 1×107 PBMC cells via tail vein injection. Three days later, the first dose was administered to the mouse once every 5 days for a total of 2 doses. The tumor volume and body weight of the mice were monitored every 2 days. At the end of the experiment, the mice were killed by cervical dislocation and the tumors were collected and weighed. The results are shown in FIG. 29. The in vivo efficacy of BCMA x CD3×bispecific antibody was dose-related. The tumor inhibition rates in 3.0 mg/kg group and 0.6 mg/kg group were 95% and 108% (BCMA x CD3×005) and 94% and 108% (BCMA×CD3×

006), respectively. The tumor-bearing mice tolerated the foregoing doses well, without weight loss and other adverse reactions.

Example 4: Construction of GPC3×CD3 κλ Bispecific Antibodies Formed by Different Types of Light Chains

1. Construction of GPC3×CD3 κλ Bispecific Antibody

A GPC3 antibody containing a κ light chain and a humanized anti-CD3 antibody containing λ light chain, with reference to Example 2, were used to construct a novel GPC3-CD3×humanized bispecific antibody having the native IgG configuration, while introduction in the GPC3 antigen arm and the CD3 arm is made of charge variants (Vκ$_{GPC3}$: Gln$_{43}$Lys; VH$_{GPC3}$: Gln$_{39}$Glu; V/λ$_{CD3}$: Gln$_{40}$Glu; V$_{HCD3}$: Gln$_{39}$Lys) (see Table 15 for sequence). The Fc portion of the bispecific antibody adopts the human IgG4 knob-into-hole structure to achieve heterodimer pairing, and through mutation of Ser$_{228}$Pro, Leu$_{235}$Glu, and Pro$_{329}$Ala, the hinge region remains stable and interaction with Fcγ receptor and C1q is reduced.

TABLE 15

| GPC3 × CD3κλ humanized bispecific antibody | | | |
| --- | --- | --- | --- |
| light chain of CD20 arm | heavy chain of CD20 arm | light chain of CD20 arm | heavy chain of CD20 arm |
| GPC3 × CD3 κλ002 | SEQ ID NO. 88 | SEQ ID NO. 90 | SEQ ID NO. 66 | SEQ ID NO. 68 |
| GPC3 × CD3 κλ003 | SEQ ID NO. 92 | SEQ ID NO. 94 | SEQ ID NO. 66 | SEQ ID NO. 68 |

GPC3×CD3 κλ002:

```
κ light chain of GPC3 arm:
                                          SEQ ID NO. 88
DVVMTQSPLSLPVTPGEPASISCRSSQSIVHSNGNTYLEWYLKKPGQSPQLLIYKVSNRFSG

VPDRFSGSGSGTDFTLKISRVEAEDVGVYFCLQVTHVPLTFGQGTKLEIKRTVAAPSVFIFP

PSDEQLKSGTASVVCLLNNFYPREAKVQWKVDNALQSGNSQESVTEQDSKDSTYSLSSTL

TLSKADYEKHKVYACEVTHQGLSSPVTKSENRGEC

Nucleotide sequence:
                                          SEQ ID NO. 89
GACGTGGTCATGACACAGAGCCCTCTGAGCCTGCCTGTGACACCTGGCGAACCTGCC

AGCATCAGCTGTAGAAGCAGCCAGAGCATCGTGCACAGCAACGGCAACACATACCTG

GAGTGGTATCTGAAGAAGCCCGGCCAGTCTCCTCAGCTGCTGATCTACAAGGTGTCCA

ACAGATTCAGCGGCGTGCCCGACAGATTCTCTGGCTCTGGATCTGGCACCGACTTCAC

CCTGAAGATCTCCAGAGTGGAAGCCGAGGACGTGGGCGTGTACTTCTGTCTCCAGGTC

ACACACGTGCCCCTGACATTTGGCCAGGGCACCAAGCTGGAAATCAAGCGAACTGTG

GCTGCACCATCTGTCTTCATCTTCCCGCCATCTGATGAGCAGTTGAAATCTGGAACTGC

CTCTGTTGTGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCAGGACAGC

AAGGACAGCACCTACAGCCTCAGCAGCACCCTGACGCTGAGCAAAGCAGACTACGAG
```

-continued

AAACACAAAGTCTACGCCTGCGAAGTCACCCATCAGGGCCTGAGCTCGCCCGTCACA

AAGAGCTTCAACAGGGGAGAGTGT

Heavy Chain (Heavy Chain 1) of GPC3 arm:

SEQ ID NO. 90

QVQLVQSGAEVKKPGSSVKVSCKASGYTFADYEIHWVREAPGQGLEWMGAIHPGSGGTA

YAQKFQGRVTLTADESSTTAYMELSSLRSEDTAVYYCTRYYSFAYWGQGTLVTVSSASTK

GPSVFPLAPCSRSTSESTAALGCLVKDYFPEPVTVSWNSGALTSGVHTFPAVLQSSGLYSLS

SVVTVPSSSLGTKTYTCNVDHKPSNTKVDKRVESKYGPPCPPCPAPEFEGGPSVFLFPPKP

KDTLMISRTPEVTCVVVDVSQEDPEVQFNWYVDGVEVHNAKTKPREEQFNSTYRVVSVL

TVLHQDWLNGKEYKCKVSNKGLASSIEKTISKAKGQPREPQVCTLPPSQEEMTKNQVSLS

CAVKGFYPSDIAVEWESNGQPENNYKTTPPVLDSDGSFFLVSKLTVDKSRWQEGNVFSCS

VMHEALHNHYTQKSLSLSLGK

Nucleotide sequence:

SEQ ID NO. 91

CAGGTTCAGCTGGTTCAGTCTGGCGCCGAAGTGAAGAAACCTGGCAGCAGCGTGAAG

GTGTCCTGCAAGGCTAGCGGCTACACCTTCGCCGACTACGAGATCCACTGGGTCCGAG

AGGCTCCAGGACAGGGACTTGAATGGATGGGCGCTATCCATCCTGGCTCTGGCGGCAC

AGCTTACGCCCAGAAATTCCAGGGCAGAGTGACCCTGACCGCCGACGAGTCTAGCAC

CACCGCCTACATGGAACTGAGCAGCCTGAGAAGCGAGGACACCGCCGTGTACTACTG

CACCCGGTACTACAGCTTCGCCTACTGGGGACAGGGAACCCTGGTCACAGTCAGCTCT

GCTAGCACCAAGGGCCCCAGCGTGTTCCCCCTGGCCCCTTGCAGCAGAAGCACCAGC

GAGAGCACAGCCGCCCTGGGCTGCCTGGTGAAGGACTACTTCCCCGAGCCCGTGACC

GTGTCCTGGAACAGCGGCGCTCTGACCAGCGGCGTGCATACCTTCCCCGCCGTGCTCC

AGAGCAGCGGACTGTACTCCCTGAGCAGCGTGGTGACCGTGCCTTCCAGCAGCCTGG

GCACCAAGACCTACACCTGCAACGTGGACCACAAGCCCAGCAACACCAAGGTGGACA

AGAGAGTGGAGAGCAAGTACGGCCCTCCCTGCCCCCCTTGCCCTGCCCCCGAGTTCGA

GGGCGGACCTAGCGTGTTCCTGTTCCCCCCCAAGCCCAAGGACACCCTGATGATCAGC

AGAACCCCCGAGGTGACCTGCGTGGTGGTGGACGTGTCCCAGGAGGACCCCGAGGTC

CAGTTTAATTGGTACGTGGACGGCGTGGAAGTGCATAACGCCAAGACCAAGCCCAGA

GAGGAGCAGTTCAACAGCACCTACAGAGTGGTGTCCGTGCTGACCGTGCTGCACCAG

GACTGGCTGAACGGCAAGGAATACAAGTGCAAGGTCTCCAACAAGGGCCTGGCCAGC

AGCATCGAGAAGACCATCAGCAAGGCCAAGGGCCAGCCACGGGAGCCCCAGGTCTGC

ACCCTGCCACCTAGCCAAGAGGAGATGACCAAGAACCAGGTGTCCCTGAGCTGTGCC

GTGAAAGGCTTCTATCCCAGCGATATCGCCGTGGAGTGGGAGAGCAACGGCCAGCCCG

AGAACAACTACAAGACCACCCCCCCTGTGCTGGACAGCGACGGCAGCTTCTTCCTGGT

TTCCAAGCTGACCGTGGACAAGTCCAGATGGCAGGAGGGCAACGTCTTCAGCTGCTC

CGTGATGCACGAGGCCCTGCACAACCACTACACCCAGAAGTCCCTGAGCCTGAGCCT

GGGCAAG

λ light chain of CD3 arm:

SEQ ID NO. 66

QAVVTQEPSLTVSPGGTVTLTCRSSTGAVTTSNYANWVQEKPGQAPRGLIGGTNKRAPWT

PARFSGSLLGGKAALTITGAQAEDEAEYYCVLWYSNLWVFGGGTKLTVLGQPKAAPSVT

LFPPSSEELQANKATLVCLISDFYPGAVTVAWKADSSPVKAGVETTTPSKQSNNKYAASSY

LSLTPEQWKSHRSYSCQVTHEGSTVEKTVAPTECS

-continued

Nucleotide sequence:

SEQ ID NO. 67

CAGGCTGTGGTCACACAAGAGCCTAGCCTGACAGTGTCTCCTGGCGGCACAGTGACC

CTGACCTGTAGATCTTCTACAGGCGCCGTGACCACCAGCAACTACGCTAATTGGGTGC

AGGAGAAGCCCGGCCAGGCTCCTAGAGGACTGATCGGCGGAACAAACAAGAGAGCC

CCTTGGACACCCGCCAGATTCTCTGGATCTCTGCTCGGCGGAAAGGCCGCTCTGACAA

TCACTGGTGCTCAGGCTGAGGACGAGGCCGAGTACTATTGTGTGCTGTGGTACAGCAA

CCTGTGGGTGTTCGGCGGAGGCACCAAACTGACAGTTCTGGGTCAGCCCAAGGCGGC

GCCCTCGGTCACTCTGTTCCCGCCCTCCTCTGAGGAGCTTCAAGCCAACAAGGCCACA

CTGGTGTGTCTCATAAGTGACTTCTATCCGGGAGCCGTGACAGTGGCCTGGAAGGCAG

ATAGCAGCCCCGTCAAGGCGGGAGTGGAGACCACCACACCCTCCAAACAAAGCAACA

ACAAGTACGCGGCCAGCAGCTACCTGAGCCTGACGCCTGAGCAGTGGAAGTCCCACA

GAAGCTACAGCTGCCAGGTCACGCATGAAGGGAGCACCGTGGAGAAGACAGTGGCCC

CTACAGAATGTTCA

Heavy chain (heavy chain 2) of CD3 arm:

SEQ ID NO. 68

EVQLVESGGGLVQPGGSLRLSCAASGFTFNTYAMNWVRKAPGKGLEWVGRIRSKYNNYA

TYYADSVKDRFTISRDDSKNSLYLQMNSLKTEDTAVYYCVRHGNFGNSYVSWFAYWGQG

TLVTVSSASTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRVESKYGPPCPPCPAPEFEG

GPSVFLFPPKPKDTLMISRTPEVTCVVVDVSQEDPEVQFNWYVDGVEVHNAKTKPREEQF

NSTYRVVSVLTVLHQDWLNGKEYKCKVSNKGLASSIEKTISKAKGQPREPQVYTLPPCQE

EMTKNQVSLWCLVKGFYPSDIAVEWESNGQPENNYKTTPPVLDSDGSFFLYSKLTVDKSR

WQEGNVFSCSVMHEALHNHYTQKSLSLSLGK

Nucleotide sequence:

SEQ ID NO. 69

GAGGTGCAGCTGGTTGAATCTGGCGGAGGACTGGTTCAGCCTGGCGGATCTCTGAGA

CTGTCTTGTGCCGCCAGCGGCTTCACCTTCAACACCTACGCTATGAACTGGGTCCGAA

AGGCCCCTGGCAAAGGACTGGAATGGGTGGGAAGAATCAGGTCCAAGTACAACAACT

ACGCCACCTACTACGCCGACAGCGTGAAGGACAGATTCACCATCAGCAGGGACGACA

GCAAGAACAGCCTGTACCTGCAGATGAACAGCCTGAAAACCGAGGACACCGCCGTGT

ACTACTGTGTCAGACACGGCAACTTCGGCAACAGCTATGTGTCTTGGTTTGCCTACTGG

GGCCAGGGCACACTGGTCACAGTTAGCTCTGCTAGCACCAAGGGCCCCAGCGTGTTCC

CCCTGGCCCCTTGCAGCAGAAGCACCAGCGAGAGCACAGCCGCCCTGGGCTGCCTGG

TGAAGGACTACTTCCCCGAGCCCGTGACCGTGTCCTGGAACAGCGGCGCTCTGACCA

GCGGCGTGCATACCTTCCCCGCCGTGCTCCAGAGCAGCGGACTGTACTCCCTGAGCAG

CGTGGTGACCGTGCCTTCCAGCAGCCTGGGCACCAAGACCTACACCTGCAACGTGGA

CCACAAGCCCAGCAACACCAAGGTGGACAAGAGAGTGGAGAGCAAGTACGGCCCTC

CCTGCCCCCCTTGCCCTGCCCCCGAGTTCGAGGGCGGACCTAGCGTGTTCCTGTTCCC

CCCCAAGCCCAAGGACACCCTGATGATCAGCAGAACCCCCGAGGTGACCTGCGTGGT

GGTGGACGTGTCCCAGGAGGACCCCGAGGTCCAGTTTAATTGGTACGTGGACGGCGT

GGAAGTGCATAACGCCAAGACCAAGCCCAGAGAGGAGCAGTTCAACAGCACCTACAG

AGTGGTGTCCGTGCTGACCGTGCTGCACCAGGACTGGCTGAACGGCAAGGAATACAA

-continued
GTGCAAGGTCTCCAACAAGGGCCTGGCCAGCAGCATCGAGAAGACCATCAGCAAGGC

CAAGGGCCAGCCACGGGAGCCCCAGGTCTACACCCTGCCACCTTGTCAAGAGGAGAT

GACCAAGAACCAGGTGTCCCTGTGGTGTCTGGTGAAAGGCTTCTATCCCAGCGATATC

GCCGTGGAGTGGGAGAGCAACGGCCAGCCCGAGAACAACTACAAGACCACCCCCCCT

GTGCTGGACAGCGACGGCAGCTTCTTCCTGTACTCCAAGCTGACCGTGGACAAGTCCA

GATGGCAGGAGGGCAACGTCTTCAGCTGCTCCGTGATGCACGAGGCCCTGCACAACC

ACTACACCCAGAAGTCCCTGAGCCTGAGCCTGGGCAAG

GPC3×CD3 κλ003:

κ light chain of GPC3 arm:
                                                           SEQ ID NO. 92
DVVMTQSPLSLPVTPGEPASISCRSSQSIVHSNGNTYLEWYLKKPGQSPQLLIYKVSNRFSG

VPDRFSGSGSGTDFTLKISRVEAEDVGVYFCLQVTHVPLTFGQGTKLEIKRTVAAPSVFIFP

PSDKKLKSGTASVVCLLNNFYPREAKVQWKVDNALQSGNSQESVTEQDSKDSTYSLSSTL

TLSKADYEKHKVYACEVTHQGLSSPVTKSENRGEC

Nucleotide sequence
                                                           SEQ ID NO. 93
GACGTGGTCATGACACAGAGCCCTCTGAGCCTGCCTGTGACACCTGGCGAACCTGCC

AGCATCAGCTGTAGAAGCAGCCAGAGCATCGTGCACAGCAACGGCAACACATACCTG

GAGTGGTATCTGAAGAAGCCCGGCCAGTCTCCTCAGCTGCTGATCTACAAGGTGTCCA

ACAGATTCAGCGGCGTGCCCGACAGATTCTCTGGCTCTGGATCTGGCACCGACTTCAC

CCTGAAGATCTCCAGAGTGGAAGCCGAGGACGTGGGCGTGTACTTCTGTCTCCAGGTC

ACACACGTGCCCCTGACATTTGGCCAGGGCACCAAGCTGGAAATCAAGCGAACTGTG

GCTGCACCATCTGTCTTCATCTTCCCGCCATCTGATAAGAAATTGAAATCTGGAACTGC

CTCTGTTGTGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCAGGACAGC

AAGGACAGCACCTACAGCCTCAGCAGCACCCTGACGCTGAGCAAAGCAGACTACGAG

AAACACAAAGTCTACGCCTGCGAAGTCACCCATCAGGGCCTGAGCTCGCCCGTCACA

AAGAGCTTCAACAGGGGAGAGTGT

Heavy Chain (Heavy Chain 1) of GPC3 arm:
                                                           SEQ ID NO. 94
QVQLVQSGAEVKKPGSSVKVSCKASGYTFADYEIHWVREAPGQGLEWMGAIHPGSGGTA

YAQKFQGRVTLTADESSTTAYMELSSLRSEDTAVYYCTRYYSFAYWGQGTLVTVSSASTK

GPSVFPLAPCSRSTSESTAALGCLVEDYFPEPVTVSWNSGALTSGVHTFPAVLQSSGLYSLS

SVVTVPSSSLGTKTYTCNVDHKPSNTKVDERVESKYGPPCPPCPAPEFEGGPSVFLFPPKPK

DTLMISRTPEVTCVVVDVSQEDPEVQFNWYVDGVEVHNAKTKPREEQFNSTYRVVSVLT

VLHQDWLNGKEYKCKVSNKGLASSIEKTISKAKGQPREPQVCTLPPSQEEMTKNQVSLSC

AVKGFYPSDIAVEWESNGQPENNYKTTPPVLDSDGSFFLVSKLTVDKSRWQEGNVFSCSV

MHEALHNHYTQKSLSLSLGK

Nucleotide sequence:
                                                           SEQ ID NO. 95
CAGGTTCAGCTGGTTCAGTCTGGCGCCGAAGTGAAGAAACCTGGCAGCAGCGTGAAG

GTGTCCTGCAAGGCTAGCGGCTACACCTTCGCCGACTACGAGATCCACTGGGTCCGAG

AGGCTCCAGGACAGGGACTTGAATGGATGGGCGCTATCCATCCTGGCTCTGGCGGCAC

AGCTTACGCCCAGAAATTCCAGGGCAGAGTGACCCTGACCGCCGACGAGTCTAGCAC

-continued

CACCGCCTACATGGAACTGAGCAGCCTGAGAAGCGAGGACACCGCCGTGTACTACTG

CACCCGGTACTACAGCTTCGCCTACTGGGGACAGGGAACCCTGGTCACAGTCAGCTCT

GCTAGCACCAAGGGCCCCAGCGTGTTCCCCCTGGCCCCTTGCAGCAGAAGCACCAGC

GAGAGCACAGCCGCCCTGGGCTGCCTGGTGGAGGACTACTTCCCCGAGCCCGTGACC

GTGTCCTGGAACAGCGGCGCTCTGACCAGCGGCGTGCATACCTTCCCCGCCGTGCTCC

AGAGCAGCGGACTGTACTCCCTGAGCAGCGTGGTGACCGTGCCTTCCAGCAGCCTGG

GCACCAAGACCTACACCTGCAACGTGGACCACAAGCCCAGCAACACCAAGGTGGACG

AGAGAGTGGAGAGCAAGTACGGCCCTCCCTGCCCCCCTTGCCCTGCCCCCGAGTTCGA

AGGCGGACCTAGCGTGTTCCTGTTCCCCCCCCAAGCCCAAGGACACCCTGATGATCAGC

AGAACCCCCGAGGTGACCTGCGTGGTGGTGGACGTGTCCCAGGAGGACCCCGAGGTC

CAGTTTAATTGGTACGTGGACGGCGTGGAAGTGCATAACGCCAAGACCAAGCCCAGA

GAGGAGCAGTTCAACAGCACCTACAGAGTGGTGTCCGTGCTGACCGTGCTGCACCAG

GACTGGCTGAACGGCAAGGAATACAAGTGCAAGGTCTCCAACAAGGGCCTGGCCAGC

AGCATCGAGAAGACCATCAGCAAGGCCAAGGGCCAGCCACGGGAGCCCCAGGTCTGC

ACCCTGCCACCTAGCCAAGAGGAGATGACCAAGAACCAGGTGTCCCTGAGCTGTGCC

GTGAAAGGCTTCTATCCCAGCGATATCGCCGTGGAGTGGGAGAGCAACGGCCAGCCCG

AGAACAACTACAAGACCACCCCCCCTGTGCTGGACAGCGACGGCAGCTTCTTCCTGGT

TTCCAAGCTGACCGTGGACAAGTCCAGATGGCAGGAGGGCAACGTCTTCAGCTGCTC

CGTGATGCACGAGGCCCTGCACAACCACTACACCCAGAAGTCCCTGAGCCTGAGCCCT

GGGCAAG

λ light chain of CD3 arm:

SEQ ID NO. 66
QAVVTQEPSLTVSPGGTVTLTCRSSTGAVTTSNYANWVQEKPGQAPRGLIGGTNKRAPWT

PARFSGSLLGGKAALTITGAQAEDEAEYYCVLWYSNLWVFGGGTKLTVLGQPKAAPSVT

LFPPSSEELQANKATLVCLISDFYPGAVTVAWKADSSPVKAGVETTTPSKQSNNKYAASSY

LSLTPEQWKSHRSYSCQVTHEGSTVEKTVAPTECS

Nucleotide sequence:

SEQ ID NO. 67
CAGGCTGTGGTCACACAAGAGCCTAGCCTGACAGTGTCTCCTGGCGGCACAGTGACC

CTGACCTGTAGATCTTCTACAGGCGCCGTGACCACCAGCAACTACGCTAATTGGGTGC

AGGAGAAGCCCGGCCAGGCTCCTAGAGGACTGATCGGCGGAACAAACAAGAGAGCC

CCTTGGACACCCGCCAGATTCTCTGGATCTCTGCTCGGCGGAAAGGCCGCTCTGACAA

TCACTGGTGCTCAGGCTGAGGACGAGGCCGAGTACTATTGTGTGCTGTGGTACAGCAA

CCTGTGGGTGTTCGGCGGAGGCACCAAACTGACAGTTCTGGGTCAGCCCAAGGCGGC

GCCCTCGGTCACTCTGTTCCCGCCCTCCTCTGAGGAGCTTCAAGCCAACAAGGCCACA

CTGGTGTGTCTCATAAGTGACTTCTATCCGGGAGCCGTGACAGTGGCCTGGAAGGCAG

ATAGCAGCCCCGTCAAGGCGGGAGTGGAGACCACCACACCCTCCAAACAAAGCAACA

ACAAGTACGCGGCCAGCAGCTACCTGAGCCTGACGCCTGAGCAGTGGAAGTCCCACA

GAAGCTACAGCTGCCAGGTCACGCATGAAGGGAGCACCGTGGAGAAGACAGTGGCCC

CTACAGAATGTTCA

-continued

Heavy chain (heavy chain 2) of CD3 arm:

SEQ ID NO. 68

```
EVQLVESGGGLVQPGGSLRLSCAASGFTFNTYAMNWVRKAPGKGLEWVGRIRSKYNNYA

TYYADSVKDRFTISRDDSKNSLYLQMNSLKTEDTAVYYCVRHGNFGNSYVSWFAYWGQG

TLVTVSSASTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRVESKYGPPCPPCPAPEFEG

GPSVFLFPPKPKDTLMISRTPEVTCVVVDVSQEDPEVQFNWYVDGVEVHNAKTKPREEQF

NSTYRVVSVLTVLHQDWLNGKEYKCKVSNKGLASSIEKTISKAKGQPREPQVYTLPPCQE

EMTKNQVSLWCLVKGFYPSDIAVEWESNGQPENNYKTTPPVLDSDGSFFLYSKLTVDKSR

WQEGNVFSCSVMHEALHNHYTQKSLSLSLGK
```

Nucleotide sequence:

SEQ ID NO. 69

```
GAGGTGCAGCTGGTTGAATCTGGCGGAGGACTGGTTCAGCCTGGCGGATCTCTGAGA

CTGTCTTGTGCCGCCAGCGGCTTCACCTTCAACACCTACGCTATGAACTGGGTCCGAA

AGGCCCCTGGCAAAGGACTGGAATGGGTGGGAAGAATCAGGTCCAAGTACAACAACT

ACGCCACCTACTACGCCGACAGCGTGAAGGACAGATTCACCATCAGCAGGGACGACA

GCAAGAACAGCCTGTACCTGCAGATGAACAGCCTGAAAACCGAGGACACCGCCGTGT

ACTACTGTGTCAGACACGGCAACTTCGGCAACAGCTATGTGTCTTGGTTTGCCTACTGG

GGCCAGGGCACACTGGTCACAGTTAGCTCTGCTAGCACCAAGGGCCCCAGCGTGTTCC

CCCTGGCCCCTTGCAGCAGAAGCACCAGCGAGAGCACAGCCGCCCTGGGCTGCCTGG

TGAAGGACTACTTCCCCGAGCCCGTGACCGTGTCCTGGAACAGCGGCGCTCTGACCA

GCGGCGTGCATACCTTCCCCGCCGTGCTCCAGAGCAGCGGACTGTACTCCCTGAGCAG

CGTGGTGACCGTGCCTTCCAGCAGCCTGGGCACCAAGACCTACACCTGCAACGTGGA

CCACAAGCCCAGCAACACCAAGGTGGACAAGAGAGTGGAGAGCAAGTACGGCCCTC

CCTGCCCCCCTTGCCCTGCCCCCGAGTTCGAGGGCGGACCTAGCGTGTTCCTGTTCCC

CCCCAAGCCCAAGGACACCCTGATGATCAGCAGAACCCCCGAGGTGACCTGCGTGGT

GGTGGACGTGTCCCAGGAGGACCCCGAGGTCCAGTTTAATTGGTACGTGGACGGCGT

GGAAGTGCATAACGCCAAGACCAAGCCCAGAGAGGAGCAGTTCAACAGCACCTACAG

AGTGGTGTCCGTGCTGACCGTGCTGCACCAGGACTGGCTGAACGGCAAGGAATACAA

GTGCAAGGTCTCCAACAAGGGCCTGGCCAGCAGCATCGAGAAGACCATCAGCAAGGC

CAAGGGCCAGCCACGGGAGCCCCAGGTCTACACCCTGCCACCTTGTCAAGAGGAGAT

GACCAAGAACCAGGTGTCCCTGTGGTGTCTGGTGAAAGGCTTCTATCCCAGCGATATC

GCCGTGGAGTGGGAGAGCAACGGCCAGCCCGAGAACAACTACAAGACCACCCCCCCT

GTGCTGGACAGCGACGGCAGCTTCTTCCTGTACTCCAAGCTGACCGTGGACAAGTCCA

GATGGCAGGAGGGCAACGTCTTCAGCTGCTCCGTGATGCACGAGGCCCTGCACAACC

ACTACACCCAGAAGTCCCTGAGCCTGAGCCTGGGCAAG
```

The plasmids encoding the corresponding antibody fragments were prepared according to the light chain (κ light chain) of GPC3 arm: light chain (Q light chain) of CD3 arm: heavy chain (heavy chain 1) of GPC3 arm: heavy chain (heavy chain 2) of CD3 arm=2:2:1:1 ratio, after mixing with 3 mg/mL PEI, co-transfecting of CHO-S cells, culture in 500 mL CD CHO AGT medium (Gibco #12490-001) at 37° C. 5% $CO_2$ at 150 rpm, 4% CHO Feed C+supplement (Gibco #A25031-05) was added at transient day 2, 4 and 6, respectively. When the cell viability decreased to about 85%, the fermentation broth was harvested, filtered and purified by Protein A affinity chromatography, and the SEC-HPLC monomer content was higher than 92%. The monomer content was further increased to above 99.5% by Butyl HP hydrophobic chromatography and Capto Q anion chromatography (Table 16).

TABLE 16

| Purification of humanized GPC3-CD3 bispecific antibody | | | | | |
| --- | --- | --- | --- | --- | --- |
| | HPLC-SEC (post Protein A) | | | HPLC-SEC (after anion chromatography) | | |
| HPLC detection | Mer | Monomer | Fragment | Mer | Monomer | Fragment |
| GPC3 × CD3 κλ002 | 2.6% | 94.2% | 3.1% | 0.0% | 100.0% | 0.0% |
| GPC3 × CD3 κλ003 | 2.2% | 93.2% | 4.5% | 0.1% | 99.5% | 0.4% |

2. Binding of GPC3×CD3 κλ Bispecific Antibody to GPC3 Stably Transfected Cells

Figure 30:
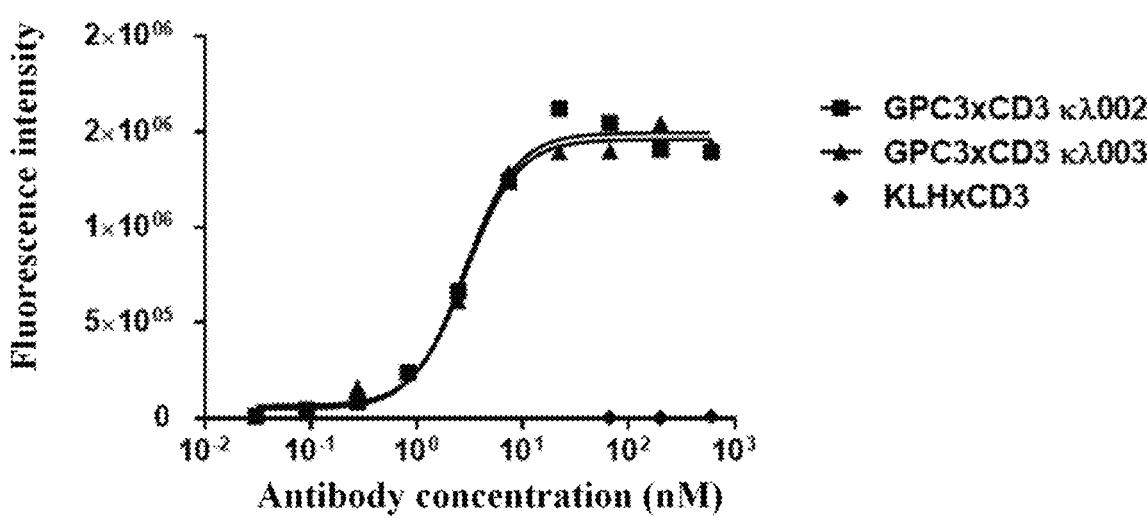
FIG. 30 shows binding of the anti-GPC3×CD3 κλ bispecific antibody to the GPC3 stably transfected cell.
Figure 30:
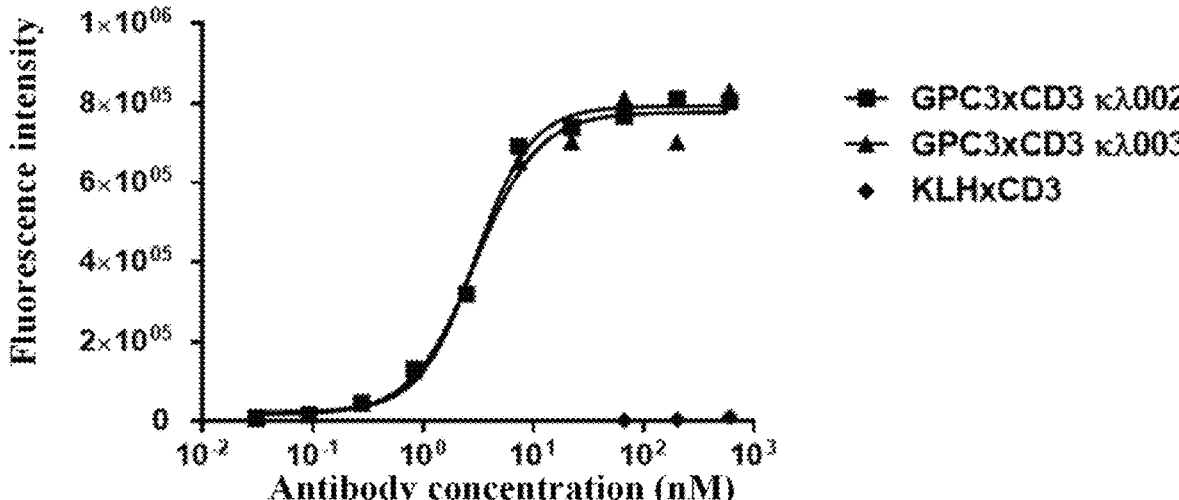
Figure 31:
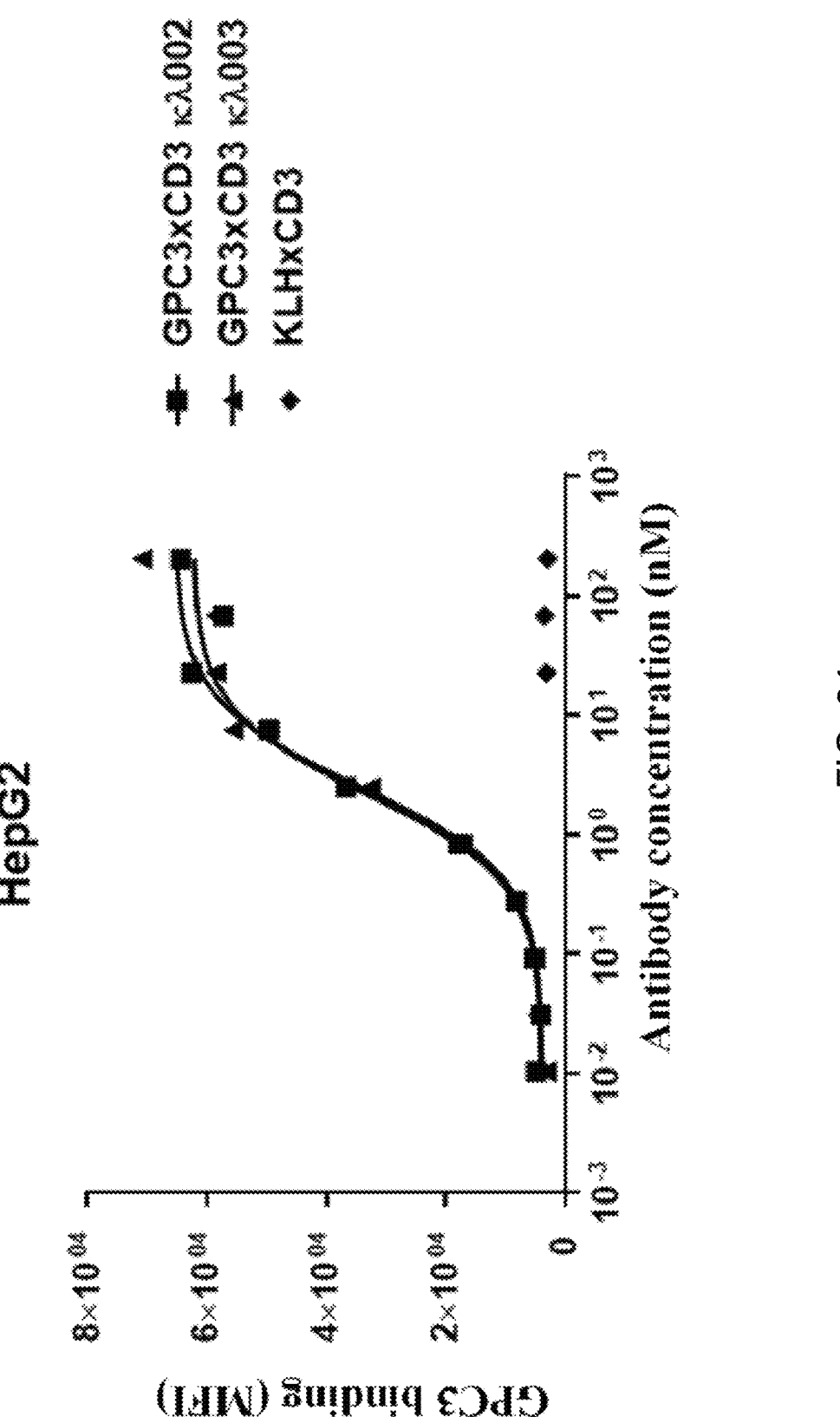
FIG. 31 shows binding of the anti-GPC3×CD3 κλ bispecific antibody to a tumor cell HepG2.

CHO-human GPC3, CHO-Cynomolgus monkey GPC3 stably transfected cells or human hepatocellular carcinoma HepG2 tumor cells in logarithmic growth phase were taken. After blocking, the cells were adjusted to 5×105 cells/ml, and 100 W/well cell suspension was added to 96-well U-shaped plate and centrifuged at 300 g for 5 min. The supernatant was discarded, 100 μL of gradient diluted antibody (with a starting concentration of 1800 nM, 3-fold dilution, 10 gradients) was added to each well, and incubated at 4° C. for 60 min. 50 μL/well Alexa Fluro647 labeled goat anti-human IgG Fc (1: 300 dilution) were added to the secondary antibody, incubated on ice for 20 min, added with 50 μL/well PI solution (1: 300) after washing once, incubated for 5 min, and flow cytometer was used to make detection. The results are shown in FIGS. 30-31 and Table 17. The GPC3×CD3 κλ bispecific antibody binds to GPC3+ cells with high affinity.

TABLE 17

| Binding ofGPC3 × CD3 κλ bispecific antibodies to GPC3 + cells | | | |
| --- | --- | --- | --- |
| EC50 | Human GPC3-CHO | Cynomolgus monkey GPC3-CHO | HepG2 |
| GPC3 × CD3 κλ002 | 2.8 nM | 3.0 nM | 2.1 nM |
| GPC3 × CD3 κλ003 | 2.9 nM | 3.0 nM | 2.5 nM |
| KLH × CD3 | Not combined | Not combined | Not combined |

3. Binding of GPC3×CD3 κλ Bispecific Antibody to Jurkat Cells

Figure 32:
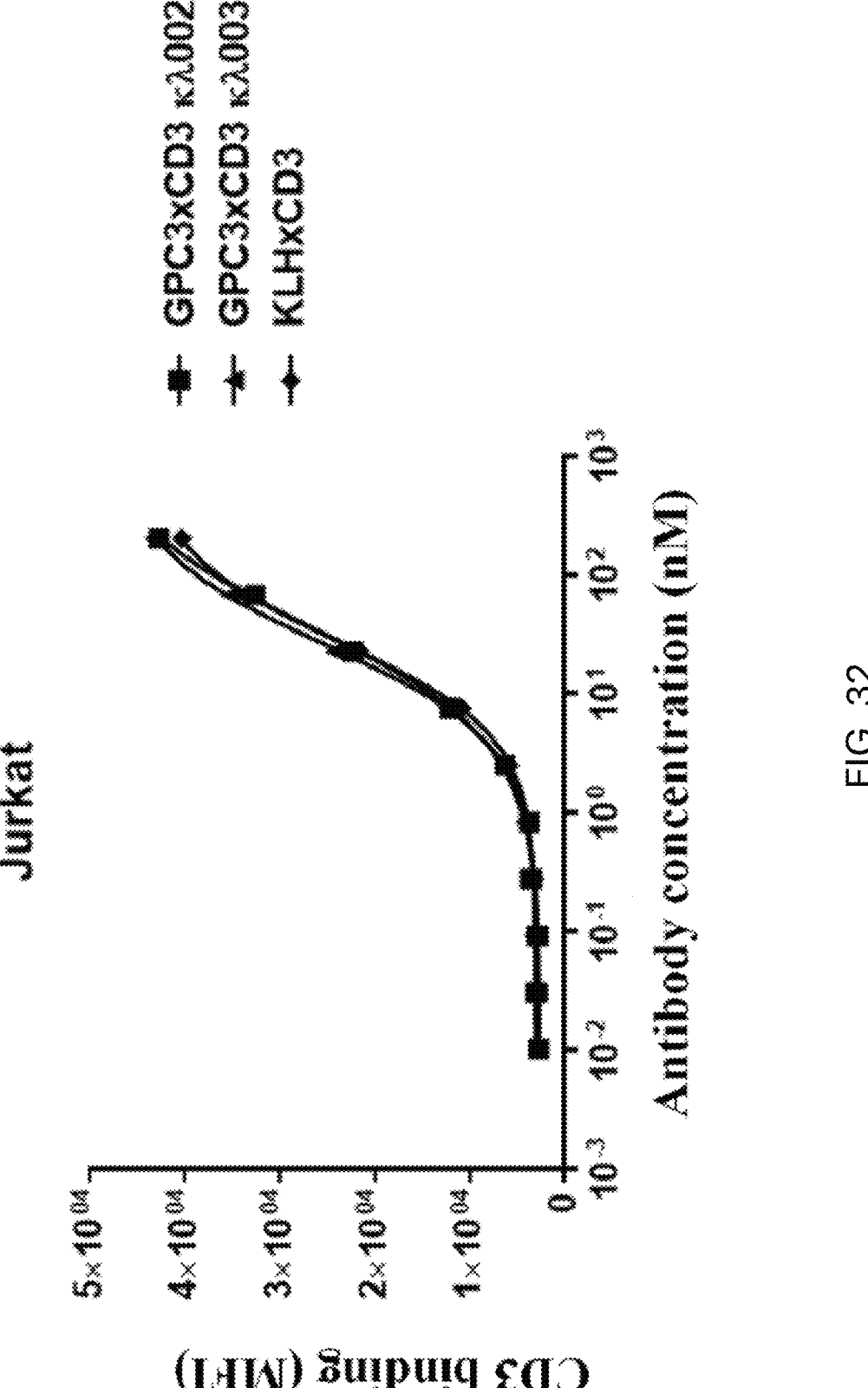
FIG. 32 shows binding of the anti-GPC3×CD3 κλ bispecific antibody to the Jurkat cell.

Jurkat cells in logarithmic growth phase were added with 200 μg/mL murine IgG (Jackson ImmunoResearch, 115-005-03) and incubated on ice for 30 minutes. The cells were adjusted to 5×105 cells/mL with 4% calf serum, 100 μL/well was added to 96-well U-plate, 300 g was centrifuged to removed the supernatant, 100 μL/well of gradient diluted antibody (initial concentration: 1800 nM, 3-fold dilution, 10 gradients) was added and incubated at 4° C. for 60 min. 50 μL/well Alexa Fluro647-labeled goat anti-human IgG Fc (1: 300 dilution) was added to the secondary antibody and incubated on ice for 20 min. 50 μL/well PI was added after washing once, incubated for 5 min, and detected with flow cytometer (BD C6). As shown in FIG. 32 and Table 18, the GPC3×CD3 κλ bispecific antibody binds with moderate affinity to human leukemia T-cell line Jurkat cells with an EC50 of about 20-40 nM.

4. Binding of GPC3×CD3 κλ Bispecific Antibody to Peripheral Blood T-Cells

Figure 33:
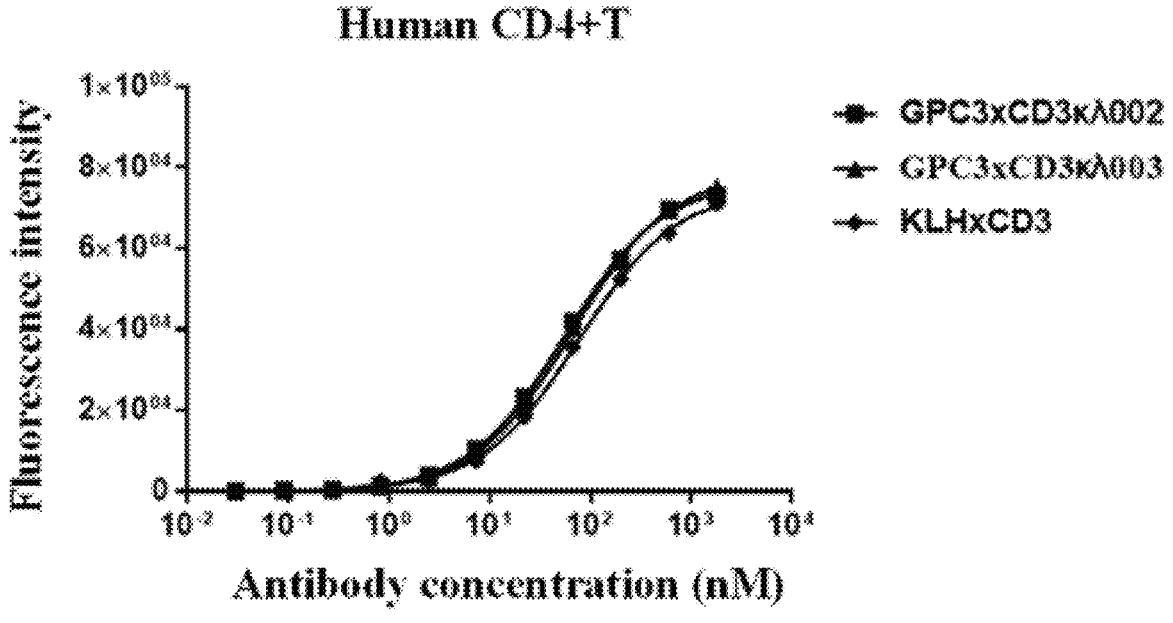
FIG. 33 shows binding of the anti-GPC3×CD3 κλ bispecific antibody to the T-cell in the peripheral blood.
Figure 33:
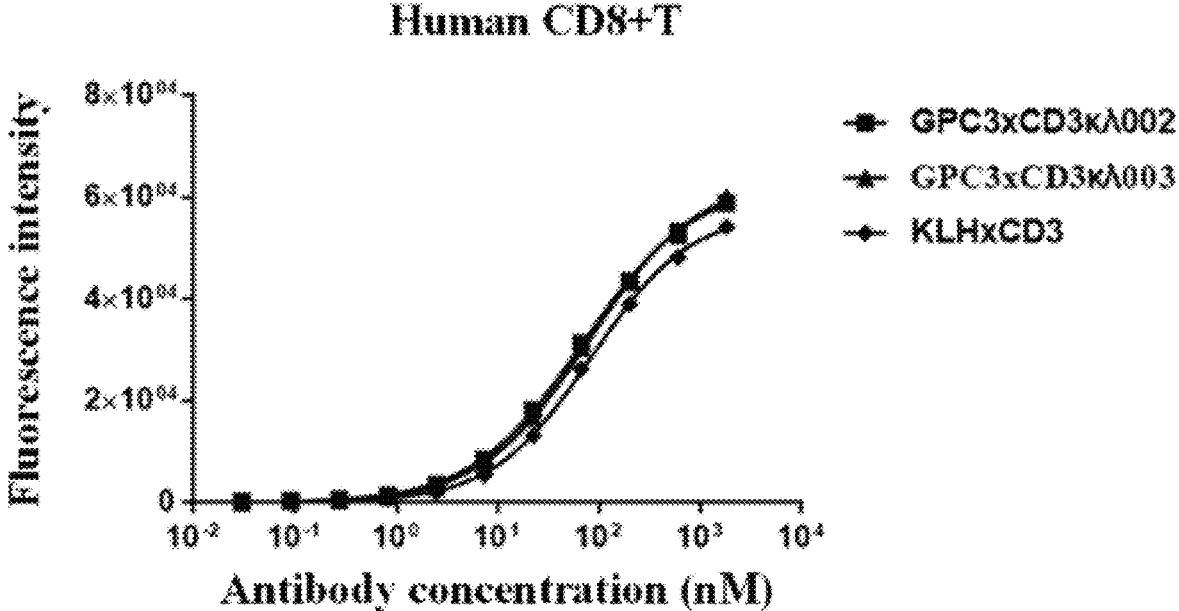

Fresh human or cynomolgus monkey peripheral blood was taken and PBMC was isolated by Ficoll. Paque Plus (GE, 17-1440-03). PBMC was adjusted to 5×105 cells/mL with 4% calf serum (Hyclone, SH30626.06), 100 μL/well was added to a 96-well U-plate, the supernatant was centrifuged off and 100 μL of gradient diluted antibody (with starting concentration of 1800 nM, 3-fold dilution, 10 gradients) was added to each well and incubated for 60 min at 4° C. 50 μL/well Alexa Fluro647 labeled goat anti-human IgG Fc (1: 300 dilution) was added to secondary antibody, with ice bath for 20 min. 50 μL/well PI was added after washing once and incubated for 5 min, and flow cytometer (BD Celesta) is used to make detection. The results are shown in FIG. 33 and Table 18. The GPC3×CD3 κλ bispecific antibody binds human peripheral blood T-cells with low affinity.

TABLE 18

| Binding of GPC3 × CD3 κλ bispecific antibodies to T-cells | | | |
| --- | --- | --- | --- |
| EC50 | Jurkat | CD4 + T | CD8 + T |
| GPC3 × CD3 κλ002 | 36 nM | 65 nM | 65 nM |
| GPC3 × CD3 κλ003 | 26 nM | 56 nM | 69 nM |
| KLH × CD3 | 27 nM | 77 nM | 84 nM |

5. TDCC Mediated by GPC3×CD3 κλ Bispecific Antibody

Figure 34A:
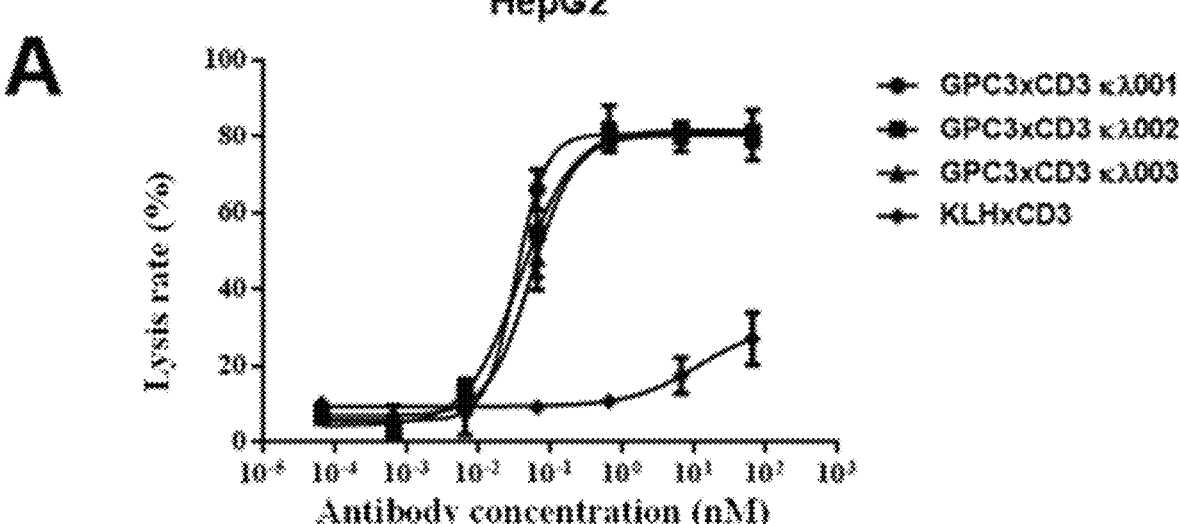
FIG. 34A and FIG. 34B show TDCC mediated by anti-GPC3×CD3 κλ antibody.
Figure 34B:
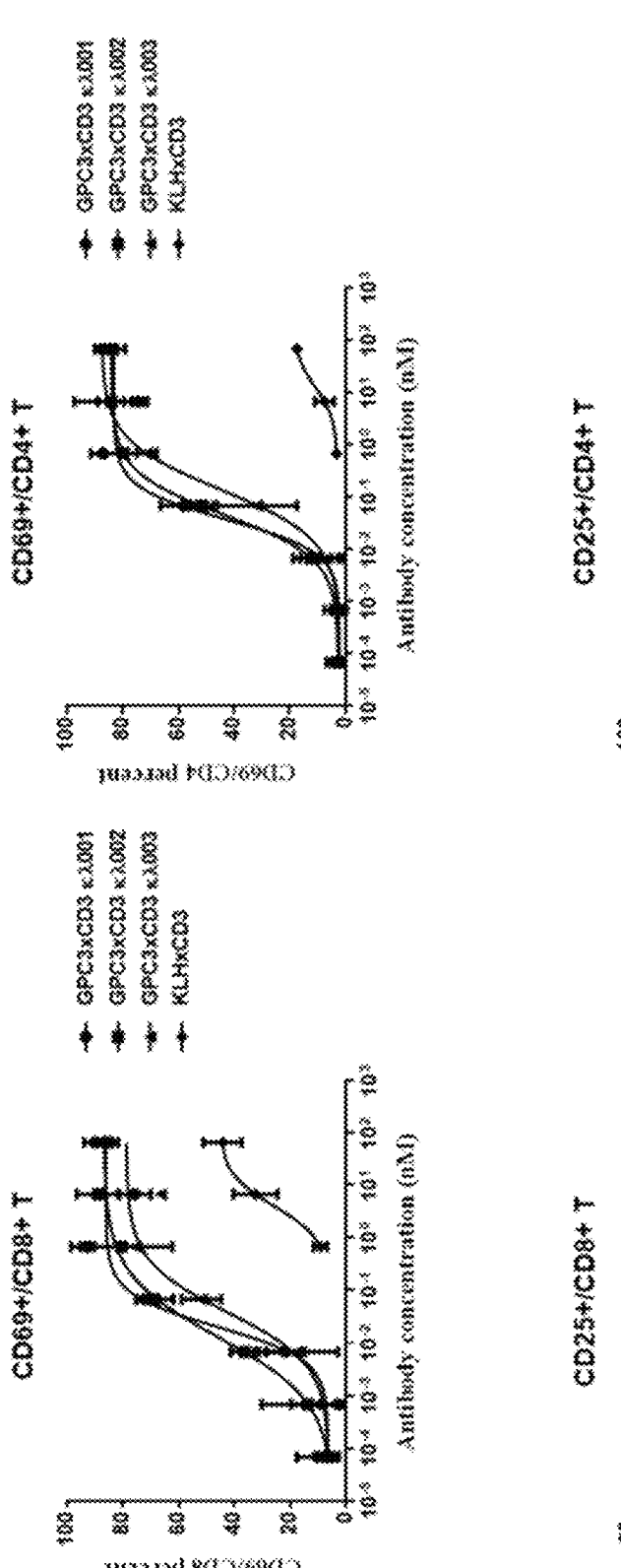
Figure 34B:
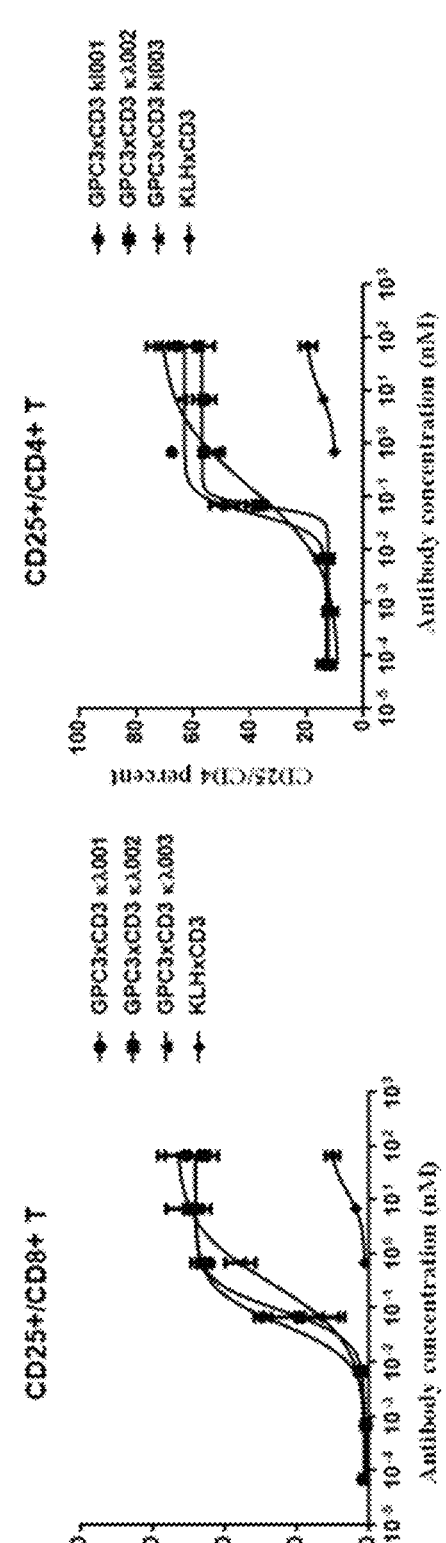

Freshly isolated PBMC was mixed with target cells in logarithmic growth phase, hepG2 cells, respectively, at an effector/target cell ratio of 10:1. 50 μL of gradient diluted antibody (with antibody concentration from 66.7 nM, 10-fold dilution, 7 gradients) was added to each well and incubated for 24 h at 37° C. in 5% $CO_2$. At the end of the incubation, 50 μL of the supernatant was transferred to a new black ELISA plate, 50 μL/well of LDH detection substrate was added, the reaction was stopped after 10 minutes and LDH release was detected. The remaining cells in the wells were washed twice with 4% calf blood, incubated with 100 μg/mL human IgG for 10 minutes, followed by T-cell activation detection antibodies (CD25-BV421, CD4-FITC, CD69-BV605 and CD8-APC) and incubated on ice for 20 minutes. The supernatant was washed and discarded, 60 μL/well PI was added, incubated on ice for 5 minutes and detected by flow cytometry. FIGS. 34A and 34B show killing of HepG2 cells and activation of T-cells, respectively, by the GPC3×CD3 κλ bispecific antibody.

6. Activation of T-Cell Activation Pathway by GPC3×CD3 κλ Bispecific Antibody

Target cells CHO-human GPC3 in logarithmic growth phase were harvested, centrifuged, the supernatant discarded and resuspended to 2×10^5 cells/ml. 50 μl/well of target cells were seeded into 96-well plates and incubated overnight at 37° C. in 5% $CO_2$. The Jurkat-NFAT-luc reporter cells in logarithmic growth phase were taken and performed with centrifugation at 300 g for 5 min. The supernatant was discarded, and it resuspended to 4×10^6 cells/ml. The 96-well plate was taken out, the supernatant, inoculate Jurkat-NFAT-luc reporter cells were 4×10^6 into the 96-well plate at 25 μL/well and added with 25 μL of gradient diluted GPC3×

Figure 35:
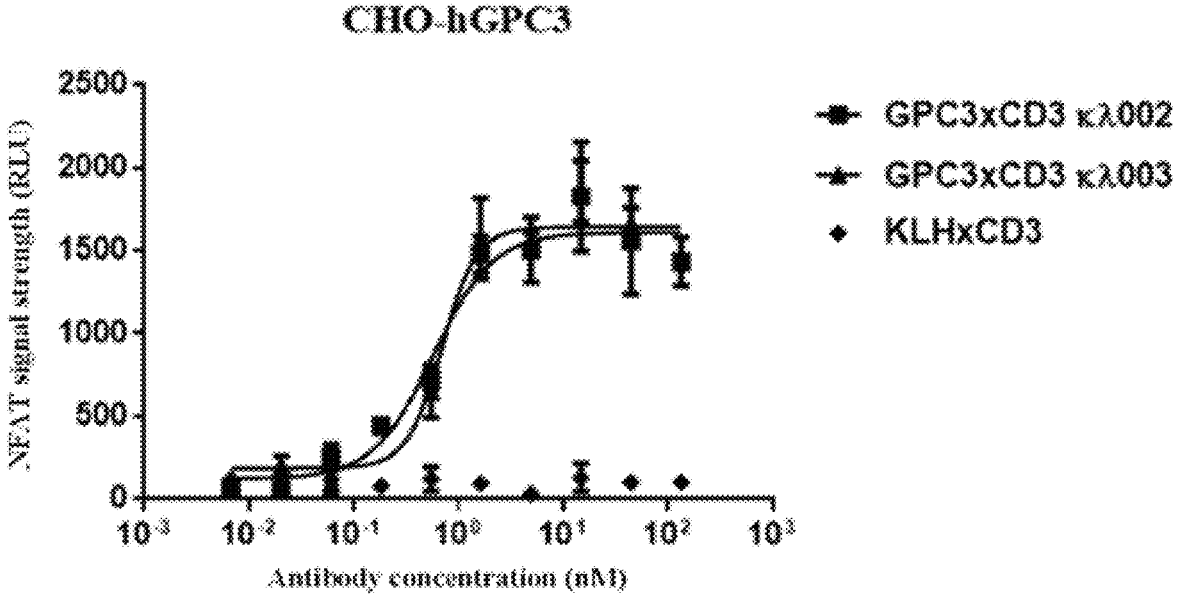
FIG. 35 shows effect of the anti-GPC3×CD3 κλ bispecific antibody on the T-cell NFAT signaling pathway.
Figure 35:
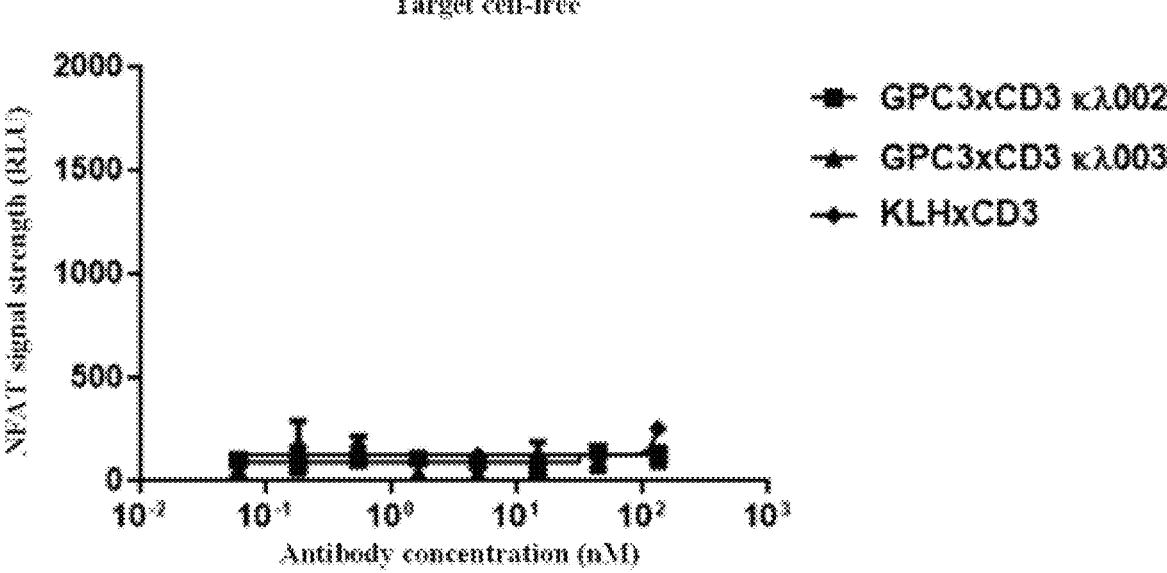

CD3 κλ bispecific antibody or control antibody KLH×CD3 (with an initial concentration of 20 g/ml, 3-fold dilution, 10 gradients) into each well, with was incubated at 37° C. for 6 h. After the incubation, 100 µL of detection reagent was added to each well according to ONE-Glo Luciferase Assay System instructions for detection in a microplate reader (MD SpectraMax i 3×). The detection results are shown in FIG. 35. The GPC3×CD3×bispecific antibody can activate the NFAT signaling pathway of T-cell when CHO-human GPC3 is used as the target cell.

7. Non-Specific Activation of GPC3×CD3κλ Bispecific Antibody PBMC

Figure 36:
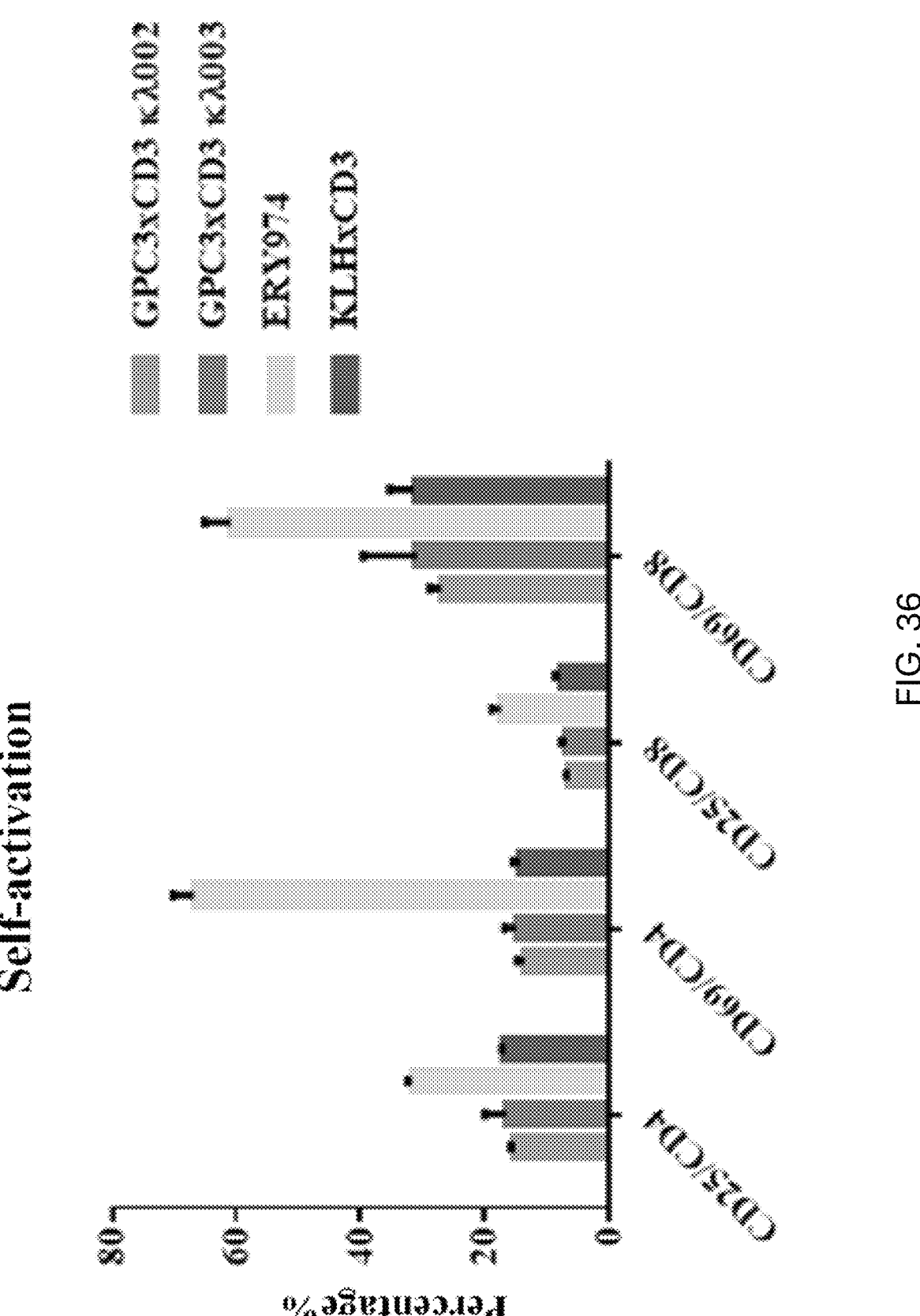
FIG. 36 shows non-specific activation of PBMC by the anti-GPC3×CD3 κλ bispecific antibody.

Freshly isolated PBMC was added with 100 L of antibody (10 gg/mL) and incubated at 37° C. in 5% $CO_2$ for 24 hours. The cells in the wells were washed twice with 4% calf blood, incubated with 100 µg/mL human IgG for 10 minutes, followed by T-cell activation detection antibodies (CD25-BV421, CD4-FITC, CD69-BV605 and CD8-APC) and incubated on ice for 20 minutes. The supernatant was washed and discarded, 60 µL/well PI was added, incubated on ice for 5 minutes and detected by flow cytometry. The positive control antibody ERY974 was prepared according to US20170267783. The results are shown in FIG. 36. In the absence of target cells, GPC3×CD3 κλ bispecific antibody had no activation of peripheral blood T-cells, comparable to the negative control KLH×CD3.

8. Immune Reconstitution of Subcutaneous HepG2 Xenograft Model in Mice

Figure 37:
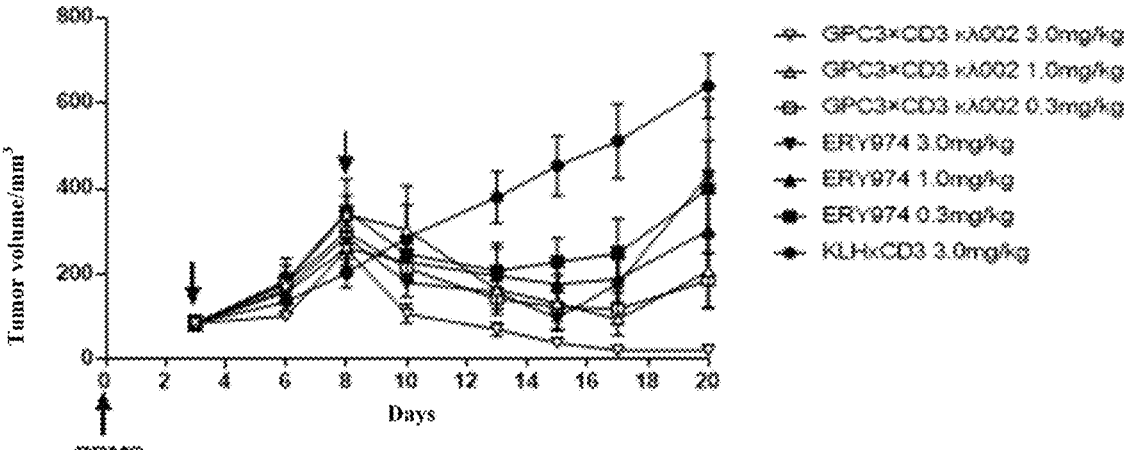
FIG. 37 shows inhibitory effect of the anti-GPC3×CD3 κλ bispecific antibody in a xenograft model of a subcutaneous HepG2 in immune-reconstituted mice.
Figure 37:
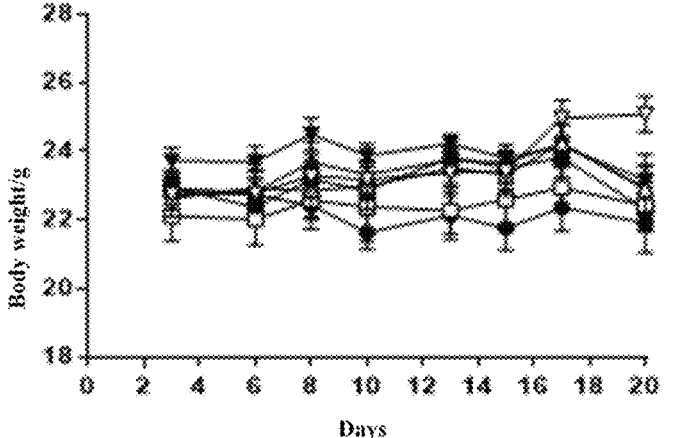

Six to eight-week-old female B-NGD mice (Bio-Tech Co. Ltd.) were subcutaneously inoculated with HepG2 cells ($7×10^6$/mouse). When the tumors grew to 60-100 mm³, they were randomly divided into high dose group (3.0 mg/kg), medium dose group (1.0 mg/kg), low dose group (0.3 mg/kg), positive control group (ERY974) and negative control group (KLH×CD3). Each mouse was injected intravenously with 1×107 PBMC cells via the tail vein. Three days later, the first dose was given to the mouse once every 5 days for a total of 2 doses. The tumor volume and body weight of the mice were monitored. At the end of the experiment, the mice were killed by cervical dislocation and the tumors were collected and weighed. The results are shown in FIG. 37. The in vivo efficacy of GPC3×CD3 κλ bispecific antibody was dose-related, and the tumor inhibition rates (low-dose to high-dose) were: 76.7%, 81.3% and 95.9%. The tumor-bearing mice tolerated the foregoing doses well, without weight loss and other adverse reactions.

9. CD3 Humanized Murine Hepa1-6/Human GPC3 Xenograft Model

Figure 38:
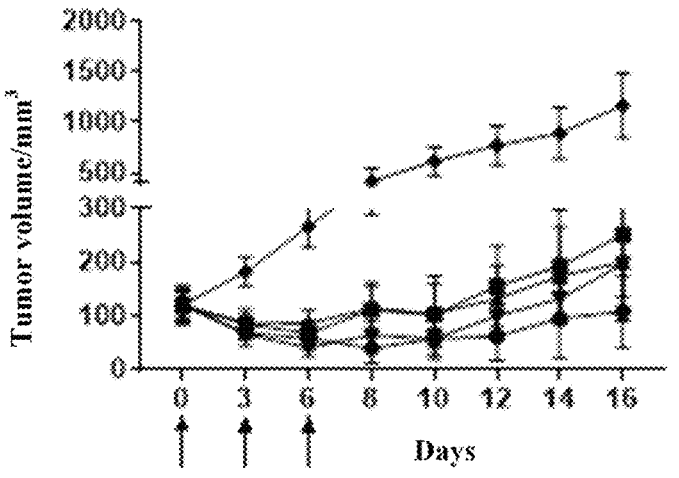
FIG. 38 shows inhibitory effect of the anti-GPC3×CD3 κλ bispecific antibody in the humanized anti-CD3 humanized murine Hepa1-6/human GPC3 xenograft model.
Figure 38:
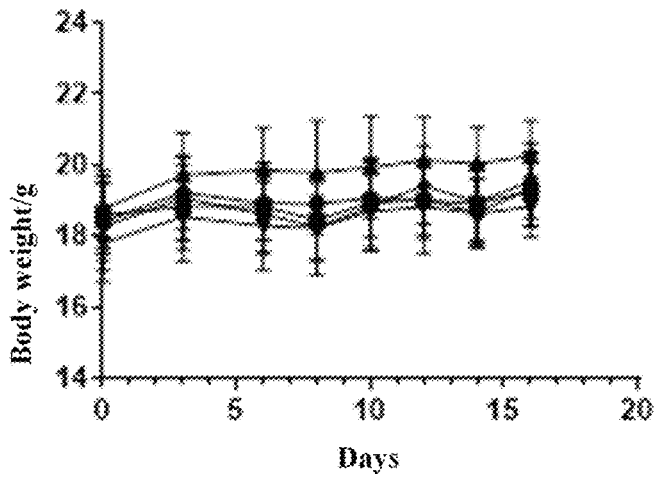

Six-week-old female C57/BL6-hCD3 mice (Bio-tech Bio-tech Co. Ltd.) were selected and inoculated with Hepa1-6/human GPC3 (6×106/mouse) subcutaneously. When the tumor volume reached 60-100 mm3, the mice were randomly divided into groups. The dose was set as 10 mg/mL in high dose group, 3 mg/mL in medium dose group low dose group 1 mg/mL, positive control group ERY974 and negative control group KLH×CD3 10 mg/kg. The dosing interval was once every 3 days for a total of 3 doses. The tumor volume and body weight of the mice were monitored. At the end of the experiment, the mice were killed by cervical dislocation and the tumors were collected and weighed. The results are shown in FIG. 38. The GPC3× CD3×bispecific antibody significantly mediated immune cells to kill tumor cells and reduce tumor-bearing volume. Its 10 mg/kg dose was comparable to ERY974.

---

40

The invention claimed is:

1. An antibody or an antigen-binding fragment thereof that binds to BCMA, comprising:
   a first light chain variable domain comprising the sequence shown in SEQ ID NO: 80, and
   a first heavy chain variable domain comprising the sequence shown in SEQ ID NO: 86.

2. The antibody or antigen-binding fragment thereof of claim 1, wherein the antibody or antigen-binding fragment thereof comprises a first light chain and a first heavy chain, wherein the first light chain comprises the first light chain variable domain and the first heavy chain comprises the first heavy chain variable domain.

3. The antibody or antigen-binding fragment thereof of claim 2, wherein:
   (i) the first light chain comprises a lysine (K) at amino acid position 42; and
   (ii) the first heavy chain comprises a glutamate (E) at amino acid position 39, and
   wherein the numbering is relative to the sequence shown in SEQ ID NOs: 80 and 86, respectively.

4. The antibody or antigen-binding fragment thereof of claim 2 wherein the first heavy chain comprises mutations Y349C, T366S, L368A, and Y407V, wherein the numbering is according to the EU numbering system.

5. The antibody or antigen-binding fragment of claim 1, wherein the antibody is IgG4 isotype.

6. The antibody or antigen-binding fragment thereof of claim 2, wherein the antibody or antigen-binding fragment thereof comprises a second light chain and a second heavy chain.

7. The antibody or antigen-binding fragment thereof of claim 6, wherein:
   (i) the second light chain comprises a glutamate (E) at amino acid position 40; and
   (ii) the second heavy chain comprises a lysine (K) at amino acid position 39.

8. The antibody or antigen-binding fragment thereof of claim 6, wherein the second heavy chain comprises a S354C mutation and a T366W mutation, wherein the numbering is according to the EU numbering system.

9. The antibody or antigen-binding fragment thereof of claim 6, wherein the first heavy chain comprises mutations Y349C, T366S, L368A, and Y407V, and wherein the second heavy chain comprises a S354C mutation and a T366W mutation, wherein the numbering is according to the EU numbering system.

10. The antibody or antigen-binding fragment thereof of claim 6, wherein the first heavy chain and the second heavy chain each, independently, comprise one or more mutations corresponding to S228P, L235E, and P329A, wherein the numbering is according to the EU numbering system.

11. The antibody or antigen-binding fragment thereof of claim 6, wherein the first heavy chain and the second heavy chain each, independently, comprise the mutations of S228P, L235E, and P329A, wherein the numbering is according to the EU numbering system.

12. The antibody or an antigen-binding fragment thereof of claim 2, wherein the first light chain is a κ type light chain.

13. The antibody or an antigen-binding fragment thereof of claim 6, wherein the second light chain is a λ type light chain.

14. The antibody or antigen-binding fragment thereof of claim 6, wherein the antibody or antigen-binding fragment thereof is multispecific.

15. The antibody or antigen-binding fragment thereof of claim 6, wherein the antibody or antigen-binding fragment thereof is multispecific and further comprises a second antigen-binding portion or antigen-binding fragment thereof that binds to a T cell antigen.

16. The antibody or antigen-binding fragment thereof of claim 15, wherein the T cell antigen is CD3.

17. The antibody or antigen-binding fragment thereof of claim 16, wherein the second antigen-binding portion or antigen-binding fragment thereof that binds to CD3 comprises:

(i) a second light chain variable domain comprising LCDR1, LCDR2, and LCDR3 comprising the amino acid sequences of: SEQ ID NO: 7, SEQ ID NO: 8, and SEQ ID NO: 21, respectively; and (ii) a second heavy chain variable domain comprising HCDR1, HCDR2, and HCDR3 comprising the amino acid sequences of: SEQ ID NO: 26, SEQ ID NO: 27, and SEQ ID NO: 28, respectively.

18. The antibody or antigen-binding fragment thereof of claim 17, wherein:

(i) the second light chain variable domain of the antigen-binding portion or antigen-binding fragment thereof that binds to CD3 comprises an amino acid sequence as shown in SEQ ID NO: 18; and (ii) the second heavy chain variable domain of the antigen-binding portion or antigen-binding fragment thereof that binds to CD3 comprises an amino acid sequence as shown in SEQ ID NO: 50.

19. The antibody or antigen-binding fragment thereof of claim 18, wherein the second antigen-binding portion or antigen-binding fragment thereof that binds to CD3 comprises:

(i) a second light chain comprising an amino acid sequence as shown in SEQ ID NO: 66; and (ii) a second heavy chain comprising an amino acid sequence as shown in SEQ ID NO: 68.

20. One or more nucleic acid molecules encoding the antibody or antigen-binding fragment of claim 1.

21. A vector comprising the one or more nucleic acid molecules of claim 20.

22. A cell comprising the one or more nucleic acid molecules of claim 20.

23. A pharmaceutical composition comprising the antibody or antigen-binding fragment thereof of claim 1 and a pharmaceutically acceptable carrier.

24. A method of treating a disease or disorder associated with BCMA in a subject, the method comprising administering the antibody or an antigen-binding fragment thereof that binds to BCMA, the antibody or antigen-binding fragment thereof comprising:

a first light chain variable domain comprising the sequence shown in SEQ ID NO: 80, and a first heavy chain variable domain comprising the sequence shown in SEQ ID NO: 86.

25. The method of claim 24, wherein the antibody or antigen-binding fragment thereof comprises a first light chain and a first heavy chain, wherein the first light chain comprises the first light chain variable domain and the first heavy chain comprises the first heavy chain variable domain.

26. The method of claim 25, wherein the antibody or antigen-binding fragment thereof comprises a second light chain and a second heavy chain.

27. The method of claim 26, wherein the antibody or antigen-binding fragment thereof is multispecific.

28. The method of claim 27, wherein the antibody or antigen-binding fragment thereof is multispecific and further comprises a second antigen-binding portion or antigen-binding fragment thereof that binds a T cell antigen.

29. The method of claim 28, wherein the T cell antigen is CD3.

30. The method of claim 29, wherein the second antigen-binding portion or antigen-binding fragment thereof that binds to CD3 comprises:

(i) a second light chain variable domain comprising LCDR1, LCDR2, and LCDR3 comprising the amino acid sequences of: SEQ ID NO: 7, SEQ ID NO: 8, and SEQ ID NO: 21, respectively; and (ii) a second heavy chain variable domain comprising HCDR1, HCDR2, and HCDR3 comprising the amino acid sequences of: SEQ ID NO: 26, SEQ ID NO: 27, and SEQ ID NO: 28, respectively.

31. The method of claim 30, wherein:

(i) the second light chain variable domain of the antigen-binding portion or antigen-binding fragment thereof that binds to CD3 comprises an amino acid sequence as shown in SEQ ID NO: 18; and (ii) the second heavy chain variable domain of the antigen-binding portion or antigen-binding fragment thereof that binds to CD3 comprises an amino acid sequence as shown in SEQ ID NO: 50.

32. The method of claim 31, wherein the second antigen-binding portion or antigen-binding fragment thereof that binds to CD3 comprises:

(i) a second light chain comprising an amino acid sequence as shown in SEQ ID NO: 66; and (ii) a second heavy chain comprising an amino acid sequence as shown in SEQ ID NO: 68.

33. A method of depleting BCMA-positive cells in a subject, the method comprising administering the antibody or an antigen-binding fragment thereof that binds to BCMA, the antibody or antigen-binding fragment thereof comprising:

a first light chain variable domain comprising the sequence shown in SEQ ID NO: 80, and a first heavy chain variable domain comprising the sequence shown in SEQ ID NO: 86.

34. The method of claim 33, wherein the antibody or antigen-binding fragment thereof comprises a first light chain and a first heavy chain, wherein the first light chain comprises the first light chain variable domain and the first heavy chain comprises the first heavy chain variable domain.

35. The method of claim 33, wherein the antibody or antigen-binding fragment thereof comprises a second light chain and a second heavy chain.

36. The method of claim 33, wherein the antibody or antigen-binding fragment thereof is multispecific.

37. The method of claim 36, wherein the antibody or antigen-binding fragment thereof is multispecific and further comprises a second antigen-binding portion or antigen-binding fragment thereof that binds a T cell antigen.

38. The method of claim 37, wherein the T cell antigen is CD3.

39. The method of claim 38, wherein the second antigen-binding portion or antigen-binding fragment thereof that binds to CD3 comprises:

a second light chain variable domain comprising LCDR1, LCDR2, and LCDR3 comprising the amino acid sequences of: SEQ ID NO: 7, SEQ ID NO: 8, and SEQ ID NO: 21, respectively; and a second heavy chain variable domain comprising HCDR1, HCDR2, and HCDR3 comprising the amino acid sequences of: SEQ ID NO: 26, SEQ ID NO: 27, and SEQ ID NO: 28, respectively.

40. The method of claim 39, wherein:

(i) the second light chain variable domain of the second antigen-binding portion or antigen-binding fragment thereof that binds to CD3 comprises an amino acid sequence as shown in SEQ ID NO: 18; and (ii) the second heavy chain variable domain of the second antigen-binding portion or antigen-binding fragment thereof that binds to CD3 comprises an amino acid sequence as shown in SEQ ID NO: 50.

41. The method of claim 40, wherein the second antigen-binding portion or antigen-binding fragment thereof that binds to CD3 comprises:

(i) a second light chain comprising an amino acid sequence as shown in SEQ ID NO: 66; and (ii) a second heavy chain comprising an amino acid sequence as shown in SEQ ID NO: 68.

\* \* \* \* \*